US008450781B2

(12) United States Patent
Rothberg et al.

(10) Patent No.: US 8,450,781 B2
(45) Date of Patent: May 28, 2013

(54) METHODS AND APPARATUS FOR MEASURING ANALYTES USING LARGE SCALE FET ARRAYS

(75) Inventors: Jonathan Rothberg, Guilford, CT (US);
Wolfgang Hinz, New Haven, CT (US);
Kim Johnson, Carlsbad, CA (US);
James Bustillo, Castro Valley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/616,599

(22) Filed: Sep. 14, 2012

(65) Prior Publication Data
US 2013/0015506 A1 Jan. 17, 2013

Related U.S. Application Data

(63) Continuation of application No. 13/149,262, filed on May 31, 2011, which is a continuation of application No. 12/002,781, filed on Dec. 17, 2007, now Pat. No. 8,262,900, which is a continuation-in-part of application No. 12/002,291, filed on Dec. 14, 2007, now Pat. No. 7,948,015.

(60) Provisional application No. 60/956,324, filed on Aug. 16, 2007, provisional application No. 60/948,748, filed on Jul. 10, 2007, provisional application No. 60/870,073, filed on Dec. 14, 2006.

(51) Int. Cl.
*G01N 27/414* (2006.01)

(52) U.S. Cl.
USPC .......................................... 257/253; 205/789

(58) Field of Classification Search
USPC ..................... 257/253; 205/789, 792, 793.5; 422/82.01–82.03; 435/6, 285.1, 287.1, 287.2; 436/103–105, 150, 182; 506/1, 9
See application file for complete search history.

(56) References Cited

U.S. PATENT DOCUMENTS 4,411,741 A 10/1983 Janata
4,490,678 A 12/1984 Kuisl et al.
(Continued)

FOREIGN PATENT DOCUMENTS

CN 102203282 9/2011
EP 0223618 5/1987
(Continued)

OTHER PUBLICATIONS

Milgrew, M. J., et al., "The development of scalable sensor arrays using standard CMOS technology", Sensors and Actuators B Chemical, vol. 103, 2004, p. 37-42.*

(Continued)

*Primary Examiner* — J. Christopher Ball

(57) ABSTRACT

Methods and apparatus relating to very large scale FET arrays for analyte measurements. ChemFET (e.g., ISFET) arrays may be fabricated using conventional CMOS processing techniques based on improved FET pixel and array designs that increase measurement sensitivity and accuracy, and at the same time facilitate significantly small pixel sizes and dense arrays. Improved array control techniques provide for rapid data acquisition from large and dense arrays. Such arrays may be employed to detect a presence and/or concentration changes of various analyte types in a wide variety of chemical and/or biological processes. In one example, chemFET arrays facilitate DNA sequencing techniques based on monitoring changes in hydrogen ion concentration (pH), changes in other analyte concentration, and/or binding events associated with chemical processes relating to DNA synthesis.

11 Claims, 76 Drawing Sheets

U.S. PATENT DOCUMENTS

| | | |
|---|---|---|
| 4,641,084 A | 2/1987 | Komatsu |
| 4,701,253 A | 10/1987 | Ligtenberg et al. |
| 4,722,830 A | 2/1988 | Urie et al. |
| 4,743,954 A | 5/1988 | Brown |
| 4,764,797 A | 8/1988 | Shaw et al. |
| 4,777,019 A | 10/1988 | Dandekar |
| 4,822,566 A | 4/1989 | Newman |
| 4,863,849 A | 9/1989 | Melamede |
| 4,864,229 A | 9/1989 | Lauks et al. |
| 4,874,499 A | 10/1989 | Smith et al. |
| 4,971,903 A | 11/1990 | Hyman |
| 5,009,766 A | 4/1991 | Lauks |
| 5,038,192 A | 8/1991 | Bonneau |
| 5,110,441 A | 5/1992 | Kinlen et al. |
| 5,113,870 A | 5/1992 | Rossenfeld |
| 5,138,251 A | 8/1992 | Koshiishi et al. |
| 5,151,759 A | 9/1992 | Vinal |
| 5,164,319 A | 11/1992 | Hafeman et al. |
| 5,284,566 A | 2/1994 | Cuomo et al. |
| 5,317,407 A | 5/1994 | Michon |
| 5,319,226 A | 6/1994 | Sohn et al. |
| 5,436,149 A | 7/1995 | Barnes |
| 5,439,839 A | 8/1995 | Jang |
| 5,466,348 A | 11/1995 | Holm-Kennedy |
| 5,490,971 A | 2/1996 | Gifford et al. |
| 5,554,339 A | 9/1996 | Cozzette et al. |
| 5,583,462 A | 12/1996 | Grasshoff |
| 5,593,838 A | 1/1997 | Zanzucchi et al. |
| 5,600,451 A | 2/1997 | Maki |
| 5,631,704 A | 5/1997 | Dickinson et al. |
| 5,637,469 A | 6/1997 | Wilding et al. |
| 5,702,964 A | 12/1997 | Lee |
| 5,793,230 A | 8/1998 | Chu et al. |
| 5,846,708 A | 12/1998 | Hollis et al. |
| 5,911,873 A | 6/1999 | McCarron et al. |
| 5,922,591 A | 7/1999 | Anderson et al. |
| 5,923,421 A | 7/1999 | Rajic et al. |
| 5,958,703 A | 9/1999 | Dower et al. |
| 5,965,452 A | 10/1999 | Kovacs |
| 6,002,299 A | 12/1999 | Thomsen |
| 6,107,032 A | 8/2000 | Kilger et al. |
| 6,210,891 B1 | 4/2001 | Nyren et al. |
| 6,255,678 B1 | 7/2001 | Sawada et al. |
| 6,274,320 B1 | 8/2001 | Rothberg et al. |
| 6,327,410 B1 | 12/2001 | Walt et al. |
| 6,355,431 B1 | 3/2002 | Chee et al. |
| 6,361,671 B1 | 3/2002 | Mathies et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,499,499 B2 | 12/2002 | Dantsker et al. |
| 6,511,803 B1 | 1/2003 | Church et al. |
| 6,518,024 B2 | 2/2003 | Choong et al. |
| 6,518,146 B1 | 2/2003 | Singh et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,602,702 B1 | 8/2003 | McDevitt et al. |
| 6,605,428 B2 | 8/2003 | Klinger et al. |
| 6,613,513 B1 | 9/2003 | Parce et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,682,899 B2 | 1/2004 | Bryan et al. |
| 6,682,936 B2 | 1/2004 | Kovacs |
| 6,700,814 B1 | 3/2004 | Nahas et al. |
| 6,780,591 B2 | 8/2004 | Williams et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,859,570 B2 | 2/2005 | Walt et al. |
| 6,888,194 B2 | 5/2005 | Yoshino |
| 6,919,211 B1 | 7/2005 | Fodor et al. |
| 6,926,865 B2 | 8/2005 | Howard |
| 6,939,451 B2 | 9/2005 | Zhao et al. |
| 6,953,958 B2 | 10/2005 | Baxter et al. |
| 6,969,488 B2 | 11/2005 | Bridgham et al. |
| 6,998,274 B2 | 2/2006 | Chee et al. |
| 7,022,288 B1 | 4/2006 | Boss |
| 7,033,754 B2 | 4/2006 | Chee et al. |
| 7,037,687 B2 | 5/2006 | Williams et al. |
| 7,049,645 B2 | 5/2006 | Sawada et al. |
| 7,060,431 B2 | 6/2006 | Chee et al. |
| 7,085,502 B2 | 8/2006 | Shushakov et al. |
| 7,087,387 B2 | 8/2006 | Gerdes et al. |
| 7,090,975 B2 | 8/2006 | Shultz et al. |
| 7,097,973 B1 | 8/2006 | Zenhausern |
| 7,105,300 B2 | 9/2006 | Parce et al. |
| 7,169,560 B2 | 1/2007 | Lapidus et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg |
| 7,223,540 B2 | 5/2007 | Pourmand et al. |
| 7,226,734 B2 | 6/2007 | Chee et al. |
| 7,238,323 B2 | 7/2007 | Knapp et al. |
| 7,244,559 B2 | 7/2007 | Rothberg et al. |
| 7,244,567 B2 | 7/2007 | Chen et al. |
| 7,264,929 B2 | 9/2007 | Rothberg et al. |
| 7,264,934 B2 | 9/2007 | Fuller |
| 7,265,929 B2 | 9/2007 | Umeda et al. |
| 7,276,749 B2 | 10/2007 | Martin et al. |
| 7,282,370 B2 | 10/2007 | Bridgham et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,323,305 B2 | 1/2008 | Leamon et al. |
| 7,335,762 B2 | 2/2008 | Rothberg et al. |
| 7,381,936 B2 | 6/2008 | Tan et al. |
| 7,394,263 B2 | 7/2008 | Pechstein et al. |
| 7,455,971 B2 | 11/2008 | Chee et al. |
| 7,462,512 B2 | 12/2008 | Levon et al. |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,515,124 B2 | 4/2009 | Yaguma et al. |
| 7,575,865 B2 | 8/2009 | Leamon et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,303 B1 | 10/2009 | Lee |
| 7,612,817 B2 | 11/2009 | Tay |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,785,790 B1 | 8/2010 | Church et al. |
| 7,859,029 B2 | 12/2010 | Lee et al. |
| 7,885,490 B2 | 2/2011 | Heideman et al. |
| 7,888,013 B2 | 2/2011 | Miyahara et al. |
| 7,888,708 B2 | 2/2011 | Yazawa et al. |
| 7,923,240 B2 | 4/2011 | Su |
| 7,932,034 B2 | 4/2011 | Esfandyarpour et al. |
| 7,948,015 B2 | 5/2011 | Rothberg et al. |
| 8,067,731 B2 | 11/2011 | Matyjaszczyk et al. |
| 8,124,936 B1 | 2/2012 | Lagna |
| 8,199,859 B2 | 6/2012 | Zerbe et al. |
| 8,217,433 B1 | 7/2012 | Fife |
| 8,231,831 B2 | 7/2012 | Hartzell et al. |
| 8,232,813 B2 | 7/2012 | Burdett et al. |
| 8,247,849 B2 | 8/2012 | Fife et al. |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |

| | | |
|---|---|---|
| 8,313,639 B2 | 11/2012 | Rothberg et al. |
| 8,317,999 B2 | 11/2012 | Rothberg et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0061529 A1 | 5/2002 | Bridgham et al. |
| 2002/0086318 A1 | 7/2002 | Manalis et al. |
| 2002/0094533 A1 | 7/2002 | Hess et al. |
| 2002/0117659 A1 | 8/2002 | Lieber et al. |
| 2002/0117694 A1 | 8/2002 | Migliorato et al. |
| 2002/0131899 A1 | 9/2002 | Kovacs |
| 2002/0132221 A1 | 9/2002 | Chee et al. |
| 2002/0137062 A1 | 9/2002 | Williams et al. |
| 2002/0168678 A1 | 11/2002 | Williams et al. |
| 2002/0172963 A1 | 11/2002 | Kelley et al. |
| 2002/0187515 A1 | 12/2002 | Chee et al. |
| 2003/0032052 A1 | 2/2003 | Hadd et al. |
| 2003/0044799 A1 | 3/2003 | Matson |
| 2003/0049624 A1 | 3/2003 | Shultz et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0077615 A1 | 4/2003 | Bridgham et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0124599 A1 | 7/2003 | Chen et al. |
| 2003/0138809 A1 | 7/2003 | Williams et al. |
| 2003/0148301 A1 | 8/2003 | Aono et al. |
| 2003/0148344 A1 | 8/2003 | Rothberg et al. |
| 2003/0157504 A1 | 8/2003 | Chee et al. |
| 2003/0186262 A1 | 10/2003 | Cailloux et al. |
| 2003/0194740 A1 | 10/2003 | Williams |
| 2003/0215857 A1 | 11/2003 | Kilger et al. |
| 2003/0224419 A1 | 12/2003 | Corcoran et al. |
| 2004/0012998 A1 | 1/2004 | Chien et al. |
| 2004/0023253 A1 | 2/2004 | Kunwar et al. |
| 2004/0038420 A1 | 2/2004 | Gelbart et al. |
| 2004/0049237 A1 | 3/2004 | Larson et al. |
| 2004/0079636 A1 | 4/2004 | Hsia et al. |
| 2004/0134798 A1 | 7/2004 | Toumazou et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0197803 A1 | 10/2004 | Yaku et al. |
| 2004/0207384 A1 | 10/2004 | Brederlow et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0017190 A1 | 1/2005 | Eversmann et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0042627 A1 | 2/2005 | Chakrabarti et al. |
| 2005/0058990 A1 | 3/2005 | Guia et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0106587 A1 | 5/2005 | Klapproth et al. |
| 2005/0119497 A1 | 6/2005 | Hong et al. |
| 2005/0130173 A1 | 6/2005 | Leamon et al. |
| 2005/0130188 A1 | 6/2005 | Walt et al. |
| 2005/0142033 A1 | 6/2005 | Glezer et al. |
| 2005/0156207 A1 | 7/2005 | Yazawa et al. |
| 2005/0181440 A1 | 8/2005 | Chee et al. |
| 2005/0191698 A1 | 9/2005 | Chee et al. |
| 2005/0212016 A1 | 9/2005 | Brunner et al. |
| 2005/0221473 A1 | 10/2005 | Dubin et al. |
| 2005/0224346 A1 | 10/2005 | Holm-Kennedy |
| 2005/0227264 A1 | 10/2005 | Nobile et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1 | 12/2005 | Fouillet et al. |
| 2006/0016699 A1 | 1/2006 | Kamahori et al. |
| 2006/0024711 A1 | 2/2006 | Lapidus et al. |
| 2006/0040297 A1 | 2/2006 | Leamon et al. |
| 2006/0051807 A1 | 3/2006 | Fuller |
| 2006/0057604 A1 | 3/2006 | Chen et al. |
| 2006/0073513 A1 | 4/2006 | Chee et al. |
| 2006/0093488 A1 | 5/2006 | Wong et al. |
| 2006/0105373 A1 | 5/2006 | Pourmand et al. |
| 2006/0115857 A1 | 6/2006 | Keen |
| 2006/0121670 A1 | 6/2006 | Stasiak |
| 2006/0134633 A1 | 6/2006 | Chen et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0183145 A1 | 8/2006 | Turner |
| 2006/0197118 A1 | 9/2006 | Migliorato et al. |
| 2006/0199193 A1 | 9/2006 | Koo et al. |
| 2006/0205061 A1 | 9/2006 | Roukes |
| 2006/0216812 A1 | 9/2006 | Okada et al. |
| 2006/0219558 A1 | 10/2006 | Hafeman et al. |
| 2006/0228721 A1 | 10/2006 | Leamon et al. |
| 2006/0244147 A1 | 11/2006 | Lee et al. |
| 2006/0246497 A1 | 11/2006 | Huang et al. |
| 2006/0269927 A1 | 11/2006 | Lieber |
| 2007/0059741 A1 | 3/2007 | Kamahori et al. |
| 2007/0069291 A1 | 3/2007 | Stuber et al. |
| 2007/0087362 A1 | 4/2007 | Church et al. |
| 2007/0087401 A1 | 4/2007 | Neilson et al. |
| 2007/0092872 A1 | 4/2007 | Rothberg et al. |
| 2007/0099208 A1 | 5/2007 | Drmanac et al. |
| 2007/0099351 A1 | 5/2007 | Peters et al. |
| 2007/0109454 A1 | 5/2007 | Chou |
| 2007/0117099 A1 | 5/2007 | Engelhardt et al. |
| 2007/0117137 A1 | 5/2007 | Jaeger |
| 2007/0138028 A1 | 6/2007 | Chodavarapu et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0032295 A1 | 2/2008 | Toumazou et al. |
| 2008/0035494 A1 | 2/2008 | Gomez et al. |
| 2008/0096216 A1 | 4/2008 | Quake |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0145910 A1 | 6/2008 | Ward et al. |
| 2008/0166727 A1 | 7/2008 | Esfandyarpour et al. |
| 2008/0176271 A1 | 7/2008 | Silver et al. |
| 2008/0186093 A1 | 8/2008 | Forbes |
| 2008/0213770 A1 | 9/2008 | Williams et al. |
| 2008/0230386 A1 | 9/2008 | Srinivasan et al. |
| 2008/0265985 A1 | 10/2008 | Toumazou et al. |
| 2008/0286762 A1 | 11/2008 | Miyahara et al. |
| 2008/0286767 A1 | 11/2008 | Miyahara et al. |
| 2009/0026082 A1 | 1/2009 | Rothberg et al. |
| 2009/0030117 A1 | 1/2009 | Lanphere et al. |
| 2009/0032401 A1 | 2/2009 | Ronaghi et al. |
| 2009/0033370 A1 | 2/2009 | Sarig et al. |
| 2009/0048124 A1 | 2/2009 | Leamon et al. |
| 2009/0062132 A1 | 3/2009 | Borner |
| 2009/0079414 A1 | 3/2009 | Levon et al. |
| 2009/0108831 A1 | 4/2009 | Levon et al. |
| 2009/0127589 A1 | 5/2009 | Rothberg et al. |
| 2009/0140763 A1 | 6/2009 | Kim |
| 2009/0143244 A1 | 6/2009 | Bridgham et al. |
| 2009/0156425 A1 | 6/2009 | Walt et al. |
| 2009/0170728 A1 | 7/2009 | Walt et al. |
| 2009/0316477 A1 | 12/2009 | Horiuchi |
| 2010/0007326 A1 | 1/2010 | Nakazato |

| | | |
|---|---|---|
| 2010/0137143 A1 | 6/2010 | Rothberg et al. |
| 2010/0156454 A1 | 6/2010 | Weir |
| 2010/0188073 A1 | 7/2010 | Rothberg et al. |
| 2010/0197507 A1 | 8/2010 | Rothberg et al. |
| 2010/0255595 A1 | 10/2010 | Toumazou et al. |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0165557 A1 | 7/2011 | Ah et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0247933 A1 | 10/2011 | Rothberg et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0287945 A1 | 11/2011 | Rothberg et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001615 A1 | 1/2012 | Levine et al. |
| 2012/0001646 A1 | 1/2012 | Bolander et al. |
| 2012/0001685 A1 | 1/2012 | Levine et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife |
| 2012/0074956 A1 | 3/2012 | Fife et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0168307 A1 | 7/2012 | Fife |
| 2012/0168784 A1 | 7/2012 | Fife et al. |
| 2012/0247977 A1 | 10/2012 | Rothberg et al. |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |

FOREIGN PATENT DOCUMENTS

| | | |
|---|---|---|
| EP | 1371974 | 12/2003 |
| EP | 1432818 | 6/2004 |
| EP | 1542009 | 6/2005 |
| EP | 2307577 | 4/2011 |
| GB | 2457851 | 9/2009 |
| GB | 2461127 B | 7/2010 |
| JP | 2002272463 | 9/2002 |
| JP | 2005-518541 | 6/2005 |
| JP | 2011-525810 | 9/2011 |
| KR | 10-0442838 | 7/2004 |
| KR | 10-0455283 | 10/2004 |
| WO | WO-89/09283 | 10/1989 |
| WO | WO-98/13523 | 4/1998 |
| WO | WO-98/46797 | 10/1998 |
| WO | WO-01/20039 | 3/2001 |
| WO | WO-01/42498 | 6/2001 |
| WO | WO-01/81896 | 11/2001 |
| WO | WO-02/077287 | 10/2002 |
| WO | WO-02/086162 | 10/2002 |
| WO | WO-03/073088 | 9/2003 |
| WO | WO-2004/040291 | 5/2004 |
| WO | WO-2005/047878 | 5/2005 |
| WO | WO-2005/054431 | 6/2005 |
| WO | WO-2005/084367 | 9/2005 |
| WO | WO-2006/005967 | 1/2006 |
| WO | WO-2006/022370 | 3/2006 |
| WO | WO-2007/086935 | 8/2007 |
| WO | WO-2008/007716 | 1/2008 |
| WO | WO-2008/058282 | 5/2008 |
| WO | WO-2008/076406 | 6/2008 |
| WO | WO-2008/107014 | 9/2008 |
| WO | WO-2009/012112 | 1/2009 |
| WO | WO-2009/158006 | 12/2009 |
| WO | WO-2010/008480 | 1/2010 |
| WO | WO-2010/047804 | 4/2010 |
| WO | WO-2010/047804 A8 | 4/2010 |
| WO | WO-2010/138182 | 12/2010 |
| WO | WO-2010/138188 | 12/2010 |
| WO | WO-2012/003359 | 1/2012 |
| WO | WO-2012/003363 | 1/2012 |
| WO | WO-2012/003368 | 1/2012 |
| WO | WO-2012/003380 | 1/2012 |
| WO | WO-2012/006222 | 1/2012 |

OTHER PUBLICATIONS

[No Author Listed], "ISFET Wikipedia article", *Wikipedia*, Last modified Nov. 7, 2006.

Ahmadian, A. et al., "Single-nucleotide polymorphism analysis by pyrosequencing", *Anal. Biochem*, vol. 280, 2000, pp. 103-110.

Akiyama, T et al., "Ion-Sensitive Field-Effect Transistors with Inorganic Gate Oxide for pH Sensing", *IEE Transactions on Electron Devices*, vol. ED-20(12), 1982, pp. 1936-1941.

AU2011226767 Search Information Statement Mailed Oct. 26, 2011, pp. 1-3.

Bandiera, L. et al., "A fully electronic sensor for the measurement of cDNA hybridization kinetics", *Biosens Bioelectron*, vol. 22, 2007, pp. 2108-2114.

Barbaro, M et al., "A CMOS, Fully Integrated Sensor for Electronic Detection of DNA Hybridization", *IEEE Electron Device Letters*, vol. 27(7), 2006, pp. 595-597.

Barbaro, M. et al., "A Conception, Modeling FET for Detection of Biomolecular Processes: Conception, Modeling, and Simulation", *IEEE Transactions on Electron Devices*, vol. 53(1), 2006, pp. 158-166.

Barbaro, M. et al., "Fully electronic DNA hybridization detection by a standard CMOS biochip", *Sensors and Actuators B Chemical*, vol. 118, 2006, pp. 41-46.

Bashford, G. et al., "Automated bead-trapping apparatus and control system for single-molecule DNA sequencing", *Optics Express*, vol. 16(5), Mar. 3, 2008, pp. 3445-3455.

Baumann, W. et al., "Microelectronic sensor system for microphysiological application on living cells", *Sensors Actuators B*, vol. 55, 1999, pp. 77-89.

Bausells, J. et al., "Ion-sensitive field-effect transistors fabricated in a commercial CMOS technology", *Sensors and Actuators B Chemical*, vol. 57, 1999, pp. 56-62.

Bergveld, P., "ISFET, Theory and Practice", *IEEE Sensor Conference*, Toronto, Oct. 2003, pp. 1-26.

Bergveld, P., "Thirty years of ISFETOLOGY What happened in the past 30 years and what may happen in the next 30 years", *Sensors and Actuators B*, vol. 88, 2003, pp. 1-20.

Besselink, G et al., "ISFET Affinity Sensor", *Methods in Biotechnology, vol. 7: Affinity Biosensors: Techniques and Protocols*, 1998, pp. 173-185.

Bobrov, P. et al., "Chemical sensitivity of an ISFET with Ta2O5 membrane in strong acid and alkaline solutions", *Sensors and Actuators B*, vol. 3, 1991, pp. 75-81.
Bousse, L. et al., "A process for the combined fabrication of ion sensors and CMOS circuits", *IEEE Electron Device Letters*, vol. 9(1), 1988, pp. 44-46.
Bousse, L. et al., "Zeta potential measurements of Ta2O5 and SiO2 thin films", *J. Colloid Interface Sci.*, vol. 147(1), 1991, pp. 22-32.
Chen, Y. et al., "Nanoscale field effect transistor for biomolecular signals amplification", *App Phys Letter*, vol. 91, 2007, pp. 243511-1-243511-3.
Chen, Y. et al., "Silicon-based nanoelectronic field-effect pH sensor with local gate control", *App Phys Letter*, vol. 89, 2006, pp. 223512-1-223512-3.
Chou, J. et al., "Letter to the Editor on Simulation of Ta2O5 gate ISEFET temperature characteristics", *Sensors and Actuators B*, vol. 80, 2001, pp. 290-291.
Chou, J. et al., "Simulation of Ta2O5 gate ISFET temperature characteristics", *Sensor and Actuators B*, vol. 71, Letter to the Editor, 2000, pp. 73-76.
Chung, W-Y et al., "ISFET interface circuit embedded with noise rejection capability", *Electronics Letters*, vol. 40(18), e-pub; 2 pages, 2004.
Chung, W-Y et al., "ISFET performance enhancement by using the improved circuit techniques", *Sensors and Actuators B*, vol. 113, 2006, pp. 555-562.
Eijkel, J. et al., "Measuring Donnan-related phenomena using a solid-state ion sensor and a concentration-step method", *J. Membrane Sci.*, vol. 127, 1997, pp. 203-221.
Eijkel, J., "Potentiometric detection and characterization of adsorbed protein using stimulus-response measurement techniques", *Thesis*, Sep. 3, 1955, pp. 1-147; 160-192.
Eltoukhy, H et al., "A 0.18um CMOS 10-6 lux Bioluminescence Detection System-on-Chip", *ISSCC 2004/Session12/Biomicrosystems/12.3*, 2004, pp. 1-3.
Eltoukhy, H. et al., "A. 0.18-um CMOS Bioluminescence Detection Lab-on-Chip", *IEEE J Solid-State Circuits*, vol. 41(3), 2006, pp. 651-662.
EP7867780.4 Examination Report Mailed Jul. 3, 2012.
Eriksson, J. et al., "Pyrosequencing technology at elevated temperature", *Electrophoresis*, vol. 25, 2004, pp. 20-27.
Esfandyarpour, H. et al., "Gate-controlled microfluidic chamber wtih magnetic bead for DNA sequencing-by-synthesis technology", *Proc 5th Intl Conf Nanochannels, Microchannels, Minnichannels*, Puebla, Mexico (Jun. 18-20, 2007), Jun. 18, 2007, pp. 1-5.
Eversmann, B. et al., "A 128 x 128 CMOS Biosensor Array for Extracellular Recording of Neural Activity", *IEEE J. Solid-State Circ.*, vol. 38(12), Dec. 12, 2003, pp. 2306-2317.
Faramarzpour, N. et al., "CMOS-Based Active Pixel for Low-Light Level Detection: Analysis and Measurements", *IEEE Trans Electron Devices*, vol. 54(12), Dec. 2007, pp. 3229-3237.
Finn, A et al., "Towards an Optimization of FET-Based Bio-Sensors", *European Cells and Materials*, vol. 4, Sup 2, 2002, pp. 21-23.
Fraden, J., "Handbook of Modern Sensors—Physics, Designs, and Applications . . . ", *17.3.2 CHEMFET Sensors*, 1996, pp. 499-501.
Fritz, J. et al., "Electronic detection of DNA by its intrinsic molecular charge", *PNAS*, 99(22), 2002, pp. 14142-14146.
GB0811656.8 Search and Examination Report Mailed Mar. 12, 2010.
GB0811656.8 Search Report Mailed Sep. 21, 2009.
GB0811657.6 Examination Report Mailed Jun. 30, 2010.
GB0811657.6 Search Report under Section 17 Mailed Oct. 26, 2009.
Gracia, I. et al., "Test Structures for ISFET Chemical Sensors", *Proc. IEEE 1992 Intl Conf Microelec Test Struct*, vol. 5, 1992, pp. 156-159.
Hammond, P. et al., "A System-on-Chip Digital pH Meter for Use in a Wireless Diagnostic Capsule", *IEEE Transactons on Biomedical Engineering*, vol. 52(4), 2005, pp. 687-694.
Hammond, P. et al., "Design of a Single-Chip pH Sensor Using a Conventional 0.6-µm CMOS Process", *IEEE Sensors Journal*, vol. 4(6), 2004, pp. 706-712.
Hammond, P. et al., "Encapsulation of a liquid-sensing microchip using SU-8 photoresist", *MicoElectronic Engineering*, vol. 73-74, 2004, pp. 893-897.
Hammond, S. et al., "Genomic sequencing and analysis of a Chinese Hampster ovary cell line using Illumina sequencing technology", *BMC Genomics*, vol. 12:67, 2011, pp. 1-8.
Han, Y., "Label-free detection of biomolecules by a field-effect transistor microarray biosensor with bio-functionalized gate surfaces", *Masters Dissertation*, 2006, pp. 1-63.
Hara, H. et al., "Dynamic response of a Ta2O5-gate pH-sensitive field-effect transistor", *Sensors Actuators B*, vol. 32, 1996, pp. 115-119.
Hermon, Z. et al., "Miniaturized bio-electronic hybrid for chemical sensing applications", *Tech Connect News*, Apr. 22, 2008, pp. 1.
Hideshima, S. et al., "Detection of tumor marker in blood serum using antibody-modified field effect transistor with optimized BSA blocking", *Sensors and Actuations B: Chemical*, vol. 161, 2012, pp. 146-150.
Hijikata, M. et al., "Identification of a Single Nucleotide Polymorphism in the MXA Gene Promoter (T/T at nt-88) Correlated with the Response of Hepatitis C Patients to Interferon", *Intervirology*, vol. 43, 2000, pp. 124-127.
Hizawa, T et al., "Fabrication of a two-dimensional pH image sensor using a charge transfer technique", *Sensors and Actuators B Chemical*, 117, 2006, pp. 509-515.
Hizawa, T. et al. "32 x 32 pH Image Sensors for Real Time Observation of Biochemical Phenomena", *Transducers & Eurosensors '07*, 14th Intl. Conf. on Solid-State, Actuators and Microsystems, Lyon, France, Jun. 10-14, 2007, pp. 1311-1312.
Jakobson, C. et al., "Low frequency noise and drift in Ion Senstive Field Effect Transistors", *Sensors Actuators B*, vol. 68, 2000, pp. 134-139.
Ji, H. et al., "A CMOS contact imager for locating individual cells", *ISCAS*, 2006, pp. 3357-3360.
Ji, H. et al., "Contact Imaging: Simulation and Experiment", *IEEE Trans Circuits Systems-I: Regular Papers*, vol. 54(8), 2007, pp. 1698-1710.
Kim, D. et al., "An FET-type charger sensor for highly sensitive detection of DNA sequence", *Biosens Bioelectron*, vol. 20(1), 2004, pp. 69-74.
Klein, M., "Time effects of ion-sensitive field-effect transistors", *Sens Act B*, vol. 17, 1989, pp. 203-208.
Koch, S et al., "Protein detection with a novel ISFET-based zeta potential analyzer", *Biosensors & Bioelectronics*, vol. 14, 1999, pp. 413-421.
Kruise, J. et al., "Detection of protein concentrations using a pH-step titration method", *Sensors Actuators B*, vol. 44, 1997, pp. 297-303.
Leamon, J. et al., "A Massively Parallel PicoTiterPlate Based Platform for Discrete Picoliter-Scale Polymerase Chain Reactions", *Electrophoresis*, vol. 24, 2003, pp. 3769-3777.
Leamon, J. et al., "Cramming More Sequencing Reactions onto Microreactors Chips", *Chemical Reviews*, vol. 107, 2007, pp. 3367-3376.
Lee, C-S et al., "Ion-sensitive Field-Effect Transistor for Biological Sensing", *Sensors*, vol. 9, 2009, pp. 7111-7131.
Li, et al., "Sequence-Specific Label-Free DNA Sensors Based on Silico Nanowires", *Nano Letters.*, vol. 4(2), 2004, pp. 245-247.
Lohrengel, M. et al., "A new microcell or microreactor for material surface investigations at large current densities", *Electrochimica Acta*, vol. 49, 2004, pp. 2863-2870.
Lui, A. et al., "A Test Chip for ISFET/CMNOS Technology Development", *Proc. of the 1996 IEEE Intl. Conf. on Microelectronic Test Structures*, vol. 9, 1996, pp. 123-128.
Margulies, M. et al., "Genome sequencing in microfabricated high-density picolitre reactors", *Nature*, vol. 437(7057), 2005, pp. 376-380.
Marshall, A. et al., "DNA chips: an array of possibilities", *Nature Biotechnology*, vol. 16, 1998, pp. 27-31.
Martinoia, S. et al., "A behavioral macromodel of the ISFET in SPICE", *Sensors Actuators B*, vol. 62, 2000, pp. 182-189.
Martinoia, S., "Development of ISFET Array-Based Microsystems for Bioelectrochemical measurements of cell populations", *Biosensors & Bioelectronics*, vol. 16, 2001, pp. 1043-1050.
Medoro, G. et al., "A Lab-on-a-Chip for Cell Detection and Manipulation", *IEEE Sensors J.* vol. 3(3), 2003, pp. 317-325.

Meyburg, S. et al., "N-Channel field-effect transistors with floating gates for extracellular recordings", *Biosens Bioelectron*, vol. 21(7), 2006, pp. 1037-1044.

Milgrew, M. et al., "A 16 x 16 CMOS proton camera array for direct extracellular imaging of hydrogen-ion activity", *IEEE Intl Solid-State Circuits Conf*, Session 32:24, 2008, pp. 590-591; 638.

Milgrew, M. et al., "A large transistor based sensor array chip for direct extracellular imaging", *Sensors and Actuators B Chemical*, vol. 111-112, 2005, pp. 347-353.

Milgrew, M. et al., "Matching the transconductance characteristics of CMOS ESFET arrays by removing trapped charge", *IEEE Trans Electron Devices*, vol. 55(4), 2008, pp. 1074-1079.

Milgrew, M. et al., "Microsensor Array Technology for Direct Extracellular Imaging", Apr. 5, 2006, pp. 1-23.

Milgrew, M. et al., "The development of scalable sensor arrays using standard CMOS technology",*Sensors and Actuators B*, vol. 103, 2004, pp. 37-42.

Milgrew, M. et al., "The fabrication of scalable multi-sensor arrays using standard CMOS technology", *2003 IEEE Custom Integrated Circuits Conference*, 2003, pp. 513-516.

Miyahara, Y. et al., "Biochip Using Micromachining Technology", *J. Institute of Electrostatics*, Japan, vol. 27(6), 2003, pp. 268-272.

Miyahara, Y. et al., "Direct Transduction of Primer Extension into Electrical Signal Using Genetic Field Effect Transistor", *Micro Total Analysis Systems 2004*, vol. 1, 2004, pp. 303-305.

Miyahara, Y. et al., "Potentiometric Detection of DNA Molecules Using Field Effect Transistor", *The Japan Society of Applied Physics*, No. 3 (Translation included), 2003, pp. 1180, 30A-S2.

Nyren, P. et al., "Enzymatic Method for Continuous Monitoring of Inorganic Pyrophosphate Synthesis", *Analytical Biochemistry*, vol. 151, 1985, pp. 504-509.

Oelbner, W. et al., "Encapsulation of ESFET sensor chips", *Sensors Actuators B*, vol. 105, 2005, pp. 104-117.

Oelbner, W. et al., "Investigation of the dynamic response behaviour of ISFET pH sensors by means of laser Doppler velocimetry (LDV)", *Sensors Actuators B*, vol. 26-27, 1995, pp. 345-348.

Offenhausser, A. et al., "Field-Effect transistor array for monitoring electrical activity from mammalian neurons in culture", *Biosensors & Bioelectronics*, vol. 12(8), 1997, pp. 819-826.

Ohno, Y. et al., "Electrolyte-Gated Graphene Field-Effect Transistors for Detecting pH and Protein Adsorption", *Nano Letters*, vol. 9(9), Jul. 28, 2009, pp. 3318-3322.

Patolsky, F. et al., "Nanowire-Based Biosensors", *Analyt Chem 1*, vol. 78(13), 2006, pp. 4261-4269.

PCT/JP2005/001987 International Search Report Mailed Apr. 5, 2005.

PCT/JP2005/015522 International Preliminary Report on Patentability Mailed Mar. 19, 2007.

PCT/JP2005/015522 International Search Report Mailed Sep. 27, 2005.

PCT/US/2009/05745 International Preliminary Report on Patentability Issued Apr. 26, 2011.

PCT/US/2009/05745 International Search Report Mailed Dec. 11, 2009.

PCT/US/2009/05745 Written Opinion Mailed Dec. 11, 2009.

PCT/US2007/025721 Declaration of Non-Establishment of International Search Report Mailed Jul. 15, 2008.

PCT/US2007/025721 International Preliminary Report on Patentability Mailed Jun. 16, 2009.

PCT/US2007/025721 Written Opinion Mailed Jun. 16, 2009.

PCT/US2009/003766 International Preliminary Report on Patentability Mailed Jan. 5, 2011.

PCT/US2009/003766 International Search Report Mailed Apr. 8, 2010.

PCT/US2009/003766 Written Opinion Mailed Apr. 8, 2010.

PCT/US2009/003797 International Search Report Mailed Mar. 12, 2010.

PCT/US2009/003797 Written Opinion Mailed Mar. 12, 2010.

PCT/US2010/001543 International Preliminary Report on Patentability Mailed Nov. 29, 2011, pp. 1-8.

PCT/US2010/001543 International Search Report and Written Opinion Mailed Oct. 13, 2010, pp. 1-12.

PCT/US2010/001553International Preliminary Report on Patentability Mailed Dec. 8, 2011, pp. 1-10.

PCT/US2010/001553 International Search Report Mailed Jul. 28, 2010, pp. 1-2.

PCT/US2010/001553 Written Opinion Mailed Jul. 14, 2010, pp. 1-6.

PCT/US2010/48835 International Search Report and Written Opinion Mailed Dec. 16, 2010, pp. 1-12.

PCT/US2011/042655 International Search Report Mailed Oct. 21, 2011, pp. 1-2.

PCT/US2011/042660 International Search Report Mailed Nov. 2, 2011.

PCT/US2011/042665 International Search Report Mailed Nov. 2, 2011.

PCT/US2011/042668 International Search Report Mailed Oct. 28, 2011.

PCT/US2011/042669 International Search Report Mailed Jan. 9, 2012, pp. 1-5.

PCT/US2011/042669 Written Opinion Mailed Jan. 9, 2012, pp. 1-5.

PCT/US2011/042683 International Search Report Mailed Feb. 16, 2012.

PCT/US2011/042683 Written Opinon Mailed Feb. 16, 2012.

Poghossian, A. et al., "Functional testing and characterization of ISFETs on wafer level by means of a micro-droplet cell", *Sensors*, vol. 6, 2006, pp. 397-404.

Pourmand, N. et al., "Direct electrical detection of DNA synthesis", *PNAS*, vol. 103(17), 2006, pp. 6466-6470.

Pouthas, F. et al., "Spatially resolved electronic detection of biopolymers", *Phys Rev*, vol. 70, 2004, pp. 031906-1-031906-8.

Premanode, B. et al., "A composite ISFED readout circuit employing current feedback", *Sensors Actuators B*, vol. 127, 2007, pp. 486-490.

Premanode, B. et al., "A novel, low power biosensor for real time monitoring of creatine and urea in peritoneal dialysis", *Sensors Actuators B*, vol. 120, 2007, pp. 732-735.

Premanode, B. et al., "Ultra-low power precision ISFET readout using global current feedback", *Electronic Lett*, vol. 42(22), 2006, 2 pages.

Purushothaman, S. et al., "Protons and single nucleotide polymorphism detection: A simple ues for the Ion Sensitive Field Effect Transistor", *Sensors and Actuators B Chemical*, vol. 114(2), 2006, pp. 964-968.

Purushothaman, S. et al., "Towards Fast Solid State DNA Sequencing", *IEEE ISCAS 2002 Proceedings*, Circuits and Systems, vol. 4, 2002, pp. IV-169-IV-172.

Rodriguez-Villegas, E., "Solution to trapped charge in FGMOS transistors", *Electronics Letters*, vol. 39(19), 2003.

Ronaghi, M. et al., "A Sequencing Method Based on Real-Time Pyrophosphate", *Science*, vol. 281, 1998, pp. 363-365.

Sakata, T. et al., "Cell-based field effect devices fo cell adhesion analysis", *Intl. Conf. on Microtechnologies in Medicine and Biology*, May 9-12, 2006, Okinawa, Japan, 2006, pp. 177-179.

Sakata, T. et al., "Detection of DNA recognition events using multi-well field effect transistor", *Biosensors and Bioelectronics* vol. 21, 2005, pp. 827-832.

Sakata, T. et al., "Detection sensitivity of genetic field effect transistor combined with charged nanoparticle-DNA conjugate", *Proc. of 2006 Intl. Conf. on Microtechnologies in Medicine and Biology*, May 9-12, 2005, Okinawa, Japan, 2006, pp. 97-100.

Sakata T. et al., "Direct detection of single nucleotide polymorphism using genetic field effect transistor", *Digest of Papers Microprocesses and Nanotechnology 2004*, Osaka, Japan, 2004 International Microprocesses and Nanotechnology Conference, 2004, pp. 226-227.

Sakata T. et al., "Direct Detection of Single-Base Extension Reaction Using Genetic Field Effect Transistor", *Proc. of 3rd Ann. Intl. IEEE EMBS Special Topic Conf. on Microtechnologies in Medicine and Biology*, Kahuku, Oahu, HI, May 12-15, 2005, pp. 219-222.

Sakata, T. et al., "Direct transduction of allele-specific primer extension into electrical signal using genetic field effect transistor", *Biosensors and Bioelectronics*, vol. 22, 2007, pp. 1311-1316.

Sakata, T. et al., "DNA Analysis Chip Based on Field-Effect Transistors", *Japanese Journal of Applies Physics*, vol. 44(4B), 2005, pp. 2854-2859.

Sakata, T. et al., "DNA Sequencing Based on Intrinsic Molecular Charges", *Angewandte Chemie International Edition 2006*, vol. 118, 2006, pp. 2283-2286.

Sakata, T. et al., "DNA Sequencing Based on Intrinsic Molecular Charges", *Angewandte Chemie International Edition 2006*, vol. 45, 2006, pp. 2225-2228.

Sakata, T. et al., "DNA Sequencing Using Genetic Field Effect Transistor", *13th Intl. Conf. on Solid-State Sensors, Actuators and Microsystems*, Jun. 5-9, 2005, Seoul, Korea, 2005, pp. 1676-1679.

Sakata, T. et al., "Immobilization of oligonucleotide probes on Si3N4 surface and its application to genetic field effect transistor", *Materials Science and Engineering: C*, vol. 24, 2004, pp. 827-832.

Sakata, T. et al., "Potential Behavior of Biochemically Modified Gold Electrode for Extended-Gate Field-Effect Transitor", *Japanese Journal of Applied Physics*, vol. 44(4B), 2005, pp. 2860-2863.

Sakata, T. et al., "Potential Response of Genetic Field Effect Transistor to Charged Nanoparticle-DNA Conjugate", *Digest of Papers Microprocesses and Nanotechnology 2005*, Tokyo, Japan, 2005 Intl Microprocesses and Nanotech Conference, Hotel Bellclassic, 2005, pp. 42-43.

Sakata, T. et al., "Potentiometric Detection of Allele Specific Oligonucleotide Hybridization Using Genetic Field Effect Transistor", *Micro Total Analysis Systems 2004*, 8th Intl. Conf. on Miniaturized Systems for Chemistry and Life Sciences, Sep. 26-30, 2004, Malmo, Sweden, 2004, pp. 300-302.

Sakata, T. et al., "Potentiometric Detection of DNA Molecules Hybridization Using Gene Field Effect Transistor and Intercalator", *Materials Research Society Symposium Proceedings*, vol. 782, Micro- and Nanosystems, Dec. 1-3, 2003, Boston, Massachusetts, 2004, pp. 393-398.

Sakata, T. et al., "Potentiometric Detection of DNA Using Genetic Transistor", *Denki Gakkai Kenkyukai Shiryo Chemical Sensor Kenkyukai*, CHS-03-51-55, pp. 1-5.

Sakata, T. et al., "Potentiometric Detection of Single Nucleotide Polymorphism by Using a Genetic Field-effect transistor", *ChemBioChem*, vol. 6, 2005, pp. 703-710.

Sakurai, T. et al., "Real-Time Monitoring of DNA Polymerase Reactions by a Micro ISFET pH Sensor", *Anal Chem*, vol. 64(17), 1992, pp. 1996-1997.

Salama, K., "CMOS luminescence detection lab-on-chip: modeling, design, and characterization", *Thesis*, Presented at Stanford University, 2005, pp. ii-78.

Salama, K., "Modeling and simulation of luminescence detection platforms", *Biosensors & Bioelectronics*, 2004, pp. 1377-1386.

Sawada, K. et al., "A novel fused sensor for photo- and ion-sensing", *Sensors Actuators B*, vol. 106, 2005, pp. 614-618.

Sawada, K. et al., "Highly sensitive ion sensors using charge transfer technique", *Sensors Actuators B*, vol. 98, 2004, pp. 69-72.

Schasfoort, R. et al., "A new approach to immunoFET operation", *Biosensors & Bioelectronics*, vol. 5, 1990, pp. 103-124.

Schasfoort, R. et al., "Field-effect flow control for microfabricated fluidic networks", *Science*, vol. 286(5441), 1999, pp. 942-945.

Schoning, M. et al., "Bio FEDs (Field-Effect Devices): State-of-the-Art and New Directions", *Electroanalysis*, vol. 18(19-20), 2006, pp. 1893-1900.

SG200903992-6 Search and Examination Report Mailed Jan. 20, 2011.

Shah, N., "Microfabrication of a parellel-array DNA pyrosequencing chip", *NNIN REU Research Accomplishments*, 2005, pp. 130-131.

Shepherd, L. et al., "A biochemical translinear principle with weak inversion ISFETs", *IEEE Trans Circuits Syst—I*, vol. 52(12), Dec. 2005, pp. 2614-2619.

Shepherd, L. et al., "A novel voltage-clamped CMOS ISFET sensor interface", *IEEE*, 2007, pp. 3331-3334.

Shepherd, L. et al., "Towards direct biochemical analysis with weak inversion ISFETS", *Intl Workshop on Biomedical. . .* , 2004, S1.5-5-S1.5-8.

Shepherd, L. et al., "Weak inversion ISFETs for ultra-low power biochemical sensing and real-time analysis", *Sensors Actuators B*, vol. 107, 2005, pp. 468-473.

Shi, Y. et al., "Radical Capillary Array Electrophoresis Microplace and Scanner for High-Performance Nucleic Acid Analysis", *Anal. Chem.*, vol. 71(23), 1999, pp. 5354-5361.

Simonian, A. L. et al., "FET based biosensors for the direct detection of organophosphate neurotoxins", *Electroanalys*, vol. 16(22), 2004, pp. 1896-1906.

Souteyrand, E. et al., "Direct detection of the hybridization of synthetic homo-oligomer DNA sequences by field effect", *J Phys Chem B*, vol. 101(15), 1997, pp. 2980-2985.

Starodub, N. et al., "Immunosensor for the determination of the herbicide simazine based on an ion-selective field-effect transistor", *Analytica Chimica Acta*, vol. 424, 2000, pp. 37-43.

Takenaka, S. et al., "DNA Sensing on a DNA Probe-Modified Electrode Using Ferrocenylnaphthalene Dimide as the Electrochemically Active Ligand", *Annal. Chem.*, vol. 72(6), 2000, pp. 1334-1341.

Tomaszewski, D. et al., "Electrical characterization of ISFETs", *J Telecomm Info Technol*, Mar. 2007, pp. 55-60.

Toumazou, C. et al., "Using transistors to linearase biochemistry", *Electronics Letters*, vol. 43(2), Jan. 18, 2007, 3 pages.

Truman, P., "Monitoring liquid transport and chemical composition in lab on . . . ", *Lab on a Chip*, vol. 6, 2006, pp. 1220-1228.

Uslu, F. et al., "Labelfree fully electronic nucleic acid detection system based on a field-effect transistor device", *Biosens & Bioelectron*, vol. 19(12), 2004, pp. 1723-1731.

Van Der Wouden, E. et al., "Directional flow induced by synchronized longitudinal and zeta-potential controlling AC-electrical fields", *Lab Chip*, vol. 6(10), 2006, pp. 1300-1305.

Van Hal, R.E.G. et al., "A general model to describe the electrostatic potential at electrolyte oxide interfaces", *Advances in Colloid and Interface Science*, vol. 69, 1996, pp. 31-62.

Van Kerkhof, J et al., "The ISFET based heparin sensor with a monolayer of protamine as affinity ligand", *Biosensors & Bioelectronics*, vol. 10(3), 1995, pp. 269-282.

Van Kerkhof, J. et al., "ISFET Responses on a stepwise change in electrolyte concentration at constant pH", *Sensors Actuators B: Chemical*, vol. 18-19, 1994, pp. 56-59.

Van Kerkhof, J., "The Development of an ISFET-based Heparin Sensor", *Thesis*, 1994.

Wagner, T et al., "'All-in-one' solid-state device based on a light-addressable potentiometric sensor platform", *Sensors and Actuators B*, vol. 117, 2006, pp. 472-479.

Wang, W. et al., "Label-free detection of small-molecule-protein interactions by using nanowire nanosensors", *Proc. of the Natl. Acad. of Sciences (PNAS)*, vol. 102(9), 2005, pp. 3208-3212.

Woias, P., "Modelling the short time response of ISFET sensors", *Sensors and Actuators B*, vol. 24-25, 1995, pp. 211-217.

Woias, P. et al., "Slow pH response effects of silicon nitride ISFET sensors", *Sensors and Actuators B*, vol. 48, 1998, pp. 501-504.

Wu, P. et al., "DNA and protein microarray printing on silicon nitride waveguide surfaces", *Biosensns Bioelectron*, vol. 21(7), 2006, pp. 1252-1263.

Xu, J-J et al., "Analytical Aspects of FET-Based Biosensors", *Frontiers in Bioscience*, vol. 10, 2005, pp. 420-430.

Yeow, T.C.W., "A very large integrated pH-ISFET sensor array chip compatible with standard CMOS processes", *Sensor and Actuators B*, vol. 44, 1997, pp. 434-440.

Yuqing, M. et al., "Ion sensitive field effect trnasducer-based biosensors", *Biotechnology Advances* , vol. 21, 2003, pp. 527-534.

Zhang, X. et al., "32-Channel Full Customized CMOS Biosensor Chip for Extracellular neural Signal Recording", *Proc. of the 2nd Intl. IEEE EMBS Conf. on Neural Engineering, Arlington, Virginia*, 2005, pp. v-viii.

Zhou, G. et al., "Quantitative detection of single nucleotide polymorphisms for a pooled sample by a bioluminometric assay coupled with modified primer extension reactions (BAMPER)", *Nuc. Acids Res.*, vol. 29(19), e93, 2001, pp. 1-11.

\* cited by examiner

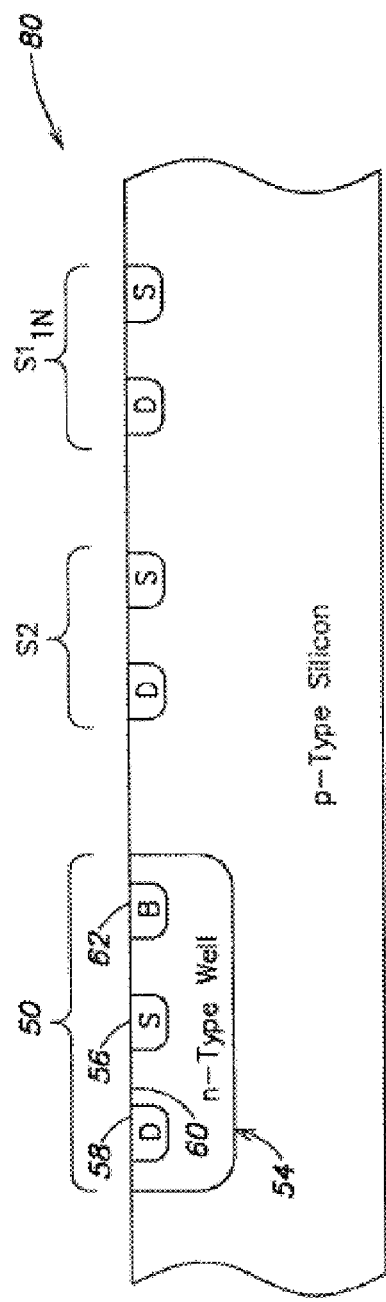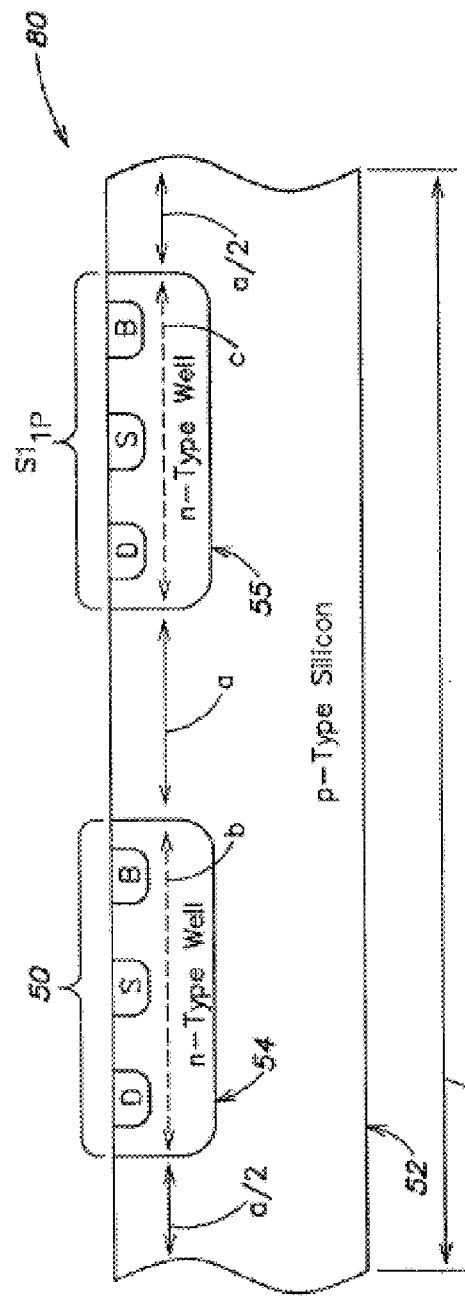
FIG. 5 (Prior Art)
FIG. 6 (Prior Art)

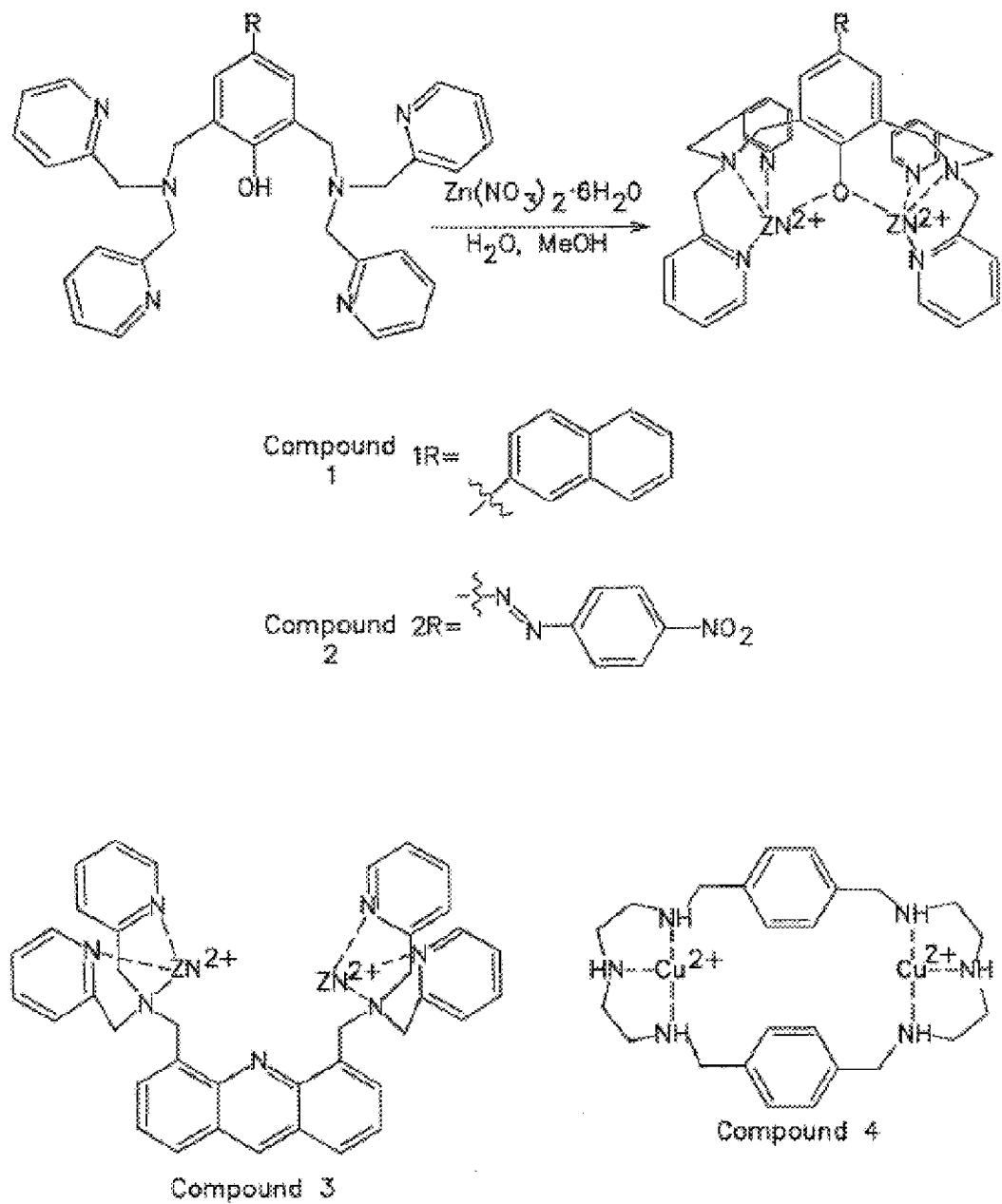
FIG. 11B(1)

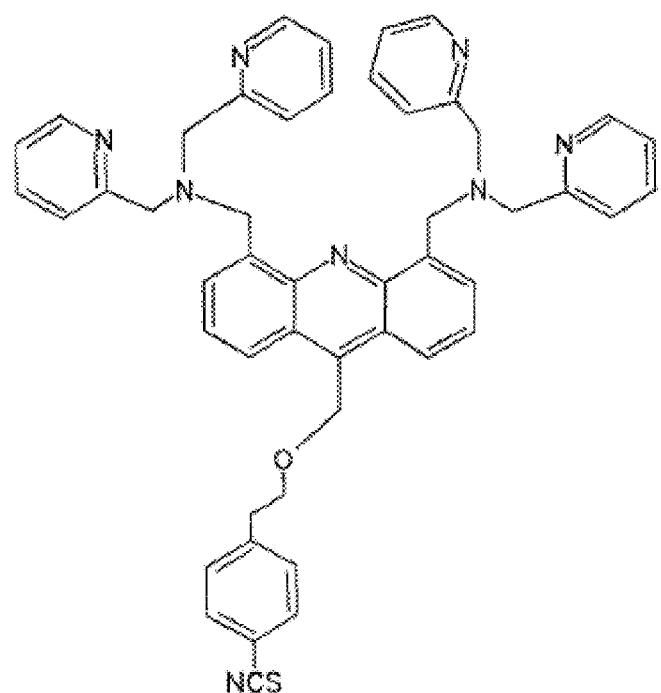
Compound 10
FIG. 11B(2)

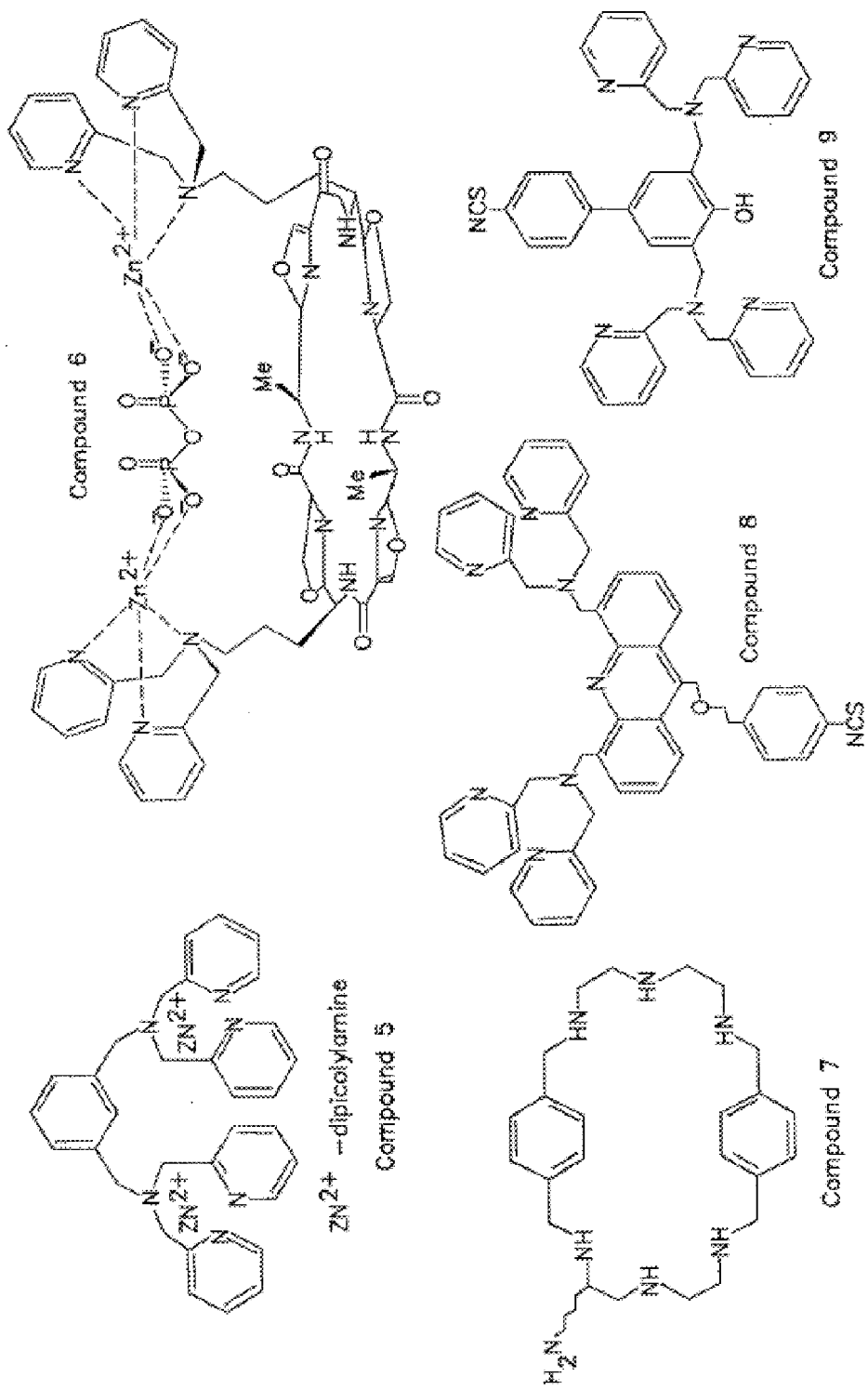
FIG. 11B(3)

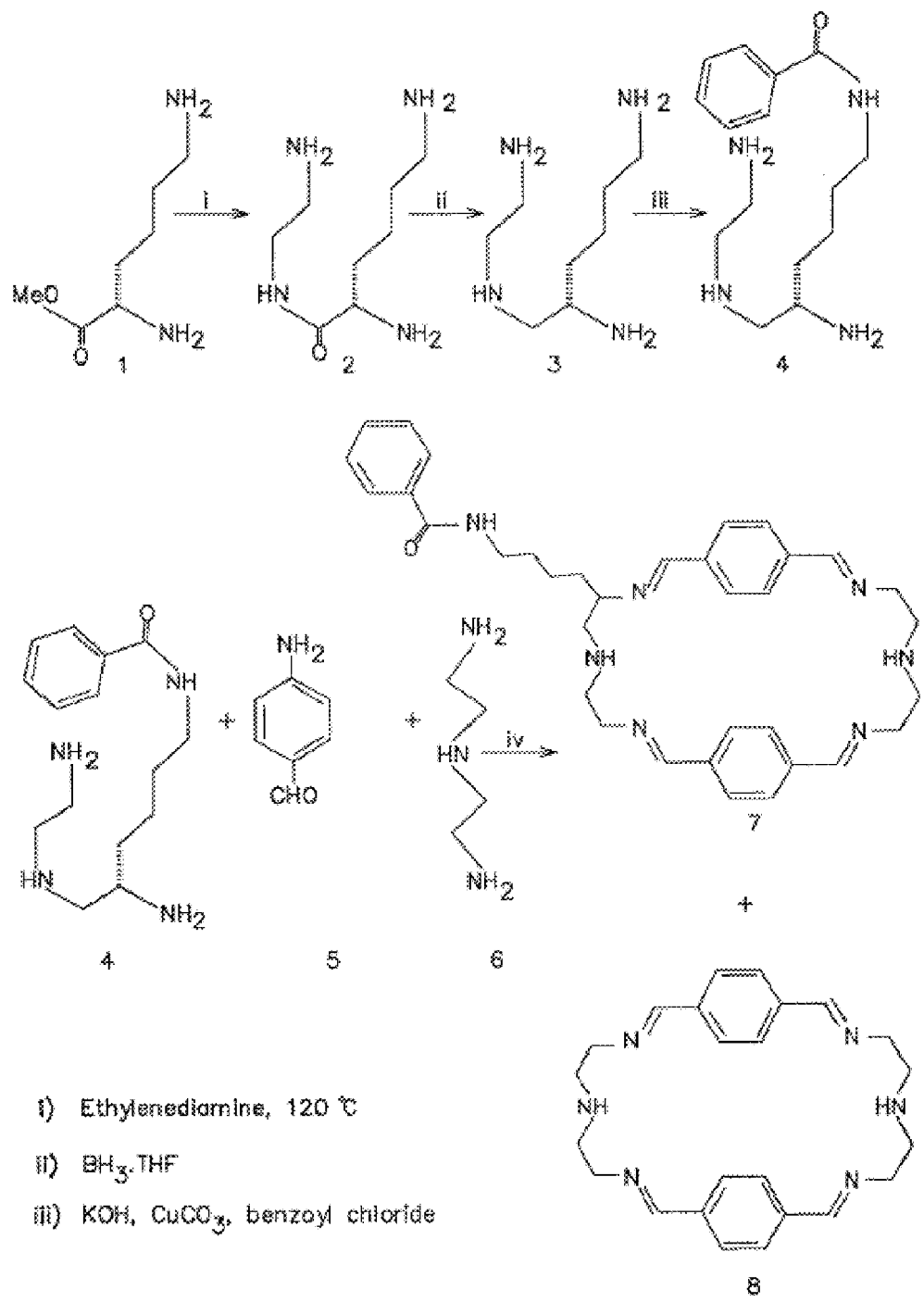
FIG. 11C(1)

iv) 1:3 ratio of 4:6, MeOH, r.t.
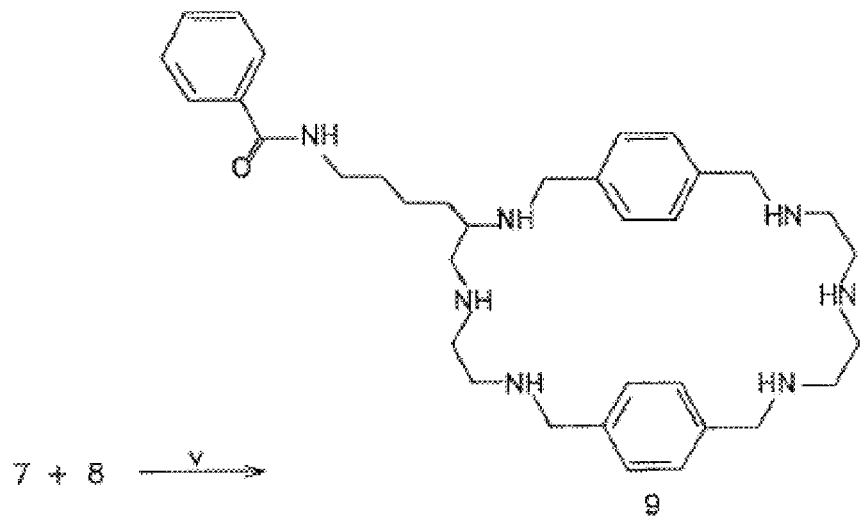
7 + 8 —v→
v) NaBH₃, MeOH
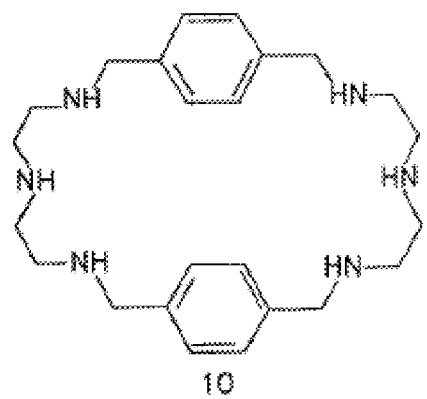
*FIG. 11C(2)*

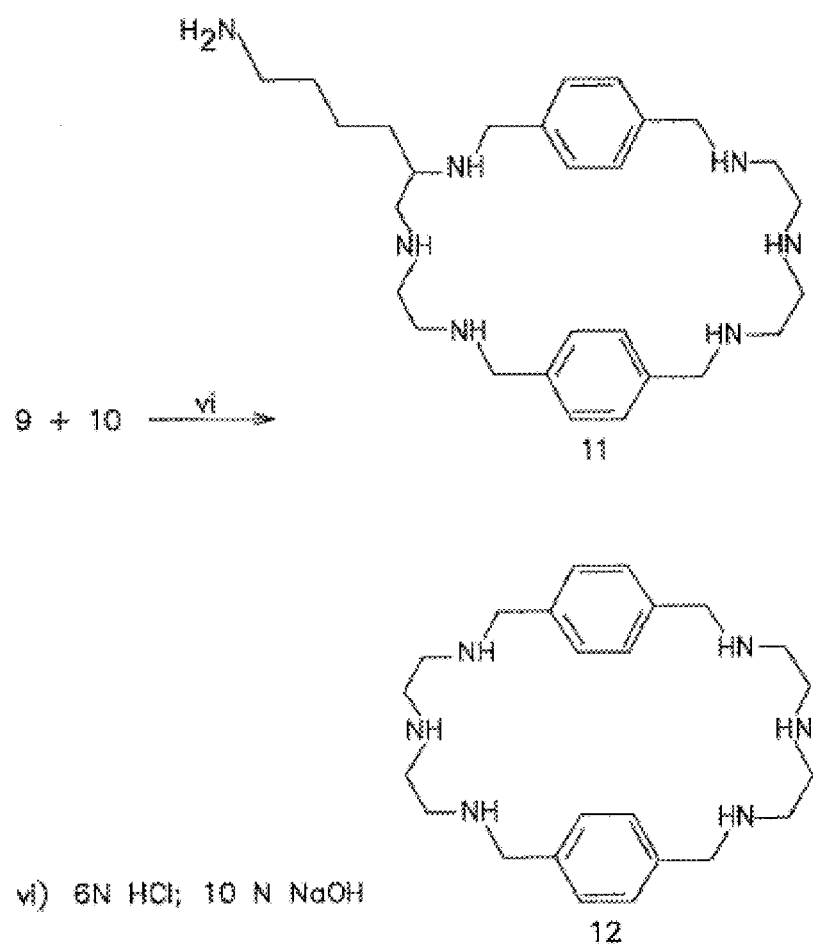
FIG. 11C(3)

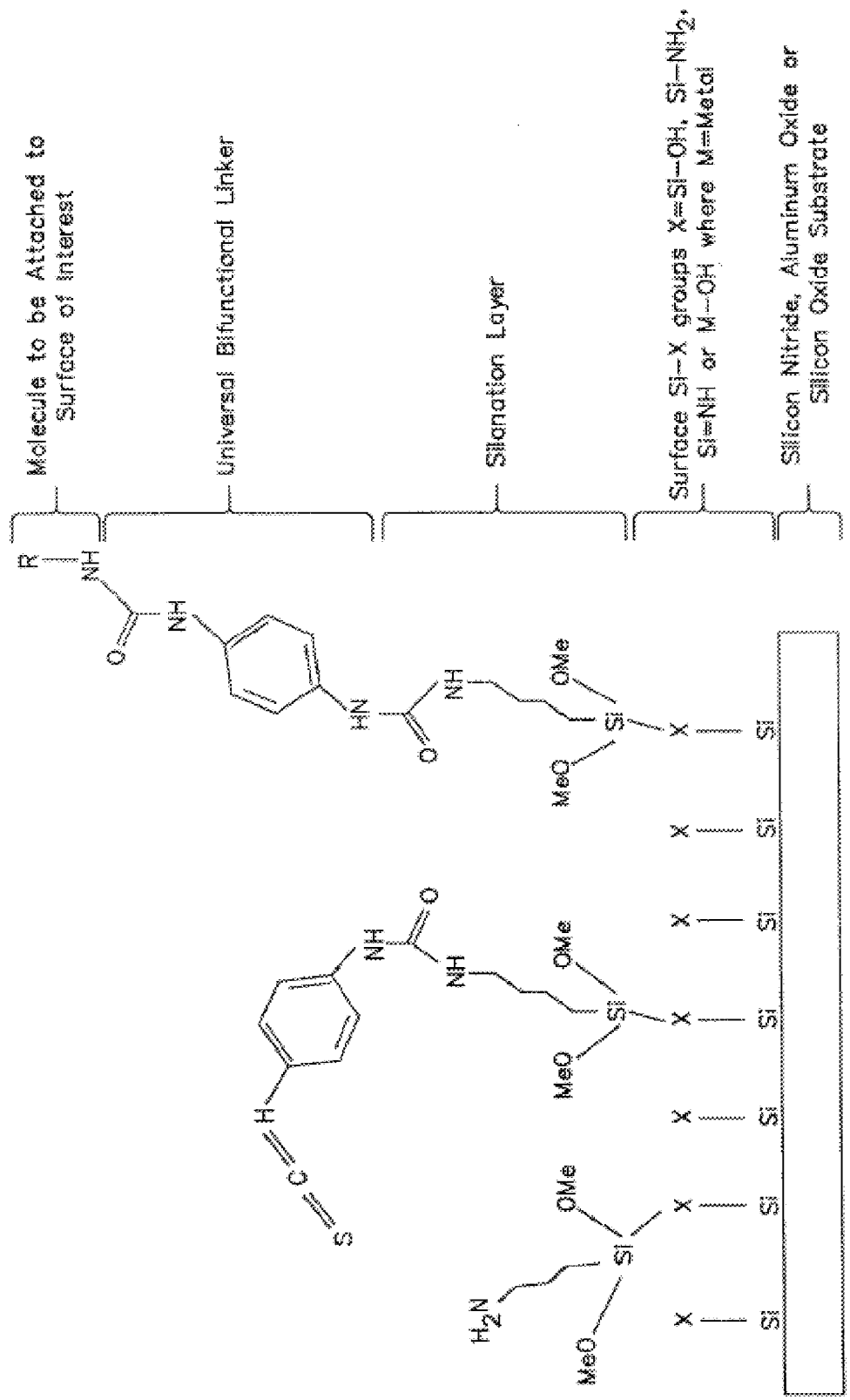
FIG. 11D(1)

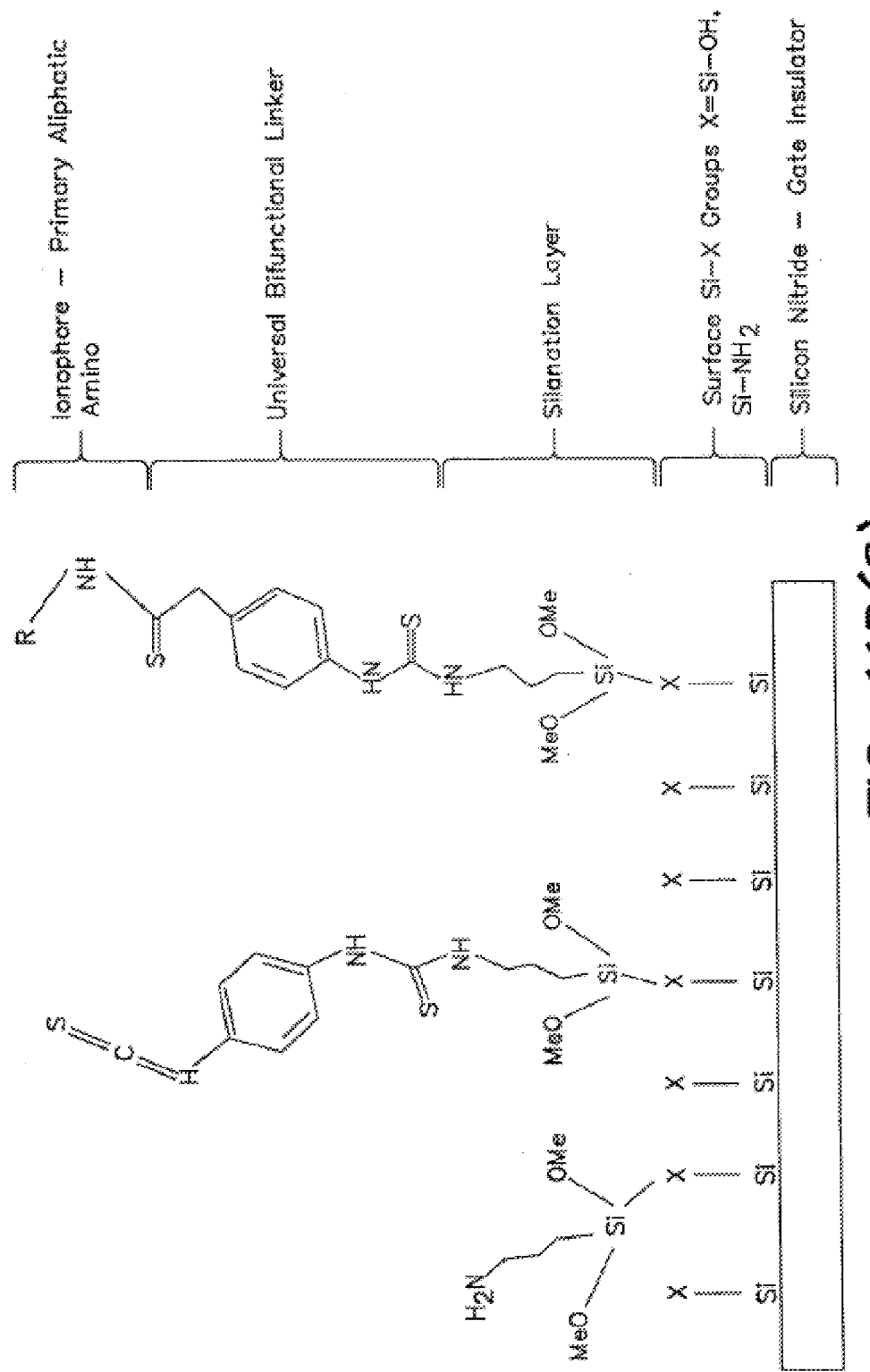
FIG. 11D(2)

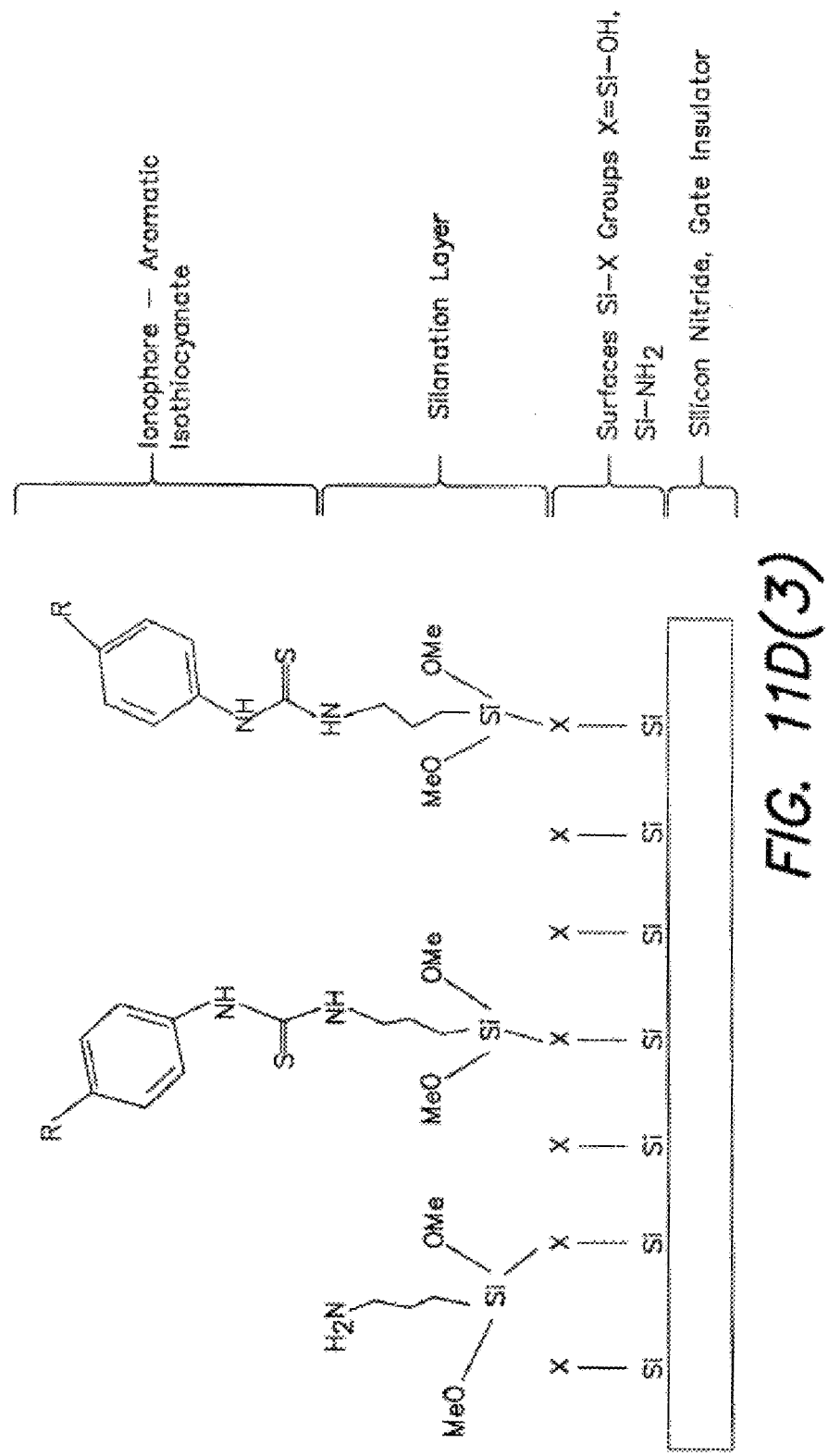
FIG. 11D(3)

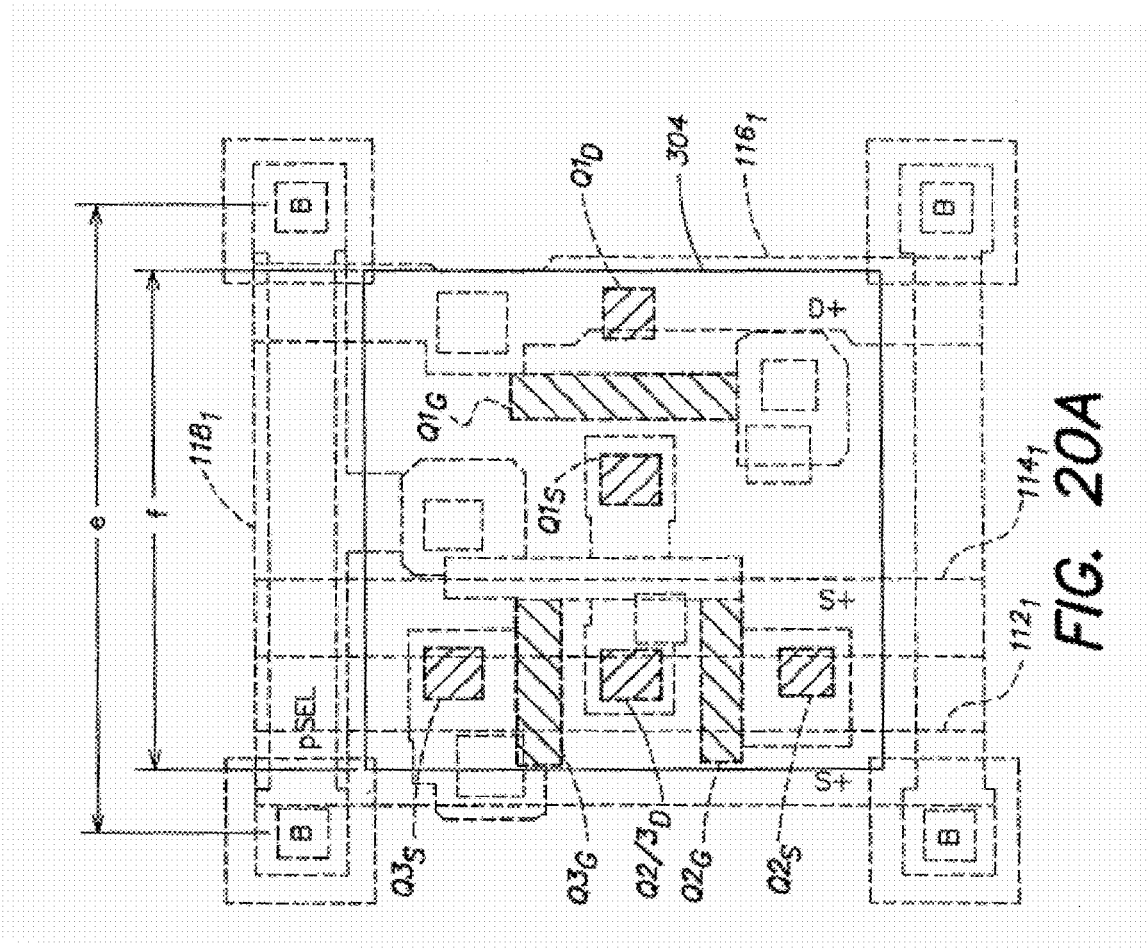

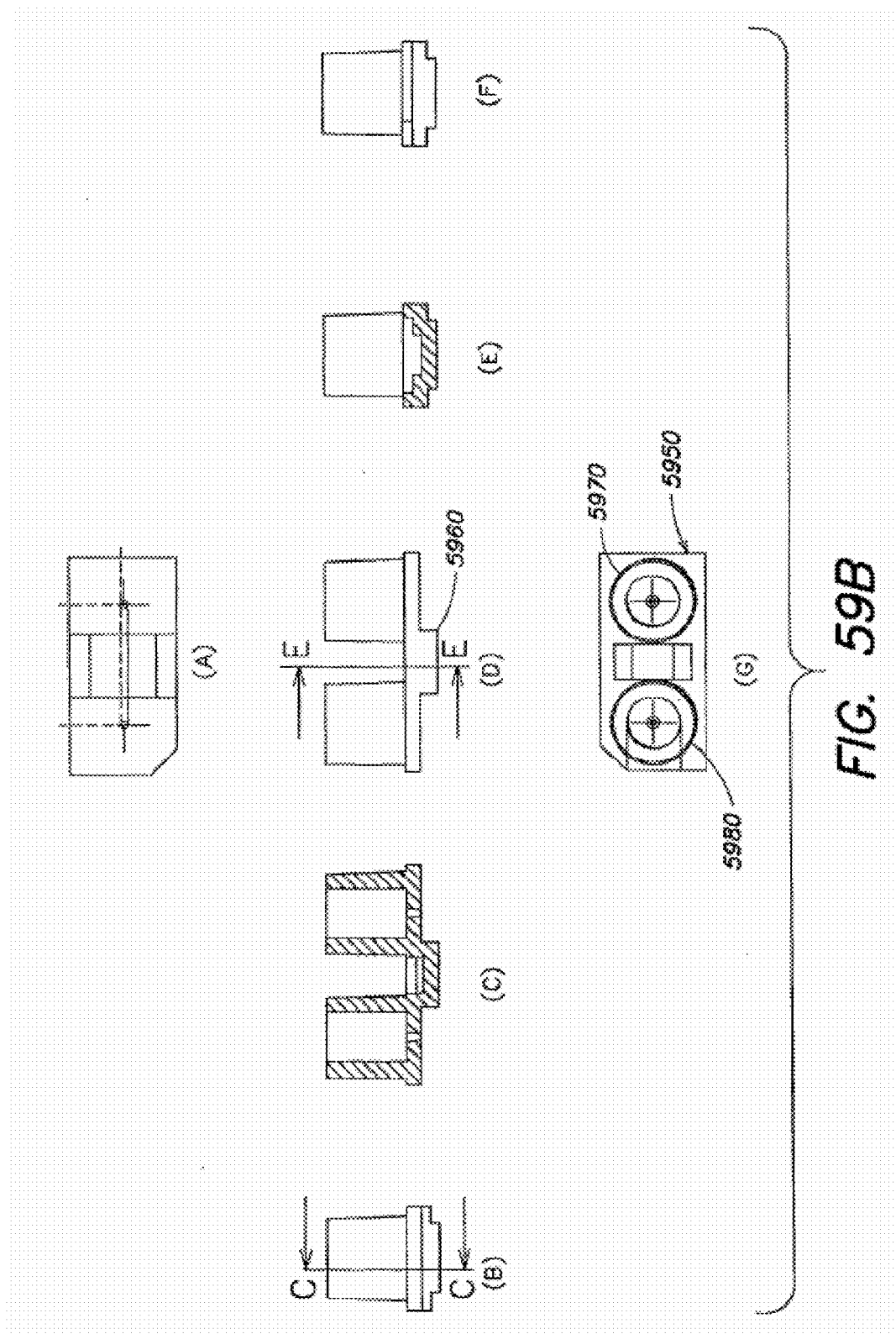

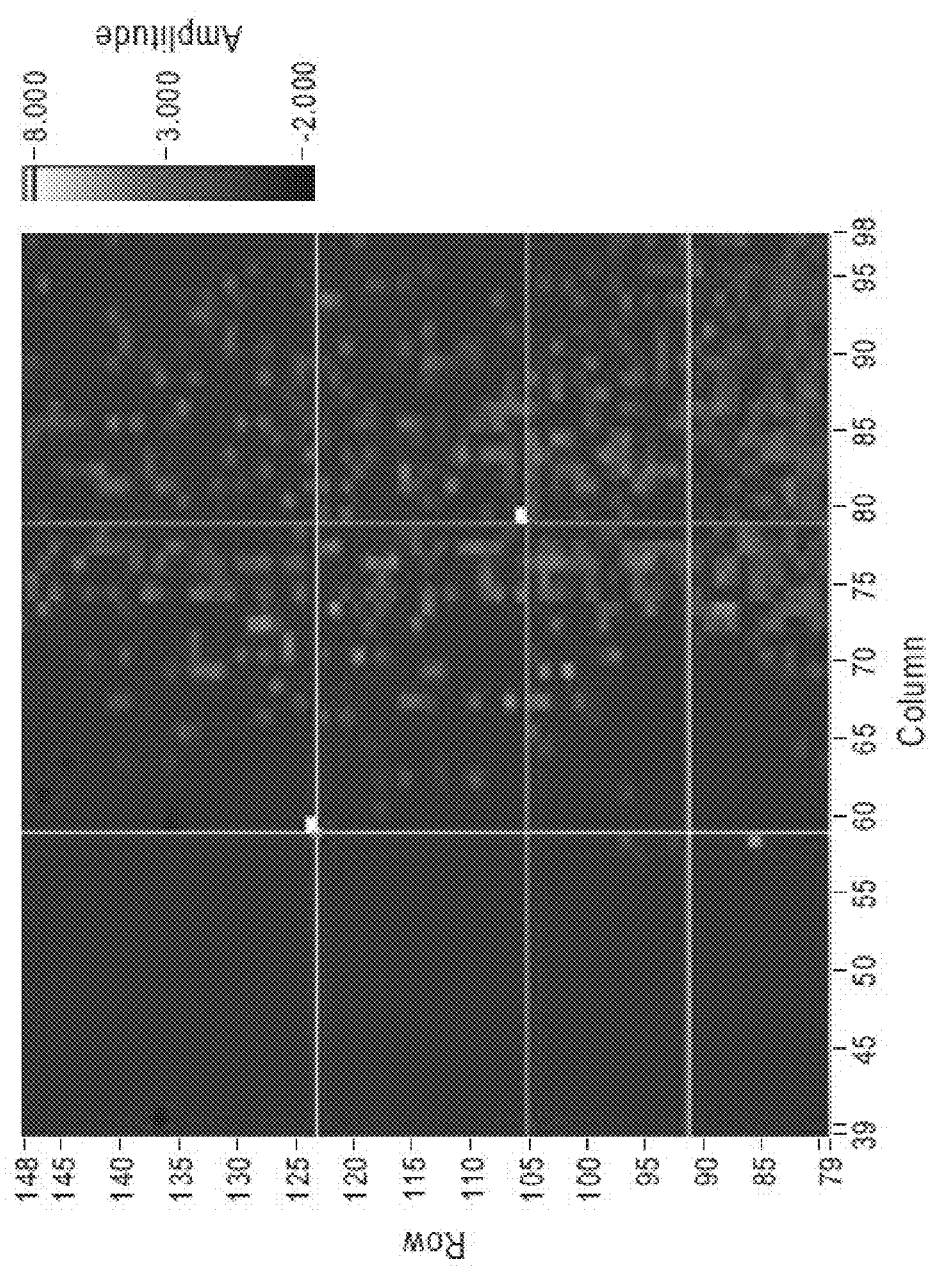
FIG. 71A (PART 1)

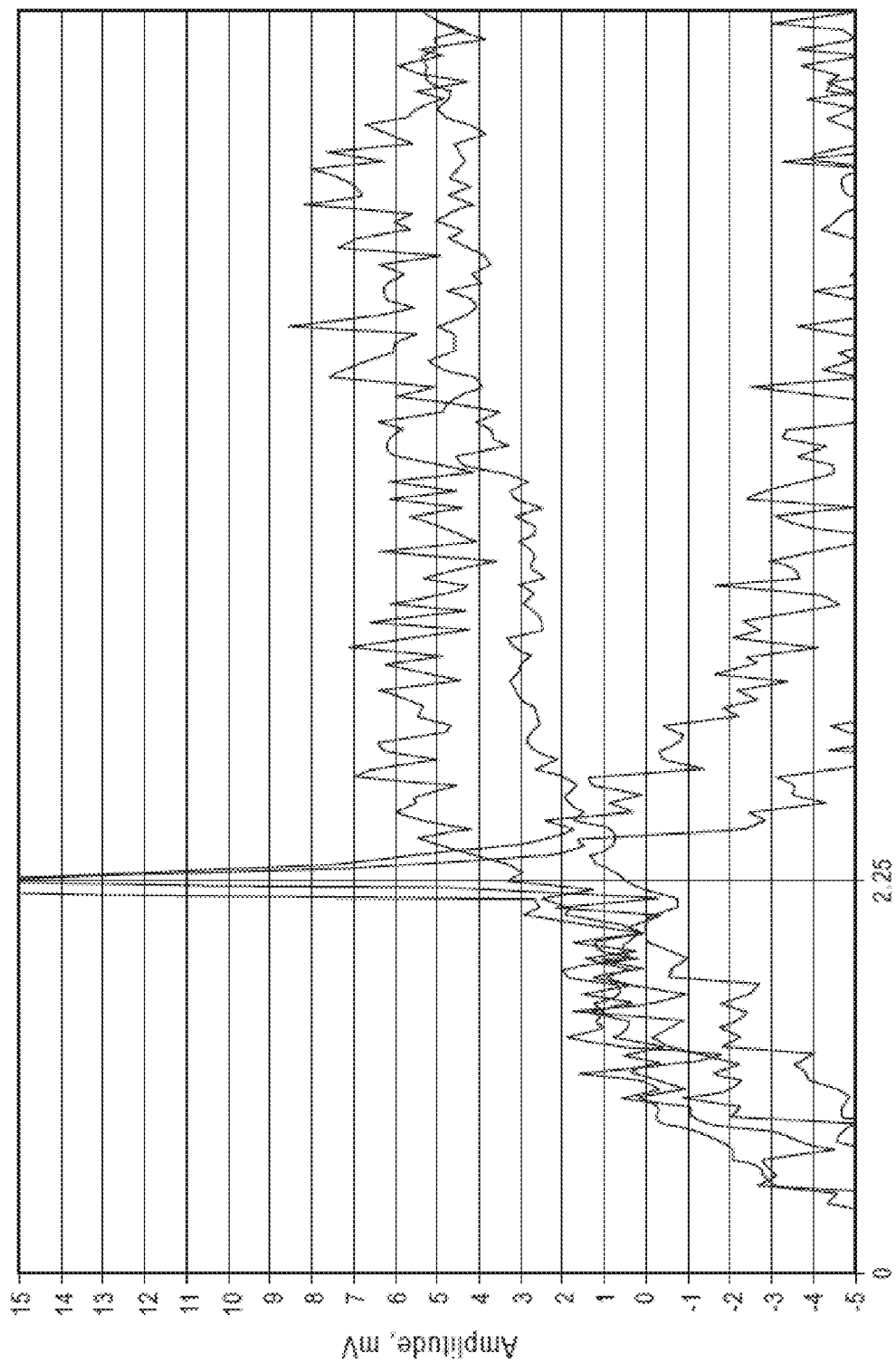
FIG. 71A (PART 2)

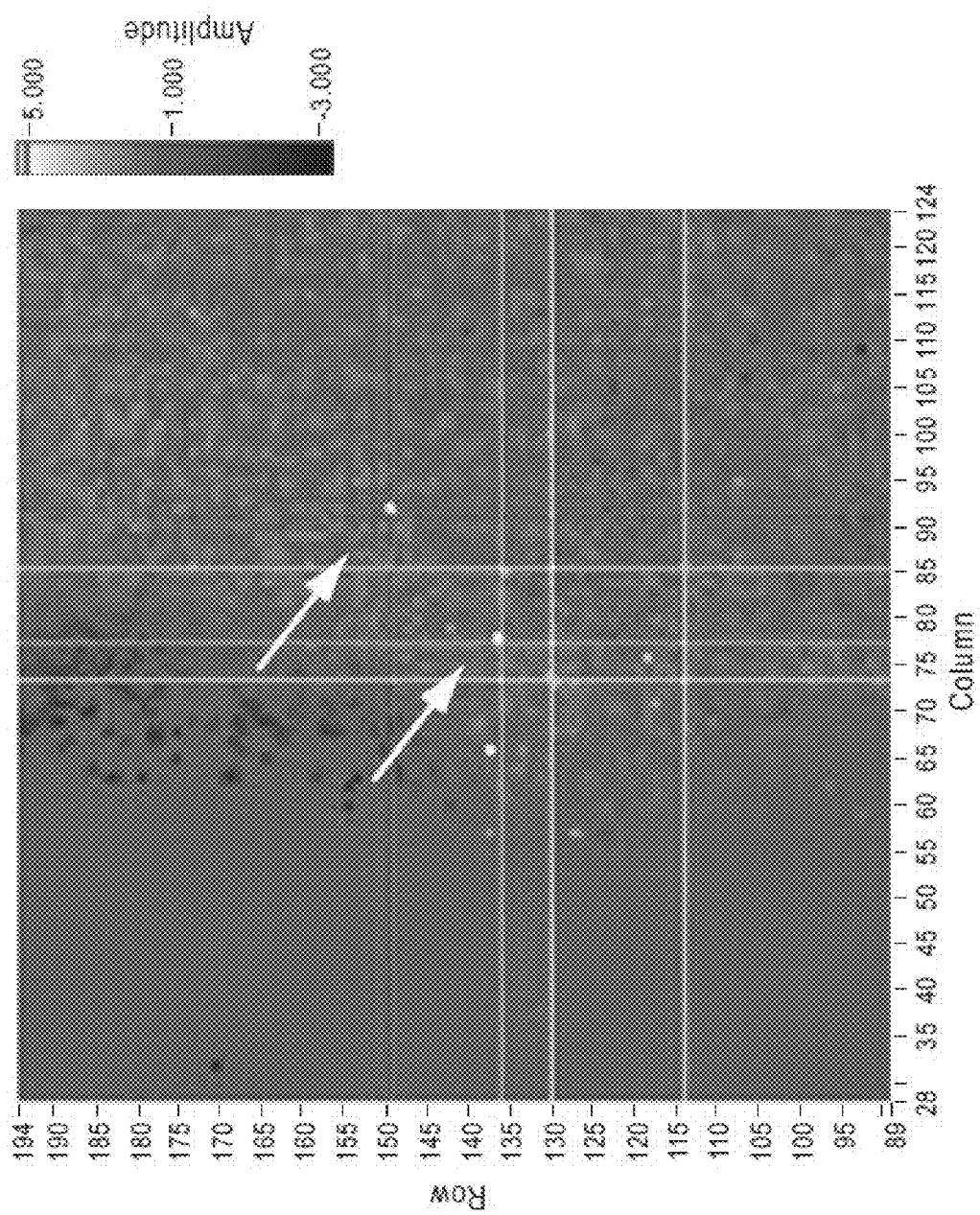
FIG. 71B (PART 1)

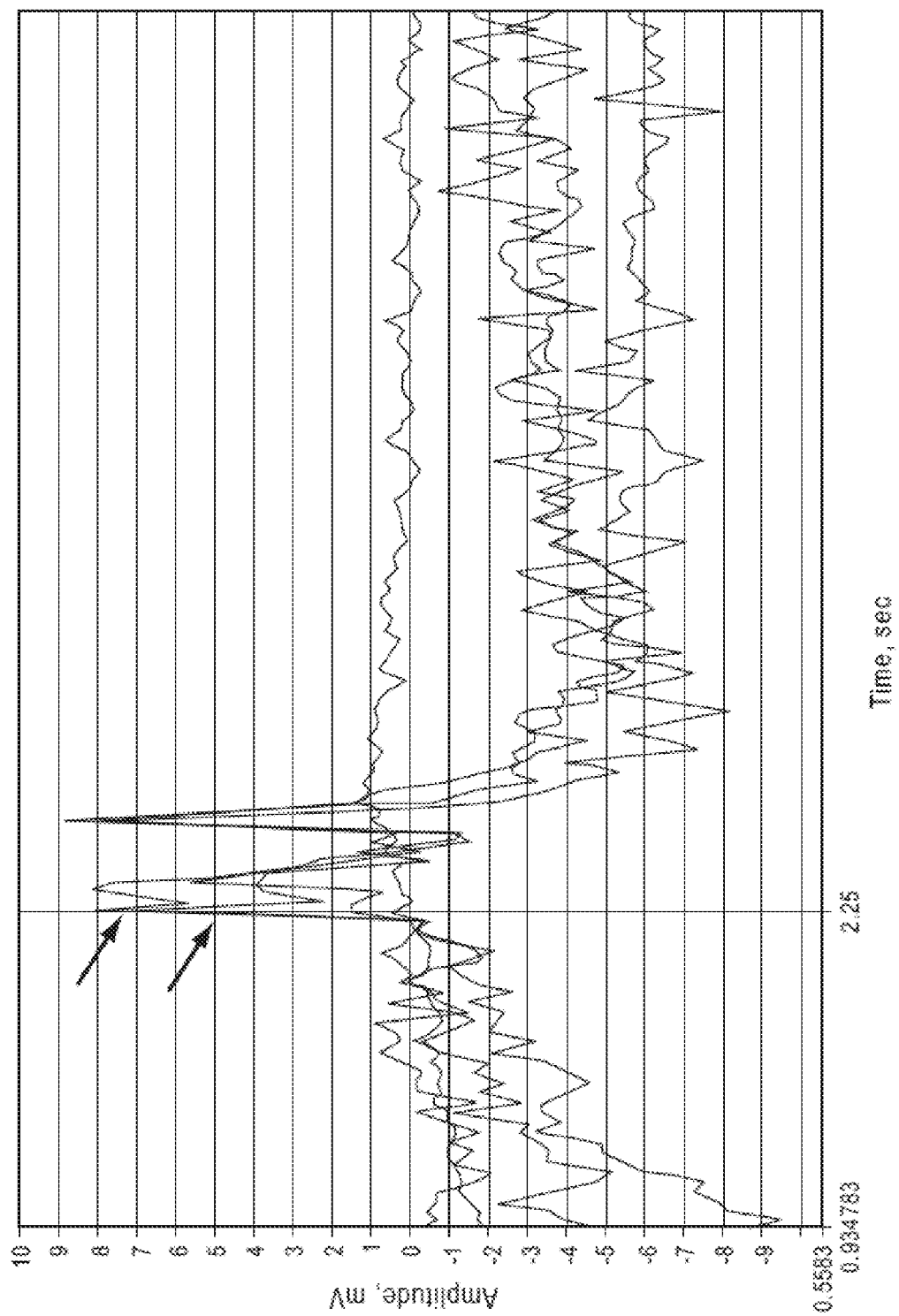

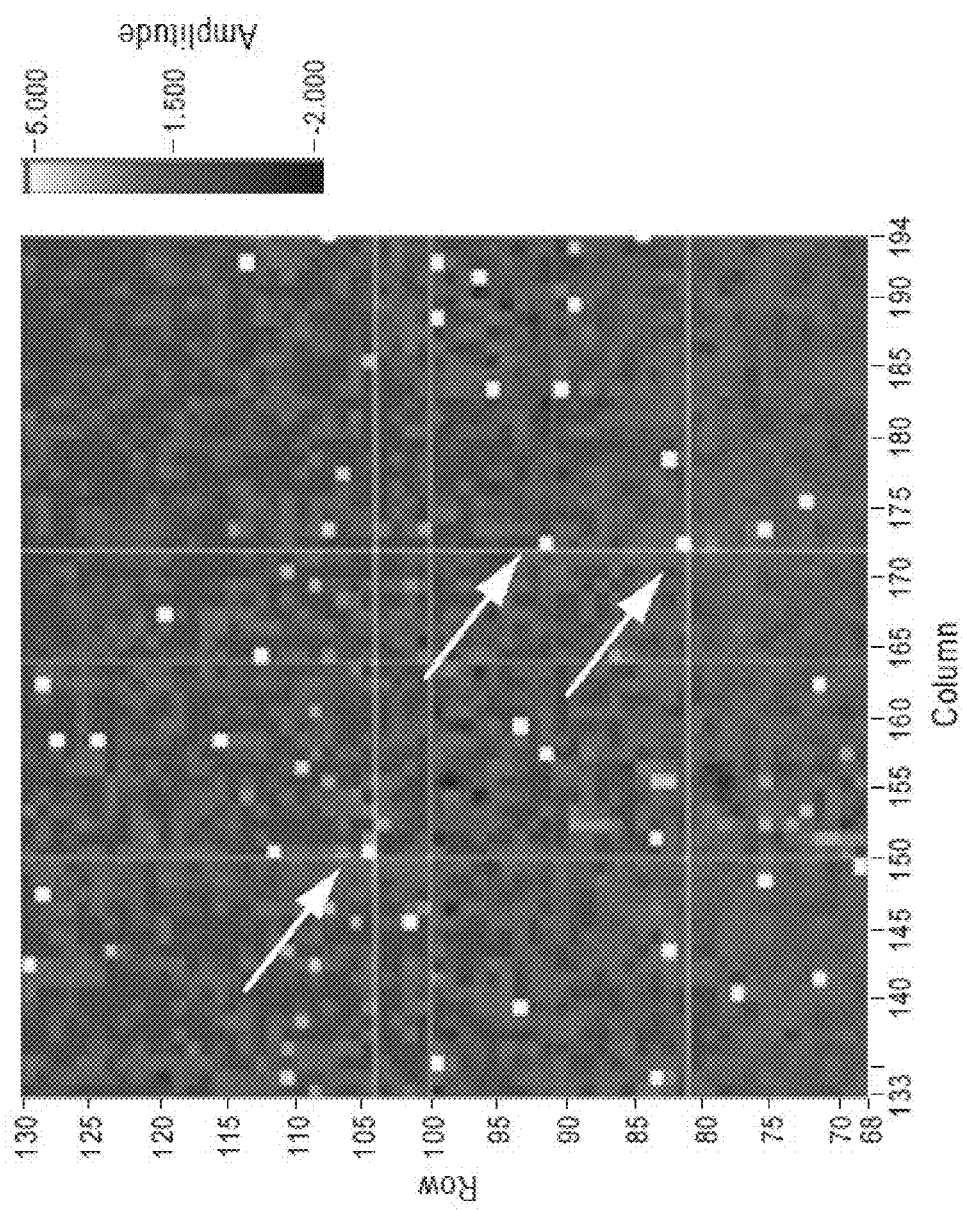
FIG. 71C (PART 1)

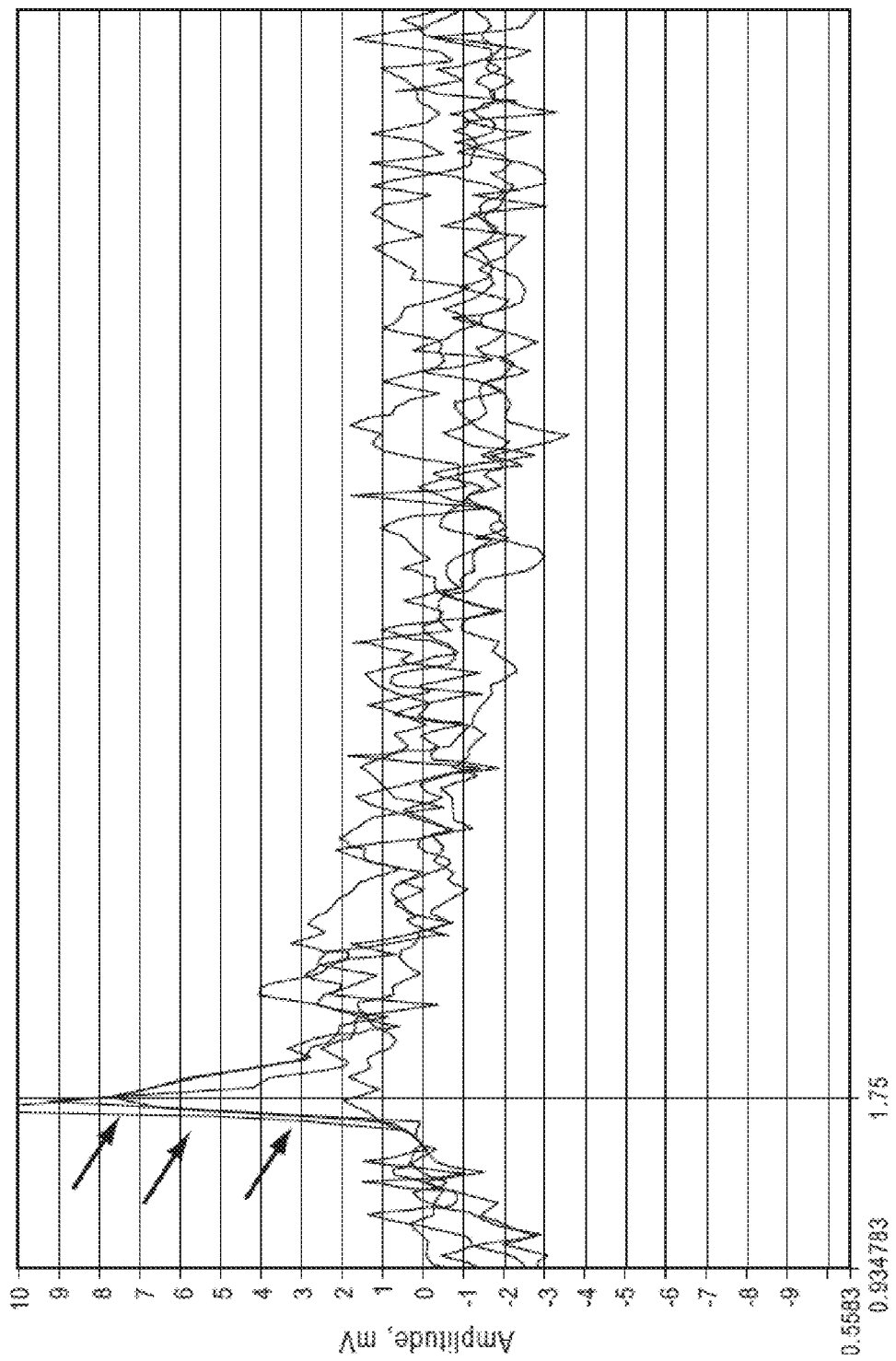
FIG. 71C (PART 2)

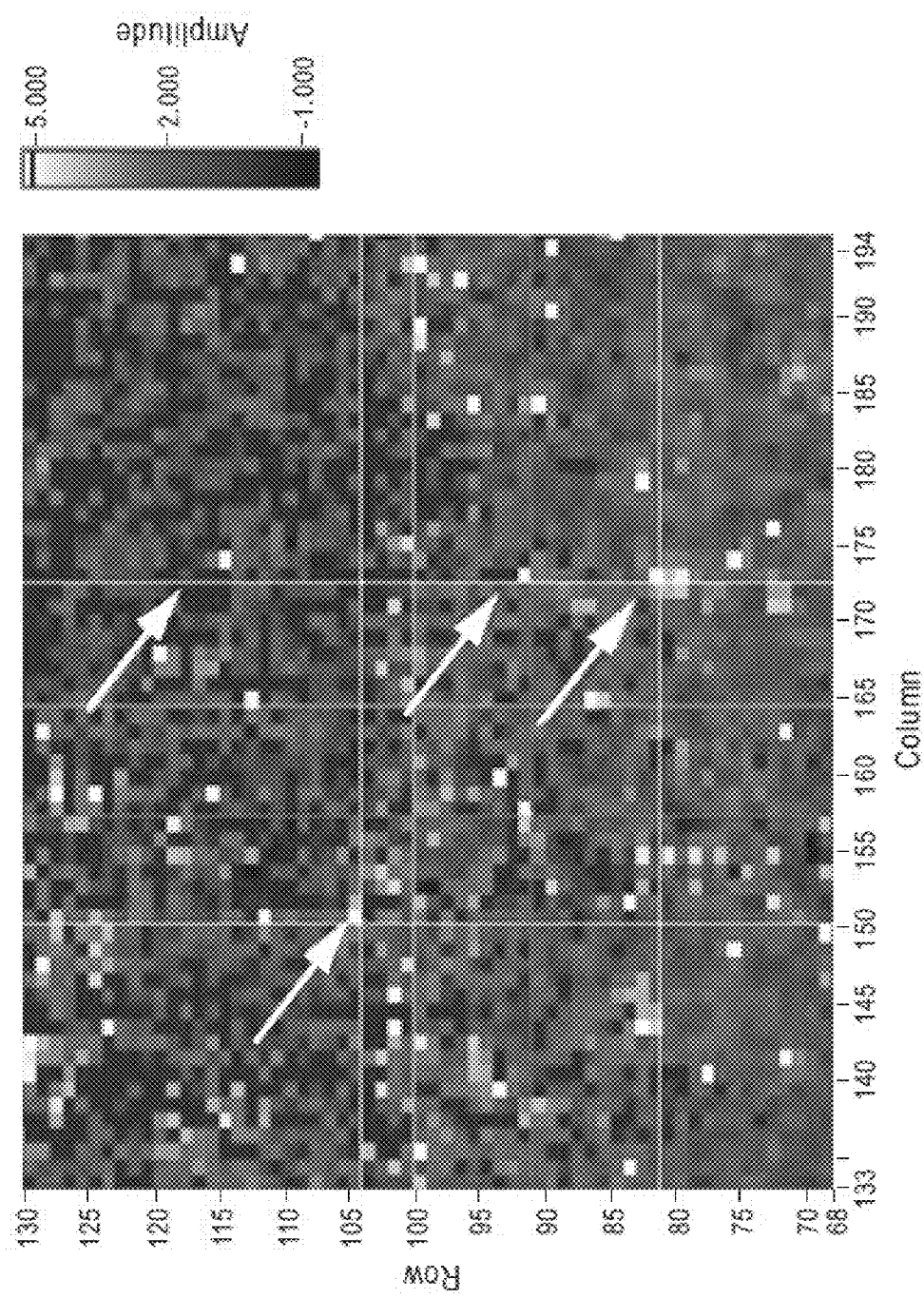
FIG. 71D (PART 1)

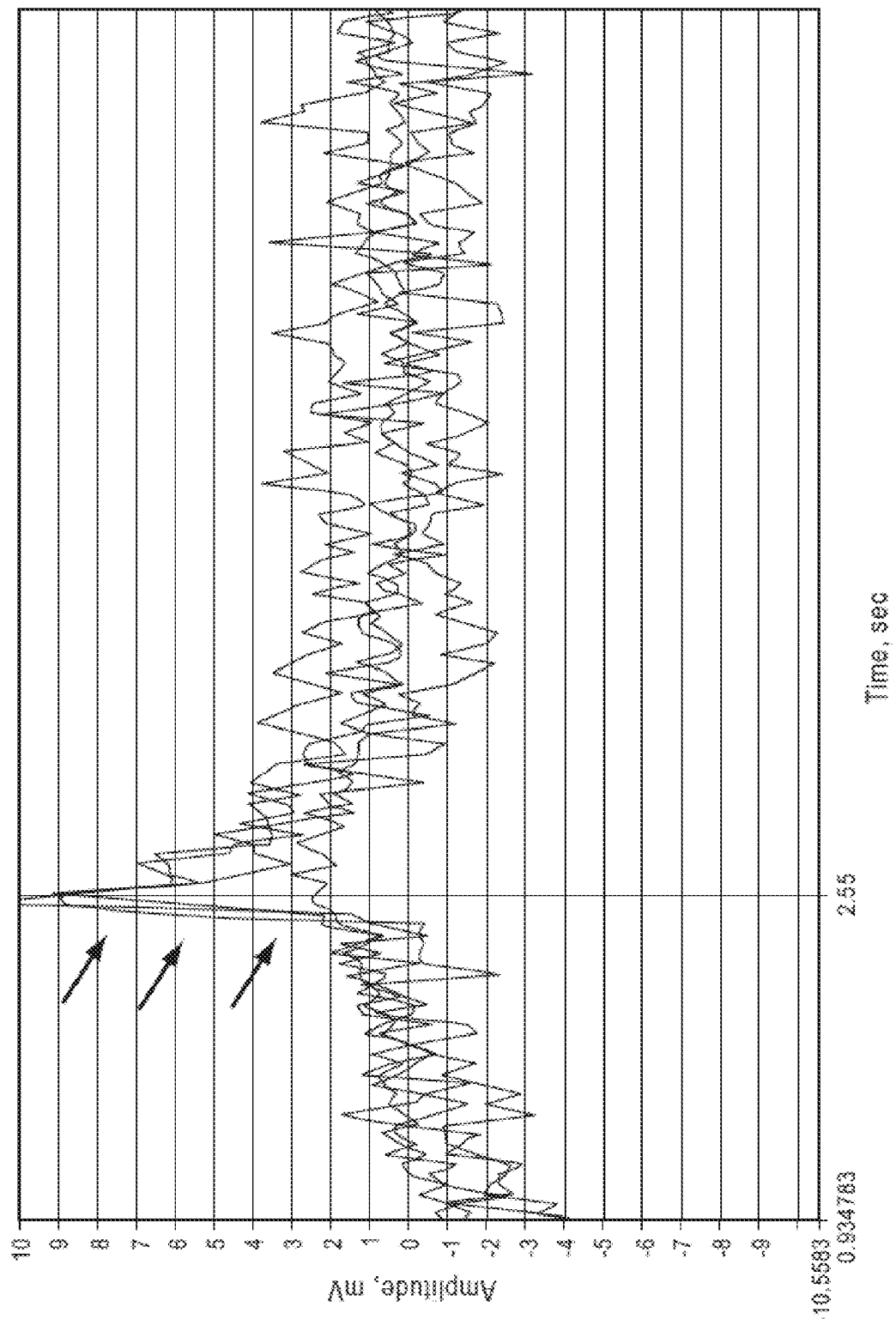
FIG. 71D (PART 2)

SEQUENCE LISTING

```
<160> NUMBER OF SEQ ID NOS: 7

<210> SEQ ID NO 1
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 1
gcaagtgccc ttaggcttca gttcaaaagt cctaactggg caaggcacac aggggatagg      60

<210> SEQ ID NO 2
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 2
ccatgtcccc ttaagccccc cccattcccc cctgaacccc caaggcacac aggggatagg      60

<210> SEQ ID NO 3
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 3
aagctcaaaa acggtaaaaa aaagccaaaa aactggaaaa caaggcacac aggggatagg      60

<210> SEQ ID NO 4
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 4
ttcgagtttt tgccattttt tttcggtttt ttgacctttt caaggcacac aggggatagg      60

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 5
```

-continued

```
actggtccag cattagccgt acgac                                              25

<210> SEQ ID NO 6
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 6
gtcgtacggc taa                                                           13

<210> SEQ ID NO 7
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 7
gtcgtacggc taat                                                          14
```

US 8,450,781 B2

METHODS AND APPARATUS FOR MEASURING ANALYTES USING LARGE SCALE FET ARRAYS

CROSS-REFERENCE TO RELATED APPLICATIONS

This application is a continuation of U.S. patent application Ser. No. 13/149,262 filed 31 May 2011, which is a continuation of U.S. patent application Ser. No. 12/002,781 filed 17 Dec. 2007, which is a continuation-in-part of U.S. application Ser. No. 12/002,291, filed 14 Dec. 2007, which claims priority to U.S. Provisional Application No. 60/956,324, filed 16 Aug. 2007, U.S. Provisional Application No. 60/948,748, filed 10 Jul. 2007, and U.S. Provisional Application No. 60/870,073, filed 14 Dec. 2007; the entire contents of each of which are incorporated herein by reference.

REFERENCE TO BIOLOGICAL SEQUENCE DISCLOSURE

This application contains nucleotide sequence and/or amino acid sequence disclosure in computer readable form and a written sequence listing, the entire contents of both of which are expressly incorporated by reference in their entirety as though fully set forth herein.

FIELD OF THE DISCLOSURE

The present disclosure is directed generally to inventive methods and apparatus relating to detection and measurement of one or more analytes via electronic sensors.

BACKGROUND

Electronic devices and components have found numerous applications in chemistry and biology (more generally, "life sciences"), especially for detection and measurement of various aspects of chemical reactions and substance composition. One such electronic device is referred to as an ion-sensitive field effect transistor, often denoted in the relevant literature as ISFET (or pHFET). ISFETs conventionally have been explored, primarily in the academic and research community, to facilitate measurement of the hydrogen ion concentration of a solution (commonly denoted as "pH").

More specifically, an ISFET is an impedance transformation device that operates in a manner similar to that of a MOSFET (Metal Oxide Semiconductor Field Effect Transistor), and is particularly configured to selectively measure ion activity in a solution (e.g., hydrogen ions in the solution are the "analyte"). A detailed theory of operation of an ISFET is given in "Thirty years of ISFETOLOGY: what happened in the past 30 years and what may happen in the next 30 years," P. Bergveld, Sens. Actuators, 88 (2003), pp. 1-20, which publication is hereby incorporated herein by reference.

FIG. 1 illustrates a cross-section of a p-type (p-channel) ISFET 50 fabricated using a conventional CMOS (Complimentary Metal Oxide Semiconductor) process. P-type ISFET fabrication is based on a p-type silicon substrate 52, in which an n-type well 54 forming a transistor "body" is formed. Highly doped p-type (p+) regions S and D, constituting a source 56 and a drain 58 of the ISFET, are formed within the n-type well 54. A highly doped n-type (n+) region B is also formed within the n-type well to provide a conductive body (or "bulk") connection 62 to the n-type well. An oxide layer 65 is disposed above the source, drain and body connection regions, through which openings are made to provide electrical connections (via electrical conductors) to these regions; for example, metal contact 66 serves as a conductor to provide an electrical connection to the drain 58, and metal contact 68 serves as a conductor to provide a common connection to the source 56 and n-type well 54, via the highly conductive body connection 62. A polysilicon gate 64 is formed above the oxide layer at a location above a region 60 of the n-type well 54, between the source 56 and the drain 58. Because it is disposed between the polysilicon gate 64 and the transistor body (i.e., the n-type well), the oxide layer 65 often is referred to as the "gate oxide."

Like a MOSFET, the operation of an ISFET is based on the modulation of charge concentration caused by a MOS (Metal-Oxide-Semiconductor) capacitance constituted by the polysilicon gate 64, the gate oxide 65 and the region 60 of the n-type well 54 between the source and the drain. When a negative voltage is applied across the gate and source regions (VGs<0 Volts), a "p-channel" 63 is created at the interface of the region 60 and the gate oxide 65 by depleting this area of electrons. This p-channel 63 extends between the source and the drain, and electric current is conducted through the p-channel when the gate-source potential $V_{GS}$ is negative enough to attract holes from the source into the channel. The gate-source potential at which the channel 63 begins to conduct current is referred to as the transistor's threshold voltage $V_{TH}$ (the transistor conducts when $V_{GS}$ has an absolute value greater than the threshold voltage $V_{TH}$). The source is so named because it is the source of the charge carriers (holes for a p-channel) that flow through the channel 63; similarly, the drain is where the charge carriers leave the channel 63.

In the ISFET 50 of FIG. 1, the n-type well 54 (transistor body), via the body connection 62, is forced to be biased at a same potential as the source 56 (i.e., $V_{SB}=0$ Volts), as seen by the metal contact 68 connected to both the source 56 and the body connection 62. This connection prevents forward biasing of the p+ source region and the n-type well, and thereby facilitates confinement of charge carriers to the area of the region 60 in which the channel 63 may be formed. Any potential difference between the source 56 and the body/n-type well 54 (a non-zero source-to-body voltage $V_{SB}$) affects the threshold voltage $V_{TH}$ of the ISFET according to a non-linear relationship, and is commonly referred to as the "body effect," which in many applications is undesirable.

As also shown in FIG. 1, the polysilicon gate 64 of the ISFET 50 is coupled to multiple metal layers disposed within one or more additional oxide layers 75 disposed above the gate oxide 65 to form a "floating gate" structure 70. The floating gate structure is so named because it is electrically isolated from other conductors associated with the ISFET; namely, it is sandwiched between the gate oxide 65 and a passivation layer 72. In the ISFET 50, the passivation layer 72 constitutes an ion-sensitive membrane that gives rise to the ion-sensitivity of the device; i.e., the presence of ions in an "analyte solution" 74 (a solution containing ions of interest) in contact with the passivation layer 72, particularly in a sensitive area 78 above the floating gate structure 70, alters the electrical characteristics of the ISFET so as to modulate a current flowing through the p-channel 63 between the source 56 and the drain 58. The passivation layer 72 may comprise any one of a variety of different materials to facilitate sensitivity to particular ions; for example, passivation layers comprising silicon nitride or silicon oxynitride generally provide sensitivity to hydrogen ion concentration (pH) in the analyte solution 74, whereas passivation layers comprising polyvinyl chloride containing valinomycin provide sensitivity to potassium ion concentration in the analyte solution (materials suitable for passivation layers and sensitive to other ions such as sodium, silver, iron, bromine, iodine, calcium, and nitrate, for example, are known).

With respect to ion sensitivity, an electric potential difference, commonly referred to as a "surface potential," arises at the solid/liquid interface of the passivation layer 72 and the analyte solution 74 as a function of the ion concentration in the sensitive area 78 due to a chemical reaction (e.g., usually involving the dissociation of oxide surface groups by the ions in the analyte solution in proximity to the sensitive area 78). This surface potential in turn affects the threshold voltage $V_{TH}$ of the ISFET; thus, it is the threshold voltage $V_{TH}$ of the ISFET that varies with changes in ion concentration in the analyte solution 74 in proximity to the sensitive area 78.

FIG. 2 illustrates an electric circuit representation of the p-channel ISFET 50 shown in FIG. 1. With reference again to FIG. 1, a reference electrode 76 (a conventional Ag/AgCl electrode) in the analyte solution 74 determines the electric potential of the bulk of the analyte solution itself and is analogous to the gate terminal of a conventional MOSFET, as shown in FIG. 2. In a linear or non-saturated operating region of the ISFET, the drain current $I_D$ is given as:

$$I_D = \beta \left( V_{GS} - V_{TH} - \frac{1}{2} V_{DS} \right) \cdot V_{DS}, \quad (1)$$

where $V_{DS}$ is the voltage between the drain and the source, and $\beta$ is a transconductance parameter (in units of Amps/Volts$^2$) given by:

$$\beta = \mu C_{ox} \left( \frac{W}{L} \right), \quad (2)$$

where $\mu$ represents the carrier mobility, $C_{ox}$ is the gate oxide capacitance per unit area, and the ratio W/L is the width to length ratio of the channel 63. If the reference electrode 76 provides an electrical reference or ground ($V_G$=0 Volts), and the drain current $I_D$ and the drain-to-source voltage $V_{DS}$ are kept constant, variations of the source voltage $V_S$ of the ISFET directly track variations of the threshold voltage $V_{TH}$, according to Eq. (1); this may be observed by rearranging Eq. (1) as:

$$V_S = -V_{TH} - \left( \frac{I_D}{\beta V_{DS}} + \frac{V_{DS}}{2} \right). \quad (3)$$

Since the threshold voltage $V_{TH}$ of the ISFET is sensitive to ion concentration as discussed above, according to Eq. (3) the source voltage $V_S$ provides a signal that is directly related to the ion concentration in the analyte solution 74 in proximity to the sensitive area 78 of the ISFET. In exemplary conventional ISFETs employing a silicon nitride or silicon oxynitride passivation layer 72 for pH-sensitivity, a threshold voltage sensitivities $\Delta V_{TH}$ (i.e., a change in threshold voltage with change in pH of the analyte solution) of approximately 30 mV/pH to 50 mV/pH have been observed (with a theoretical maximum sensitivity of 59.2 mV/pH at 298 degrees Kelvin).

Prior research efforts to fabricate ISFETs for pH measurements based on conventional CMOS processing techniques typically have aimed to achieve high signal linearity over a pH range from 1-14. Using an exemplary threshold sensitivity of approximately 50 mV/pH, and considering Eq. (3) above, this requires a linear operating range of approximately 700 mV for the source voltage $V_S$. As discussed above in connection with FIG. 1, the threshold voltage $V_{TH}$ of ISFETs (as well as MOSFETs) is affected by any voltage $V_{SB}$ between the source and the body (n-type well 54). More specifically, the threshold voltage $V_{TH}$ is a nonlinear function of a nonzero source-to-body voltage $V_{SB}$. Accordingly, so as to avoid compromising linearity due to a difference between the source and body voltage potentials (i.e., to mitigate the "body effect"), as shown in FIG. 1 the source 56 and body connection 62 of the ISFET 50 often are coupled to a common potential via the metal contact 68. This body-source coupling also is shown in the electric circuit representation of the ISFET 50 shown in FIG. 2.

Previous efforts to fabricate two-dimensional arrays of ISFETs based on the ISFET design of FIG. 1 have resulted in a maximum of 256 ISFET sensor elements, or "pixels," in an array (i.e., a 16 pixel by 16 pixel array). Exemplary research in ISFET array fabrication are reported in the publications "A large transistor-based sensor array chip for direct extracellular imaging," M. J. Milgrew, M. O. Riehle, and D. R. S. Cumming, *Sensors and Actuators, B: Chemical*, 111-112, (2005), pp. 347-353, and "The development of scalable sensor arrays using standard CMOS technology," M. J. Milgrew, P. A. Hammond, and D. R. S. Cumming, *Sensors and Actuators, B: Chemical*, 103, (2004), pp. 37-42, which publications are incorporated herein by reference and collectively referred to hereafter as "Milgrew et al." Other research efforts relating to the realization of ISFET arrays are reported in the publications "A very large integrated pH-ISFET sensor array chip compatible with standard CMOS processes," T. C. W. Yeow, M. R. Haskard, D. E. Mulcahy, H. I. Seo and D. H. Kwon, Sensors and Actuators B: Chemical, 44, (1997), pp. 434-440 and "Fabrication of a two-dimensional pH image sensor using a charge transfer technique," Hizawa, T., Sawada, K., Takao, H., Ishida, M., *Sensors and Actuators, B: Chemical* 117 (2), 2006, pp. 509-515, which publications also are incorporated herein by reference.

FIG. 3 illustrates one column $85_j$ of a two-dimensional ISFET array according to the design of Milgrew et al. The column $85_j$ includes sixteen (16) pixels $80_1$ through $80_{16}$ and, as discussed further below in connection with FIG. 7, a complete two-dimensional array includes sixteen (16) such columns $85_j$ (j=1, 2, 3, . . . 16) arranged side by side. As shown in FIG. 3, a given column $85_j$ includes a current source $i_{SOURCEj}$ that is shared by all pixels of the column, and ISFET bias/readout circuitry $82_j$ (including current sink $I_{SINKj}$) that is also shared by all pixels of the column. Each ISFET pixel $80_1$ through $80_{16}$ includes a p-channel ISFET 50 having an electrically coupled source and body (as shown in FIGS. 1 and 2), plus two switches S1 and S2 that are responsive to one of sixteen row select signals ($RSEL_1$ through $RSEL_{16}$, and their complements). As discussed below in connection with FIG. 7, a row select signal and its complement are generated simultaneously to "enable" or select a given pixel of the column $85_j$, and such signal pairs are generated in some sequence to successively enable different pixels of the column one at a time.

As shown in FIG. 3, the switch S2 of each pixel 80 in the design of Milgrew et al. is implemented as a conventional n-channel MOSFET that couples the current source $I_{SOURCEj}$ to the source of the ISFET 50 upon receipt of the corresponding row select signal. The switch S1 of each pixel 80 is implemented as a transmission gate, i.e., a CMOS pair including an n-channel MOSFET and a p-channel MOSFET, that couples the source of the ISFET 50 to the bias/readout circuitry 82*j* upon receipt of the corresponding row select signal and its complement. An example of the switch S1₁ of the pixel 80₁ is shown in FIG. 4, in which the p-channel MOSFET of the transmission gate is indicated as S1$_{1P}$ and the n-channel MOSFET is indicated as S1$_{1N}$. In the design of Milgrew et al., a transmission gate is employed for the switch S1 of each pixel so that, for an enabled pixel, any ISFET source voltage within the power supply range V$_{DD}$ to V$_{SS}$ may be applied to the bias/readout circuitry 82$_j$ and output by the column as the signal V$_{Sj}$. From the foregoing, it should be appreciated that each pixel 80 in the ISFET sensor array design of Milgrew et al. includes four transistors, i.e., a p-channel ISFET, a CMOS-pair transmission gate including an n-channel MOSFET and a p-channel MOSFET for switch S1, and an n-channel MOSFET for switch S2.

As also shown in FIG. 3, the bias/readout circuitry 82$_j$ employs a source-drain follower configuration in the form of a Kelvin bridge to maintain a constant drain-source voltage V$_{DSj}$ and isolate the measurement of the source voltage V$_{DSj}$ from the constant drain current I$_{SOURCEj}$ for the ISFET of an enabled pixel in the column 85$_j$. To this end, the bias/readout circuitry 82$_j$ includes two operational amplifiers A1 and A2, a current sink I$_{SINKj}$, and a resistor R$_{SDJ}$. The voltage developed across the resistor R$_{SDJ}$ due to the current I$_{SINKj}$ flowing through the resistor is forced by the operational amplifiers to appear across the drain and source of the ISFET of an enabled pixel as a constant drain-source voltage V$_{DSj}$. Thus, with reference again to Eq. (3), due to the constant V$_{DSj}$ and the constant I$_{SOURCEj}$, the source voltage V$_{Sj}$ of the ISFET of the enabled pixel provides a signal corresponding to the ISFETs threshold voltage V$_{TH}$, and hence a measurement of pH in proximity to the ISFETs sensitive area (see FIG. 1). The wide dynamic range for the source voltage V$_{Sj}$ provided by the transmission gate S1 ensures that a full range of pH values from 1-14 may be measured, and the source-body connection of each ISFET ensures sufficient linearity of the ISFETs threshold voltage over the full pH measurement range.

In the column design of Milgrew et al. shown in FIG. 3, it should be appreciated that for the Kelvin bridge configuration of the column bias/readout circuitry 82$_j$ to function properly, a p-channel ISFET 50 as shown in FIG. 1 must be employed in each pixel; more specifically, an alternative implementation based on the Kelvin bridge configuration is not possible using an n-channel ISFET. With reference again to FIG. 1, for an n-channel ISFET based on a conventional CMOS process, the n-type well 54 would not be required, and highly doped n-type regions for the drain and source would be formed directly in the p-type silicon substrate 52 (which would constitute the transistor body). For n-channel FET devices, the transistor body typically is coupled to electrical ground. Given the requirement that the source and body of an ISFET in the design of Milgrew et al. are electrically coupled together to mitigate nonlinear performance due to the body effect, this would result in the source of an n-channel ISFET also being connected to electrical ground (i.e., V$_S$=V$_B$=0 Volts), thereby precluding any useful output signal from an enabled pixel. Accordingly, the column design of Milgrew et al. shown in FIG. 3 requires p-channel ISFETs for proper operation.

It should also be appreciated that in the column design of Milgrew et al. shown in FIG. 3, the two n-channel MOSFETs required to implement the switches S1 and S2 in each pixel cannot be formed in the n-type well 54 shown in FIG. 1, in which the p-channel ISFET for the pixel is formed; rather, the n-channel MOSFETs are formed directly in the p-type silicon substrate 52, beyond the confines of the n-type well 54 for the ISFET. FIG. 5 is a diagram similar to FIG. 1, illustrating a wider cross-section of a portion of the p-type silicon substrate 52 corresponding to one pixel 80 of the column 85$_j$ shown in FIG. 3, in which the n-type well 54 containing the drain 58, source 56 and body connection 62 of the ISFET 50 is shown alongside a first n-channel MOSFET corresponding to the switch S2 and a second n-channel MOSFET S1$_{1N}$ constituting one of the two transistors of the transmission gate S1₁ shown in FIG. 4.

Furthermore, in the design of Milgrew et al., the p-channel MOSFET required to implement the transmission gate S1 in each pixel (e.g., see S1$_{1P}$ in FIG. 4) cannot be formed in the same n-type well in which the p-channel ISFET 50 for the pixel is formed. In particular, because the body and source of the p-channel ISFET are electrically coupled together, implementing the p-channel MOSFET S1$_{1P}$ in the same n-well as the p-channel ISFET 50 would lead to unpredictable operation of the transmission gate, or preclude operation entirely. Accordingly, two separate n-type wells are required to implement each pixel in the design of Milgrew et al. FIG. 6 is a diagram similar to FIG. 5, showing a cross-section of another portion of the p-type silicon substrate 52 corresponding to one pixel 80, in which the n-type well 54 corresponding to the ISFET 50 is shown alongside a second n-type well 55 in which is formed the p-channel MOSFET S1$_{1P}$ constituting one of the two transistors of the transmission gate S1₁ shown in FIG. 4. It should be appreciated that the drawings in FIGS. 5 and 6 are not to scale and may not exactly represent the actual layout of a particular pixel in the design of Milgrew et al.; rather these figures are conceptual in nature and are provided primarily to illustrate the requirements of multiple n-wells, and separate n-channel MOSFETs fabricated outside of the n-wells, in the design of Milgrew et al.

The array design of Milgrew et al. was implemented using a 0.35 micrometer (μm) conventional CMOS fabrication process. In this process, various design rules dictate minimum separation distances between features. For example, according to the 0.35 μm CMOS design rules, with reference to FIG. 6, a distance "a" between neighboring n-wells must be at least three (3) micrometers. A distance "a/2" also is indicated in FIG. 6 to the left of the n-well 54 and to the right of the n-well 55 to indicate the minimum distance required to separate the pixel 80 shown in FIG. 6 from neighboring pixels in other columns to the left and right, respectively. Additionally, according to the 0.35 μm CMOS design rules, a distance "b" shown in FIG. 6 representing the width in cross-section of the n-type well 54 and a distance "c" representing the width in cross-section of the n-type well 55 are each on the order of approximately 3 μm to 4 μm (within the n-type well, an allowance of 1.2 μm is made between the edge of the n-well and each of the source and drain, and the source and drain themselves have a width on the order of 0.7 μm). Accordingly, a total distance "d" shown in FIG. 6 representing the width of the pixel 80 in cross-section is on the order of approximately 12 μm to 14 μm. In one implementation, Milgrew et al. report an array based on the column/pixel design shown in FIG. 3 comprising geometrically square pixels each having a dimension of 12.8 μm by 12.8 μm.

In sum, the ISFET pixel design of Milgrew et al. is aimed at ensuring accurate hydrogen ion concentration measurements over a pH range of 1-14. To ensure measurement linearity, the source and body of each pixel's ISFET are electrically coupled together. To ensure a full range of pH measurements, a transmission gate S1 is employed in each pixel to transmit the source voltage of an enabled pixel. Thus, each pixel of Milgrew's array requires four transistors (p-channel ISFET, p-channel MOSFET, and two n-channel MOSFETs) and two separate n-wells (FIG. 6). Based on a 0.35 micrometer conventional CMOS fabrication process and the corresponding design rules, the pixels of such an array have a minimum size appreciably greater than 10 µm, i.e., on the order of approximately 12 µm to 14 µm.

FIG. 7 illustrates a complete two-dimensional pixel array 95 according to the design of Milgrew et al., together with accompanying row and column decoder circuitry and measurement readout circuitry. The array 95 includes sixteen columns $85_1$ through $85_{16}$ of pixels, each column having sixteen pixels as discussed above in connection with FIG. 3 (i.e., a 16 pixel by 16 pixel array). A row decoder 92 provides sixteen pairs of complementary row select signals, wherein each pair of row select signals simultaneously enables one pixel in each column $85_1$ through $85_{16}$ to provide a set of column output signals from the array 95 based on the respective source voltages $V_{S1}$ through $V_{S16}$ of the enabled row of ISFETs. The row decoder 92 is implemented as a conventional four-to-sixteen decoder (i.e., a four-bit binary input $ROW_1$-$ROW_4$ to select one of $2^4$ outputs). The set of column output signals $V_{S1}$ through $V_{S16}$ for an enabled row of the array is applied to switching logic 96, which includes sixteen transmission gates S1 through S16 (one transmission gate for each output signal). As above, each transmission gate of the switching logic 96 is implemented using a p-channel MOSFET and an n-channel MOSFET to ensure a sufficient dynamic range for each of the output signals $V_{S1}$ through $V_{S16}$. The column decoder 94, like the row decoder 92, is implemented as a conventional four-to-sixteen decoder and is controlled via the four-bit binary input $COL_1$-$COL_4$ to enable one of the transmission gates S1 through S16 of the switching logic 96 at any given time, so as to provide a single output signal $V_S$ from the switching logic 96. This output signal $V_S$ is applied to a 10-bit analog to digital converter (ADC) 98 to provide a digital representation $D_1$-$D_{10}$ of the output signal $V_S$ corresponding to a given pixel of the array.

As noted earlier, individual ISFETs and arrays of ISFETs similar to those discussed above have been employed as sensing devices in a variety of applications involving chemistry and biology. In particular, ISFETs have been employed as pH sensors in various processes involving nucleic acids such as DNA. Some examples of employing ISFETs in various life-science related applications are given in the following publications, each of which is incorporated herein by reference: Massimo Barbaro, Annalisa Bonfiglio, Luigi Raffo, Andrea Alessandrini, Paolo Facci and Inrich Barak, "Fully electronic DNA hybridization detection by a standard CMOS biochip," *Sensors and Actuators B: Chemical*, Volume 118, Issues 1-2, 2006, pp. 41-46; Toshinari Sakurai and Yuzuru Husimi, "Real-time monitoring of DNA polymerase reactions by a micro ISFET pH sensor," *Anal. Chem.*, 64 (17), 1992, pp 1996-1997; S. Purushothaman, C. Toumazou, J. Georgiou, "Towards fast solid state DNA sequencing," *Circuits and Systems*, vol. 4, 2002, pp. IV-169 to IV-172; S. Purushothaman, C. Toumazou, C. P. Ou, "Protons and single nucleotide polymorphism detection: A simple use for the Ion Sensitive Field Effect Transistor," *Sensors and Actuators B: Chemical*, Vol. 114, no. 2, 2006, pp. 964-968; A. L. Simonian, A. W. Flounders, J. R. Wild, "FET-Based Biosensors for The Direct Detection of Organophosphate Neurotoxins," *Electroanalysis*, Vol. 16, No. 22, 2004, pp. 1896-1906; C. Toumazou, S. Purushothaman, "Sensing Apparatus and Method," United States Patent Application 2004-0134798, published Jul. 15, 2004; and T. W. Koo, S. Chan, X. Su, Z. Jingwu, M. Yamakawa, V. M. Dubin, "Sensor Arrays and Nucleic Acid Sequencing Applications," United States Patent Application 2006-0199193, published Sep. 7, 2006.

In general, the development of rapid and sensitive nucleic acid sequencing methods utilizing automated DNA sequencers has significantly advanced the understanding of biology. The term "sequencing" refers to the determination of a primary structure (or primary sequence) of an unbranched biopolymer, which results in a symbolic linear depiction known as a "sequence" that succinctly summarizes much of the atomic-level structure of the sequenced molecule. "DNA sequencing" particularly refers to the process of determining the nucleotide order of a given DNA fragment. Analysis of entire genomes of viruses, bacteria, fungi, animals and plants is now possible, but such analysis generally is limited due to the cost and throughput of sequencing. More specifically, present conventional sequencing methods are limited in terms of the accuracy of the sequence, the length of individual templates that can be sequenced, the cost of the sequence, and the rate of sequence determination.

Despite improvements in sample preparation and sequencing technologies, none of the present conventional sequencing strategies, including those to date that may involve ISFETs, has provided the cost reductions required to increase throughput to levels required for analysis of large numbers of individual human genomes. It is necessary to sequence a large number of individual genomes to understand the genetic basis of disease and aging. In addition, a large number of cancers will need to be sequenced to understand the somatic changes underlying cancer. Some recent efforts have made significant gains in both the ability to prepare genomes for sequencing and to sequence large numbers of templates simultaneously. However, these and other efforts are still limited by the relatively large size of the reaction volumes needed to prepare templates that are detectable by these systems, as well as the need for special nucleotide analogues, and complex enzymatic or fluorescent methods to read out the bases.

SUMMARY

Applicants have recognized and appreciated that large arrays of ISFETs may be particularly configured and employed to facilitate DNA sequencing techniques based on monitoring changes in chemical processes relating to DNA synthesis. More generally, Applicants have recognized and appreciated that large arrays of chemically-sensitive FETs may be employed to detect and measure concentrations/levels of a variety of analytes (e.g., hydrogen ions, other ions, non-ionic molecules or compounds, binding events, etc.) in a host of chemical and/or biological processes (chemical reactions, cell cultures, neural activity, nucleic acid sequencing, etc.) in which valuable information may be obtained based on such analyte measurements.

Accordingly, various embodiments of the present disclosure is directed generally to inventive methods and apparatus relating to large scale FET arrays for measuring one or more analytes. In the various embodiments disclosed herein, FET arrays include multiple "chemFETs," or chemically-sensitive field-effect transistors, that act as chemical sensors. An ISFET, as discussed above, is a particular type of chemFET that is configured for ion detection, and ISFETs may be employed in various embodiments disclosed herein. Other types of chemFETs contemplated by the present disclosure include ENFETs, which are configured for sensing of specific enzymes. It should be appreciated, however, that the present disclosure is not limited to ISFETs and ENFETs, but more generally relates to any FET that is configured for some type of chemical sensitivity.

According to yet other embodiments, the present disclosure is directed generally to inventive methods and apparatus relating to the delivery to the above-described large scale chemFET arrays of appropriate chemical samples to evoke corresponding responses. The chemical samples may comprise (liquid) analyte samples in small reaction volumes, to facilitate high speed, high-density determination of chemical (e.g., ion or other constituent) concentration or other measurements on the analyte.

For example, some embodiments are directed to a "very large scale" two-dimensional chemFET sensor array (e.g., greater than 256 k sensors), in which one or more chemFET-containing elements or "pixels" constituting the sensors of such an array are configured to monitor one or more independent chemical reactions or events occurring in proximity to the pixels of the array. In some exemplary implementations, the array may be coupled to one or more microfluidics structures that form one or more reaction chambers, or "wells" or "microwells," over individual sensors or groups of sensors of the array, and apparatus which delivers analyte samples to the wells and removes them from the wells between measurements. Even when microwells are not employed, the sensor array may be coupled to one or more microfluidics structures for the delivery of one or more analytes to the pixels and for removal of analyte(s) between measurements. Accordingly, inventive aspects of this disclosure, which are desired to be protected, include the various microfluidic structures which may be employed to flow reagents/analytes to and from the wells or pixels, the methods of manufacture of the array of wells, methods and structures for coupling the wells with the pixels of the array, and methods and apparatus for loading the wells with DNA-bearing beads when the apparatus is used for DNA sequencing or related analysis.

A unique reference electrode and its coupling to the flow cell are also shown.

In various embodiments, an analyte of particular interest is hydrogen ions, and large scale ISFET arrays according to the present disclosure are specifically configured to measure pH. In other embodiments, the chemical reactions being monitored may relate to DNA synthesis processes, or other chemical and/or biological processes, and chemFET arrays may be specifically configured to measure pH or one or more other analytes that provide relevant information relating to a particular chemical process of interest. In various aspects, the chemFET arrays are fabricated using conventional CMOS processing technologies, and are particularly configured to facilitate the rapid acquisition of data from the entire array (scanning all of the pixels to obtain corresponding pixel output signals).

With respect to analyte detection and measurement, it should be appreciated that in various embodiments discussed in greater detail below, one or more analytes measured by a chemFET array according to the present disclosure may include any of a variety of chemical substances that provide relevant information regarding a chemical process or chemical processes of interest (e.g., binding of multiple nucleic acid strands, binding of an antibody to an antigen, etc.). In some aspects, the ability to measure levels or concentrations of one or more analytes, in addition to merely detecting the presence of an analyte, provides valuable information in connection with the chemical process or processes. In other aspects, mere detection of the presence of an analyte or analytes of interest may provide valuable information.

A chemFET array according to various inventive embodiments of the present disclosure may be configured for sensitivity to any one or more of a variety of analytes/chemical substances. In one embodiment, one or more chemFETs of an array may be particularly configured for sensitivity to one or more analytes representing one or more binding events (e.g., associated with a nucleic acid sequencing process), and in other embodiments different chemFETs of a given array may be configured for sensitivity to different analytes. For example, in one embodiment, one or more sensors (pixels) of the array may include a first type of chemFET configured to be chemically sensitive to a first analyte, and one or more other sensors of the array may include a second type of chemFET configured to be chemically sensitive to a second analyte different from the first analyte. In one exemplary implementation, the first analyte may represent a first binding event associated with a nucleic acid sequencing process, and the second analyte may represent a second binding event associated with the nucleic acid sequencing process. Of course, it should be appreciated that more than two different types of chemFETs may be employed in any given array to detect and/or measure different types of analytes/binding events. In general, it should be appreciated in any of the embodiments of sensor arrays discussed herein that a given sensor array may be "homogeneous" and include chemFETs of substantially similar or identical types to detect and/or measure a same type of analyte (e.g., pH or other ion concentration), or a sensor array may be "heterogeneous" and include chemFETs of different types to detect and/or measure different analytes.

In yet other aspects, Applicants have specifically improved upon the ISFET array design of Milgrew et al. discussed above in connection with FIGS. 1-7, as well as other conventional ISFET array designs, so as to significantly reduce pixel size, and thereby increase the number of pixels of a chemFET array for a given semiconductor die size (i.e., increase pixel density). In various embodiments, this increase in pixel density is accomplished while at the same time increasing the signal-to-noise ratio (SNR) of output signals corresponding to respective measurements relating to monitored chemical processes, and the speed with which such output signals may be read from the array. In particular, Applicants have recognized and appreciated that by relaxing requirements for chemFET linearity and focusing on a more limited measurement output signal range (e.g., output signals corresponding to a pH range of from approximately 7 to 9 rather than 1 to 14), individual pixel complexity and size may be significantly reduced, thereby facilitating the realization of very large scale dense chemFET arrays. Applicants have also recognized and appreciated that alternative less complex approaches to pixel selection in an chemFET array (e.g., alternatives to the row and column decoder approach employed in the design of Milgrew et al. as shown in FIG. 7, whose complexity scales with array size) facilitate rapid acquisition of data from significantly large and dense arrays.

With respect to chemFET array fabrication, Applicants have further recognized and appreciated that various techniques employed in a conventional CMOS fabrication process, as well as various post-fabrication processing steps (wafer handling, cleaning, dicing, packaging, etc.), may in some instances adversely affect performance of the resulting chemFET array. For example, with reference again to FIG. 1, one potential issue relates to trapped charge that may be induced in the gate oxide 65 during etching of metals associated with the floating gate structure 70, and how such trapped charge may affect chemFET threshold voltage $V_{TH}$. Another potential issue relates to the density/porosity of the chemFET passivation layer (e.g., see ISFET passivation layer 72 in FIG. 1) resulting from low-temperature material deposition processes commonly employed in aluminum metal-based CMOS fabrication. While such low-temperature processes generally provide an adequate passivation layer for conventional CMOS devices, they may result in a somewhat low-density and porous passivation layer which may be potentially problematic for chemFETs in contact with an analyte solution; in particular, a low-density porous passivation layer over time may absorb and become saturated with analytes or other substances in the solution, which may in turn cause an undesirable time-varying drift in the chemFETs threshold voltage $V_{TH}$. This phenomenon in turn impedes accurate measurements of one or more particular analytes of interest. In view of the foregoing, other inventive embodiments disclosed herein relate to methods and apparatus which mitigate potentially adverse effects on chemFET performance that may arise from various aspects of fabrication and post-fabrication processing/handling of chemFET arrays.

Accordingly, one embodiment of the present invention is directed to an apparatus, comprising an array of CMOS-fabricated sensors, each sensor comprising one chemically-sensitive field effect transistor (chemFET) and occupying an area on a surface of the array of ten micrometers by ten micrometers or less.

Another embodiment is directed to a sensor array, comprising a two-dimensional array of electronic sensors including at least 512 rows and at least 512 columns of the electronic sensors, each sensor comprising one chemically-sensitive field effect transistor (chemFET) configured to provide at least one output signal representing a presence and/or concentration of an analyte proximate to a surface of the two-dimensional array.

Another embodiment is directed to an apparatus, comprising an array of CMOS-fabricated sensors, each sensor comprising one chemically-sensitive field effect transistor (chemFET). The array of CMOS-fabricated sensors includes more than 256 sensors, and a collection of chemFET output signals from all chemFETs of the array constitutes a frame of data. The apparatus further comprises control circuitry coupled to the array and configured to generate at least one array output signal to provide multiple frames of data from the array at a frame rate of at least 1 frame per second. In one aspect, the frame rate may be at least 10 frames per second. In another aspect, the frame rate may be at least 20 frames per second. In yet other aspects, the frame rate may be at least 30, 40, 50, 70 or up to 100 frames per second.

Another embodiment is directed to an apparatus, comprising an array of CMOS-fabricated sensors, each sensor comprising a chemically-sensitive field effect transistor (chemFET). The chemFET comprises a floating gate structure, and a source and a drain having a first semiconductor type and fabricated in a region having a second semiconductor type, wherein there is no electrical conductor that electrically connects the region having the second semiconductor type to either the source or the drain.

Another embodiment is directed to an apparatus, comprising an array of electronic sensors, each sensor consisting of three field effect transistors (FETs) including one chemically-sensitive field effect transistor (chemFET).

Another embodiment is directed to an apparatus, comprising an array of electronic sensors, each sensor comprising three or fewer field effect transistors (FETs), wherein the three or fewer FETs includes one chemically-sensitive field effect transistor (chemFET).

Another embodiment is directed to an apparatus, comprising an array of electronic sensors, each sensor comprising a plurality of field effect transistors (FETs) including one chemically-sensitive field effect transistor (chemFET), and a plurality of electrical conductors electrically connected to the plurality of FETs, wherein the plurality of FETs are arranged such that the plurality of electrical conductors includes no more than four conductors traversing an area occupied by each sensor and interconnecting multiple sensors of the array.

Another embodiment is directed to an apparatus, comprising an array of CMOS-fabricated sensors, each sensor comprising a plurality of field effect transistors (FETs) including one chemically-sensitive field effect transistor (chemFET), wherein all of the FETs in each sensor are of a same channel type and implemented in a single semiconductor region of an array substrate.

Another embodiment is directed to a sensor array, comprising a plurality of electronic sensors arranged in a plurality of rows and a plurality of columns. Each sensor comprises one chemically-sensitive field effect transistor (chemFET) configured to provide at least one output signal representing a presence and/or a concentration of an analyte proximate to a surface of the array. For each column of the plurality of columns, the array further comprises column circuitry configured to provide a constant drain current and a constant drain-to-source voltage to respective chemFETs in the column, the column circuitry including two operational amplifiers and a diode-connected FET arranged in a Kelvin bridge configuration with the respective chemFETs to provide the constant drain-to-source voltage.

Another embodiment is directed to a sensor array, comprising a plurality of electronic sensors arranged in a plurality of rows and a plurality of columns. Each sensor comprises one chemically-sensitive field effect transistor (chemFET) configured to provide at least one output signal representing a concentration of ions in an analyte proximate to a surface of the array. The array further comprises at least one row select shift register to enable respective rows of the plurality of rows, and at least one column select shift register to acquire chemFET output signals from respective columns of the plurality of columns.

Another embodiment is directed to an apparatus, comprising an array of CMOS-fabricated sensors, each sensor comprising a chemically-sensitive field effect transistor (chemFET). The chemFET comprises a floating gate structure, and a source and a drain having a first semiconductor type and fabricated in a region having a second semiconductor type, wherein there is no electrical conductor that electrically connects the region having the second semiconductor type to either the source or the drain. The array includes a two-dimensional array of at least 512 rows and at least 512 columns of the CMOS-fabricated sensors. Each sensor consists of three field effect transistors (FETs) including the chemFET, and each sensor includes a plurality of electrical conductors electrically connected to the three FETs. The three FETs are arranged such that the plurality of electrical conductors includes no more than four conductors traversing an area occupied by each sensor and interconnecting multiple sensors of the array. All of the FETs in each sensor are of a same channel type and implemented in a single semiconductor region of an array substrate. A collection of chemFET output signals from all chemFETs of the array constitutes a frame of data. The apparatus further comprises control circuitry coupled to the array and configured to generate at least one array output signal to provide multiple frames of data from the array at a frame rate of at least 20 frames per second.

Another embodiment is directed to a method for processing an array of CMOS-fabricated sensors, each sensor comprising a chemically-sensitive field effect transistor (chemFET). The method comprises: A) dicing a semiconductor wafer including the array to form at least one diced portion including the array; and B) performing a forming gas anneal on the at least one diced portion.

Another embodiment is directed to a method for processing an array of CMOS-fabricated sensors. Each sensor comprises a chemically-sensitive field effect transistor (chemFET) having a chemically-sensitive passivation layer of silicon nitride and/or silicon oxynitride deposited via plasma enhanced chemical vapor deposition (PECVD). The method comprises depositing at least one additional passivation material on the chemically-sensitive passivation layer so as to reduce a porosity and/or increase a density of the passivation layer.

In another aspect, the invention provides a method for sequencing a nucleic acid comprising disposing a plurality of template nucleic acids into a plurality of reaction chambers, wherein the plurality of reaction chambers is in contact with a chemical-sensitive field effect transistor (chemFET) array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, detecting the incorporation of the one or more known nucleotide triphosphates by a change in current at the at least one chemFET. The array may be comprised of at least two, at least three, at least four, at least five, at least six, at least seven, at least eight, at least nine, at least ten, at least 100, at least 500, at least 1000, at least $10^4$, at least $10^5$, at least $10^6$, at least $10^7$, or more chemFET (or chemFET sensors, or sensors, as the terms are used interchangeably herein).

In another aspect, the invention provides a method for sequencing a nucleic acid comprising disposing a plurality of template nucleic acids into a plurality of reaction chambers, wherein the plurality of reaction chambers is in contact with a chemical-sensitive field effect transistor (chemFET) array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, detecting the incorporation of the one or more known nucleotide triphosphates by a change in current at the at least one chemFET, wherein the chemFET array is any of the foregoing arrays.

In another aspect, the invention provides a method for sequencing a nucleic acid comprising disposing a plurality of template nucleic acids into a plurality of reaction chambers, wherein the plurality of reaction chambers is in contact with a chemical-sensitive field effect transistor (chemFET) array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, and detecting the incorporation of the one or more known nucleotide triphosphates by a change in current at the at least one chemFET within the array, wherein a center-to-center distance between adjacent reaction chambers is 1-10 μm.

In another aspect, the invention provides a method for sequencing a nucleic acid comprising disposing a plurality of template nucleic acids into a plurality of reaction chambers, wherein the plurality of reaction chambers is in contact with a chemical-sensitive field effect transistor (chemFET) array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, detecting the incorporation of the one or more known nucleotide triphosphates by the generation of sequencing reaction byproduct, wherein (a) the chemFET array comprises more than 256 sensors, or (b) a center-to-center distance between adjacent reaction chambers (or "pitch") is 1-10 μm.

In yet another aspect, the invention provides a method for sequencing a nucleic acid comprising fragmenting a target nucleic acid to generate a plurality of fragmented nucleic acids, attaching each of the plurality of fragmented nucleic acids to individual beads to generate a plurality of beads each attached to a single fragmented nucleic acid, amplifying the number of fragmented nucleic acids on each bead, delivering the plurality of beads attached to amplified fragmented nucleic acids to a chemical-sensitive field effect transistor (chemFET) array having a separate reaction chamber for each sensor in the array, wherein only one bead is situated in each reaction chamber, and performing a sequencing reaction simultaneously in the plurality of reaction chambers.

In still another aspect, the invention provides a method for sequencing nucleic acids comprising fragmenting a target nucleic acid to generate a plurality of fragmented nucleic acids, amplifying each fragmented nucleic acid separately in the presence of a bead and binding amplified copies of the fragmented nucleic acid to the bead, thereby producing a plurality of beads each having attached multiple identical copies of a fragmented nucleic acid, delivering the plurality of beads each having attached multiple identical copies of a fragmented nucleic acid to a chemical-sensitive field effect transistor (chemFET) array having a separate reaction chamber for each chemFET sensor in the array, wherein only one bead is situated in each reaction chamber, and performing a sequencing reaction simultaneously in the plurality of reaction chambers.

In another aspect, the invention provides a method for sequencing a nucleic acid comprising disposing a plurality of template nucleic acids into a plurality of reaction chambers, wherein the plurality of reaction chambers is in contact with an chemical-sensitive field effect transistor (chemFET) array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, and detecting a change in the level of a sequencing byproduct as an indicator of incorporation of the one or more known nucleotide triphosphates.

The change in the level may an increase or a decrease in a level relative to that level prior to incorporation of the one or more known nucleotide triphosphates. The change in the level may be read as a change in current at a chemFET sensor or a change in pH, but it is not so limited.

In one embodiment, the sequencing byproduct is inorganic pyrophosphate (PPi). In a related embodiment, PPi is detected by binding to a PPi receptor on the surface of one or more chemFET sensors in the array.

Various embodiments apply equally to the methods disclosed herein and they are recited once for brevity. In some embodiments, the center-to-center distance between adjacent reaction chambers is about 2-9 μm, about 2 μm, about 5 μm, or about 9 μm. In some embodiments, the chemFET array comprises more than 256 sensors (and optionally more than 256 corresponding reaction chambers (or wells), more than $10^3$ sensors (and optionally more than $10^3$ corresponding reaction chambers), more than $10^4$ sensors (and optionally more than $10^4$ corresponding reaction chambers), more than $10^5$ sensors (and optionally more than $10^5$ corresponding reaction chambers), or more than $10^6$ sensors (and optionally more than $10^6$ corresponding reaction chambers). In some embodiments, the chemFET array comprises at least 512 rows and at least 512 columns of sensors.

In some embodiments, the sequencing reaction byproduct is inorganic pyrophosphate (PPi). In some embodiments, PPi is measured directly. In some embodiments, the PPi is measured in the absence of a PPi receptor. In some embodiments, the sequencing reaction byproduct is hydrogen ions. In some embodiments, the sequencing reaction byproduct is inorganic phosphate (Pi). In still other embodiments, the chemFET detects changes in any combination of the byproducts, optionally in combination with other parameters, as described herein.

In another aspect, the invention provides a method for sequencing a nucleic acid comprising disposing a plurality of template nucleic acids into a plurality of reaction chambers, wherein the plurality of reaction chambers is in contact with an chemical-sensitive field effect transistor (chemFET) array comprising at least one chemFET for each reaction chamber, and wherein each of the template nucleic acids is hybridized to a sequencing primer and is bound to a polymerase, synthesizing a new nucleic acid strand by incorporating one or more known nucleotide triphosphates sequentially at the 3' end of the sequencing primer, directly detecting release of inorganic pyrophosphate (PPi) as an indicator of incorporation of the one or more known nucleotide triphosphates.

In some embodiments, the PPi is directly detected by binding to a PPi receptor immobilized on the chemFET. In some embodiments, the PPi is directly detected by the chemFET in the absence of a PPi receptor.

In another aspect, the invention provides a method for sequencing nucleic acids comprising fragmenting a template nucleic acid to generate a plurality of fragmented nucleic acids, attaching one strand from each of the plurality of fragmented nucleic acids individually to beads to generate a plurality of beads each having a single stranded fragmented nucleic acid attached thereto, delivering the plurality of beads having a single stranded fragmented nucleic acid attached thereto to a chemFET array having a separate reaction chamber for each sensor in the area, and wherein only one bead is situated in each reaction chamber, and performing a sequencing reaction simultaneously in the plurality of chambers.

In another aspect, the invention provides an apparatus comprising a chemical-sensitive field effect transistor (chemFET) having disposed on its surface a PPi receptor.

In still another aspect, the invention provides an apparatus comprising a chemical-sensitive field effect transistor (chemFET) array comprising a plurality of chemFET sensors each having a PPi receptor disposed on its surface, wherein the plurality is a subset of the chemFET sensors in the array. In a related embodiment, the array comprises at least three chemFET sensors. The subset may represent 10%, 25%, 33%, 50%, 75% or more of the sensors in the array.

In some embodiments, the PPi selective receptor is Compound 1, Compound 2, Compound 3, Compound 4, Compound 5, Compound 6, Compound 7, Compound 8, Compound 9 or Compound 10 as shown in FIG. 11B. In some embodiments, the chemFET is present in an array of chemFETs, each of which has disposed on its surface a PPi selective receptor. In some embodiments, the identical PPi selective receptors are disposed on each chemFET of the array. In some embodiments, the array comprises more than 256 sensors. In some embodiments, the array comprises at least 512 rows and at least 512 columns of sensors. In some embodiments, the chemFET is located at a bottom of a reaction chamber.

In another aspect, the invention provides an apparatus comprising a chemical-sensitive field effect transistor (chemFET) array having disposed on its surface a biological array.

The biological array may be a nucleic acid array, a protein array including but not limited to an enzyme array, an antibody array and an antibody fragment array, a cell array, and the like. The chemical array may be an organic small molecule array, or an inorganic molecule array, but it is not so limited. The chemFET array may comprise at least 5, 10, $10^2$, $10^3$, $10^4$, $10^5$, $10^6$ or more sensors. The biological or chemical array may be arranged into a plurality of "cells" or spatially defined regions and each of these regions is situated over a different sensor in the chemFET array, in some embodiments.

In yet another aspect, the invention provides a method for detecting a nucleic acid comprising contacting a nucleic acid array disposed on a chemFET array with a sample, and detecting binding of a nucleic acid from the sample to one or more regions on the nucleic acid array.

In another aspect, the invention provides a method for detecting a protein comprising contacting a protein array disposed on a chemFET array with a sample, and detecting binding of a protein from the sample to one or more regions on the protein array.

In yet another aspect, the invention provides a method for detecting a nucleic acid comprising contacting a protein array disposed on a chemFET array with a sample, and detecting binding of a nucleic acid from the sample to one or more regions on the protein array.

In another aspect, the invention provides a method for detecting an antigen comprising contacting an antibody array disposed on a chemFET array with a sample, and detecting binding of a antigen from the sample to one or more regions on the antibody array.

In another aspect, the invention provides a method for detecting an enzyme substrate or inhibitor comprising contacting an enzyme array disposed on a chemFET array with a sample, and detecting binding of an entity from the sample to one or more regions on the enzyme array.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead being placed upon generally illustrating the various concepts discussed herein.

FIG. 5 is a diagram similar to FIG. 1, illustrating a wider cross-section of a portion of a substrate corresponding to one pixel of the array column shown in FIG. 3, in which the ISFET is shown alongside two n-channel MOSFETs also included in the pixel.

FIG. 6 is a diagram similar to FIG. 5, illustrating a cross-section of another portion of the substrate corresponding to one pixel of the array column shown in FIG. 3, in which the ISFET is shown alongside the p-channel MOSFET of the transmission gate shown in FIG. 4.

FIG. 11B provides the chemical structures of ten PPi receptors (compounds 1 through 10).

FIG. 11C is a schematic of a synthesis protocol for compound 4 from FIG. 11 B.

FIG. 11D is a schematic illustrating a variety of chemistries that can be applied to the passivation layer in order to bind molecular recognition compounds (such as but not limited to PPi receptors).

FIG. 20A illustrates a top view of a chip layout design for a pixel of the chemFET array shown in FIG. 20, according to another inventive embodiment of the present disclosure.

FIGS. 59A-59C are illustrations of the pieces for two examples of two-piece injection molded parts for forming a flow cell.

FIG. 71A is a screen capture showing pixels with signal occurring after dATP was added (first) resulting in a 4 base extension in template 4 (see Tables 1 and 2) (left panel) and a plot of voltage versus frame (or time) for the arrowed pixels (right panel).

FIG. 71B is a screen capture showing pixels with signal occurring after dCTP was added next resulting in a 4 base extension in template 1 (see Tables 1, 2) (left panel) and a plot of voltage versus frame (or time) for the arrowed pixels (right panel).

FIG. 71C is a screen capture showing pixels with signal occurring after dGTP was added next resulting in extension of templates 1, 2 and 4 (see Tables 1, 2) (left panel) and a plot of voltage versus frame (or time) for the arrowed pixels (right panel).

FIG. 71D is a screen capture showing pixels with signal occurring after dTTP was added and run-off occurred (due the presence of all 4 dNTP) in all 4 templates (see Tables 1, 2) (left panel) and a plot of voltage versus frame (or time) for the arrowed pixels (right panel).

DETAILED DESCRIPTION

Figure 1:
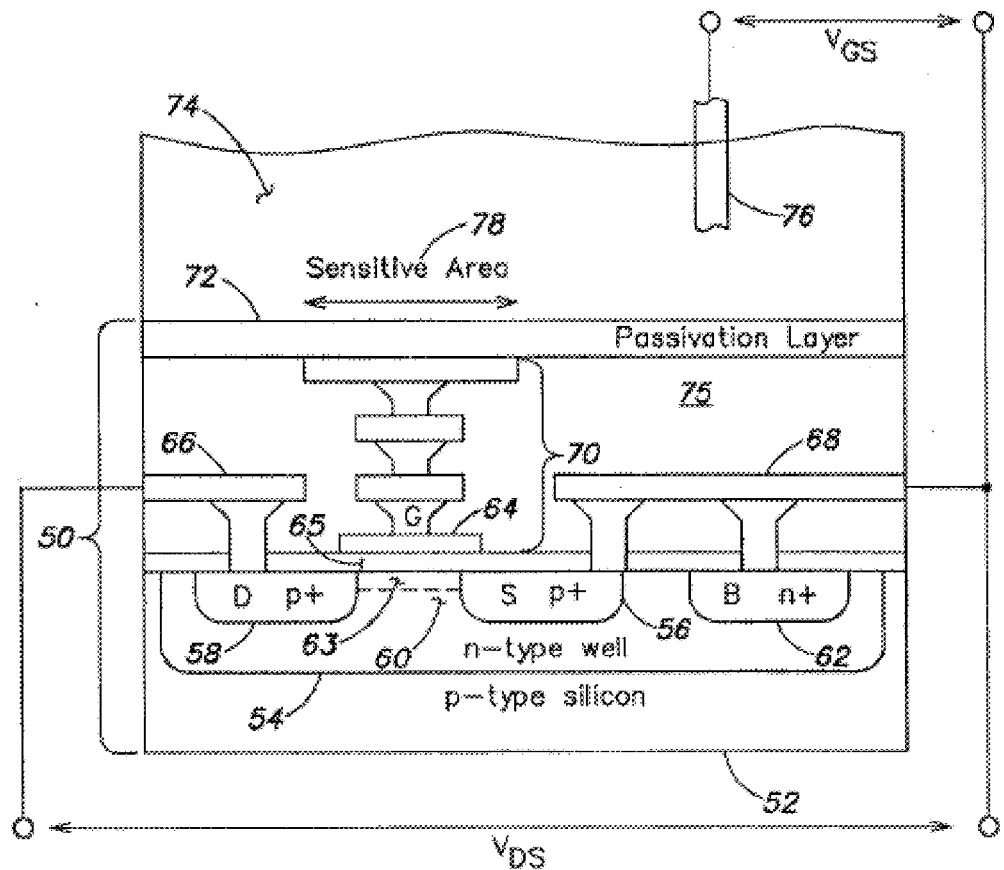
FIG. 1 illustrates a cross-section of a p-type (p-channel) ion-sensitive field effect transistor (ISFET) fabricated using a conventional CMOS process.
Figure 2:
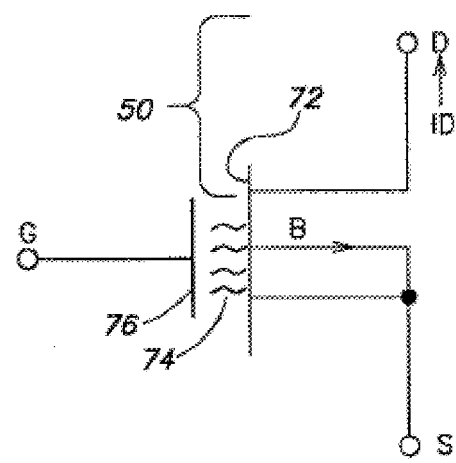
FIG. 2 illustrates an electric circuit representation of the p-channel ISFET shown in FIG. 1.

Following below are more detailed descriptions of various concepts related to, and embodiments of, inventive methods and apparatus relating to large scale chemFET arrays for analyte measurements. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Various inventive embodiments according to the present disclosure are directed at least in part to a semiconductor-based/microfluidic hybrid system that combines the power of microelectronics with the biocompatibility of a microfluidic system. In some examples below, the microelectronics portion of the hybrid system is implemented in CMOS technology for purposes of illustration. It should be appreciated, however, that the disclosure is not intended to be limiting in this respect, as other semiconductor-based technologies may be utilized to implement various aspects of the microelectronics portion of the systems discussed herein.

One embodiment disclosed herein is directed to a large sensor array (e.g., a two-dimensional array) of chemically-sensitive field effect transistors (chemFETs), wherein the individual chemFET sensor elements or "pixels" of the array are configured to detect analyte concentration changes in a host of chemical and/or biological processes (chemical reactions, cell cultures, neural activity, nucleic acid sequencing processes, etc.) occurring in proximity to the array. Examples of chemFETs contemplated by various embodiments discussed in greater detail below include, but are not limited to, ion-sensitive field effect transistors (ISFETs) and enzyme-sensitive field effect transistors (ENFETs). In one exemplary implementation, one or more microfluidic structures is/are fabricated above the chemFET sensor array to provide for containment and/or confinement of a chemical reaction in which an analyte of interest may be produced. For example, in one implementation, the microfluidic structure(s) may be configured as one or more "wells" (e.g., small reaction chambers) disposed above one or more sensors of the array, such that the one or more sensors over which a given well is disposed detect and measure analyte concentration in the given well.

In some embodiments, such a chemFET array/microfluidics hybrid structure may be used to analyze solution(s)/material(s) of interest containing nucleic acids. For example, such structures may be employed to process nucleic acids in a multitude of ways that utilize sequencing of nucleic acids. In various aspects, such sequencing can be performed to determine the identity of a sequence of nucleic acids, for single nucleotide polymorphism detection in nucleic acid fragments, for nucleic acid expression profiling (comparing the nucleic acid expression profile between two or more states—e.g., comparing between diseased and normal tissue or comparing between untreated tissue and tissue treated with drug, enzymes, radiation or chemical treatment), for haplotyping (comparing genes or variations in genes on each of the two alleles present in a human subject), for karyotyping (diagnostically comparing one or more genes in a test tissue—typically from an embryo/fetus prior to conception to detect birth defects—with the same genes from "normal" karyotyped subjects), and for genotyping (comparing one or more genes in a first individual of a species with the same genes in other individuals of the same species). It should be appreciated, however, that while some illustrative examples of the concepts disclosed herein are applied in the context of nucleic acid processing, application of the concepts disclosed herein relating to chemFET sensor arrays is not limited to these examples.

Figure 8:
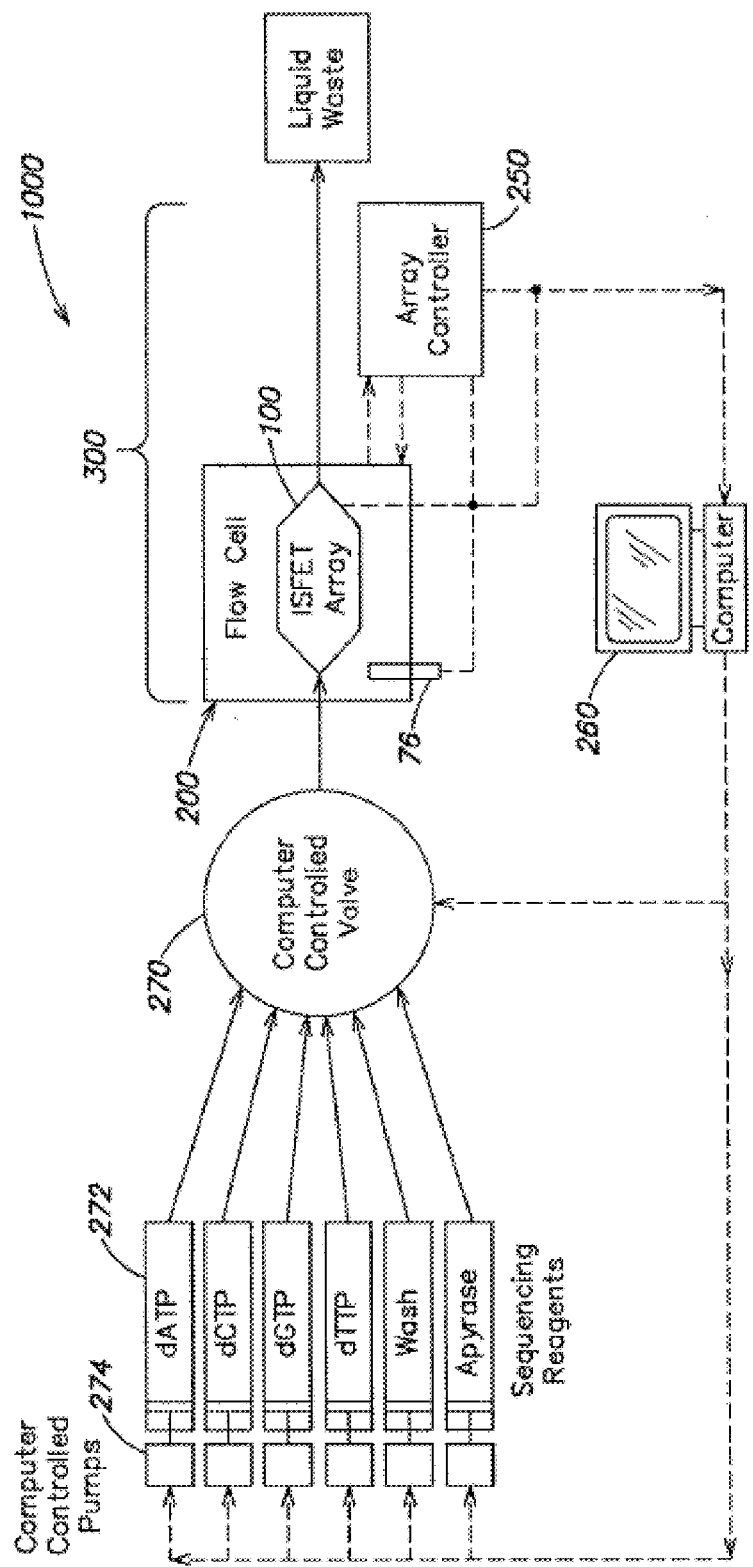
FIG. 8 generally illustrates a nucleic acid processing system comprising a large scale chemFET array, according to one inventive embodiment of the present disclosure.

FIG. 8 generally illustrates a nucleic acid processing system 1000 comprising a large scale chemFET array, according to one inventive embodiment of the present disclosure. In the discussion that follows, the chemFET sensors of the array are described for purposes of illustration as ISFETs configured for sensitivity to hydrogen ion concentration. However, it should be appreciated that the present disclosure is not limited in this respect, and that in any of the embodiments discussed herein in which ISFETs are employed as an illustrative example, other types of chemFETs may be similarly employed in alternative embodiments, as discussed in further detail below. In one aspect, the system 1000 includes a semiconductor/microfluidics hybrid structure 300 comprising an ISFET sensor array 100 and a microfluidics flow cell 200. In another aspect, the flow cell 200 is configured to facilitate the sequencing of a nucleic acid template disposed in the flow cell via the controlled admission to the flow cell of a number of sequencing reagents 272 (e.g., bases dATP, dCTP, dGTP, dTTP and other reagents). As illustrated in FIG. 8, the admission of the sequencing reagents to the flow cell 200 may be accomplished via one or more valves 270 and one or more pumps 274 that are controlled by computer 260.

In the system 1000 of FIG. 8, according to one embodiment the ISFET sensor array 100 monitors pH changes occurring in different portions of the flow cell 200 due to chemical reactions between one or more of the bases constituting the sequencing reagents 272 and the nucleic acid template. In other embodiments discussed in greater detail below, the FET sensor array may be particularly configured for sensitivity to other analytes that may provide relevant information about the chemical reactions of interest. Via an array controller 250 (also under operation of the computer 260), the ISFET array may be controlled so as to acquire data relating to analyte measurements, and collected data may be processed by the computer 260 to yield meaningful information associated with the processing of the nucleic acid template. For example, in one implementation, pH change generally is proportional to the number of a particular type of base (e.g., one of dATP, dCTP, dGTP, dTTP) added to the nucleic acid template. Such a pH change may be represented by a change in output voltage of one or more ISFETs of the array 100 in proximity to the reaction(s) between a given type of base and the template. Thus, the magnitude of the voltage change in an output signal of a given pixel of the array may be used to determine the number of bases of a particular type added to the template disposed in the flow cell above the given pixel.

In one aspect, the flow cell 200 of the system 1000 shown in FIG. 8 may comprise a number of wells (not shown in FIG. 8) disposed above corresponding sensors of the ISFET array 100. A number of techniques may be used to admit the various processing materials to the wells of such a flow cell. For example, the flow cell first may be loaded with a nucleic acid template to be sequenced by centrifuging into the wells "beads" containing the nucleic acid template; alternatively, such beads may enter the wells by gravity. In another example, instead of employing beads, the wells can be coated with a set of primer pairs, and the nucleic acid template provided to the flow cell with adapters that complement the primer pairs (immobilization materials can be added to the sensor array 100, or to individual dies as part of the chip packaging, or immediately before the processing of the nucleic acid). Other methods involving solgels may be used to immobilize a nucleic acid template near the surface of the ISFET array 100.

Once a nucleic acid template is loaded into respective wells of the flow cell 200, bridge amplification can then be performed in the wells, the product denatured, and sequencing by synthesis or ligation then performed. Other methods of amplification in the wells (with the products captured in the wells) are envisioned, including rolling circle amplification, or other strategies using isothermal or non-isothermal amplification techniques such as PCR. As illustrated in FIG. 8, reagents including bases may be admitted to the flow cell (e.g., via the computer controlled valve 270 and pumps 274) and diffuse into the wells, or reagents may be added to the flow cell by other means such as an ink jet. In yet another example, the flow cell 200 may not contain any wells, and diffusion properties of the reagents may be exploited to limit cross-talk between respective sensors of the ISFET array 100.

In sum, the flow cell 200 in the system of FIG. 8 may be configured in a variety of manners to provide one or more analytes in proximity to the ISFET array 100; for example, a nucleic acid template (DNA) may be directly attached or applied in suitable proximity to one or more pixels of the sensor array 100, or on a support material (e.g., one or more "beads") located above the sensor array. Processing reagents (e.g., enzymes) can also be placed on the sensors directly, or on one or more solid supports in proximity to the array, and the device used without wells or beads for a number of biosensor applications where the enzymes result in a sensor-detectable product (e.g., ion concentration change).

With respect to the ISFET array 100 of the system 1000 shown in FIG. 8, in one embodiment the array 100 is implemented as an integrated circuit designed and fabricated using standard CMOS processes (e.g., 0.35 micrometer process, 0.18 micrometer process), comprising all the sensors and electronics needed to monitor/measure one or more analytes. With reference again to FIG. 1, one or more reference electrodes 76 to be employed in connection with the ISFET array 100 may be placed in the flow cell 200 (e.g., disposed in "unused" wells of the flow cell) or otherwise exposed to a reference (e.g., one or more of the sequencing reagents 172) to establish a base line against which changes in analyte concentration proximate to respective ISFETs of the array 100 are compared. The reference electrode(s) 76 may be electrically coupled to the array 100, the array controller 250 or directly to the computer 260 to facilitate analyte measurements based on voltage signals obtained from the array 100; in some implementations, the reference electrode(s) may be coupled to an electric ground or other predetermined potential, or the reference electrode voltage may be measured with respect to ground, to establish an electric reference for ISFET output signal measurements, as discussed further below.

The ISFET array 100 is not limited to any particular size, as one- or two-dimensional arrays, including as few as two to 256 pixels (e.g., 16 by 16 pixels in a two-dimensional implementation) or as many as 54 mega-pixels (e.g., 7400 by 7400 pixels in a two-dimensional implementation) or even greater may be fabricated and employed for various chemical/biological analysis purposes pursuant to the concepts disclosed herein. In one embodiment of the exemplary system shown in FIG. 8, the individual ISFET sensors of the array may be configured for sensitivity to hydrogen ions; however, it should also be appreciated that the present disclosure is not limited in this respect, as individual sensors of an ISFET sensor array may be particularly configured for sensitivity to other types of ion concentrations for a variety of applications (materials sensitive to other ions such as sodium, silver, iron, bromine, iodine, calcium, and nitrate, for example, are known).

More generally, a chemFET array according to various embodiments of the present disclosure may be configured for sensitivity to any one or more of a variety of analytes/chemical substances. In one embodiment, one or more chemFETs of an array may be particularly configured for sensitivity to one or more analytes representing one or more binding events (e.g., associated with a nucleic acid sequencing process), and in other embodiments different chemFETs of a given array may be configured for sensitivity to different analytes. For example, in one embodiment, one or more sensors (pixels) of the array may include a first type of chemFET configured to be chemically sensitive to a first analyte, and one or more other sensors of the array may include a second type of chemFET configured to be chemically sensitive to a second analyte different from the first analyte. In one exemplary implementation, the first analyte may represent a first binding event associated with a nucleic acid sequencing process, and the second analyte may represent a second binding event associated with the nucleic acid sequencing process. Of course, it should be appreciated that more than two different types of chemFETs may be employed in any given array to detect and/or measure different types of analytes/binding events. In general, it should be appreciated in any of the embodiments of sensor arrays discussed herein that a given sensor array may be "homogeneous" and include chemFETs of substantially similar or identical types to detect and/or measure a same type of analyte (e.g., pH or other ion concentration), or a sensor array may be "heterogeneous" and include chemFETs of different types to detect and/or measure different analytes. For simplicity of discussion, again the example of an ISFET is discussed below in various embodiments of sensor arrays, but the present disclosure is not limited in this respect, and several other options for analyte sensitivity are discussed in further detail below (e.g., in connection with FIG. 11A).

In exemplary implementations based on 0.35 micrometer CMOS processing techniques (or CMOS processing techniques capable of smaller feature sizes), each pixel of the ISFET array 100 may include an ISFET and accompanying enable/select components, and may occupy an area on a surface of the array of approximately ten micrometers by ten micrometers (i.e., 100 micrometers$^2$) or less; stated differently, arrays having a pitch (pixel-to-pixel spacing) on the order of 10 micrometers or less may be realized. An array pitch on the order of 10 micrometers or less using a 0.35 micrometer CMOS processing technique constitutes a significant improvement in terms of size reduction with respect to prior attempts to fabricate ISFET arrays, which resulted in pixel sizes on the order of at least 12 micrometers or greater.

More specifically, in some embodiments discussed further below based on the inventive concepts disclosed herein, an array pitch of approximately nine (9) micrometers allows an ISFET array including over 256,000 pixels (i.e., a 512 by 512 array), together with associated row and column select and bias/readout electronics, to be fabricated on a 7 millimeter by 7 millimeter semiconductor die, and a similar sensor array including over four million pixels (i.e., a 2048 by 2048 array, over 4 Mega-pixels) to be fabricated on a 21 millimeter by 21 millimeter die. In other examples, an array pitch of approximately 5 micrometers allows an ISFET array including approximately 1.55 Mega-pixels (i.e., a 1348 by 1152 array) and associated electronics to be fabricated on a 9 millimeter by 9 millimeter die, and an ISFET sensor array including over 14 Mega-pixels and associated electronics on a 22 millimeter by 20 millimeter die. In yet other implementations, using a CMOS fabrication process in which feature sizes of less than 0.35 micrometers are possible (e.g., 0.18 micrometer CMOS processing techniques), ISFET sensor arrays with a pitch significantly below 5 micrometers may be fabricated (e.g., array pitch of 2.6 micrometers or pixel area of less than 8 or 9 micrometers$^2$), providing for significantly dense ISFET arrays. Of course, it should be appreciated that pixel sizes greater than 10 micrometers (e.g., on the order of approximately 20, 50, 100 micrometers or greater) may be implemented in various embodiments of chemFET arrays according to the present disclosure.

In other aspects of the system shown in FIG. 8, one or more array controllers 250 may be employed to operate the ISFET array 100 (e.g., selecting/enabling respective pixels of the array to obtain output signals representing analyte measurements). In various implementations, one or more components constituting one or more array controllers may be implemented together with pixel elements of the arrays themselves, on the same integrated circuit (IC) chip as the array but in a different portion of the IC chip, or off-chip. In connection with array control, analog-to-digital conversion of ISFET output signals may be performed by circuitry implemented on the same integrated circuit chip as the ISFET array, but located outside of the sensor array region (locating the analog to digital conversion circuitry outside of the sensor array region allows for smaller pitch and hence a larger number of sensors, as well as reduced noise). In various exemplary implementations discussed further below, analog-to-digital conversion can be 4-bit, 8-bit, 12-bit, 16-bit or other bit resolutions depending on the signal dynamic range required.

Having provided a general overview of the role of a chemFET (e.g., ISFET) array 100 in an exemplary system 1000 for measuring one or more analytes in connection with nucleic acid processing, following below are more detailed descriptions of exemplary chemFET arrays according to various inventive embodiments of the present disclosure that may be employed in a variety of applications including, but not limited to, nucleic acid processing. Again, for purposes of illustration, chemFET arrays according to the present disclosure are discussed below using the particular example of an ISFET array, but other types of chemFETs may be employed in alternative embodiments.

An noted above, various inventive embodiments disclosed herein specifically improve upon the ISFET array design of Milgrew et al. discussed above in connection with FIGS. 1-7, as well as other prior ISFET array designs, so as to significantly reduce pixel size and array pitch, and thereby increase the number of pixels of an ISFET array for a given semiconductor die size (i.e., increase pixel density). In some implementations, an increase in pixel density is accomplished while at the same time increasing the signal-to-noise ratio (SNR) of output signals corresponding to respective measurements relating to one or more chemical properties of one or more analytes and the speed with which such output signals may be read from the array. In particular, Applicants have recognized and appreciated that by relaxing requirements for ISFET linearity and focusing on a more limited signal output/measurement range (e.g., signal outputs corresponding to a pH range of from approximately 7 to 9 rather than 1 to 14), individual pixel complexity and size may be significantly reduced, thereby facilitating the realization of very large scale dense ISFET arrays.

Figure 9:
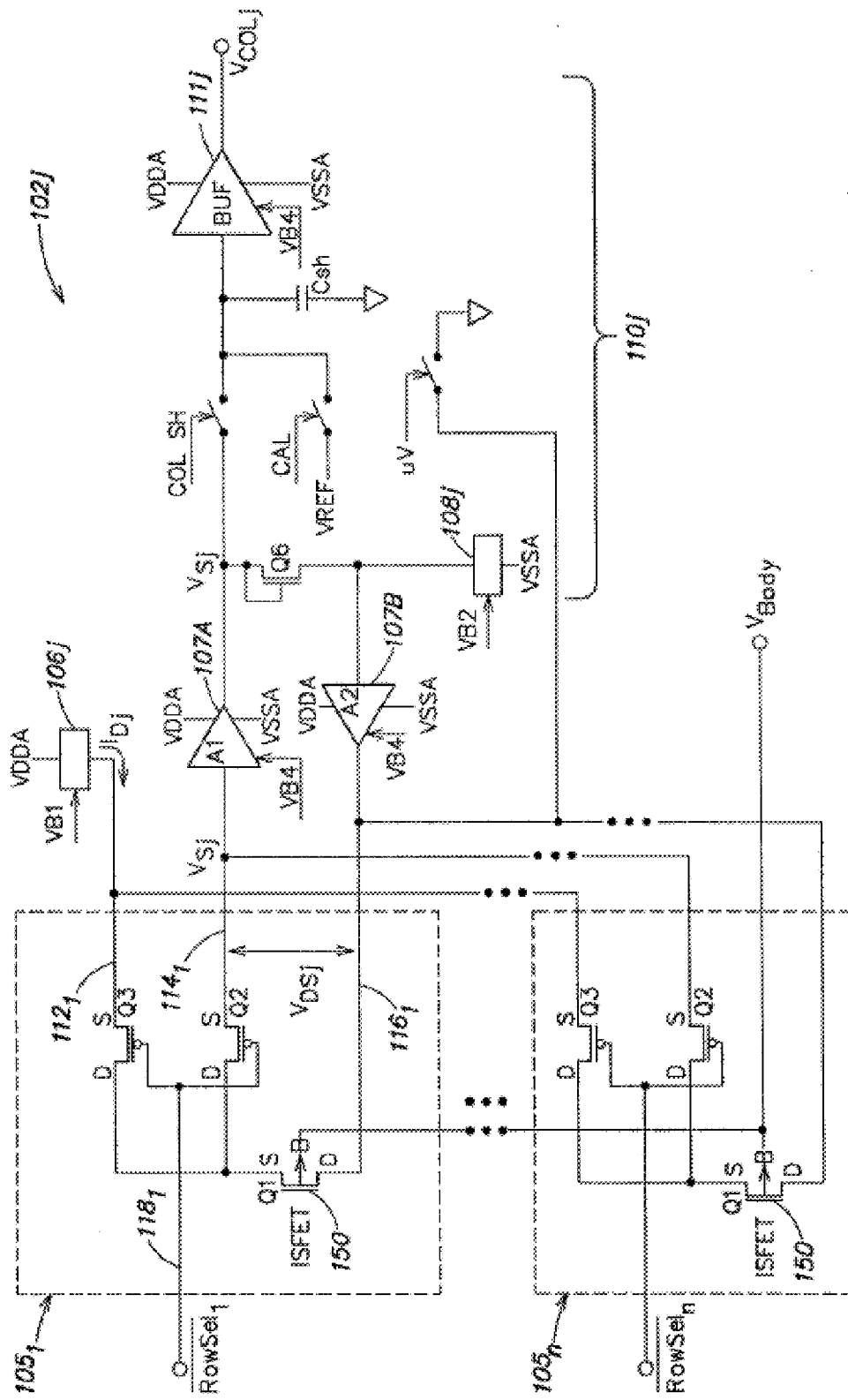
FIG. 9 illustrates one column of an chemFET array similar to that shown in FIG. 8, according to one inventive embodiment of the present disclosure.

To this end, FIG. 9 illustrates one column 102 of an ISFET array 100, according to one inventive embodiment of the present disclosure, in which ISFET pixel design is appreciably simplified to facilitate small pixel size. The column $102_j$ includes n pixels, the first and last of which are shown in FIG. 9 as the pixels $105_1$ and $105_n$. As discussed further below in connection with FIG. 13, a complete two-dimensional ISFET array 100 based on the column design shown in FIG. 9 includes m such columns $102_j$ (j=1, 2, 3, ... m) with successive columns of pixels generally arranged side by side.

In one aspect of the embodiment shown in FIG. 9, each pixel $105_1$ through $105_n$ of the column $102_j$ includes only three components, namely, an ISFET 150 (also labeled as Q1) and two MOSFET switches Q2 and Q3. The MOSFET switches Q2 and Q3 are both responsive to one of n row select signals ($\overline{RowSel}_1$ through $\overline{RowSel}_n$, logic low active) so as to enable or select a given pixel of the column $102_j$. Using pixel $105_1$ as an example that applies to all pixels of the column, the transistor switch Q3 couples a controllable current source $106_j$ via the line $112_1$ to the source of the ISFET 150 upon receipt of the corresponding row select signal via the line $118_1$. The transistor switch Q2 couples the source of the ISFET 150 to column bias/readout circuitry $110_j$ via the line $114_1$ upon receipt of the corresponding row select signal. The drain of the ISFET 150 is directly coupled via the line $116_1$ to the bias/readout circuitry $110_j$. Thus, only four signal lines per pixel, namely the lines $112_1$, $114_1$, $116_1$ and $118_1$, are required to operate the three components of the pixel $105_1$. In an array of m columns, a given row select signal is applied simultaneously to one pixel of each column (e.g., at same positions in respective columns).

Figure 3:
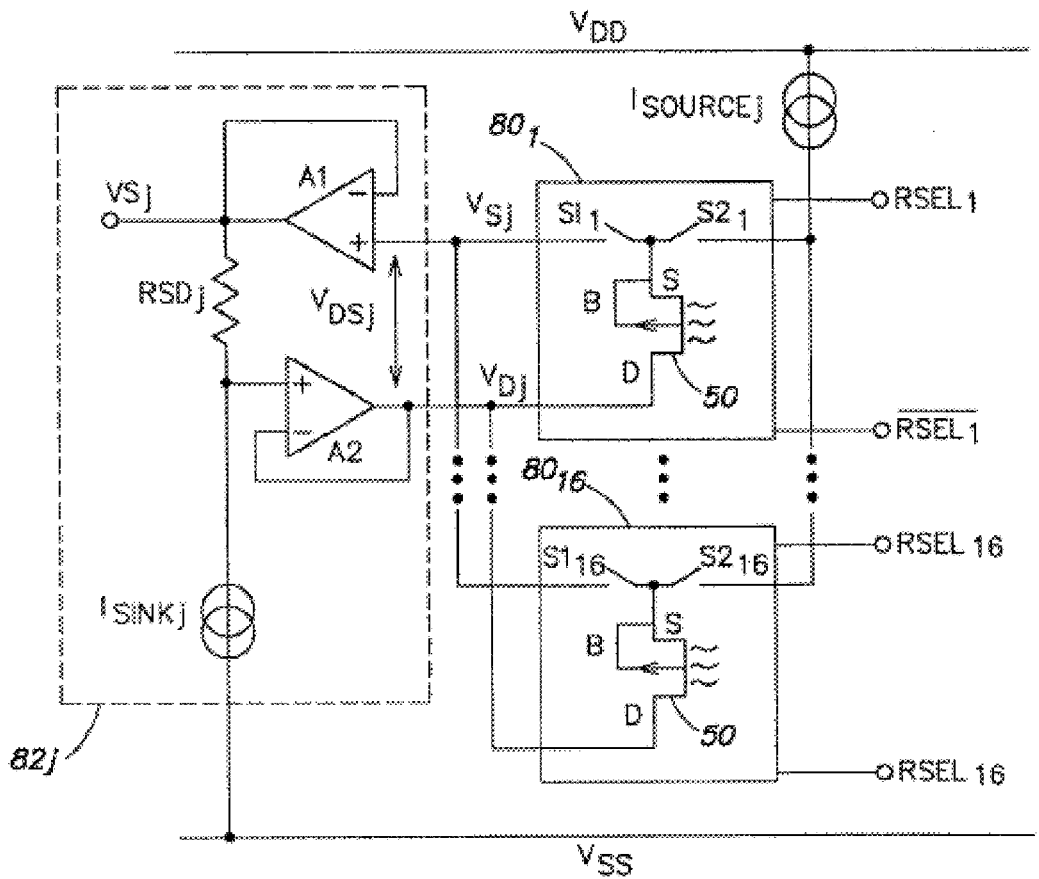
FIG. 3 illustrates one column of a two-dimensional ISFET array based on the ISFET shown in FIG. 1.
Figure 4:
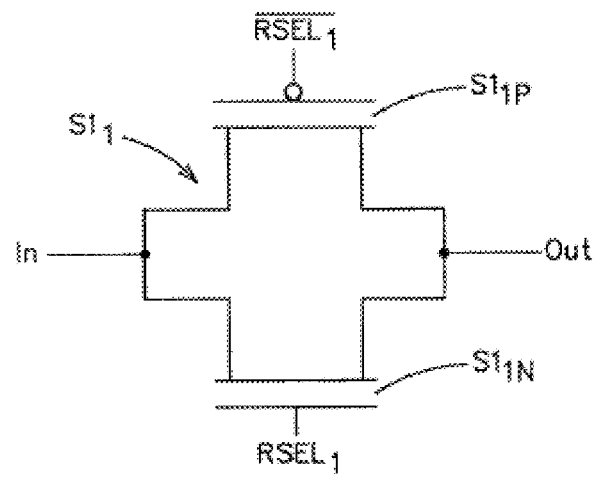
FIG. 4 illustrates a transmission gate including a p-channel MOSFET and an n-channel MOSFET that is employed in each pixel of the array column shown in FIG. 3.
Figure 7:
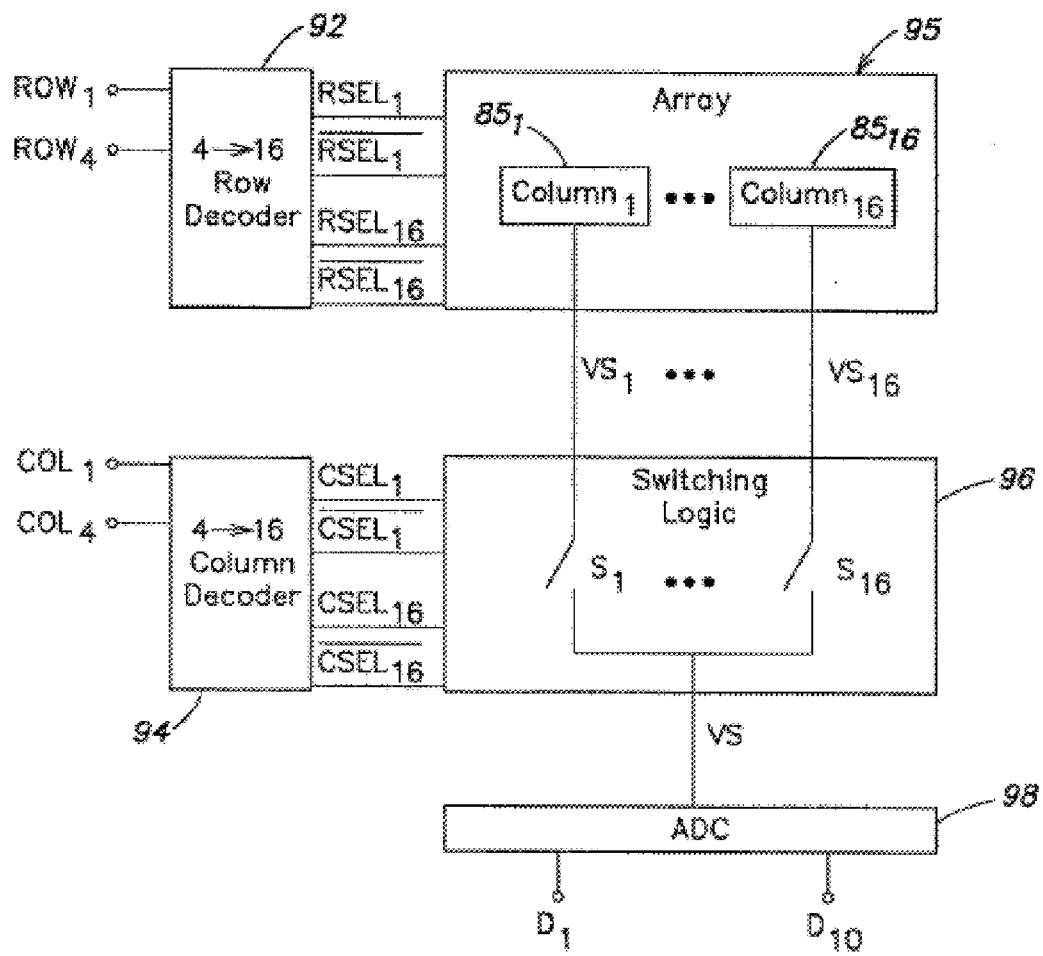
FIG. 7 illustrates an example of a complete two-dimensional ISFET pixel array based on the column design of FIG. 3, together with accompanying row and column decoder circuitry and measurement readout circuitry.

As illustrated in FIG. 9, the design for the column $102_j$ according to one embodiment is based on general principles similar to those discussed above in connection with the column design of Milgrew et al. shown FIG. 3. In particular, the ISFET of each pixel, when enabled, is configured with a constant drain current $I_{Dj}$ and a constant drain-to-source voltage $V_{DSj}$ to obtain an output signal $V_{Sj}$ from an enabled pixel according to Eq. (3) above. To this end, the column $102_j$ includes a controllable current source $106_j$, coupled to an analog circuitry positive supply voltage VDDA and responsive to a bias voltage VB1, that is shared by all pixels of the column to provide a constant drain current $I_{Dj}$ to the ISFET of an enabled pixel. In one aspect, the current source $106_j$ is implemented as a current mirror including two long-channel length and high output impedance MOSFETs. The column also includes bias/readout circuitry $110_j$ that is also shared by all pixels of the column to provide a constant drain-to-source voltage to the ISFET of an enabled pixel. The bias/readout circuitry $110_j$ is based on a Kelvin Bridge configuration and includes two operational amplifiers 107A (A1) and 107B (A2) configured as buffer amplifiers and coupled to analog circuitry positive supply voltage VDDA and the analog supply voltage ground VSSA. The bias/readout circuitry also includes a controllable current sink $108_j$ (similar to the current source $106_j$) coupled to the analog ground VSSA and responsive to a bias voltage VB2, and a diode-connected MOSFET Q6. The bias voltages VB1 and VB2 are set/controlled in tandem to provide a complimentary source and sink current. The voltage developed across the diode-connected MOSFET Q6 as a result of the current drawn by the current sink $108_j$ is forced by the operational amplifiers to appear across the drain and source of the ISFET of an enabled pixel as a constant drain-source voltage $V_{DSj}$.

By employing the diode-connected MOSFET Q6 in the bias/readout circuitry $110_j$ of FIG. 9, rather than the resistor $R_{SDj}$ as shown in the design of Milgrew et al. illustrated in FIG. 3, a significant advantage is provided in a CMOS fabrication process; specifically, matching resistors can be fabricated with error tolerances generally on the order of ±20%, whereas MOSFET matching in a CMOS fabrication process is on the order of ±1% or better. The degree to which the component responsible for providing a constant ISFET drain-to-source voltage $V_{DSj}$ can be matched from column to column significantly affects measurement accuracy (e.g., offset) from column to column. Thus, employing the MOSFET Q6 rather than a resistor appreciably mitigates measurement offsets from column-to-column. Furthermore, whereas the thermal drift characteristics of a resistor and an ISFET may be appreciably different, the thermal drift characteristics of a MOSFET and ISFET are substantially similar, if not virtually identical; hence, any thermal drift in MOSFET Q6 virtually cancels any thermal drift from ISFET Q1, resulting in greater measurement stability with changes in array temperature.

In FIG. 9, the column bias/readout circuitry $110_j$ also includes sample/hold and buffer circuitry to provide an output signal $V_{COLj}$ from the column. In particular, after one of the pixels $105_1$ through $105_n$ is enabled or selected via the transistors Q2 and Q3 in each pixel, the output of the amplifier 107A (A1), i.e., a buffered $V_{Sj}$, is stored on a column sample and hold capacitor $C_{sh}$ via operation of a switch (e.g., a transmission gate) responsive to a column sample and hold signal COL SH. Examples of suitable capacitances for the sample and hold capacitor include, but are not limited to, a range of from approximately 500 fF to 2 pF. The sampled voltage is buffered via a column output buffer amplifier $111j$ (BUF) and provided as the column output signal $V_{COLj}$. As also shown in FIG. 9, a reference voltage VREF may be applied to the buffer amplifier $111j$, via a switch responsive to a control signal CAL, to facilitate characterization of column-to-column non-uniformities due to the buffer amplifier $111j$ and thus allow post-read data correction.

Figure 9A:
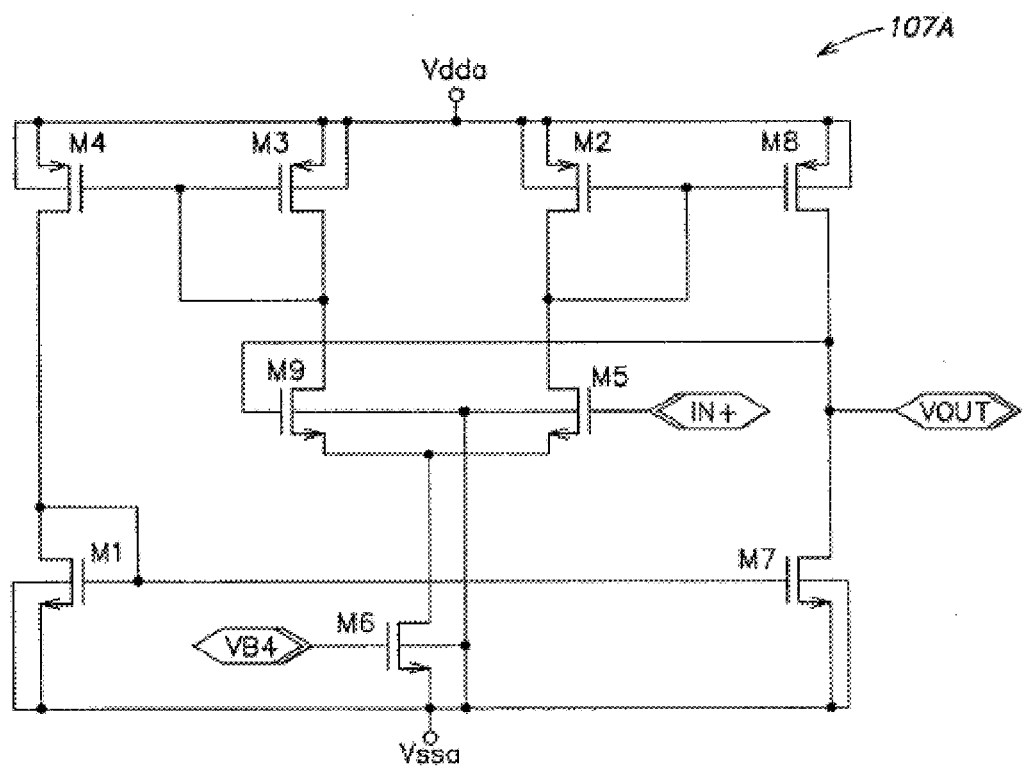
FIG. 9A illustrates a circuit diagram for an exemplary amplifier employed in the array column shown in FIG. 9.
Figure 9B:
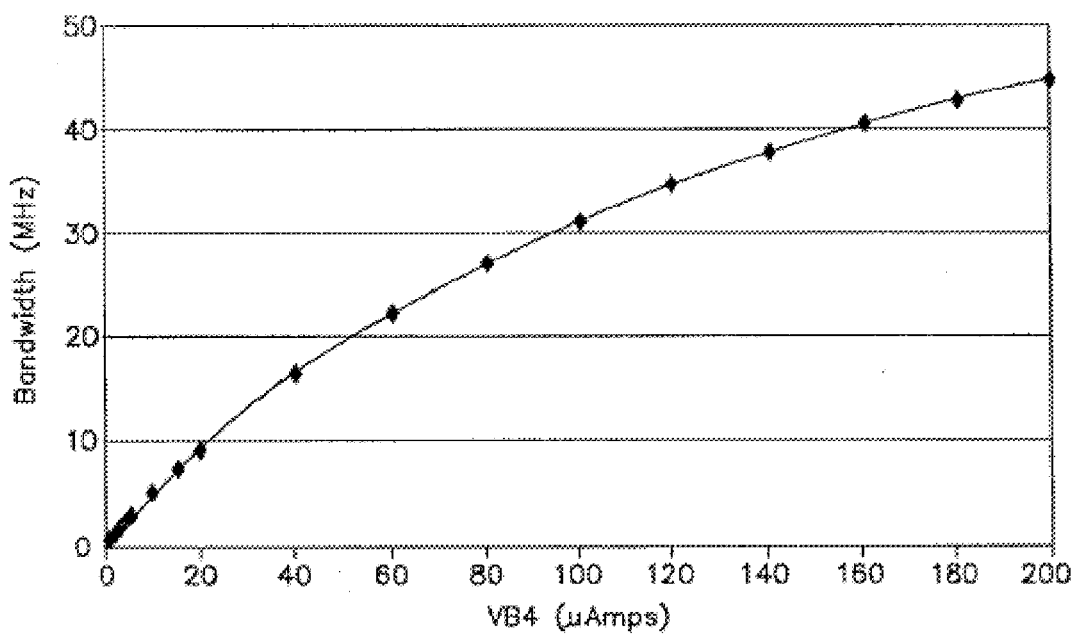
FIG. 9B is a graph of amplifier bias vs. bandwidth, according to one inventive embodiment of the present disclosure.

FIG. 9A illustrates an exemplary circuit diagram for one of the amplifiers 107A of the bias/readout circuitry $110_j$ (the amplifier 107B is implemented identically), and FIG. 9B is a graph of amplifier bias vs. bandwidth for the amplifiers 107A and 107B. As shown in FIG. 9A, the amplifier 107A employs an arrangement of multiple current mirrors based on nine MOSFETs (M1 through M9) and is configured as a unity gain buffer, in which the amplifier's inputs and outputs are labeled for generality as IN+ and VOUT, respectively. The bias voltage VB4 (representing a corresponding bias current) controls the transimpedance of the amplifier and serves as a bandwidth control (i.e., increased bandwidth with increased current). With reference again to FIG. 9, due to the sample and hold capacitor Csh, the output of the amplifier 107A essentially drives a filter when the sample and hold switch is closed. Accordingly, to achieve appreciably high data rates, the bias voltage VB4 may be adjusted to provide higher bias currents and increased amplifier bandwidth. From FIG. 9B, it may be observed that in some exemplary implementations, amplifier bandwidths of at least 40 MHz and significantly greater may be realized. In some implementations, amplifier bandwidths as high as 100 MHz may be appropriate to facilitate high data acquisition rates and relatively lower pixel sample or "dwell" times (e.g., on the order of 10 to 20 microseconds).

In another aspect of the embodiment shown in FIG. 9, unlike the pixel design of Milgrew et al. shown in FIG. 3, the pixels $105_1$ through $105_n$ do not include any transmission gates or other devices that require both n-channel and p-channel FET components; in particular, the pixels $105_1$ through $105_n$ of this embodiment include only FET devices of a same type (i.e., only n-channel or only p-channel). For purposes of illustration, the pixels $105_1$ and $105_n$ illustrated in FIG. 9 are shown as comprising only p-channel components, i.e., two p-channel MOSFETs Q2 and Q3 and a p-channel ISFET 150. By not employing a transmission gate to couple the source of the ISFET to the bias/readout circuitry $110_j$ some dynamic range for the ISFET output signal (i.e., the ISFET source voltage $V_S$) may be sacrificed. However, Applicants have recognized and appreciated that by potentially foregoing some output signal dynamic range (and thereby potentially limiting measurement range for a given chemical property, such as pH), the requirement of different type FET devices (both n-channel and p-channel) in each pixel may be eliminated and the pixel component count reduced. As discussed further below in connection with FIGS. 10-12, this significantly facilitates pixel size reduction. Thus, in one aspect, there is a beneficial tradeoff between reduced dynamic range and smaller pixel size.

In yet another aspect of the embodiment shown in FIG. 9, unlike the pixel design of Milgrew et al., the ISFET 150 of each pixel $105_1$ through $105_n$ does not have its body connection tied to its source (i.e., there is no electrical conductor coupling the body connection and source of the ISFET such that they are forced to be at the same electric potential during operation). Rather, the body connections of all ISFETs of the array are tied to each other and to a body bias voltage $V_{BODY}$. While not shown explicitly in FIG. 9, the body connections for the MOSFETs Q2 and Q3 likewise are not tied to their respective sources, but rather to the body bias voltage $V_{BODY}$. In one exemplary implementation based on pixels having all p-channel components, the body bias voltage $V_{BODY}$ is coupled to the highest voltage potential available to the array (e.g., VDDA), as discussed further below in connection with FIG. 17.

By not tying the body connection of each ISFET to its source, the possibility of some non-zero source-to-body voltage $V_{SB}$ may give rise to the "body effect," as discussed above in connection with FIG. 1, which affects the threshold voltage $V_{TH}$ of the ISFET according to a nonlinear relationship (and thus, according to Eq. (3), may affect measurements of chemical properties, such as pH). However, Applicants have recognized and appreciated that by focusing on a reduced ISFET output signal dynamic range, any body effect that may arise in the ISFET from a non-zero source-to-body voltage may be relatively minimal. Thus, any measurement nonlinearity that may result over the reduced dynamic range may be ignored as insignificant or taken into consideration and compensated (e.g., via array calibration and data processing techniques, as discussed further below in connection with FIG. 17). Applicants have also recognized and appreciated that by not tying each ISFET source to its body connection, all of the FETs constituting the pixel may share a common body connection, thereby further facilitating pixel size reduction, as discussed further below in connection with FIGS. 10-12. Accordingly, in another aspect, there is a beneficial tradeoff between reduced linearity and smaller pixel size.

Figure 10:
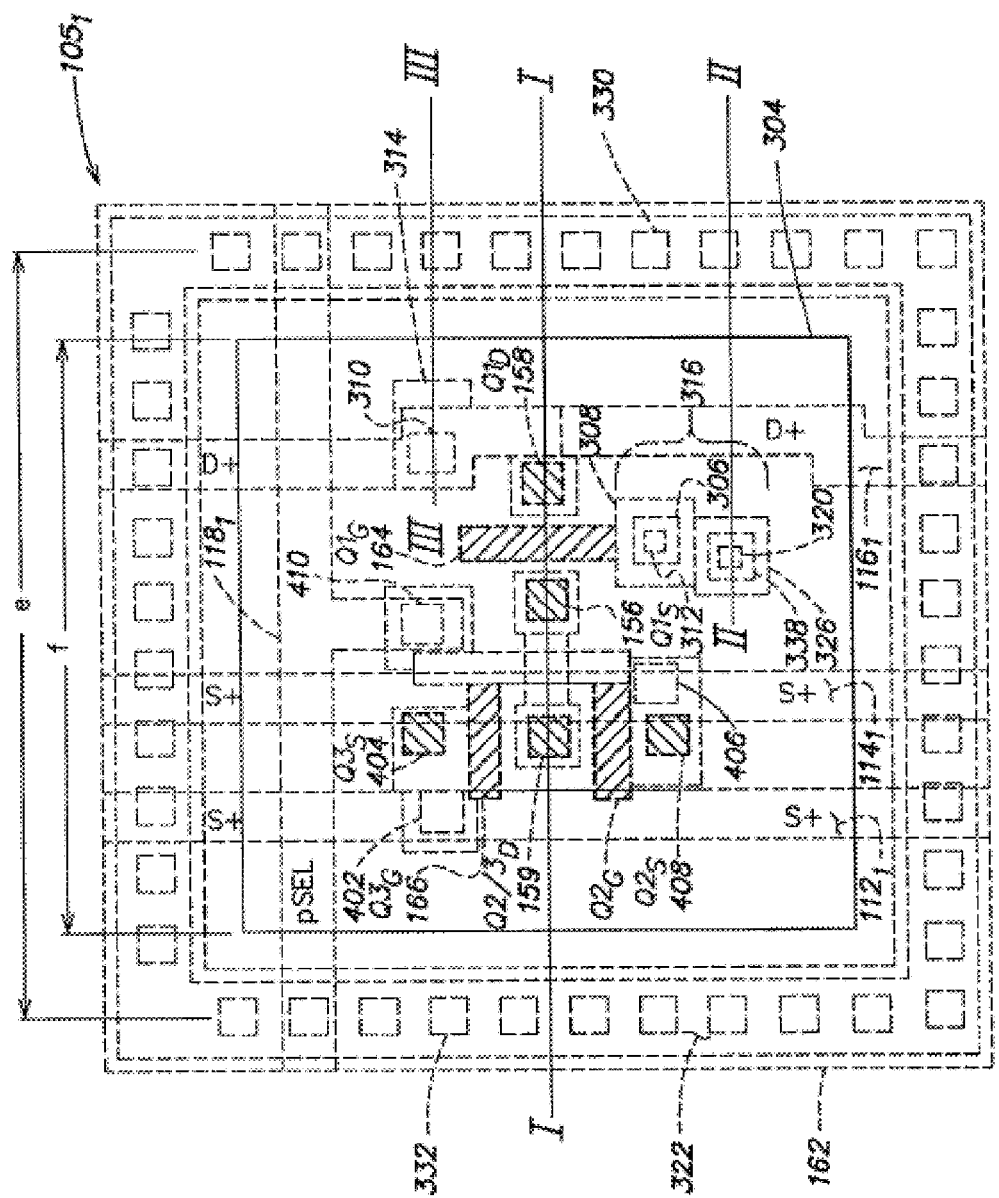
FIG. 10 illustrates a top view of a chip layout design for a pixel of the column of an chemFET array shown in FIG. 9, according to one inventive embodiment of the present disclosure.
Figure 11A:
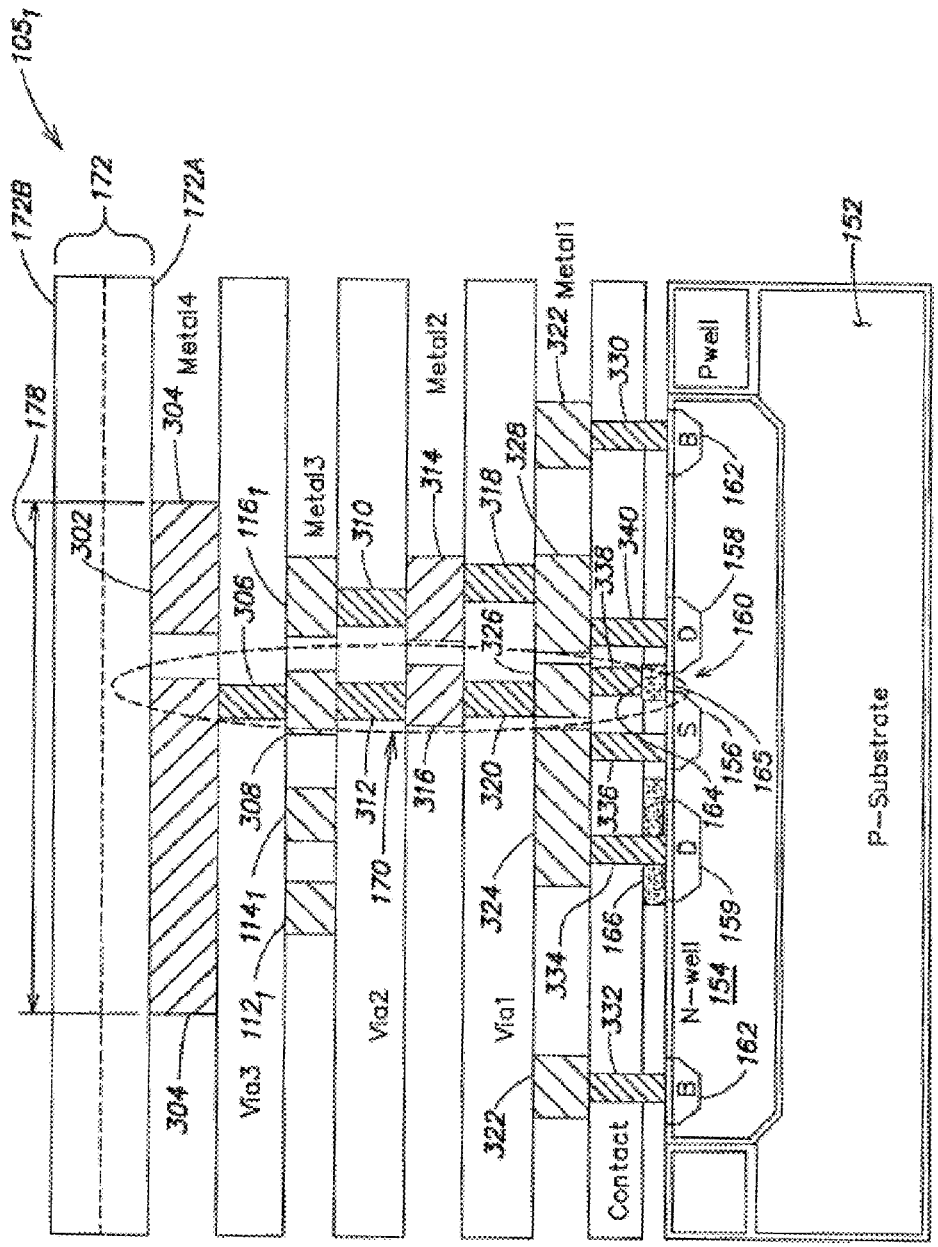
FIG. 11A shows a composite cross-sectional view along the line I-I of the pixel shown in FIG. 10, including additional elements on the right half of FIG. 10 between the lines II-II and III-III, illustrating a layer-by-layer view of the pixel fabrication according to one inventive embodiment of the present disclosure.

FIG. 10 illustrates a top view of a chip layout design for the pixel $105_1$ shown in FIG. 9, according to one inventive embodiment of the present disclosure. FIG. 11A shows a composite cross-sectional view along the line I-I of the pixel shown in FIG. 10, including additional elements on the right half of FIG. 10 between the lines II-II and III-III, illustrating a layer-by-layer view of the pixel fabrication, and FIGS. 12A through 12L provide top views of each of the fabrication layers shown in FIG. 11A (the respective images of FIGS. 12A through 12L are superimposed one on top of another to create the pixel chip layout design shown in FIG. 10). In one exemplary implementation, the pixel design illustrated in FIGS. 10-12 may be realized using a standard 4-metal, 2-poly, 0.35 micrometer CMOS process to provide a geometrically square pixel having a dimension "e" as shown in FIG. 10 of approximately 9 micrometers, and a dimension "f" corresponding to the ISFET sensitive area of approximately 7 micrometers.

In the top view of FIG. 10, the ISFET 150 (labeled as Q1 in FIG. 10) generally occupies the right center portion of the pixel illustration, and the respective locations of the gate, source and drain of the ISFET are indicated as $Q1_G$, $Q1_S$ and $Q1_D$. The MOSFETs Q2 and Q3 generally occupy the left center portion of the pixel illustration; the gate and source of the MOSFET Q2 are indicated as $Q2_G$ and $Q2_S$, and the gate and source of the MOSFET Q3 are indicated as $Q3_G$ and $Q3_S$. In one aspect of the layout shown in FIG. 10, the MOSFETs Q2 and Q3 share a drain, indicated as $Q2/3_D$. In another aspect, it may be observed generally from the top view of FIG. 10 that the ISFET is formed such that its channel lies along a first axis of the pixel (e.g., parallel to the line I-I), while the MOSFETs Q2 and Q3 are formed such that their channels lie along a second axis perpendicular to the first axis. FIG. 10 also shows the four lines required to operate the pixel, namely, the line $112_1$ coupled to the source of Q3, the line $114_1$ coupled to the source of Q2, the line $116_1$ coupled to the drain of the ISFET, and the row select line $118_1$ coupled to the gates of Q2 and Q3. With reference to FIG. 9, it may be appreciated that all pixels in a given column share the lines 112, 114 and 116 (e.g., running vertically across the pixel in FIG. 10), and that all pixels in a given row share the line 118 (e.g., running horizontally across the pixel in FIG. 10); thus, based on the pixel design of FIG. 9 and the layout shown in FIG. 10, only four metal lines need to traverse each pixel.

With reference now to the cross-sectional view of FIG. 11A, highly doped p-type regions 156 and 158 (lying along the line I-I in FIG. 10) in n-well 154 constitute the source (S) and drain (D) of the ISFET, between which lies a region 160 of the n-well in which the ISFETs p-channel is formed below the ISFETs polysilicon gate 164 and a gate oxide 165. According to one aspect of the inventive embodiment shown in FIGS. 10 and 11, all of the FET components of the pixel $105_1$ are fabricated as p-channel FETs in the single n-type well 154 formed in a p-type semiconductor substrate 152. This is possible because, unlike the design of Milgrew et al., 1) there is no requirement for a transmission gate in the pixel; and 2) the ISFETs source is not tied to the n-well's body connection. More specifically, highly doped n-type regions 162 provide a body connection (B) to the n-well 154 and, as shown in FIG. 10, the body connection B is coupled to a metal conductor 322 around the perimeter of the pixel $105_1$. However, the body connection is not directly electrically coupled to the source region 156 of the ISFET (i.e., there is no electrical conductor coupling the body connection and source such that they are forced to be at the same electric potential during operation), nor is the body connection directly electrically coupled to the gate, source or drain of any component in the pixel. Thus, the other p-channel FET components of the pixel, namely Q2 and Q3, may be fabricated in the same n-well 154.

In the composite cross-sectional view of FIG. 11A, a highly doped p-type region 159 is also visible (lying along the line I-I in FIG. 10), corresponding to the shared drain (D) of the MOSFETs Q2 and Q3. For purposes of illustration, a polysilicon gate 166 of the MOSFET Q3 also is visible in FIG. 11A, although this gate does not lie along the line I-I in FIG. 10, but rather "behind the plane" of the cross-section along the line I-I. However, for simplicity, the respective sources of the MOSFETs Q2 and Q3 shown in FIG. 10, as well as the gate of Q2, are not visible in FIG. 11A, as they lie along the same axis (i.e., perpendicular to the plane of the figure) as the shared drain (if shown in FIG. 11A, these elements would unduly complicate the composite cross-sectional view of FIG. 11A).

Above the substrate, gate oxide, and polysilicon layers shown in FIG. 11A, a number of additional layers are provided to establish electrical connections to the various pixel components, including alternating metal layers and oxide layers through which conductive vias are formed. Pursuant to the 4-Metal CMOS process, these layers are labeled in FIG. 11A as "Contact," "Metal1," "Via1," "Metal2," "Via2," "Metal3," "Via3," and "Metal4." To facilitate an understanding particularly of the ISFET electrical connections, the composite cross-sectional view of FIG. 11A shows additional elements of the pixel fabrication on the right side of the top view of FIG. 10 between the lines II-II and III-III. With respect to the ISFET electrical connections, the topmost metal layer 304 corresponds to the ISFETs sensitive area 178, above which is disposed an analyte-sensitive passivation layer 172. The topmost metal layer 304, together with the ISFET polysilicon gate 164 and the intervening conductors 306, 308, 312, 316, 320, 326 and 338, form the ISFETs "floating gate" structure 170, in a manner similar to that discussed above in connection with a conventional ISFET design shown in FIG. 1. An electrical connection to the ISFETs drain is provided by the conductors 340, 328, 318, 314 and 310 coupled to the line $116_1$. The ISFETs source is coupled to the shared drain of the MOSFETs Q2 and Q3 via the conductors 334 and 336 and the conductor 324 (which lies along the line I-I in FIG. 10). The body connections 162 to the n-well 154 are electrically coupled to a metal conductor 322 around the perimeter of the pixel on the "Metal1" layer via the conductors 330 and 332.

As indicated above, FIGS. 12A through 12L provide top views of each of the fabrication layers shown in FIG. 11A (the respective images of FIGS. 12A through 12L are superimposed one on top of another to create the pixel chip layout design shown in FIG. 10). In FIG. 12, the correspondence between the lettered top views of respective layers and the cross-sectional view of FIG. 11A is as follows: A) n-type well 154; B) Implant; C) Diffusion; D) polysilicon gates 164 (ISFET) and 166 (MOSFETs Q2 and Q3); E) contacts; F) Metal1; G) Via1; H) Metal2; I) Via2; J) Metal3; K) Via3; L) Metal4 (top electrode contacting ISFET gate). The various reference numerals indicated in FIGS. 12A through 12L correspond to the identical features that are present in the composite cross-sectional view of FIG. 11A.

Thus, the pixel chip layout design shown in FIGS. 10, 11, and 12A through 12L illustrates that, according to one embodiment, FET devices of a same type may be employed for all components of the pixel, and that all components may be implemented in a single well. This dramatically reduces the area required for the pixel, thereby facilitating increased pixel density in a given area.

In one exemplary implementation, the gate oxide 165 for the ISFET may be fabricated to have a thickness on the order of approximately 75 Angstroms, giving rise to a gate oxide capacitance per unit area $C_{ox}$ of 4.5 fF/$\mu m^2$. Additionally, the polysilicon gate 164 may be fabricated with dimensions corresponding to a channel width W of 1.2 μm and a channel length L of from 0.35 to 0.6 μm (i.e., W/L ranging from approximately 2 to 3.5), and the doping of the region 160 may be selected such that the carrier mobility for the p-channel is 190 cm$^2$/V·s (i.e., 1.9E10 μm$^2$/V·s). From Eq. (2) above, this results in an ISFET transconductance parameter β on the order of approximately 170 to 300 μA/V$^2$. In other aspects of this exemplary implementation, the analog supply voltage VDDA is 3.3 Volts, and VB1 and VB2 are biased so as to provide a constant ISFET drain current $I_{Dj}$ on the order of 5 μA (in some implementations, VB1 and VB2 may be adjusted to provide drain currents from approximately 1 μA to 20 μA). Additionally, the MOSFET Q6 (see bias/readout circuitry 110$_j$ in FIG. 9) is sized to have a channel width to length ratio (e.g., W/L of approximately 50) such that the voltage across Q6, given $I_{Dj}$ of 5 μA, is 800 mV (i.e., $V_{DSj}$=800 mV). From Eq. (3), based on these exemplary parameters, this provides for pixel output voltages $V_{Sj}$ over a range of approximately 0.5 to 2.5 Volts for ISFET threshold voltage changes over a range of approximately 0 to 2 Volts.

With respect to the analyte-sensitive passivation layer 172 shown in FIG. 11A, in exemplary CMOS implementations the passivation layer may be significantly sensitive to hydrogen ion concentration and may include silicon nitride ($Si_3N_4$) and/or silicon oxynitride ($Si_2N_2O$). In conventional CMOS processes, a passivation layer may be formed by one or more successive depositions of these materials, and is employed generally to treat or coat devices so as to protect against contamination and increase electrical stability. The material properties of silicon nitride and silicon oxynitride are such that a passivation layer comprising these materials provides scratch protection and serves as a significant barrier to the diffusion of water and sodium, which can cause device metallization to corrode and/or device operation to become unstable. A passivation layer including silicon nitride and/or silicon oxynitride also provides ion-sensitivity in ISFET devices, in that the passivation layer contains surface groups that may donate or accept protons from an analyte solution with which they are in contact, thereby altering the surface potential and the device threshold voltage $V_{TH}$, as discussed above in connection with FIG. 1.

For CMOS processes involving aluminum as the metal (which has a melting point of approximately 650 degrees Celsius), a silicon nitride and/or silicon oxynitride passivation layer generally is formed via plasma-enhanced chemical vapor deposition (PECVD), in which a glow discharge at 250-350 degrees Celsius ionizes the constituent gases that form silicon nitride or silicon oxynitride, creating active species that react at the wafer surface to form a laminate of the respective materials. In one exemplary process, a passivation layer having a thickness on the order of approximately 1.0 to 1.5 μm may be formed by an initial deposition of a thin layer of silicon oxynitride (on the order of 0.2 to 0.4 μm) followed by a slighting thicker deposition of silicon oxynitride (on the order of 0.5 μm) and a final deposition of silicon nitride (on the order of 0.5 μm). Because of the low deposition temperature involved in the PECVD process, the aluminum metallization is not adversely affected.

However, Applicants have recognized and appreciated that while a low temperature PECVD process provides adequate passivation for conventional CMOS devices, the low-temperature process results in a generally low-density and somewhat porous passivation layer, which in some cases may adversely affect ISFET threshold voltage stability. In particular, during ISFET device operation, a low-density porous passivation layer over time may absorb and become saturated with ions from the solution, which may in turn cause an undesirable time-varying drift in the ISFETs threshold voltage $V_{TH}$, making accurate measurements challenging.

In view of the foregoing, in one embodiment a CMOS process that uses tungsten metal instead of aluminum may be employed to fabricate ISFET arrays according to the present disclosure. The high melting temperature of Tungsten (above 3400 degrees Celsius) permits the use of a higher temperature low pressure chemical vapor deposition (LPCVD) process (e.g., approximately 700 to 800 degrees Celsius) for a silicon nitride or silicon oxynitride passivation layer. The LPCVD process typically results in significantly more dense and less porous films for the passivation layer, thereby mitigating the potentially adverse effects of ion absorption from the analyte solution leading to ISFET threshold voltage drift.

In yet another embodiment in which an aluminum-based CMOS process is employed to fabricate ISFET arrays according to the present disclosure, the passivation layer 172 shown in FIG. 11A may comprise additional depositions and/or materials beyond those typically employed in a conventional CMOS process. For example, the passivation layer 172 may include initial low-temperature plasma-assisted depositions (PECVD) of silicon nitride and/or silicon oxynitride as discussed above; for purposes of the present discussion, these conventional depositions are illustrated in FIG. 11A as a first portion 172A of the passivation layer 172. In one embodiment, following the first portion 172A, one or more additional passivation materials are disposed to form at least a second portion 172B to increase density and reduce porosity of (and absorption by) the overall passivation layer 172. While one additional portion 172B is shown primarily for purposes of illustration in FIG. 11A, it should be appreciated that the disclosure is not limited in this respect, as the overall passivation layer 172 may comprise two or more constituent portions, in which each portion may comprise one or more layers/depositions of same or different materials, and respective portions may be configured similarly or differently.

Examples of materials suitable for the second portion 172B (or other additional portions) of the passivation layer 172 for particular sensitivity to hydrogen ions include, but are not limited to, silicon nitride, silicon oxynitride, aluminum oxide ($Al_2O_3$), tantalum oxide ($Ta_3O_5$), tin oxide ($SnO_2$) and silicon dioxide ($SiO_2$). In one aspect, the second portion 172B (or other additional portions) may be deposited via a variety of relatively low temperature processes including, but not limited to, RF sputtering, DC magnetron sputtering, thermal or e-beam evaporation, and ion-assisted depositions. In another aspect, a pre-sputtering etch process may be employed, prior to deposition of the second portion 172B, to remove any native oxide residing on the first portion 172A (alternatively, a reducing environment, such as an elevated temperature hydrogen environment, may be employed to remove native oxide residing on the first portion 172A). In yet another aspect, a thickness of the second portion 172B may be on the order of approximately 0.04 μm to 0.06 μm (400 to 600 Angstroms) and a thickness of the first portion may be on the order of 1.0 to 1.5 as discussed above. In some exemplary implementations, the first portion 172A may include multiple layers of silicon oxynitride and silicon nitride having a combined thickness of 1.0 to 1.5 μm, and the second portion 172B may include a single layer of either aluminum oxide or tantalum oxide having a thickness of approximately 400 to 600 Angstroms. Again, it should be appreciated that the foregoing exemplary thicknesses are provided primarily for purposes of illustration, and that the disclosure is not limited in these respects.

Thus it is to be understood that the chemFET arrays described herein may be used to detect various analytes and, by doing so, may monitor a variety of reactions and/or interactions. It is also to be understood that the emphasis on hydrogen ion detection (in the form of a pH change) is for the sake of convenience and brevity and that other analytes (including other ions) can be substituted for hydrogen in these descriptions.

The chemFETs, including ISFETs, described herein are capable of detecting any analyte that is itself capable of inducing a change in electric field. The analyte need not be charged in order to be detected by the sensor. For example, depending on the embodiment, the analyte may be positively charged (i.e., a cation), negatively charged (i.e., an anion), zwitterionic (i.e., capable of having two equal and opposite charges but overall neutral), and polar yet neutral. This list is not intended as exhaustive as other analyte classes as well as species within each class will be readily contemplated by those of ordinary skill in the art based on the disclosure provided herein.

In the broadest sense of the invention, passivation layer may or may not be coated and the analyte may or may not interact with the passivation layer. As an example, the passivation layer may be comprised of silicon nitride and the analyte may be something other than hydrogen ions. As a specific example, the passivation layer may be comprised of silicon nitride and the analyte may be inorganic pyrophosphate (PPi). In these instances, PPi is detected directly (i.e., in the absence of PPi receptors attached to the passivation layer either directly or indirectly).

If the analyte being detected is hydrogen (or alternatively hydroxide), then it is preferable to use weak buffers so that changes in either ionic species can be detected at the passivation layer. If the analyte being detected is something other than hydrogen (or hydroxide) but there is some possibility of a pH change in the solution during the reaction or detection step, then it is preferable to use a strong buffer so that changes in pH do not interfere with the detection of the analyte. A buffer is an ionic molecule that resists changes in pH. Buffers are able to neutralize acids or bases added to or generated in a solution, resulting in no effective pH change in the solution. It is to be understood that any buffer is suitable provided it has a pKa in the desired range. A suitable buffer is one that functions in about the pH range of 6 to 9, and more preferably 6.5 to 8.5. The strength of a buffer is a relative term since it depends on the nature, strength and concentration of the acid or base added to or generated in the solution of interest. A weak buffer is a buffer that allows detection (and therefore is not able to otherwise control) pH changes of about at least +/−0.005, 0.01, 0.015, 0.02, 0.03, 0.04, 0.05, 0.10, 0.15, 0.20, 0.25, 0.30, 0.35, 0.45, 0.50, or more. In some embodiments, the pH change is on the order of about 0.005 (e.g., per nucleotide incorporation) and is preferably an increase in pH. A strong buffer is a buffer that controls pH changes of about at least +/−0.005, 0.01, 0.015, 0.02, 0.03, 0.04, 0.05, 0.10, 0.15, 0.20, 0.25, 0.30, 0.35, 0.45, 0.50, or more. Buffer strength can be varied by varying the concentration of the buffer species itself. Thus low concentration buffers can be low strength buffers. Examples include those having less than 1 mM (e.g., 50-100 μM) buffer species. A non-limiting example of a weak buffer suitable for the sequencing reactions described herein wherein pH change is the readout is 0.1 mM Tris or Tricine. Examples of suitable weak buffers are provided in the Examples and are also known in the art. Higher concentration buffers can be stronger buffers. Examples include those having 1-25 mM buffer species. A non-limiting example of a strong buffer suitable for the sequencing reactions described herein wherein PPi is read directly is 1, 5 or 25 mM (or more) Tris or Tricine. One of ordinary skill in the art will be able to determine the optimal buffer for use in the reactions and detection methods encompassed by the invention.

In some embodiments, the passivation layer and/or the molecules coated thereon dictate the analyte specificity of the array readout.

Detection of hydrogen ions (in the form of pH) can be carried out using a passivation layer made of silicon nitride ($Si_3N_4$), silicon oxynitride ($Si_2N_2O$), silicon oxide ($SiO_2$), aluminum oxide ($Al_2O_3$), tantalum pentoxide ($Ta_2O_5$), tin oxide or stannic oxide ($SnO_2$), and the like.

The passivation layer can also detect other ion species directly including but not limited to calcium, potassium, sodium, iodide, magnesium, chloride, lithium, lead, silver, cadmium, nitrate, phosphate, dihydrogen phosphate, and the like.

In some embodiments, the passivation layer is coated with a receptor for the analyte of interest. The receptor binds selectively to the analyte of interest. As used herein, a receptor that binds selectively to an analyte is a molecule that binds preferentially to that analyte (i.e., its binding affinity for that analyte is greater than its binding affinity for any other analyte). Its binding affinity for the analyte of interest may be 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 100-fold or more than its binding affinity for any other analyte. In addition to its relative binding affinity, the receptor must also have an absolute binding affinity that is sufficiently high to efficiently bind the analyte of interest (i.e., it must have a sufficient sensitivity). Receptors having binding affinities in the picomolar to micromolar range are suitable. Preferably such interaction are reversible.

The receptor may be of any nature (e.g., chemical, nucleic acid, peptide, lipid, combinations thereof and the like). The analyte too may be of any nature provided there exists a receptor that binds to it selectively and in some instances specifically. It is to be understood however that the invention further contemplates detection of analytes in the absence of a receptor. An example of this is the detection of PPi and Pi by the passivation layer in the absence of PPi or Pi receptors.

In one aspect, the invention contemplates receptors that are ionophores. As used herein, an ionophore is a molecule that binds selectively to an ionic species, whether anion or cation. In the context of the invention, the ionophore is the receptor and the ion to which it binds is the analyte. Ionophores of the invention include art-recognized carrier ionophores (i.e., small lipid-soluble molecules that bind to a particular ion)

derived from microorganisms. Various ionophores are commercially available from sources such as Calbiochem.

Detection of some ions can be accomplished through using the passivation layer itself or through the use of receptors coated onto the passivation layer. For example, potassium can be detected selectively using the polysiloxane, valinomycin, or salinomycin; sodium can be detected selectively using monensin, nystatin, or SQI-Pr; calcium can be detected selectively using ionomycin, calcimycine (A23187), or CA 1001 (ETH 1001).

Receptors able to bind more than one ion can also be used in some instances. For example, beauvericin can be used to detect calcium and/or barium ions, nigericin can be used to detect potassium, hydrogen and/or lead ions, and gramicidin can be used to detect hydrogen, sodium and/or potassium ions. One of ordinary skill in the art will recognize that these compounds can be used in applications in which single ion specificity is not required or in which it is unlikely (or impossible) that other ions which the compounds bind will be present or generated.

Figure 11E:
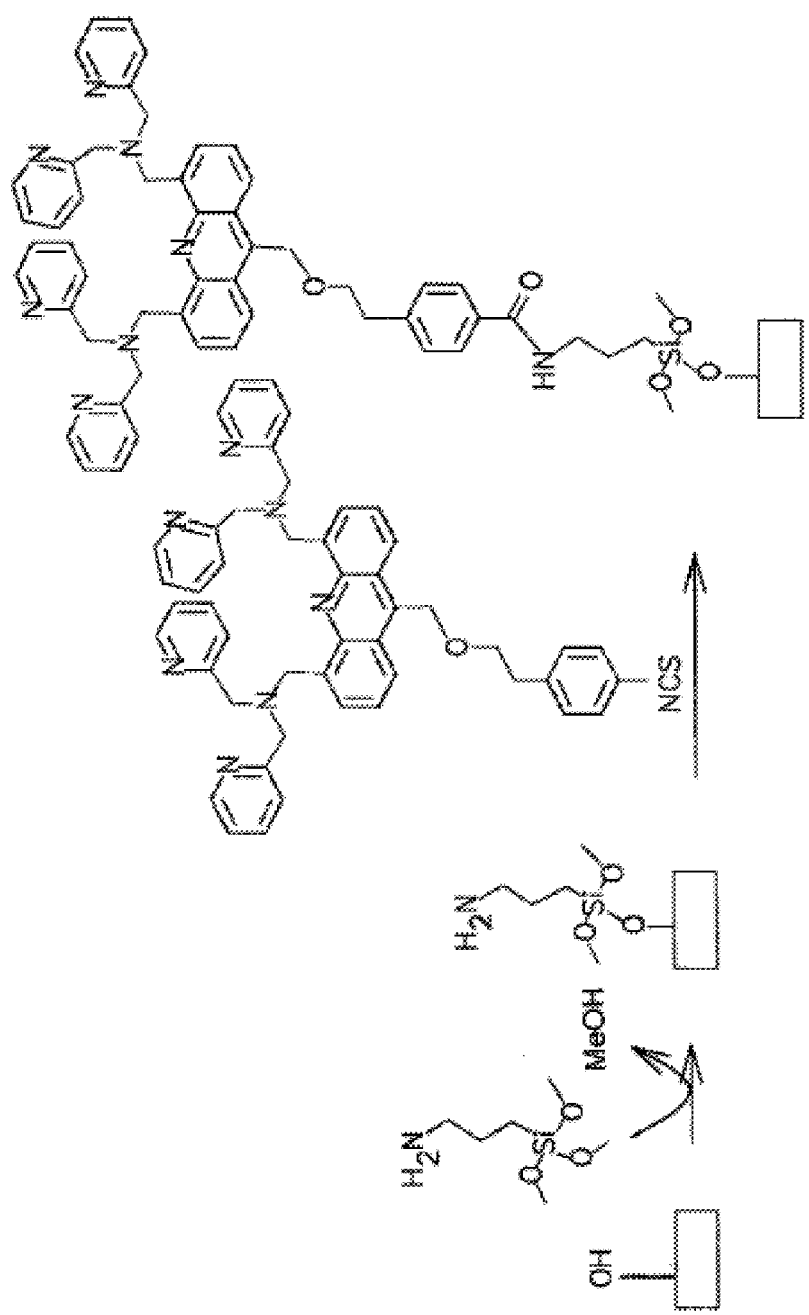
FIG. 11E is a schematic of attachment of compound 10 from FIG. 11B to a metal oxide surface.

In other embodiments, including but not limited to nucleic acid sequencing applications, receptors that bind selectively to inorganic pyrophosphate (PPi) can be used. Examples of PPi receptors include those compounds shown in FIG. 11B (compounds 1-10). Compound 1 is described in Angew Chem Int Ed 2004 43:4777-4780 and US 2005/0119497 A1 and is referred to as p-naphthyl-bis[(bis(2-pyridylmethyl)amino)methyl]phenol. Compound 2 is described in J Am Chem Soc 2003 125:7752-7753 and US 2005/0119497 A1 and is referred to as p-(p-nitrophenylazo)-bis[(bis(2-pyridylmethyl-1)amino)methyl]phenol (or its dinuclear Zn complex). Compound 3 is described in Sensors and Actuators B 1995 29:324-327. Compound 4 is described in Angew Chem Int Ed 2002 41(20):3811-3814. Compound 5 is described in WO 2007/002204 and is referred to therein as bis-$Zn^{2+}$-dipicolylamine ($Zn^{2+}$-DPA). Synthesis schemes for compounds 1 and 2 are shown provided in US 2005/0119497 A1. An exemplary synthesis for compound 4 is shown in FIG. 11C. Attachment of compound 10 to a metal oxide surface is shown in FIG. 11E.

As another example, receptors for neurotoxins are described in Simonian Electroanalysis 2004, 16: 1896-1906.

Receptors may be attached to the passivation layer covalently or non-covalently. Covalent attachment of a receptor to the passivation layer may be direct or indirect (e.g., through a linker). FIG. 11D illustrates the use of silanol chemistry to covalently bind receptors to the passivation layer. Receptors may be immobilized on the passivation layer using for example aliphatic primary amines (bottom left panel) or aryl isothiocyanates (bottom right panel). In these and other embodiments, the passivation layer which itself may be comprised of silicon nitride, aluminum oxide, silicon oxide, tantalum pentoxide, or the like, is bonded to a silanation layer via its reactive surface groups. For greater detail on silanol chemistry for covalent attachment to the FET surface, reference can be made to at least the following publications: for silicon nitride, see Sensors and Actuators B 1995 29:324-327, Jpn J Appl Phys 1999 38:3912-3917 and Langmuir 2005 21:395-402; for silicon oxide, see Protein Sci 1995 4:2532-2544 and Am Biotechnol Lab 2002 20(7):16-18; and for aluminum oxide, see Colloids and Surfaces 1992 63:1-9, Sensors and Accuators B 2003 89:40-47, and Bioconjugate Chem 1997 8:424-433. The receptor is then conjugated to the silanation layer reactive groups. This latter binding can occur directly or indirectly through the use of a bifunctional linker, as illustrated in FIG. 11D. A bifunctional linker is a compound having at least two reactive groups to which two entities may be bound. In some instances, the reactive groups are located at opposite ends of the linker. In some embodiments, the bifunctional linker is a universal bifunctional linker such as that shown in FIG. 11D. A universal linker is a linker that can be used to link a variety of entities. It should be understood that the chemistries shown in FIG. 11D are meant to be illustrative and not limiting.

The bifunctional linker may be a homo-bifunctional linker or a hetero-bifunctional linker, depending upon the nature of the molecules to be conjugated. Homo-bifunctional linkers have two identical reactive groups. Hetero-bifunctional linkers are have two different reactive groups. Various types of commercially available linkers are reactive with one or more of the following groups: primary amines, secondary amines, sulphydryls, carboxyls, carbonyls and carbohydrates. Examples of amine-specific linkers are bis(sulfosuccinimidyl) suberate, bis[2-(succinimidooxycarbonyloxy)ethyl]sulfone, disuccinimidyl suberate, disuccinimidyl tartarate, dimethyl adipimate.2HCl, dimethyl pimelimidate.2HCl, dimethyl suberimidate.2HCl, and ethylene glycolbis-[succinimidyl-[succinate]]. Linkers reactive with sulfhydryl groups include bismaleimidohexane, 1,4-di-[3'-(2'-pyridyldithio)-propionamido)]butane, 1-[p-azidosalicylamido]-4-kodoacetamidol butane, and N-[4-(p-azidosalicylamido) butyl]-3'-[2'-pyridyldithio]propionamide. Linkers preferentially reactive with carbohydrates include azidobenzoyl hydrazine. Linkers preferentially reactive with carboxyl groups include 4-[p-azidosalicylamido]butylamine.

Heterobifunctional linkers that react with amines and sulfhydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional linkers that react with carboxyl and amine groups include 1-ethyl-3-[3-dimethylaminopropyl]-carbodiimide hydrochloride. Heterobifunctional linkers that react with carbohydrates and sulfhydryls include 4-[N-maleimidomethyl]-cyclohexane-1-carboxylhydrazide. 2HCl, 4-(4-N-maleimidophenyl)-butyric acid hydrazide.2HCl, and 3-[2-pyridyldithio]propionyl hydrazide.

Alternatively, receptors may be non-covalently coated onto the passivation layer. Non-covalent deposition of the receptor to the passivation layer may involve the use of a polymer matrix. The polymer may be naturally occurring or non-naturally occurring and may be of any type including but not limited to nucleic acid (e.g., DNA, RNA, PNA, LNA, and the like, or mimics, derivatives, or combinations thereof), amino acid (e.g., peptides, proteins (native or denatured), and the like, or mimics, derivatives, or combinations thereof, lipids, polysaccharides, and functionalized block copolymers. The receptor may be adsorbed onto and/or entrapped within the polymer matrix.

Alternatively, the receptor may be covalently conjugated or crosslinked to the polymer (e.g., it may be "grafted" onto a functionalized polymer).

An example of a suitable peptide polymer is poly-lysine (e.g., poly-L-lysine). Examples of other polymers include block copolymers that comprise polyethylene glycol (PEG), polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes, alkyl cellulose, hydroxyalkyl celluloses, cellulose ethers, cellulose esters, nitrocelluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, polyvinyl chloride, polystyrene, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), poly(lactide-glycolide), copolyoxalates, polycaprolactones, polyesteramides, polyorthoesters, polyhydroxybutyric acid, polyanhydrides, poly(styrene-b-isobutylene-b-styrene) (SIBS) block copolymer, ethylene vinyl acetate, poly(meth) acrylic acid, polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, albumin and other hydrophilic proteins, zein and other prolamines and hydrophobic proteins, copolymers and mixtures thereof, and chemical derivatives thereof including substitutions and/or additions of chemical groups, for example, alkyl, alkylene, hydroxylations, oxidations, and other modifications routinely made by those skilled in the art.

Another issue that relates to ISFET threshold voltage stability and/or predictability involves trapped charge that may accumulate on metal layers of CMOS-fabricated devices as a result of various processing activities during or following array fabrication (e.g., back-end-of-line processing such as plasma metal etching, wafer cleaning, dicing, packaging, handling, etc.). In particular, with reference to FIG. 11A, trapped charge may in some instances accumulate on one or more of the various conductors 304, 306, 308, 312, 316, 320, 326, 338, and 164 constituting the ISFETs floating gate structure 170. This phenomenon also is referred to in the relevant literature as the "antenna effect."

One opportunity for trapped charge to accumulate includes plasma etching of the topmost metal layer 304. Applicants have recognized and appreciated that other opportunities for charge to accumulate on one or more conductors of the floating gate structure includes wafer dicing, during which the abrasive process of a dicing saw cutting through a wafer generates static electricity, and/or various post-processing wafer handling/packaging steps, where automated machinery that handles/transports wafers may be sources of electrostatic discharge (ESD) to conductors of the floating gate structure. If there is no connection to the silicon substrate (or other semi-conductor substrate) to provide an electrical path to bleed off such charge accumulation, charge may build up to the point of causing undesirable changes or damage to the gate oxide 165 (e.g., charge injection into the oxide, or low-level oxide breakdown to the underlying substrate). Trapped charge in the gate oxide or at the gate oxide-semiconductor interface in turn can cause undesirable and/or unpredictable variations in ISFET operation and performance.

In view of the foregoing, other inventive embodiments of the present disclosure are directed to methods and apparatus for improving ISFET performance by reducing trapped charge or mitigating the antenna effect. In one embodiment, trapped charge may be reduced after a sensor array has been fabricated, while in other embodiments the fabrication process itself may be modified to reduce trapped charge that could be induced by some conventional process steps. In yet other embodiments, both "during fabrication" and "post fabrication" techniques may be employed in combination to reduce trapped charge and thereby improve ISFET performance.

With respect to alterations to the fabrication process itself to reduce trapped charge, in one embodiment the thickness of the gate oxide 165 shown in FIG. 11A may be particularly selected so as to facilitate bleeding of accumulated charge to the substrate; in particular, a thinner gate oxide may allow a sufficient amount of built-up charge to pass through the gate oxide to the substrate below without becoming trapped. In another embodiment based on this concept, a pixel may be designed to include an additional "sacrificial" device, i.e., another transistor having a thinner gate oxide than the gate oxide 165 of the ISFET. The floating gate structure of the ISFET may then be coupled to the gate of the sacrificial device such that it serves as a "charge bleed-off transistor." Of course, it should be appreciated that some trade-offs for including such a sacrificial device include an increase in pixel size and complexity.

In another embodiment, the topmost metal layer 304 of the ISFETs floating gate structure 170 shown in FIG. 11A may be capped with a dielectric prior to plasma etching to mitigate trapped charge. As discussed above, charge accumulated on the floating gate structure may in some cases be coupled from the plasma being used for metal etching. Typically, a photoresist is applied over the metal to be etched and then patterned based on the desired geometry for the underlying metal. In one exemplary implementation, a capping dielectric layer (e.g., an oxide) may be deposited over the metal to be etched, prior to the application of the photoresist, to provide an additional barrier on the metal surface against charge from the plasma etching process. In one aspect, the capping dielectric layer may remain behind and form a portion of the passivation layer 172.

In yet another embodiment, the metal etch process for the topmost metal layer 304 may be modified to include wet chemistry or ion-beam milling rather than plasma etching. For example, the metal layer 304 could be etched using an aqueous chemistry selective to the underlying dielectric (e.g., see http://www.transene.com/aluminum.html, hereby incorporated herein by reference). Another alternative approach employs ion-milling rather than plasma etching for the metal layer 304. Ion-milling is commonly used to etch materials that cannot be readily removed using conventional plasma or wet chemistries. The ion-milling process does not employ an oscillating electric field as does a plasma, so that charge build-up does not occur in the metal layer(s). Yet another metal etch alternative involves optimizing the plasma conditions so as to reduce the etch rate (i.e. less power density).

In yet another embodiment, architecture changes may be made to the metal layer to facilitate complete electrical isolation during definition of the floating gate. In one aspect, designing the metal stack-up so that the large area ISFET floating gate is not connected to anything during its final definition may require a subsequent metal layer serving as a "jumper" to realize the electrical connection to the floating gate of the transistor. This "jumper" connection scheme prevents charge flow from the large floating gate to the transistor.

This method may be implemented as follows (M=metal layer): i) M1 contacting Poly gate electrode; ii) M2 contacting M1; iii) M3 defines floating gate and separately connects to M2 with isolated island; iv) M4 jumper, having very small area being etched over the isolated islands and connections to floating gate M3, connects the M3 floating gate to the M1/M2/M3 stack connected to the Poly gate immediately over the transistor active area; and v) M3 to M4 interlayer dielectric is removed only over the floating gate so as to expose the bare M3 floating gate. In the method outlined immediately above, step v) need not be done, as the ISFET architecture according to some embodiments discussed above leaves the M4 passivation in place over the M4 floating gate. In one aspect, removal may nonetheless improve ISFET performance in other ways (i.e. sensitivity). In any case, the final chemically-sensitive passivation layer may be a thin sputter-deposited ion-sensitive metal-oxide layer. It should be appreciated that the over-layer jumpered architecture discussed above may be implemented in the standard CMOS fabrication flow to allow any of the first three metal layers to be used as the floating gates (i.e. M1, M2 or M3).

With respect to post-fabrication processes to reduce trapped charge, in one embodiment a "forming gas anneal" may be employed as a post-fabrication process to mitigate potentially adverse effects of trapped charge. In a forming gas anneal, CMOS-fabricated ISFET devices are heated in a hydrogen and nitrogen gas mixture. The hydrogen gas in the mixture diffuses into the gate oxide 165 and neutralizes certain forms of trapped charges. In one aspect, the forming gas anneal need not necessarily remove all gate oxide damage that may result from trapped charges; rather, in some cases, a partial neutralization of some trapped charge is sufficient to significantly improve ISFET performance. In exemplary annealing processes according to the present disclosure, ISFETs may be heated for approximately 30 to 60 minutes at approximately 400 to 425 degrees Celsius in a hydrogen/nitrogen mixture that includes 10% to 15% hydrogen. In one particular implementation, annealing at 425 degrees Celsius at 30 minutes in a hydrogen/nitrogen mixture that includes 10% hydrogen is observed to be particularly effective at improving ISFET performance. For aluminum CMOS processes, the temperature of the anneal should be kept at or below 450 degrees Celsius to avoid damaging the aluminum metallurgy. In another aspect of an annealing process according to the present disclosure, the forming gas anneal is performed after wafers of fabricated ISFET arrays are diced, so as to ensure that damage due to trapped charge induced by the dicing process itself, and/or other pre-dicing processing steps (e.g., plasma etching of metals) may be effectively ameliorated.

In yet other processes for mitigating potentially adverse effects of trapped charge according to embodiments of the present disclosure, a variety of "electrostatic discharge {ESD}-sensitive protocols" may be adopted during any of a variety of wafer post-fabrication handling/packaging steps. For example, in one exemplary process, anti-static dicing tape may be employed to hold wafer substrates in place (e.g., during the dicing process). Also, although high-resistivity (e.g., 10 MΩ) deionized water conventionally is employed in connection with cooling of dicing saws, according to one embodiment of the present disclosure less resistive/more conductive water may be employed for this purpose to facilitate charge conduction via the water; for example, deionized water may be treated with carbon dioxide to lower resistivity and improve conduction of charge arising from the dicing process. Furthermore, conductive and grounded die-ejection tools may be used during various wafer dicing/handling/packaging steps, again to provide effective conduction paths for charge generated during any of these steps, and thereby reduce opportunities for charge to accumulate on one or more conductors of the floating gate structure of respective ISFETs of an array.

Figure 12:
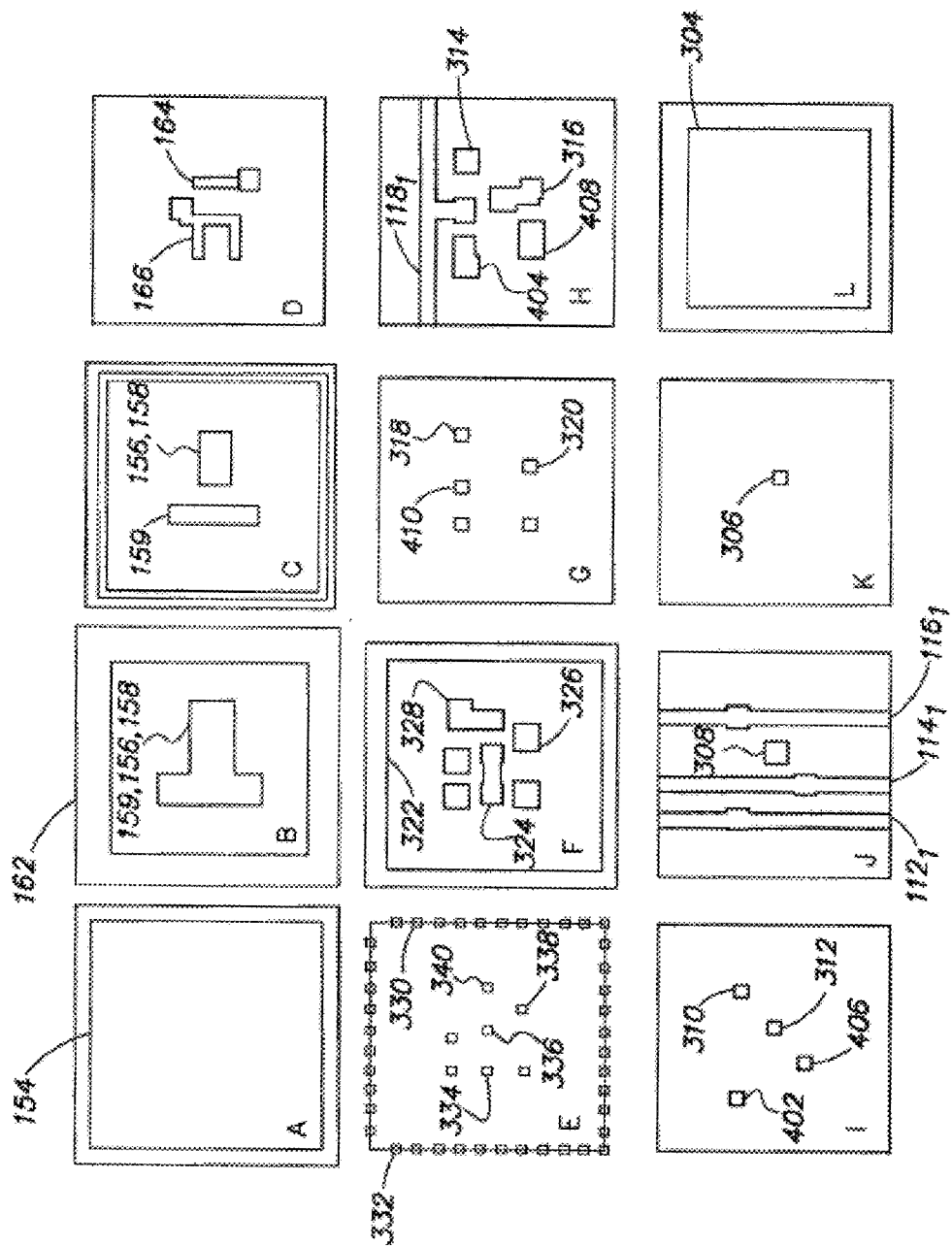
FIGS. 12A through 12L provide top views of each of the fabrication layers shown in FIG. 11A, according to one inventive embodiment of the present disclosure.

In yet another embodiment involving a post-fabrication process to reduce trapped charge, the gate oxide region of an ISFET may be irradiated with UV radiation. With reference again to FIG. 11A, in one exemplary implementation based on this embodiment, an optional hole or window 302 is included during fabrication of an ISFET array in the top metal layer 304 of each pixel of the array, proximate to the ISFET floating gate structure. This window is intended to allow UV radiation, when generated, to enter the ISFETs gate region; in particular, the various layers of the pixel $105_1$. as shown in FIGS. 11 and 12 A-L, are configured such that UV radiation entering the window 302 may impinge in an essentially unobstructed manner upon the area proximate to the polysilicon gate 164 and the gate oxide 165.

To facilitate a UV irradiation process to reduce trapped charge, Applicants have recognized and appreciated that materials other than silicon nitride and silicon oxynitride generally need to be employed in the passivation layer 172 shown in FIG. 11A, as silicon nitride and silicon oxynitride significantly absorb UV radiation. In view of the foregoing, these materials need to be substituted with others that are appreciably transparent to UV radiation, examples of which include, but are not limited to, phososilicate glass (PSG) and boron-doped phososilicate glass (BPSG). PSG and BPSG, however, are not impervious to hydrogen and hydroxyl ions; accordingly, to be employed in a passivation layer of an ISFET designed for pH sensitivity, PSG and BPSG may be used together with an ion-impervious material that is also significantly transparent to UV radiation, such as aluminum oxide ($Al_2O_3$), to form the passivation layer. For example, with reference again to FIG. 11A, PSG or BPSG may be employed as a substitute for silicon nitride or silicon oxynitride in the first portion 172A of the passivation layer 172, and a thin layer (e.g., 400 to 600 Angstroms) of aluminum oxide may be employed in the second portion 172B of the passivation layer 172 (e.g., the aluminum oxide may be deposited using a post-CMOS lift-off lithography process).

In another aspect of an embodiment involving UV irradiation, each ISFET of a sensor array must be appropriately biased during a UV irradiation process to facilitate reduction of trapped charge. In particular, high energy photons from the UV irradiation, impinging upon the bulk silicon region 160 in which the ISFET conducting channel is formed, create electron-hole pairs which facilitate neutralization of trapped charge in the gate oxide as current flows through the ISFETs conducting channel. To this end, an array controller, discussed further below in connection with FIG. 17, generates appropriate signals for biasing the ISFETs of the array during a UV irradiation process. In particular, with reference again to FIG. 9, each of the signals $\overline{RowSel_1}$ through $\overline{RowSel_n}$ is generated so as to enable/select (i.e., turn on) all rows of the sensor array at the same time and thereby couple all of the ISFETs of the array to respective controllable current sources $106_j$ in each column. With all pixels of each column simultaneously selected, the current from the current source $106_j$ of a given column is shared by all pixels of the column. The column amplifiers 107A and 107B are disabled by removing the bias voltage VB4, and at the same time the output of the amplifier 107B, connected to the drain of each ISFET in a given column, is grounded via a switch responsive to a control signal "UV". Also, the common body voltage $V_{BODY}$ for all ISFETs of the array is coupled to electrical ground (i.e., $V_{BODY}$=0 Volts) (as discussed above, during normal operation of the array, the body bias voltage $V_{BODY}$ is coupled to the highest voltage potential available to the array, e.g., VDDA). In one exemplary procedure, the bias voltage VB1 for all of the controllable current sources $106_j$ is set such that each pixel's ISFET conducts approximately 1 μA of current. With the ISFET array thusly biased, the array then is irradiated with a sufficient dose of UV radiation (e.g., from an EPROM eraser generating approximately 20 milliWatts/cm$^2$ of radiation at a distance of approximately one inch from the array for approximately 1 hour). After irradiation, the array may be allowed to rest and stabilize over several hours before use for measurements of chemical properties such as ion concentration.

Figure 13:
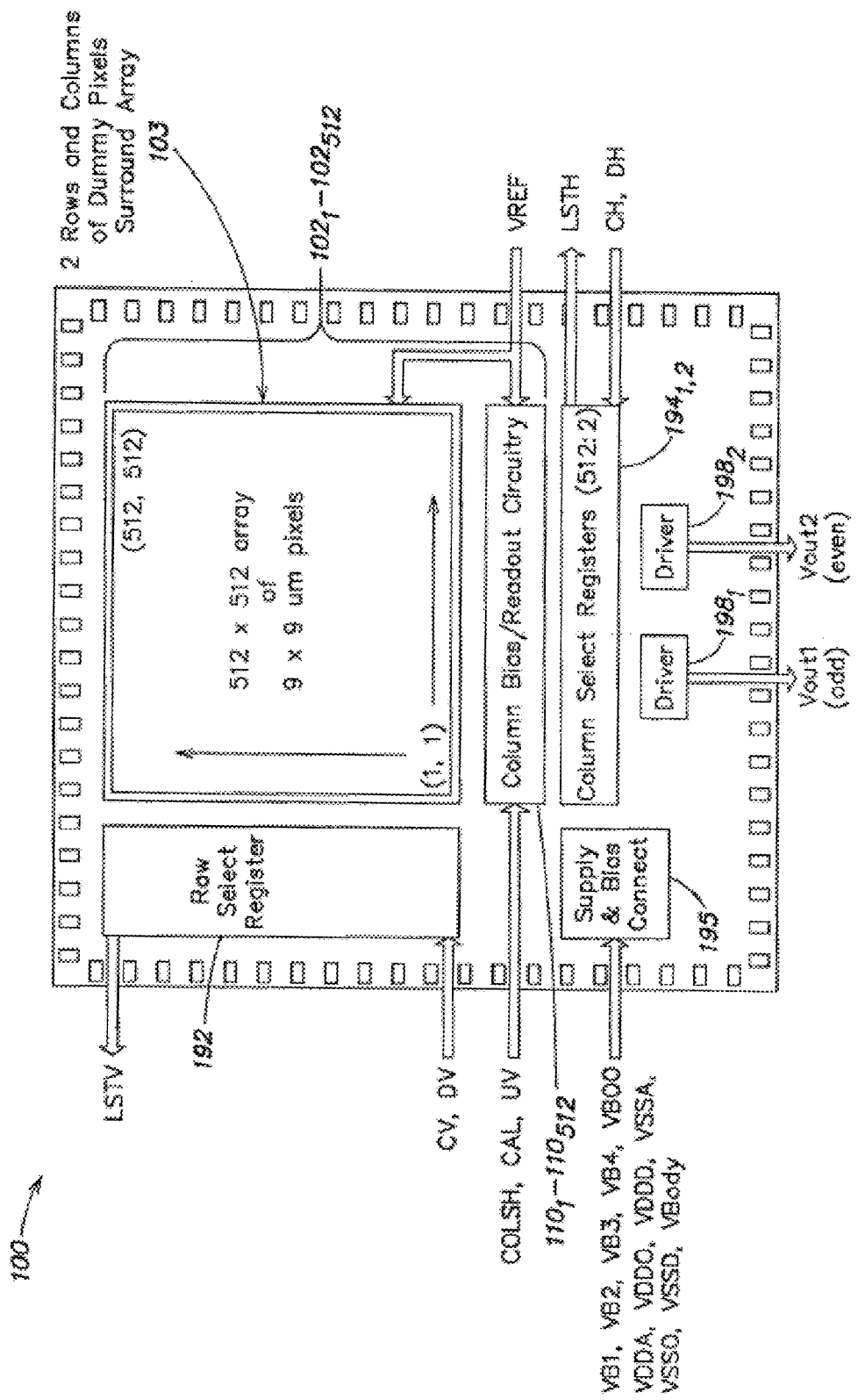
FIG. 13 illustrates a block diagram of an exemplary CMOS IC chip implementation of an chemFET sensor array similar to that shown in FIG. 8, based on the column and pixel designs shown in FIGS. 9-12, according to one inventive embodiment of the present disclosure.

FIG. 13 illustrates a block diagram of an exemplary CMOS IC chip implementation of an ISFET sensor array 100 based on the column and pixel designs discussed above in connection with FIGS. 9-12, according to one embodiment of the present disclosure. In one aspect of this embodiment, the array 100 includes 512 columns $102_1$ through $102_{512}$ with corresponding column bias/readout circuitry $110_1$ through $110_{512}$ (one for each column, as shown in FIG. 9), wherein each column includes 512 geometrically square pixels $105_1$ through $105_{512}$, each having a size of approximately 9 micrometers by 9 micrometers (i.e., the array is 512 columns by 512 rows). In another aspect, the entire array (including pixels together with associated row and column select circuitry and column bias/readout circuitry) may be fabricated on a semiconductor die as an application specific integrated circuit (ASIC) having dimensions of approximately 7 millimeters by 7 millimeters. While an array of 512 by 512 pixels is shown in the embodiment of FIG. 13, it should be appreciated that arrays may be implemented with different numbers of rows and columns and different pixel sizes according to other embodiments, as discussed further below in connection with FIGS. 19-23.

Also, as discussed above, it should be appreciated that arrays according to various embodiments of the present invention may be fabricated according to conventional CMOS fabrications techniques, as well as modified CMOS fabrication techniques (e.g., to facilitate realization of various functional aspects of the chemFET arrays discussed herein, such as additional deposition of passivation materials, process steps to mitigate trapped charge, etc.) and other semiconductor fabrication techniques beyond those conventionally employed in CMOS fabrication. Additionally, various lithography techniques may be employed as part of an array fabrication process. For example, in one exemplary implementation, a lithography technique may be employed in which appropriately designed blocks are "stitched" together by overlapping the edges of a step and repeat lithography exposures on a wafer substrate by approximately 0.2 micrometers. In a single exposure, the maximum die size typically is approximately 21 millimeters by 21 millimeters. By selectively exposing different blocks (sides, top & bottoms, core, etc.) very large chips can be defined on a wafer (up to a maximum, in the extreme, of one chip per wafer, commonly referred to as "wafer scale integration").

In one aspect of the array 100 shown in FIG. 13, the first and last two columns $102_1$, $102_2$, $102_{511}$ and $102_{512}$, as well as the first two pixels $105_1$ and $105_2$ and the last two pixels $105_{511}$ and $105_{512}$ of each of the columns $102_3$ through $102_{510}$ (e.g., two rows and columns of pixels around a perimeter of the array) may be configured as "reference" or "dummy" pixels 103. With reference to FIG. 11A, for the dummy pixels of an array, the topmost metal layer 304 of each dummy pixel's ISFET (coupled ultimately to the ISFETs polysilicon gate 164) is tied to the same metal layer of other dummy pixels and is made accessible as a terminal of the chip, which in turn may be coupled to a reference voltage VREF. As discussed above in connection with FIG. 9, the reference voltage VREF also may be applied to the bias/readout circuitry of respective columns of the array. In some exemplary implementations discussed further below, preliminary test/evaluation data may be acquired from the array based on applying the reference voltage VREF and selecting and reading out dummy pixels, and/or reading out columns based on the direct application of VREF to respective column buffers (e.g., via the CAL signal), to facilitate offset determination (e.g., pixel-to-pixel and column-to-column variances) and array calibration.

In FIG. 13, various power supply and bias voltages required for array operation (as discussed above in connection with FIG. 9) are provided to the array via electrical connections (e.g., pins, metal pads) and labeled for simplicity in block 195 as "supply and bias connections." The array 100 of FIG. 13 also includes a row select shift register 192, two sets of column select shift registers $194_{1,2}$ and two output drivers $198_1$ and $198_2$ to provide two parallel output signals from the array, Vout1 and Vout2, representing sensor measurements. The various power supply and bias voltages, control signals for the row and column shift registers, and control signals for the column bias/readout circuitry shown in FIG. 13 are provided by an array controller, as discussed further below in connection with FIG. 17, which also reads the output signals Vout1 and Vout2 (and other optional status/diagnostic signals) from the array 100. In another aspect of the array embodiment shown in FIG. 13, configuring the array such that multiple regions (e.g., multiple columns) of the array may be read at the same time via multiple parallel array outputs (e.g., Vout1 and Vout2) facilitates increased data acquisition rates, as discussed further below in connection with FIGS. 17 and 18. While FIG. 13 illustrates an array having two column select registers and parallel output signals Vout1 and Vout2 to acquire data simultaneously from two columns at a time, it should be appreciated that, in other embodiments, arrays according to the present disclosure may be configured to have only one measurement signal output, or more than two measurement signal outputs; in particular, as discussed further below in connection with FIGS. 19-23, more dense arrays according to other inventive embodiments may be configured to have four our more parallel measurement signal outputs and simultaneously enable different regions of the array to provide data via the four our more outputs.

Figure 14:
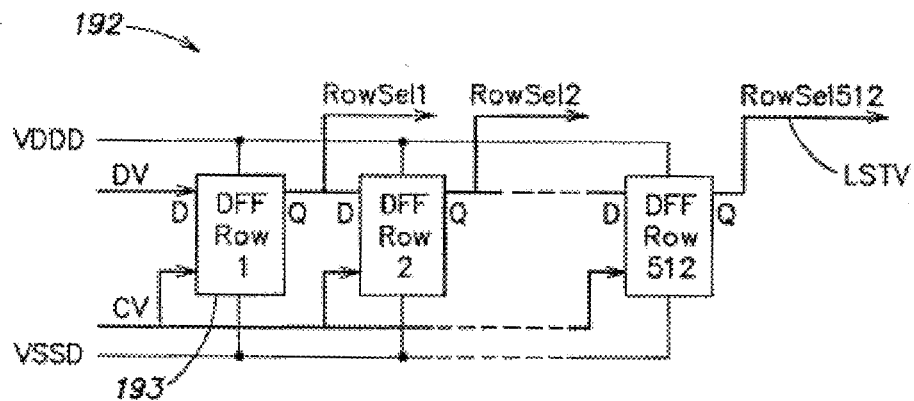
FIG. 14 illustrates a row select shift register of the array shown in FIG. 13, according to one inventive embodiment of the present disclosure.
Figure 15:
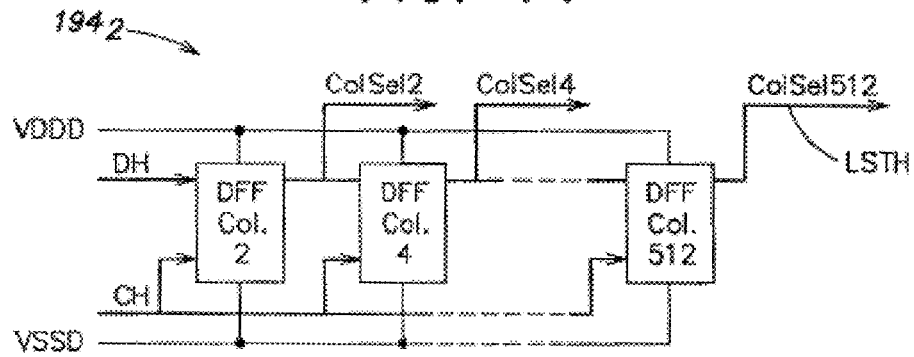
FIG. 15 illustrates one of two column select shift registers of the array shown in FIG. 13, according to one inventive embodiment of the present disclosure.
Figure 16:
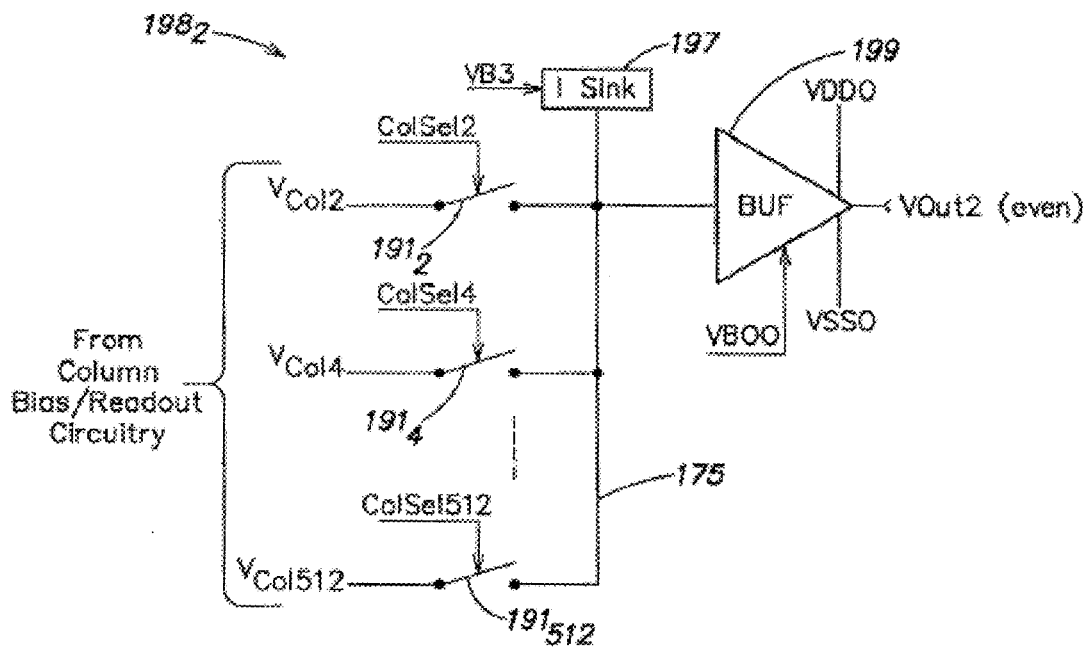
FIG. 16 illustrates one of two output drivers of the array shown in FIG. 13, according to one inventive embodiment of the present disclosure.

FIG. 14 illustrates the row select shift register 192, FIG. 15 illustrates one of the column select shift registers $194_2$ and FIG. 16 illustrates one of the output drivers $198_2$ of the array 100 shown in FIG. 13, according to one exemplary implementation. As shown in FIGS. 14 and 15, the row and column select shift registers are implemented as a series of D-type flip-flops coupled to a digital circuitry positive supply voltage VDDD and a digital supply ground VSSD. In the row and column shift registers, a data signal is applied to a D-input of first flip-flop in each series and a clock signal is applied simultaneously to a clock input of all of the flip-flops in the series. For each flip-flop, a "Q" output reproduces the state of the D-input upon a transition (e.g., falling edge) of the clock signal. With reference to FIG. 14, the row select shift register 192 includes 512 D-type flip-flops, in which a first flip-flop 193 receives a vertical data signal DV and all flip-flops receive a vertical clock signal CV. A "Q" output of the first flip-flop 193 provides the first row select signal RowSel$_1$ and is coupled to the D-input of the next flip-flop in the series. The Q outputs of successive flip-flops are coupled to the D-inputs of the next flip-flop in the series and provide the row select signals $RowSel_2$ through $RowSel_{512}$ with successive falling edge transitions of the vertical clock signal CV, as discussed further below in connection with FIG. 18. The last row select signal $RowSel_{512}$ also may be taken as an optional output of the array 100 as the signal LSTV (Last STage Vertical), which provides an indication (e.g., for diagnostic purposes) that the last row of the array has been selected. While not shown explicitly in FIG. 14, each of the row select signals $RowSel_1$ through $RowSel_{512}$ is applied to a corresponding inverter, the output of which is used to enable a given pixel in each column (as illustrated in FIG. 9 by the signals $\overline{RowSel_1}$ through $\overline{RowSel_n}$).

Regarding the column select shift registers $194_1$ and $194_2$, these are implemented in a manner similar to that of the row select shift registers, with each column select shift register comprising 256 series-connected flip-flops and responsible for enabling readout from either the odd columns of the array or the even columns of the array. For example, FIG. 15 illustrates the column select shift register $194_2$, which is configured to enable readout from all of the even numbered columns of the array in succession via the column select signals $ColSel_2$, $ColSel_4$, ... $COLSEL_{512}$, whereas another column select shift register $194_1$ is configured to enable readout from all of the odd numbered columns of the array in succession (via column select signals $ColSel_1$, $ColSel_3$, ... $ColSel_{511}$). Both column select shift registers are controlled simultaneously by the horizontal data signal DH and the horizontal clock signal CH to provide the respective column select signals, as discussed further below in connection with FIG. 18. As shown in FIG. 15, the last column select signal $ColSel_{512}$ also may be taken as an optional output of the array 100 as the signal LSTH (Last STage Horizontal), which provides an indication (e.g., for diagnostic purposes) that the last column of the array has been selected.

With reference again for the moment to FIG. 7, Applicants have recognized and appreciated that an implementation for array row and column selection based on shift registers, as discussed above in connection with FIGS. 13-15, is a significant improvement to the row and column decoder approach employed in various prior art ISFET array designs, including the design of Milgrew et al. shown in FIG. 7. In particular, regarding the row decoder 92 and the column decoder 94 shown in FIG. 7, the complexity of implementing these components in an integrated circuit array design increases dramatically as the size of the array is increased, as additional inputs to both decoders are required. For example, an array having 512 rows and columns as discussed above in connection with FIG. 13 would require nine inputs ($2^9$=512) per row and column decoder if such a scheme were employed for row and column selection; similarly, arrays having 7400 rows and 7400 columns, as discussed below in connection with other embodiments, would require 13 inputs ($2^{13}$=8192) per row and column decoder. In contrast, the row and column select shift registers shown in FIGS. 14 and 15 require no additional input signals as array size is increased, but rather additional D-type flip-flops (which are routinely implemented in a CMOS process). Thus, the shift register implementations shown in FIGS. 14 and 15 provide an easily scalable solution to array row and column selection.

In the embodiment of FIG. 13, the "odd" column select shift register $194_1$ provides odd column select signals to an "odd" output driver $198_1$ and the even column select shift register $194_2$ provides even column select signals to an "even" output driver $198_2$. Both output drivers are configured similarly, and an example of the even output driver $198_2$ is shown in FIG. 16. In particular, FIG. 16 shows that respective even column output signals $V_{COL2}$, $V_{COL4}$, ... $V_{COL512}$ (refer to FIG. 9 for the generic column signal output $V_{COLj}$) are applied to corresponding switches $191_2$, $191_4$, ... $191_{512}$, responsive to the even column select signals $ColSel_2$, $ColSel_4$, ... $ColSel_{512}$ provided by the column select register $194_2$, to successively couple the even column output signals to the input of a buffer amplifier 199 (BUF) via a bus 175. In FIG. 16, the buffer amplifier 199 receives power from an output buffer positive supply voltage VDDO and an output buffer supply ground VSSO, and is responsive to an output buffer bias voltage VBO0 to set a corresponding bias current for the buffer output. Given the high impedance input of the buffer amplifier 199, a current sink 197 responsive to a bias voltage VB3 is coupled to the bus 175 to provide an appropriate drive current (e.g., on the order of approximately 100 μA) for the output of the column output buffer (see the buffer amplifier 111j of FIG. 9) of a selected column. The buffer amplifier 199 provides the output signal Vout2 based on the selected even column of the array; at the same time, with reference to FIG. 13, a corresponding buffer amplifier of the "odd" output driver $198_1$ provides the output signal Vout1 based on a selected odd column of the array.

In one exemplary implementation, the switches of both the even and odd output drivers $198_1$ and $198_2$ (e.g., the switches $191_2$, $191_4$, ... $191_{512}$ shown in FIG. 16) may be implemented as CMOS-pair transmission gates (including an n-channel MOSFET and a p-channel MOSFET; see FIG. 4), and inverters may be employed so that each column select signal and its complement may be applied to a given transmission gate switch 191 to enable switching. Each switch 191 has a series resistance when enabled or "on" to couple a corresponding column output signal to the bus 175; likewise, each switch adds a capacitance to the bus 175 when the switch is off. A larger switch reduces series resistance and allows a higher drive current for the bus 175, which generally allows the bus 175 to settle more quickly; on the other hand, a larger switch increases capacitance of the bus 175 when the switch is off, which in turn increases the settling time of the bus 175. Hence, there is a trade-off between switch series resistance and capacitance in connection with switch size.

The ability of the bus 175 to settle quickly following enabling of successive switches in turn facilitates rapid data acquisition from the array. To this end, in some embodiments the switches 191 of the output drivers $198_1$ and $198_2$ are particularly configured to significantly reduce the settling time of the bus 175. Both the n-channel and the p-channel MOSFETs of a given switch add to the capacitance of the bus 175; however, n-channel MOSFETs generally have better frequency response and current drive capabilities than their p-channel counterparts. In view of the foregoing, Applicants have recognized and appreciated that some of the superior characteristics of n-channel MOSFETs may be exploited to improve settling time of the bus 175 by implementing "asymmetric" switches in which respective sizes for the n-channel MOSFET and p-channel MOSFET of a given switch are different.

For example, in one embodiment, with reference to FIG. 16, the current sink 197 may be configured such that the bus 175 is normally "pulled down" when all switches $191_2$, $191_4$, ... $191_{512}$ are open or off (not conducting). Given a somewhat limited expected signal dynamic range for the column output signals based on ISFET measurements, when a given switch is enabled or on (conducting), in many instances most of the conduction is done by the n-channel MOSFET of the CMOS-pair constituting the switch. Accordingly, in one aspect of this embodiment, the n-channel MOSFET and the p-channel MOSFET of each switch 191 are sized differently; namely, in one exemplary implementation, the n-channel MOSFET is sized to be significantly larger than the p-channel MOSFET. More specifically, considering equally-sized n-channel and p-channel MOSFETs as a point of reference, in one implementation the n-channel MOSFET may be increased to be about 2 to 2.5 times larger, and the p-channel MOSFET may be decreased in size to be about 8 to 10 times smaller, such that the n-channel MOSFET is approximately 20 times larger than the p-channel MOSFET. Due to the significant decrease is size of the p-channel MOSFET and the relatively modest increase in size of the n-channel MOSFET, the overall capacitance of the switch in the off state is notably reduced, and there is a corresponding notable reduction in capacitance for the bus 175; at the same time, due to the larger n-channel MOSFET, there is a significant increase in current drive capability, frequency response and transconductance of the switch, which in turn results in a significant reduction in settling time of the bus 175.

While the example above describes asymmetric switches 191 for the output drivers $198_1$ and $198_2$ in which the n-channel MOSFET is larger than the p-channel MOSFET, it should be appreciated that in another embodiment, the converse may be implemented, namely, asymmetric switches in which the p-channel MOSFET is larger than the n-channel MOSFET. In one aspect of this embodiment, with reference again to FIG. 16, the current sink 197 may alternatively serve as a source of current to appropriately drive the output of the column output buffer (see the buffer amplifier 111$j$ of FIG. 9) of a selected column, and be configured such that the bus 175 is normally "pulled up" when all switches $191_2$, $191_4$, ... $191_{512}$ are open or off (not conducting). In this situation, most of the switch conduction may be accomplished by the p-channel MOSFET of the CMOS-pair constituting the switch. Benefits of reduced switch capacitance (and hence reduced bus capacitance) may be realized in this embodiment, although the overall beneficial effect of reduced settling time for the bus 175 may be somewhat less than that described previously above, due to the lower frequency response of p-channel MOSFETs as compared to n-channel MOSFETs. Nevertheless, asymmetric switches based on larger p-channel MOSFETs may still facilitate a notable reduction in bus settling time, and may also provide for circuit implementations in which the column output buffer amplifier (111$j$ of FIG. 9) may be a body-tied source follower with appreciably increased gain.

In yet another embodiment directed to facilitating rapid settling of the bus 175 shown in FIG. 16, it may be appreciated that fewer switches 191 coupled to the bus 175 results in a smaller bus capacitance. With this in mind, and with reference again to FIG. 13, in yet another embodiment, more than two output drivers $198_1$ and $198_2$ may be employed in the ISFET array 100 such that each output driver handles a smaller number of columns of the array. For example, rather than having all even columns handled by one driver and all odd columns handled by another, the array may include four column select registers $194_{1,2,3,4}$ and four corresponding output drivers $198_{1,2,3,4}$ such that each output driver handles one-fourth of the total columns of the array, rather than one-half of the columns. In such an implementation, each output driver would accordingly have half the number of switches 191 as compared with the embodiment discussed above in connection with FIG. 16, and the bus 175 of each output driver would have a corresponding lower capacitance, thereby improving bus settling time. While four output drivers are discussed for purposes of illustration in this example, it should be appreciated that the present disclosure is not limited in this respect, and virtually any number of output drivers greater than two may be employed to improve bus settling time in the scenario described above. Other array embodiments in which more than two output drivers are employed to facilitate rapid data acquisition from the array are discussed in greater detail below (e.g., in connection with FIGS. 19-23).

In one aspect of the array design discussed above in connection with FIGS. 13-16, separate analog supply voltage connections (for VDDA, VSSA), digital supply voltage connections (for VDDD, VSSD) and output buffer supply voltage connections (for VDDO, VSSO) are provided on the array to facilitate noise isolation and reduce signal cross-talk amongst various array components, thereby increasing the signal-to-noise ratio (SNR) of the output signals Vout1 and Vout2. In one exemplary implementation, the positive supply voltages VDDA, VDDD and VDDO each may be approximately 3.3 Volts. In another aspect, these voltages respectively may be provided "off chip" by one or more programmable voltage sources, as discussed further below in connection with FIG. 17.

Figure 17:
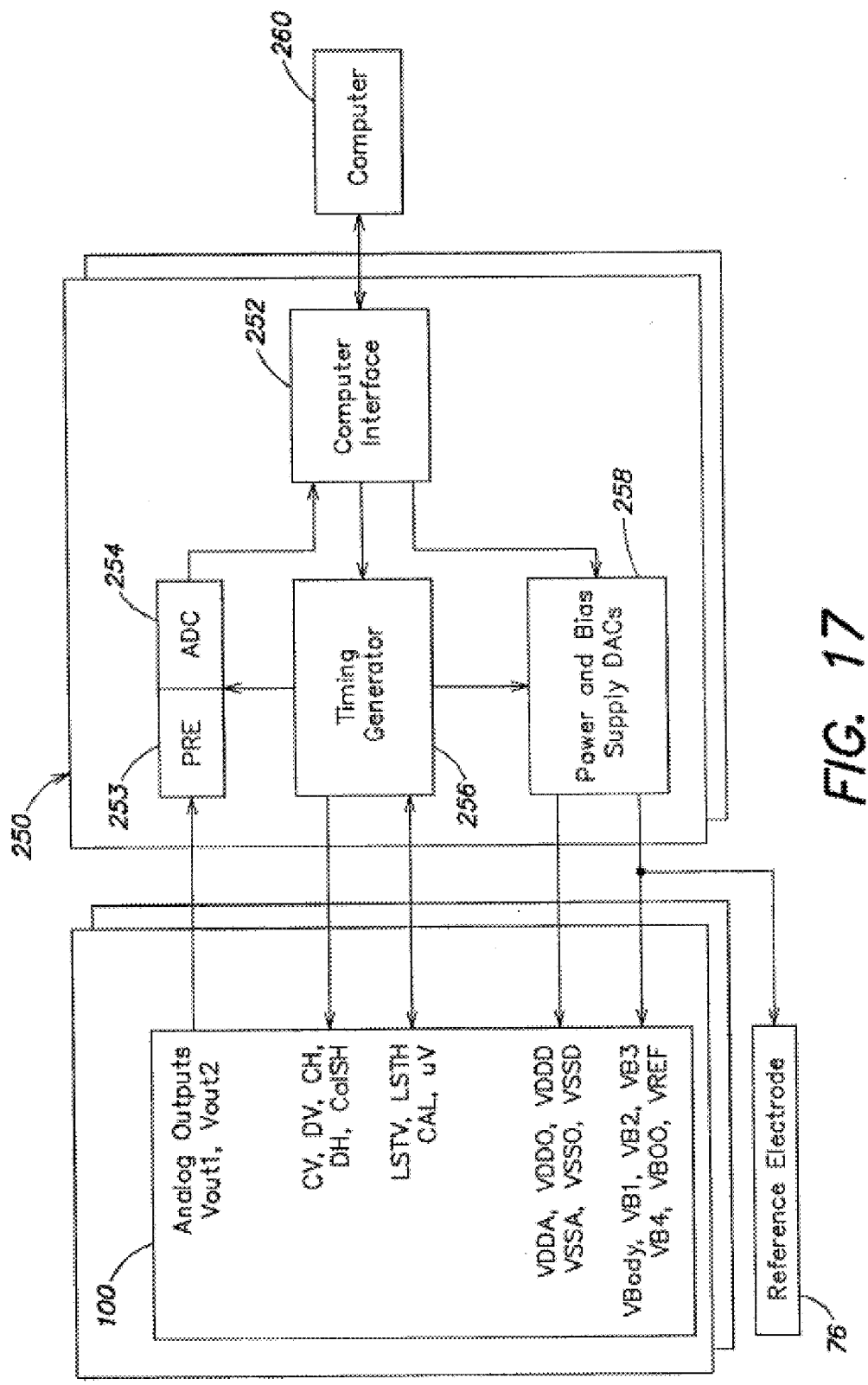
FIG. 17 illustrates a block diagram of the chemFET sensor array of FIG. 13 coupled to an array controller, according to one inventive embodiment of the present disclosure.

FIG. 17 illustrates a block diagram of the sensor array 100 of FIG. 13 coupled to an array controller 250, according to one inventive embodiment of the present disclosure. In various exemplary implementations, the array controller 250 may be fabricated as a "stand alone" controller, or as a computer compatible "card" forming part of a computer 260, as discussed above in connection with FIG. 8. In one aspect, the functions of the array controller 250 may be controlled by the computer 260 through an interface block 252 (e.g., serial interface, via USB port or PCI bus, Ethernet connection, etc.), as shown in FIG. 17. In one embodiment, the array controller 250 is fabricated as a printed circuit board into which the array 100 plugs, similar to a conventional IC chip (e.g., the array 100 is configured as an ASIC that plugs into the array controller). In one aspect of such an embodiment, all or portions of the array controller 250 may be implemented as a field programmable gate array (FPGA) configured to perform various array controller functions described in further detail below.

Generally, the array controller 250 provides various supply voltages and bias voltages to the array 100, as well as various signals relating to row and column selection, sampling of pixel outputs and data acquisition. In particular, the array controller 250 reads the two analog output signals Vout1 (odd columns) and Vout2 (even columns) including multiplexed respective pixel voltage signals from the array 100 and then digitizes these respective pixel signals to provide measurement data to the computer 260, which in turn may store and/or process the data. In some implementations, the array controller 250 also may be configured to perform or facilitate various array calibration and diagnostic functions, and an optional array UV irradiation treatment as discussed above in connection with FIG. 11A.

As illustrated in FIG. 17, the array controller 250 generally provides to the array 100 the analog supply voltage and ground (VDDA, VSSA), the digital supply voltage and ground (VDDD, VSSD), and the buffer output supply voltage and ground (VDDO, VSSO). In one exemplary implementation, each of the supply voltages VDDA, VDDD and VDDO is approximately 3.3 Volts. As discussed above, in one aspect each of these power supply voltages is provided to the array 100 via separate conducting paths to facilitate noise isolation. In another aspect, these supply voltages may originate from respective power supplies/regulators, or one or more of these supply voltages may originate from a common source in a power supply 258 of the array controller 250. The power supply 258 also may provide the various bias voltages required for array operation (e.g., VB1, VB2, VB3, VB4, VBO0, $V_{BODY}$) and the reference voltage VREF used for array diagnostics and calibration. In another aspect, the power supply 258 includes one or more digital-to-analog converters (DACs) that may be controlled by the computer 260 to allow any or all of the bias voltages, reference voltage, and supply voltages to be changed under software control (i.e., programmable bias settings). For example, a power supply 258 responsive to computer control may facilitate adjustment of the bias voltages VB1 and VB2 for pixel drain current, VB3 for column bus drive, VB4 for column amplifier bandwidth, and VBO0 for column output buffer current drive. In some aspects, one or more bias voltages may be adjusted to optimize settling times of signals from enabled pixels. Additionally, the common body voltage $V_{BODY}$ for all ISFETs of the array may be grounded during an optional post-fabrication UV irradiation treatment to reduce trapped charge, and then coupled to a higher voltage (e.g., VDDA) during diagnostic analysis, calibration, and normal operation of the array for measurement/data acquisition. Likewise, the reference voltage VREF may be varied to facilitate a variety of diagnostic and calibration functions.

As also shown in FIG. 17, the reference electrode 76 which is typically employed in connection with an analyte solution to be measured by the array 100 (as discussed above in connection with FIG. 1), may be coupled to the power supply 258 to provide a reference potential for the pixel output voltages. For example, in one implementation the reference electrode 76 may be coupled to a supply ground (e.g., the analog ground VSSA) to provide a reference for the pixel output voltages based on Eq. (3) above. In other exemplary implementations, the reference electrode voltage may be set by placing a solution/sample of interest having a known pH level in proximity to the sensor array 100 and adjusting the reference electrode voltage until the array output signals Vout1 and Vout2 provide pixel voltages at a desired reference level, from which subsequent changes in pixel voltages reflect local changes in pH with respect to the known reference pH level. In general, it should be appreciated that a voltage associated with the reference electrode 76 need not necessarily be identical to the reference voltage VREF discussed above (which may be employed for a variety of array diagnostic and calibration functions), although in some implementations the reference voltage VREF provided by the power supply 258 may be used to set the voltage of the reference electrode 76.

Regarding data acquisition from the array 100, in one embodiment the array controller 250 of FIG. 17 may include one or more preamplifiers 253 to further buffer the output signals Vout1 and Vout2 from the sensor array and provide selectable gain. In one aspect, the array controller 250 may include one preamplifier for each output signal (e.g., two preamplifiers for two analog output signals). In other aspects, the preamplifiers may be configured to accept input voltages from 0.0 to 3.3 Volts, may have programmable/computer selectable gains (e.g., 1, 2, 5, 10 and 20) and low noise outputs (e.g., <10 nV/sqrtHz), and may provide low pass filtering (e.g., bandwidths of 5 MHz and 25 MHz). In yet another aspect, the preamplifiers may have a programmable/computer selectable offset for input and/or output voltage signals to set a nominal level for either to a desired range.

The array controller 250 of FIG. 17 also comprises one or more analog-to-digital converters 254 (ADCs) to convert the sensor array output signals Vout1 and Vout2 to digital outputs (e.g., 10-bit or 12-bit) so as to provide data to the computer 260. In one aspect, one ADC may be employed for each analog output of the sensor array, and each ADC may be coupled to the output of a corresponding preamplifier (if preamplifiers are employed in a given implementation). In another aspect, the ADC(s) may have a computer-selectable input range (e.g., 50 mV, 200 mV, 500 mV, 1 V) to facilitate compatibility with different ranges of array output signals and/or preamplifier parameters. In yet other aspects, the bandwidth of the ADC(s) may be greater than 60 MHz, and the data acquisition/conversion rate greater than 25 MHz (e.g., as high as 100 MHz or greater).

In the embodiment of FIG. 17, ADC acquisition timing and array row and column selection may be controlled by a timing generator 256. In particular, the timing generator provides the digital vertical data and clock signals (DV, CV) to control row selection, the digital horizontal data and clock signals (DH, CH) to control column selection, and the column sample and hold signal COL SH to sample respective pixel voltages for an enabled row, as discussed above in connection with FIG. 9. In some implementations, the timing generator 256 may be implemented by a microprocessor executing code and configured as a multi-channel digital pattern generator to provide appropriately timed control signals. In one exemplary implementation, the timing generator 256 may be implemented as a field-programmable gate array (FPGA).

Figure 18:
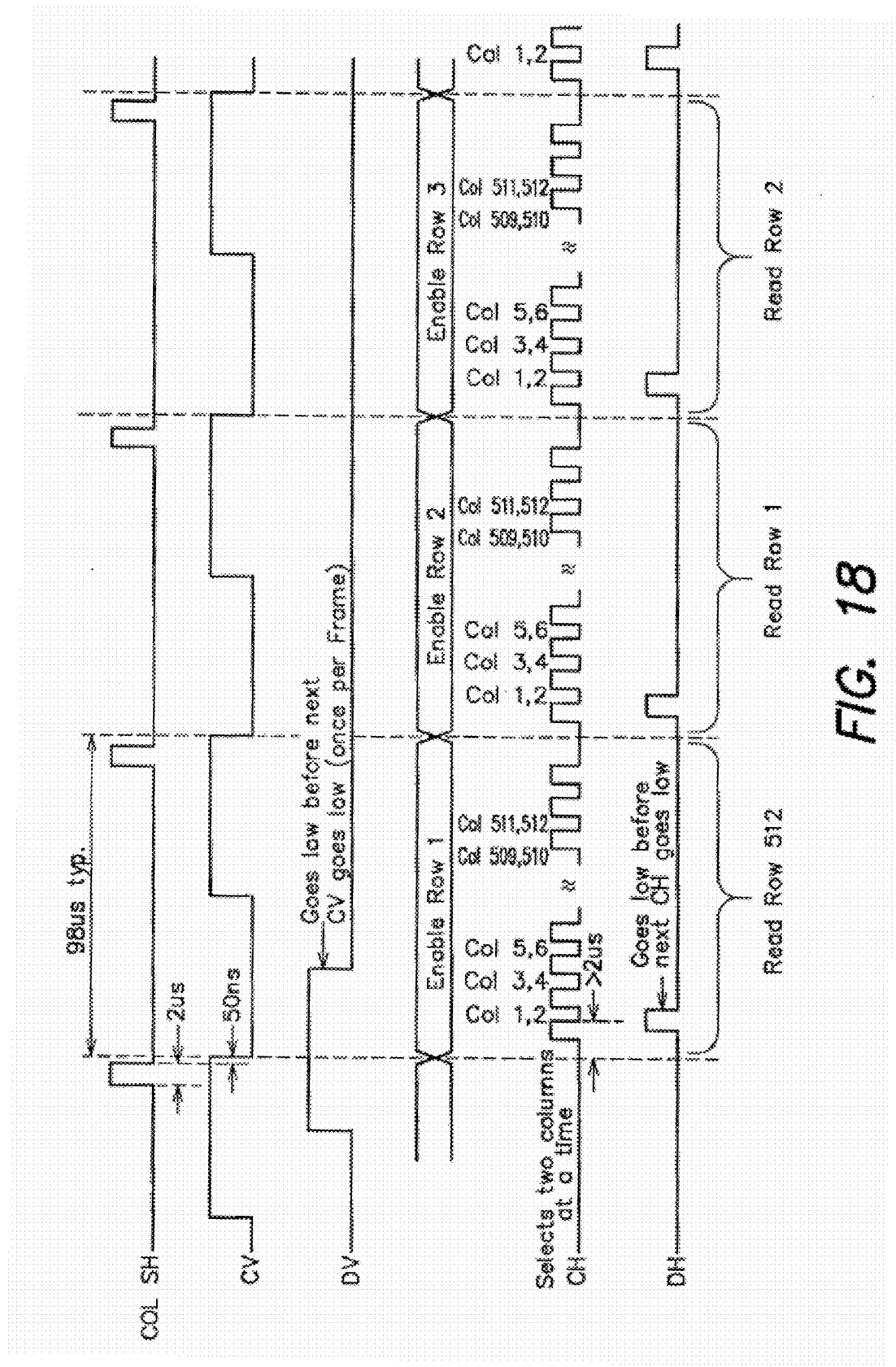
FIG. 18 illustrates an exemplary timing diagram for various signals provided by the array controller of FIG. 17, according to one inventive embodiment of the present disclosure.

FIG. 18 illustrates an exemplary timing diagram for such signals, as provided by the timing generator 256, to acquire pixel data from the sensor array 100. For purposes of the following discussion, a "frame" is defined as a data set that includes a value (e.g., pixel output signal or voltage $V_S$) for each pixel in the array, and a "frame rate" is defined as the rate at which successive frames may be acquired from the array. In the example of FIG. 18, an exemplary frame rate of 20 frames/sec is chosen to illustrate operation of the array (i.e., row and column selection and signal acquisition); however, it should be appreciated that arrays and array controllers according to the present disclosure are not limited in this respect, as different frame rates, including lower frame rates (e.g., 1 to 10 frames/second) or higher frame rates (e.g., 25, 30, 40, 50, 60, 70 to 100 frames/sec., etc.), with arrays having the same or higher numbers of pixels, are possible. In some exemplary applications, a data set may be acquired that includes many frames over several seconds to conduct an experiment on a given analyte or analytes. Several such experiments may be performed in succession, in some cases with pauses in between to allow for data transfer/processing and/or washing of the sensor array ASIC and reagent preparation for a subsequent experiment.

In one implementation, the array controller 250 controls the array 100 to enable rows successively, one at a time. For example, with reference again for the moment to FIG. 9, a first row of pixels is enabled via the row select signal $\overline{\text{RowSel}_1}$. The enabled pixels are allowed to settle for some time period, after which the COL SH signal is asserted briefly to close the sample/hold switch in each column and store on the column's sample/hold capacitor Csh the voltage value output by the first pixel in the column. This voltage is then available as the column output voltage $V_{COLj}$ applied to one of the two (odd and even column) array output drivers $198_1$ and $198_2$ (e.g., see FIG. 16). The COL SH signal is then de-asserted, thereby opening the sample/hold switches in each column and decoupling the column output buffer 111j from the column amplifiers 107A and 107B. Shortly thereafter, the second row of pixels is enabled via the row select signal $\overline{\text{RowSel}_2}$. During the time period in which the second row of pixels is allowed to settle, the column select signals are generated two at a time (one odd and one even; odd column select signals are applied in succession to the odd output driver, even column select signals are applied in succession to the even output driver) to read the column output voltages associated with the first row. Thus, while a given row in the array is enabled and settling, the previous row is being read out, two columns at a time. By staggering row selection and sampling/readout, and by reading multiple columns at a time for a given row, a frame of data may be acquired from the array in a significantly streamlined manner.

FIG. 18 illustrates the timing details of the foregoing process for an exemplary frame rate of 20 frames/sec. Given this frame rate and 512 rows in the array, each row must be read out in approximately 98 microseconds, as indicated by the vertical delineations in FIG. 18. Accordingly, the vertical clock signal CV has a period of 98 microseconds (i.e., a clock frequency of over 10 kHz), with a new row being enabled on a trailing edge (negative transition) of the CV signal. The left side of FIG. 18 reflects the beginning of a new frame cycle, at which point the vertical data signal DV is asserted before a first trailing edge of the CV signal and de-asserted before the next trailing edge of the CV signal (for data acquisition from successive frames, the vertical data signal is reasserted again only after row 512 is enabled). Also, immediately before each trailing edge of the CV signal (i.e., new row enabled), the COL SH signal is asserted for 2 microseconds, leaving approximately 50 nanoseconds before the trailing edge of the CV signal.

In FIG. 18, the first occurrence of the COL SH signal is actually sampling the pixel values of row 512 of the array. Thus, upon the first trailing edge of the CV signal, the first row is enabled and allowed to settle (for approximately 96 microseconds) until the second occurrence of the COL SH signal. During this settling time for the first row, the pixel values of row 512 are read out via the column select signals. Because two column select signals are generated simultaneously to read 512 columns, the horizontal clock signal CH must generate 256 cycles within this period, each trailing edge of the CH signal generating one odd and one even column select signal. As shown in FIG. 18, the first trailing edge of the CH signal in a given row is timed to occur two microseconds after the selection of the row to allow for settling of the voltage values stored on the sample/hold capacitors $C_{sh}$ and provided by the column output buffers. Also for each row, the horizontal data signal DH is asserted before the first trailing edge of the CH signal and de-asserted before the next trailing edge of the CH signal. The last two columns (e.g., 511 and 512) are selected before the occurrence of the COL SH signal which, as discussed above, occurs approximately two microseconds before the next row is enabled. Thus, 512 columns are read, two at a time, within a time period of approximately 94 microseconds (i.e., 98 microseconds per row, minus two microseconds at the beginning and end of each row). This results in a data rate for each of the array output signals Vout1 and Vout2 of approximately 2.7 MHz. In another aspect, the ADC(s) 254 may be controlled by the timing generator 256 to sample the output signals Vout1 and Vout2 at a significantly higher rate to provide multiple digitized samples for each pixel measurement, which may then be averaged (e.g., the ADC data acquisition rate may be approximately 100 MHz to sample the 2.7 MHz array output signals, thereby providing as many as approximately 35-40 samples per pixel measurement).

In addition to controlling the sensor array and ADCs, the timing generator 256 may be configured to facilitate various array calibration and diagnostic functions, as well as an optional UV irradiation treatment. To this end, the timing generator may utilize the signal LSTV indicating the selection of the last row of the array and the signal LSTH to indicate the selection of the last column of the array. The timing generator 256 also may be responsible for generating the CAL signal which applies the reference voltage VREF to the column buffer amplifiers, and generating the UV signal which grounds the drains of all ISFETs in the array during a UV irradiation process (see FIG. 9). The timing generator also may provide some control function over the power supply 258 during various calibration and diagnostic functions, or UV irradiation, to appropriately control supply or bias voltages; for example, during UV irradiation, the timing generator may control the power supply to couple the body voltage $V_{BODY}$ to ground while the UV signal is activated to ground the ISFET drains. With respect to array calibration and diagnostics, as well as UV irradiation, in some implementations the timing generator may receive specialized programs from the computer 260 to provide appropriate control signals. In one aspect, the computer 260 may use various data obtained from dummy pixels of the array, as well as column information based on the application of the CAL signal and the reference voltage VREF, to determine various calibration parameters associated with a given array and/or generate specialized programs for calibration and diagnostic functions.

With respect to the computer interface 252 of the array controller 250, in one exemplary implementation the interface is configured to facilitate a data rate of approximately 200 MB/sec to the computer 260, and may include local storage of up to 400 MB or greater. The computer 260 is configured to accept data at a rate of 200 MB/sec, and process the data so as to reconstruct an image of the pixels (e.g., which may be displayed in false-color on a monitor). For example, the computer may be configured to execute a general-purpose program with routines written in C++ or Visual Basic to manipulate the data and display is as desired.

Having discussed several aspects of an exemplary ISFET array and an array controller according to the present disclosure, FIGS. 19-23 illustrate block diagrams of alternative CMOS IC chip implementations of ISFET sensor arrays having greater numbers of pixels, according to yet other inventive embodiments. In one aspect, each of the ISFET arrays discussed further below in connection with FIGS. 19-23 may be controlled by an array controller similar to that shown in FIG. 17, in some cases with minor modifications to accommodate higher numbers of pixels (e.g., additional preamplifiers 253 and analog-to-digital converters 254).

Figure 19:
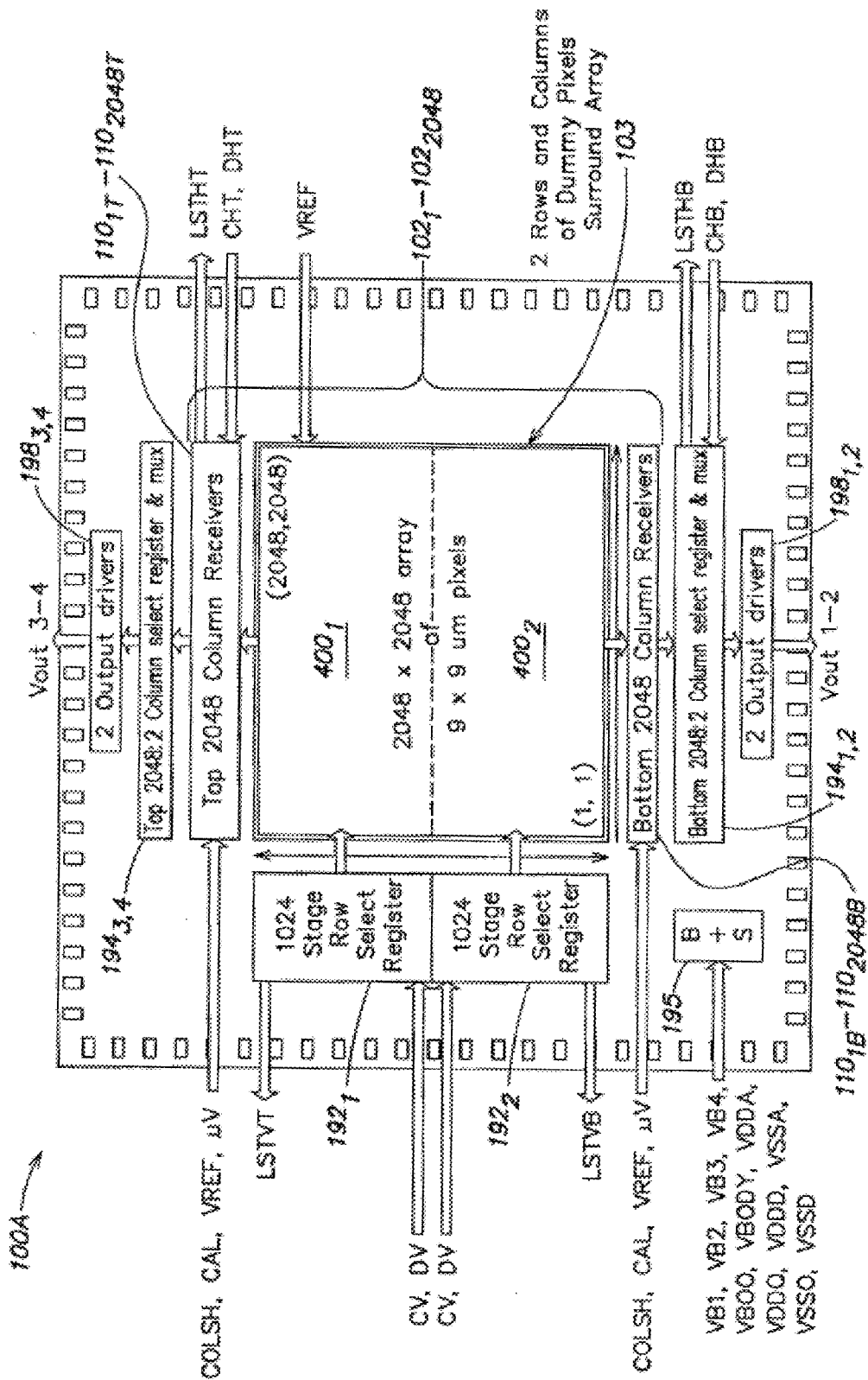
FIGS. 19-20 illustrate block diagrams of alternative CMOS IC chip implementations of chemFET sensor arrays, according to other inventive embodiments of the present disclosure.

FIG. 19 illustrates a block diagram of an ISFET sensor array 100A based on the column and pixel designs discussed above in connection with FIGS. 9-12 and a 0.35 micrometer CMOS fabrication process, according to one inventive embodiment. The array 100A includes 2048 columns $102_1$ through $102_{2048}$, wherein each column includes 2048 geometrically square pixels $105_1$ through $105_{2048}$, each having a size of approximately 9 micrometers by 9 micrometers. Thus, the array includes over four million pixels (>4 Mega-pixels) and, in one exemplary implementation, the complete array (ISFET pixels and associated circuitry) may be fabricated as an integrated circuit chip having dimensions of approximately 20.5 millimeters by 20.5 millimeters.

In one aspect of the embodiment shown in FIG. 19, the array 100A may be configured, at least in part, as multiple groups of pixels that may be respectively controlled. For example, each column of pixels may be divided into top and bottom halves, and the collection of pixels in respective top halves of columns form a first group $400_1$ of rows (e.g., a top group, rows 1-1024) and the collection of pixels in respective bottom halves of columns form a second group $400_2$ of rows (e.g., a bottom group, rows 1025-2048). In turn, each of the first and second (e.g., top and bottom) groups of rows is associated with corresponding row select registers, column bias/readout circuitry, column select registers, and output drivers. In this manner, pixel selection and data acquisition from each of the first and second groups of rows $400_1$ and $400_2$ is substantially similar to pixel selection and data acquisition from the entire array 100 shown in FIG. 13; stated differently, in one aspect, the array 100A of FIG. 19 substantially comprises two simultaneously controlled "sub-arrays" of different pixel groups to provide for significantly streamlined data acquisition from higher numbers of pixels.

In particular, FIG. 19 shows that row selection of the first group $400_1$ of rows may be controlled by a first row select register $192_1$, and row selection of the second group $400_2$ of rows may be controlled by a second row select register $192_2$. In one aspect, each of the row select registers $192_1$ and $192_2$ may be configured as discussed above in connection with FIG. 14 to receive vertical clock (CV) and vertical data (DV) signals and generate row select signals in response; for example the first row select register $192_1$ may generate the signals $\overline{\text{RowSel}_1}$ through $\overline{\text{RowSel}_{1024}}$ and the second row select register $192_2$ may generate the signals $\overline{\text{RowSel}_{1025}}$ through $\overline{\text{RowSel}_{2048}}$. In another aspect, both row select registers $192_1$ and $192_2$ may simultaneously receive common vertical clock and data signals, such that two rows of the array are enabled at any given time, one from the top group and another from the bottom group.

For each of the first and second groups of rows, the array 100A of FIG. 19 further comprises column bias/readout circuitry $110_{1T}$-$110_{2048T}$ (for the first row group $400_1$) and $110_{1B}$-$110_{2048B}$ (for the second row group $400_2$), such that each column includes two instances of the bias/readout circuitry $110j$ shown in FIG. 9. The array 100A also comprises two column select registers $192_{1,2}$ (odd and even) and two output drivers $198_{1,2}$ (odd and even) for the second row group $400_2$, and two column select registers $192_{3,4}$ (odd and even) and two output drivers $198_{3,4}$ (odd and even) for the first row group $400_1$ (i.e., a total of four column select registers and four output drivers). The column select registers receive horizontal clock signals (CHT and CHB for the first row group and second row group, respectively) and horizontal data signals (DHT and DHB for the first row group and second row group, respectively) to control odd and even column selection. In one implementation, the CHT and CHB signals may be provided as common signals, and the DHT and DHB may be provided as common signals, to simultaneously read out four columns at a time from the array (i.e., one odd and one even column from each row group); in particular, as discussed above in connection with FIGS. 13-18, two columns may be simultaneously read for each enabled row and the corresponding pixel voltages provided as two output signals. Thus, via the enablement of two rows at any given time, and reading of two columns per row at any given time, the array 100A may provide four simultaneous output signals Vout1, Vout2, Vout3 and Vout4.

In one exemplary implementation of the array 100A of FIG. 19, in which complete data frames (all pixels from both the first and second row groups $400_1$ and $400_2$) are acquired at a frame rate of 20 frames/sec, 1024 pairs of rows are successively enabled for periods of approximately 49 microseconds each. For each enabled row, 1024 pixels are read out by each column select register/output driver during approximately 45 microseconds (allowing 2 microseconds at the beginning and end of each row, as discussed above in connection with FIG. 18). Thus, in this example, each of the array output signals Vout1, Vout2, Vout3 and Vout4 has a data rate of approximately 23 MHz. Again, it should be appreciated that in other implementations, data may be acquired from the array 100A of FIG. 19 at frame rates other than 20 frames/sec (e.g., 50-100 frames/sec).

Like the array 100 of FIG. 13, in yet other aspects the array 100A of FIG. 19 may include multiple rows and columns of dummy or reference pixels 103 around a perimeter of the array to facilitate preliminary test/evaluation data, offset determination an/or array calibration. Additionally, various power supply and bias voltages required for array operation (as discussed above in connection with FIG. 9) are provided to the array 100A in block 195, in a manner similar to that discussed above in connection with FIG. 13.

Figure 20:
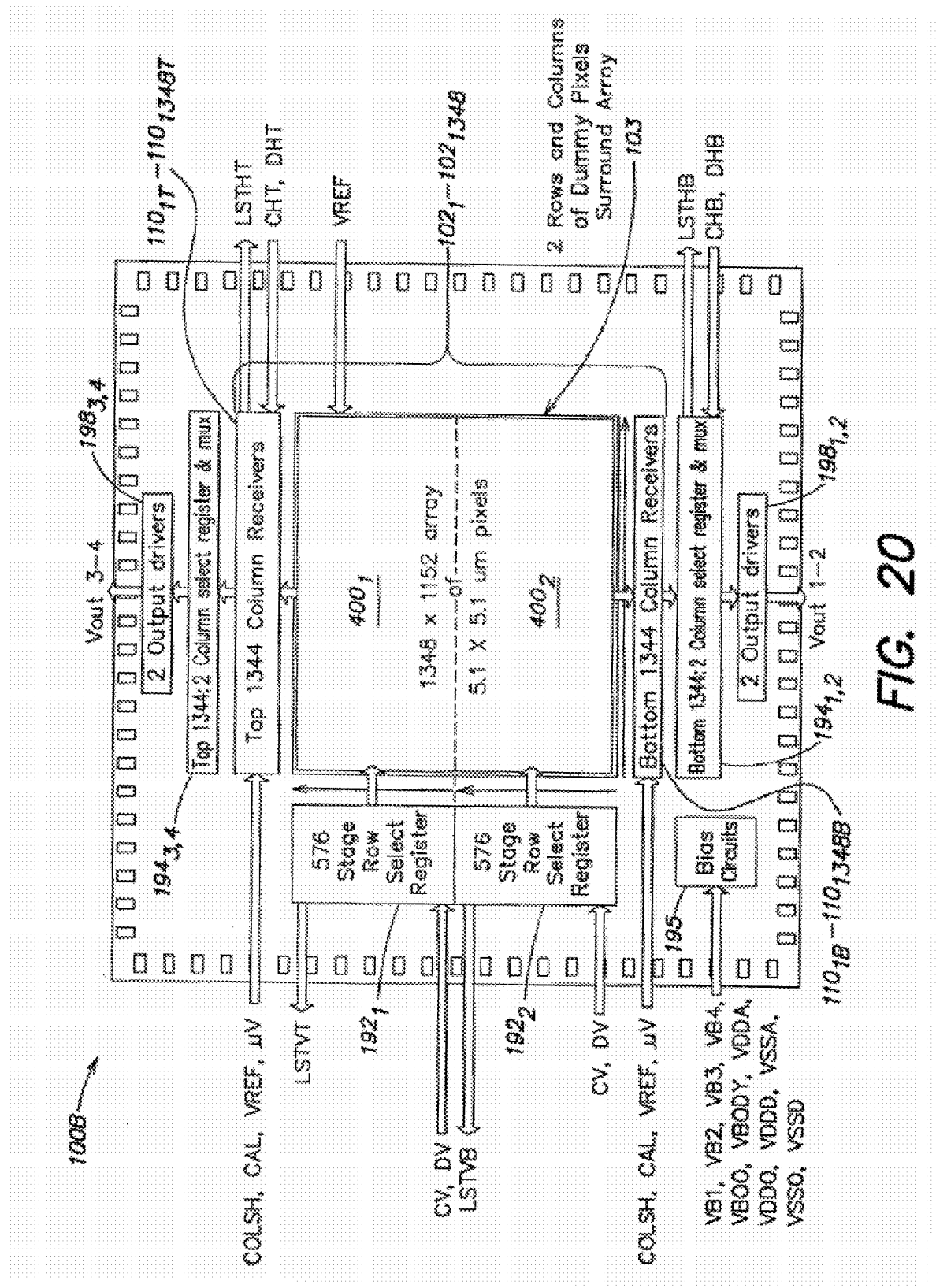

FIG. 20 illustrates a block diagram of an ISFET sensor array 100B based on a 0.35 micrometer CMOS fabrication process and having a configuration substantially similar to the array 100A discussed above in FIG. 19, according to yet another inventive embodiment. While the array 100B also is based generally on the column and pixel designs discussed above in connection with FIGS. 9-12, the pixel size/pitch in the array 100B is smaller than that of the pixel shown in FIG. 10. In particular, with reference again to FIGS. 10 and 11, the dimension "e" shown in FIG. 10 is substantially reduced in the embodiment of FIG. 20, without affecting the integrity of the active pixel components disposed in the central region of the pixel, from approximately 9 micrometers to approximately 5 micrometers; similarly, the dimension "f" shown in FIG. 10 is reduced from approximately 7 micrometers to approximately 4 micrometers. Stated differently, some of the peripheral area of the pixel surrounding the active components is substantially reduced with respect to the dimensions given in connection with FIG. 10, without disturbing the top-view and cross-sectional layout and design of the pixel's active components as shown in FIGS. 10 and 11. A top view of such a pixel 105A is shown in FIG. 20A, in which the dimension "e" is 5.1 micrometers and the dimension "f" is 4.1 micrometers. In one aspect of this pixel design, to facilitate size reduction, fewer body connections B are included in the pixel 105A (e.g., one at each corner of the pixel) as compared to the pixel shown in FIG. 10, which includes several body connections B around the entire perimeter of the pixel.

As noted in FIG. 20, the array 100B includes 1348 columns $102_1$ through $102_{1348}$, wherein each column includes 1152 geometrically square pixels $105A_1$ through $105A_{1152}$, each having a size of approximately 5 micrometers by 5 micrometers. Thus, the array includes over 1.5 million pixels (>1.5 Mega-pixels) and, in one exemplary implementation, the complete array (ISFET pixels and associated circuitry) may be fabricated as an integrated circuit chip having dimensions of approximately 9 millimeters by 9 millimeters. Like the array 100A of FIG. 19, in one aspect the array 100B of FIG. 20 is divided into two groups of rows $400_1$ and $400_2$, as discussed above in connection with FIG. 19. In one exemplary implementation, complete data frames (all pixels from both the first and second row groups $400_1$ and $400_2$) are acquired at a frame rate of 50 frames/sec, thereby requiring 576 pairs of rows to be successively enabled for periods of approximately 35 microseconds each. For each enabled row, 674 pixels are read out by each column select register/output driver during approximately 31 microseconds (allowing 2 microseconds at the beginning and end of each row, as discussed above in connection with FIG. 18). Thus, in this example, each of the array output signals Vout1, Vout2, Vout3 and Vout4 has a data rate of approximately 22 MHz. Again, it should be appreciated that in other implementations, data may be acquired from the array 100B of FIG. 20 at frame rates other than 50 frames/sec.

Figure 21:
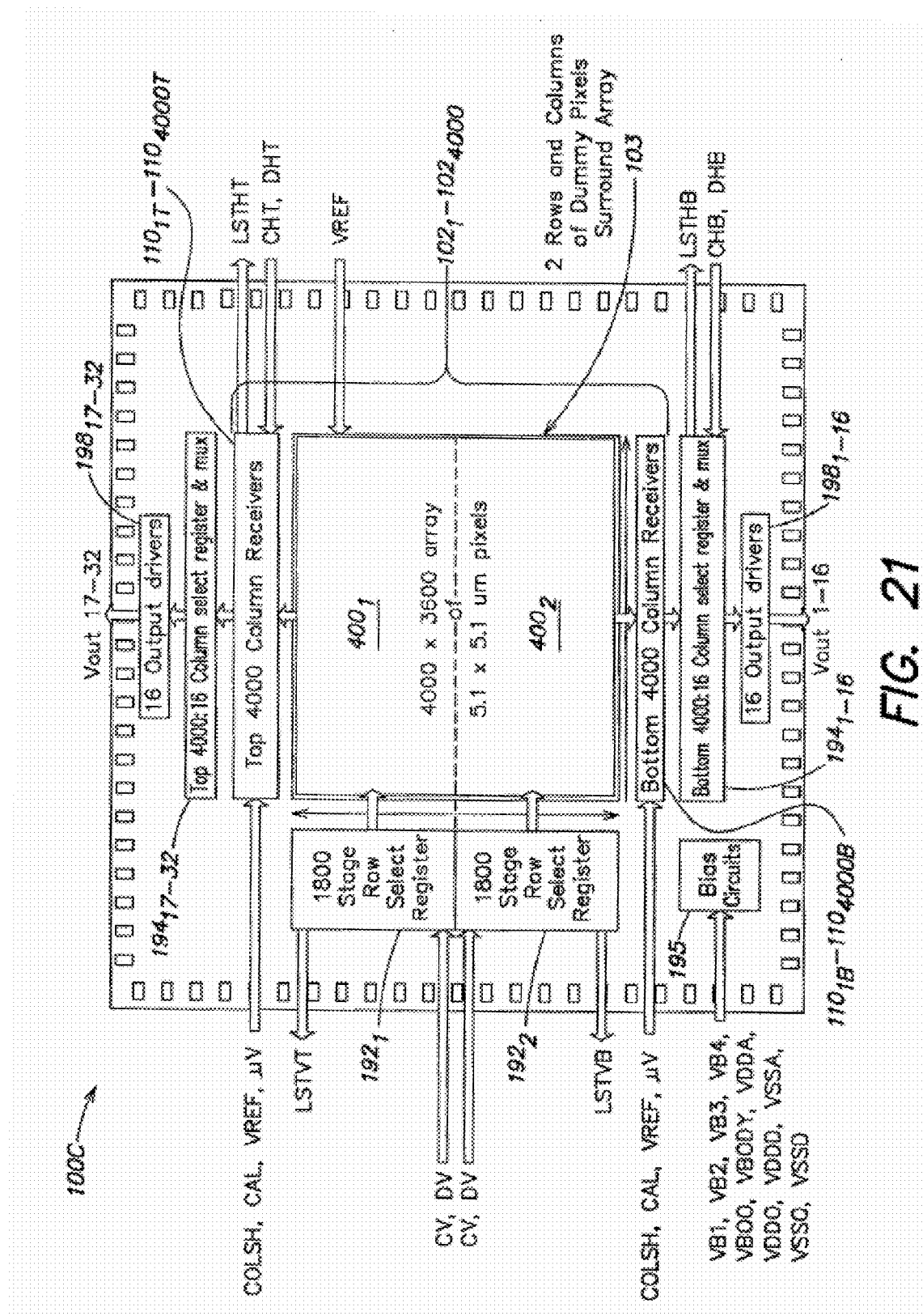
FIGS. 21-23 illustrate block diagrams of additional alternative CMOS IC chip implementations of chemFET sensor arrays, according to other inventive embodiments of the present disclosure.

FIG. 21 illustrates a block diagram of an ISFET sensor array 100C based on a 0.35 micrometer CMOS fabrication process and incorporating the smaller pixel size discussed above in connection with FIGS. 20 and 20A (5.1 micrometer square pixels), according to yet another embodiment. As noted in FIG. 21, the array 100C includes 4000 columns $102_1$ through $102_{4000}$, wherein each column includes 3600 geometrically square pixels $105A_1$ through $105A_{3600}$, each having a size of approximately 5 micrometers by 5 micrometers. Thus, the array includes over 14 million pixels (>14 Megapixels) and, in one exemplary implementation, the complete array (ISFET pixels and associated circuitry) may be fabricated as an integrated circuit chip having dimensions of approximately 22 millimeters by 22 millimeters. Like the arrays 100A and 100B of FIGS. 19 and 20, in one aspect the array 100C of FIG. 21 is divided into two groups of rows $400_1$ and $400_2$. However, unlike the arrays 100A and 100B, for each row group the array 100C includes sixteen column select registers and sixteen output drivers to simultaneously read sixteen pixels at a time in an enabled row, such that thirty-two output signals Vout1-Vout32 may be provided from the array 100C. In one exemplary implementation, complete data frames (all pixels from both the first and second row groups $400_1$ and $400_2$) may be acquired at a frame rate of 50 frames/sec, thereby requiring 1800 pairs of rows to be successively enabled for periods of approximately 11 microseconds each. For each enabled row, 250 pixels (4000/16) are read out by each column select register/output driver during approximately 7 microseconds (allowing 2 microseconds at the beginning and end of each row). Thus, in this example, each of the array output signals Vout1-Vout32 has a data rate of approximately 35 MHz. As with the previous embodiments, it should be appreciated that in other implementations, data may be acquired from the array 100C at frame rates other than 50 frames/sec.

Figure 22:
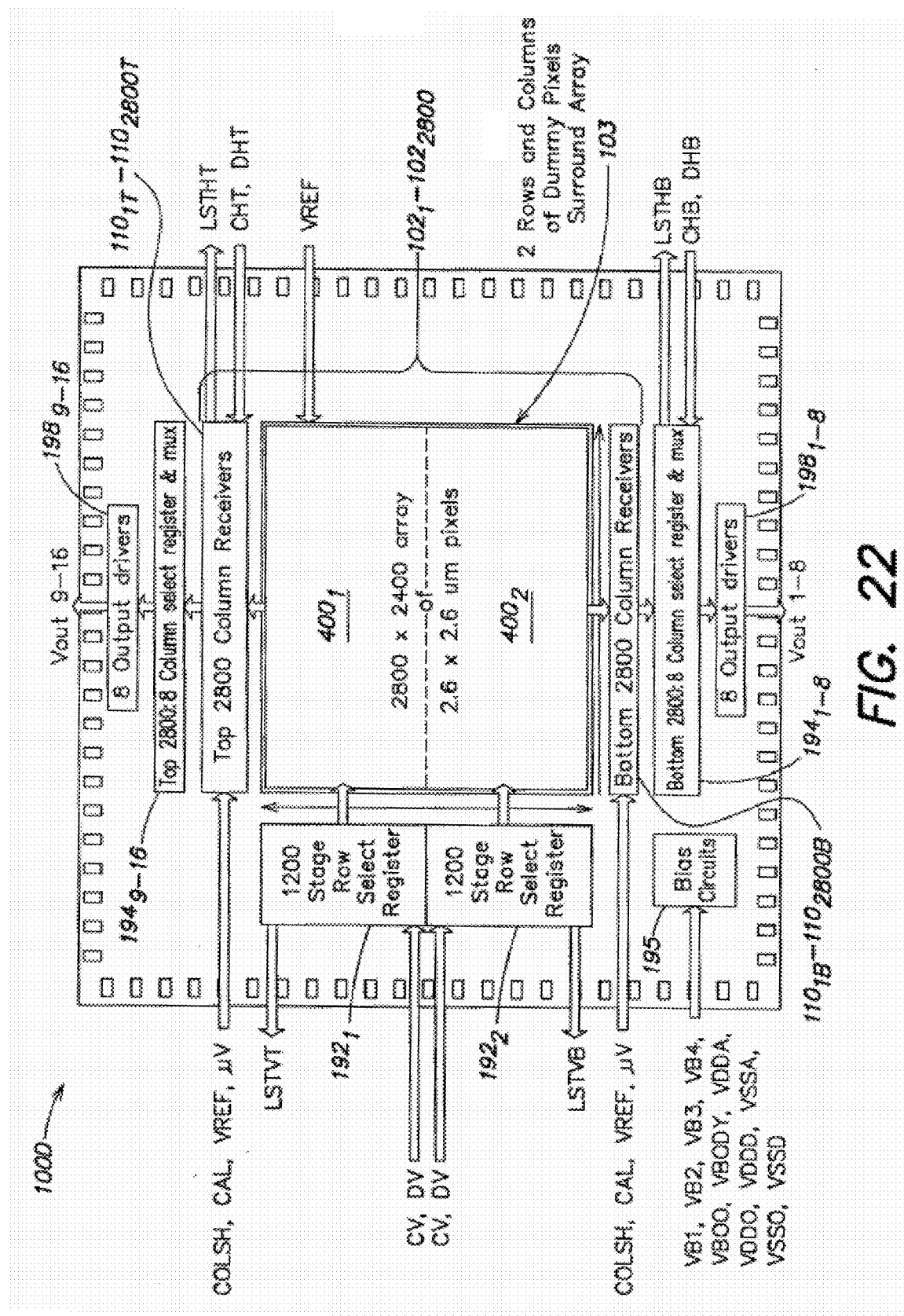
Figure 23:
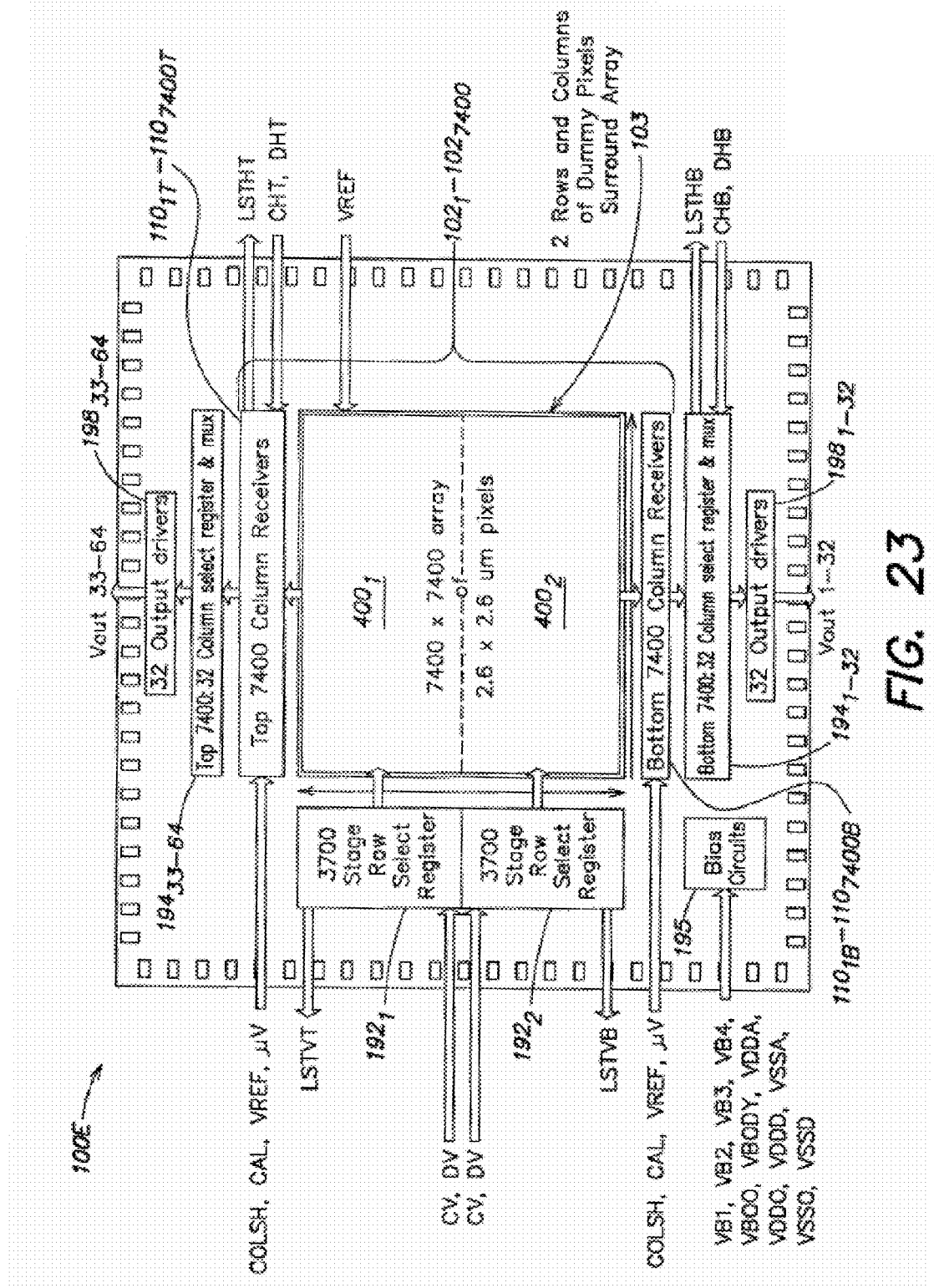

While the exemplary arrays discussed above in connection with FIGS. 13-21 are based on a 0.35 micrometer conventional CMOS fabrication process, it should be appreciated that arrays according to the present disclosure are not limited in this respect, as CMOS fabrication processes having feature sizes of less than 0.35 micrometers may be employed (e.g., 0.18 micrometer CMOS processing techniques) to fabricate such arrays. Accordingly, ISFET sensor arrays with a pixel size/pitch significantly below 5 micrometers may be fabricated, providing for significantly denser ISFET arrays. For example, FIGS. 22 and 23 illustrate respective block diagrams of ISFET sensor arrays 100D and 100E according to yet other embodiments based on a 0.18 micrometer CMOS fabrication process, in which a pixel size of 2.6 micrometers is achieved. The pixel design itself is based substantially on the pixel 105A shown in FIG. 20A, albeit on a smaller scale due to the 0.18 micrometer CMOS process.

The array 100D of FIG. 22 includes 2800 columns $102_1$ through $102_{2800}$, wherein each column includes 2400 geometrically square pixels each having a size of approximately 2.6 micrometers by 2.6 micrometers. Thus, the array includes over 6.5 million pixels (>6.5 Mega-pixels) and, in one exemplary implementation, the complete array (ISFET pixels and associated circuitry) may be fabricated as an integrated circuit chip having dimensions of approximately 9 millimeters by 9 millimeters. Like the arrays 100A, 100B and 100C of FIGS. 19-21, in one aspect the array 100D of FIG. 22 is divided into two groups of rows $400_1$ and $400_2$. However, unlike the arrays 100A, 100B, and 100C, for each row group the array 100D includes eight column select registers and eight output drivers to simultaneously read eight pixels at a time in an enabled row, such that sixteen output signals Vout1-Vout16 may be provided from the array 100D. In one exemplary implementation, complete data frames (all pixels from both the first and second row groups $400_1$ and $400_2$) may be acquired at a frame rate of 50 frames/sec, thereby requiring 1200 pairs of rows to be successively enabled for periods of approximately 16-17 microseconds each. For each enabled row, 350 pixels (2800/8) are read out by each column select register/output driver during approximately 14 microseconds (allowing 1 to 2 microseconds at the beginning and end of each row). Thus, in this example, each of the array output signals Vout1-Vout16 has a data rate of approximately 25 MHz. As with the previous embodiments, it should be appreciated that in other implementations, data may be acquired from the array 100D at frame rates other than 50 frames/sec.

The array 100E of FIG. 23 includes 7400 columns $102_1$ through $102_{7400}$, wherein each column includes 7400 geometrically square pixels each having a size of approximately 2.6 micrometers by 2.6 micrometers. Thus, the array includes over 54 million pixels (>54 Mega-pixels) and, in one exemplary implementation, the complete array (ISFET pixels and associated circuitry) may be fabricated as an integrated circuit chip having dimensions of approximately 21 millimeters by 21 millimeters. Like the arrays 100A-100D of FIGS. 19-22, in one aspect the array 100E of FIG. 23 is divided into two groups of rows $400_1$ and $400_2$. However, unlike the arrays 100A-100D, for each row group the array 100E includes thirty-two column select registers and thirty-two output drivers to simultaneously read thirty-two pixels at a time in an enabled row, such that sixty-four output signals Vout1-Vout64 may be provided from the array 100E. In one exemplary implementation, complete data frames (all pixels from both the first and second row groups $400_1$ and $400_2$) may be acquired at a frame rate of 100 frames/sec, thereby requiring 3700 pairs of rows to be successively enabled for periods of approximately 3 microseconds each. For each enabled row, 230 pixels (7400/32) are read out by each column select register/output driver during approximately 700 nanoseconds. Thus, in this example, each of the array output signals Vout1-Vout64 has a data rate of approximately 328 MHz. As with the previous embodiments, it should be appreciated that in other implementations, data may be acquired from the array 100D at frame rates other than 100 frames/sec.

Thus, in various examples of ISFET arrays based on the inventive concepts disclosed herein, an array pitch of approximately nine (9) micrometers (e.g., a sensor surface area of less than ten micrometers by ten micrometers) allows an ISFET array including over 256,000 pixels (i.e., a 512 by 512 array), together with associated row and column select and bias/readout electronics, to be fabricated on a 7 millimeter by 7 millimeter semiconductor die, and a similar sensor array including over four million pixels (i.e., a 2048 by 2048 array, over 4 Mega-pixels) to be fabricated on a 21 millimeter by 21 millimeter die. In other examples, an array pitch of approximately 5 micrometers allows an ISFET array including approximately 1.55 Mega-pixels (i.e., a 1348 by 1152 array) and associated electronics to be fabricated on a 9 millimeter by 9 millimeter die, and an ISFET sensor array including over 14 Mega-pixels and associated electronics on a 22 millimeter by 20 millimeter die. In yet other implementations, using a CMOS fabrication process in which feature sizes of less than 0.35 micrometers are possible (e.g., 0.18 micrometer CMOS processing techniques), ISFET sensor arrays with a pixel size/pitch significantly below 5 micrometers may be fabricated (e.g., array pitch of 2.6 micrometers or pixel/sensor area of less than 8 or 9 micrometers$^2$), providing for significantly dense ISFET arrays.

In the embodiments of ISFET arrays discussed above, array pixels employ a p-channel ISFET, as discussed above in connection with FIG. 9. It should be appreciated, however, that ISFET arrays according to the present disclosure are not limited in this respect, and that in other embodiments pixel designs for ISFET arrays may be based on an n-channel ISFET. In particular, any of the arrays discussed above in connection with FIGS. 13 and 19-23 may be implemented with pixels based on n-channel ISFETs.

Figure 24:
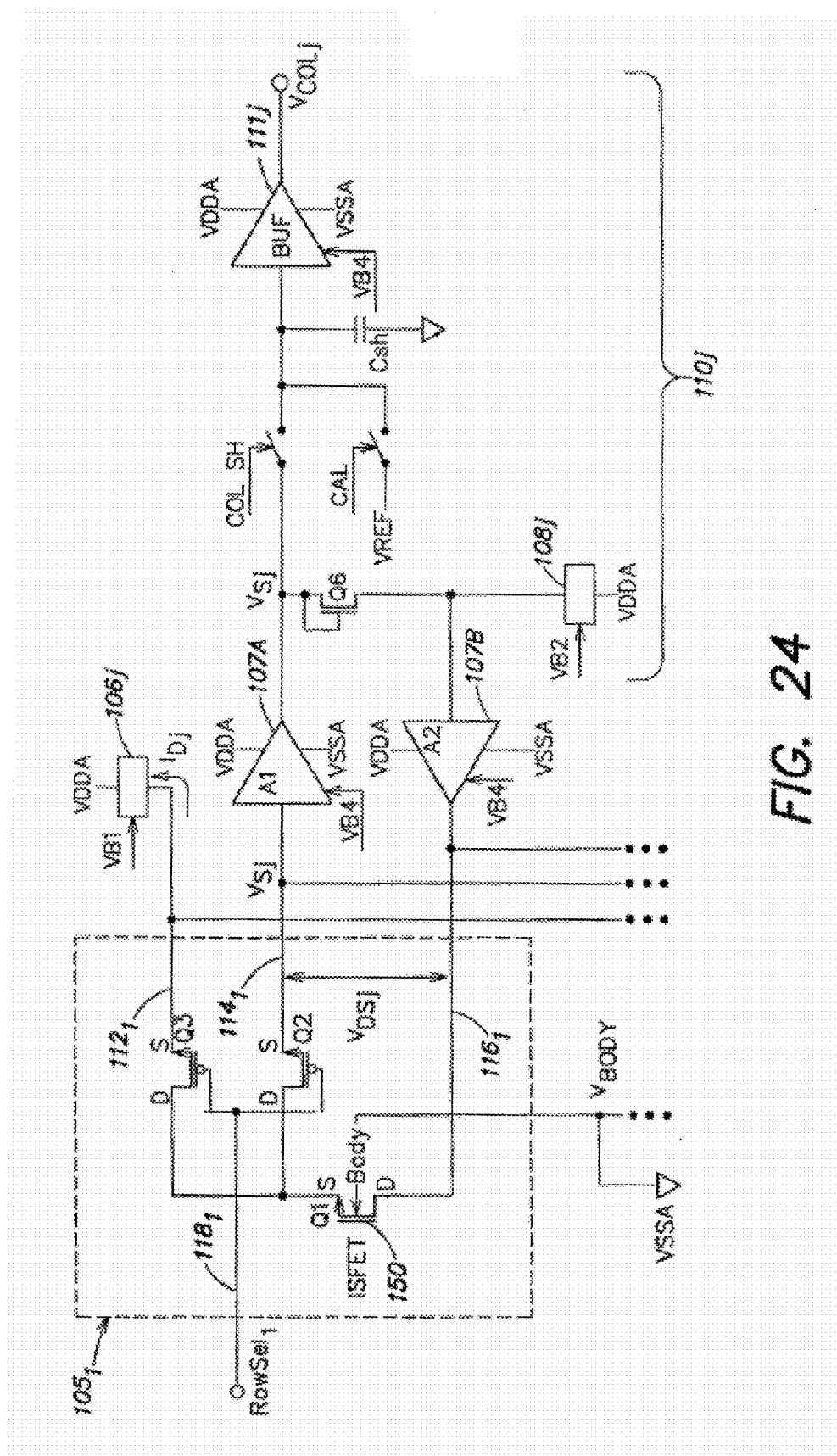
FIG. 24 illustrates the pixel design of FIG. 9 implemented with an n-channel chemFET and accompanying n-channel MOSFETs, according to another inventive embodiment of the present disclosure.

For example, FIG. 24 illustrates the pixel design of FIG. 9 implemented with an n-channel ISFET and accompanying n-channel MOSFETs, according to another inventive embodiment of the present disclosure. More specifically, FIG. 24 illustrates one exemplary pixel $105_1$ of an array column (i.e., the first pixel of the column), together with column bias/readout circuitry $110j$, in which the ISFET 150 (Q1) is an n-channel ISFET. Like the pixel design of FIG. 9, the pixel design of FIG. 24 includes only three components, namely, the ISFET 150 and two n-channel MOSFET switches Q2 and Q3, responsive to one of n row select signals (RowSel$_1$ through RowSel$_n$, logic high active). No transmission gates are required in the pixel of FIG. 24, and all devices of the pixel are of a "same type," i.e., n-channel devices. Also like the pixel design of FIG. 9, only four signal lines per pixel, namely the lines $112_1$, $114_1$, $116_1$ and $118_1$ are required to operate the three components of the pixel $105_1$ shown in FIG. 24. In other respects, the pixel designs of FIG. 9 and FIG. 24 are similar, in that they are both configured with a constant drain current $I_{Dj}$ and a constant drain-to-source voltage $V_{DSj}$ to obtain an output signal $V_{Sj}$ from an enabled pixel.

One of the primary differences between the n-channel ISFET pixel design of FIG. 24 and the p-channel ISFET design of FIG. 9 is the opposite direction of current flow through the pixel. To this end, in FIG. 24, the element 106, is a controllable current sink coupled to the analog circuitry supply voltage ground VSSA, and the element 108, of the bias/readout circuitry $110j$ is a controllable current source coupled to the analog positive supply voltage VDDA. Additionally, the body connection of the ISFET 150 is not tied to its source, but rather to the body connections of other ISFETs of the array, which in turn is coupled to the analog ground VSSA, as indicated in FIG. 24.

Figure 25:
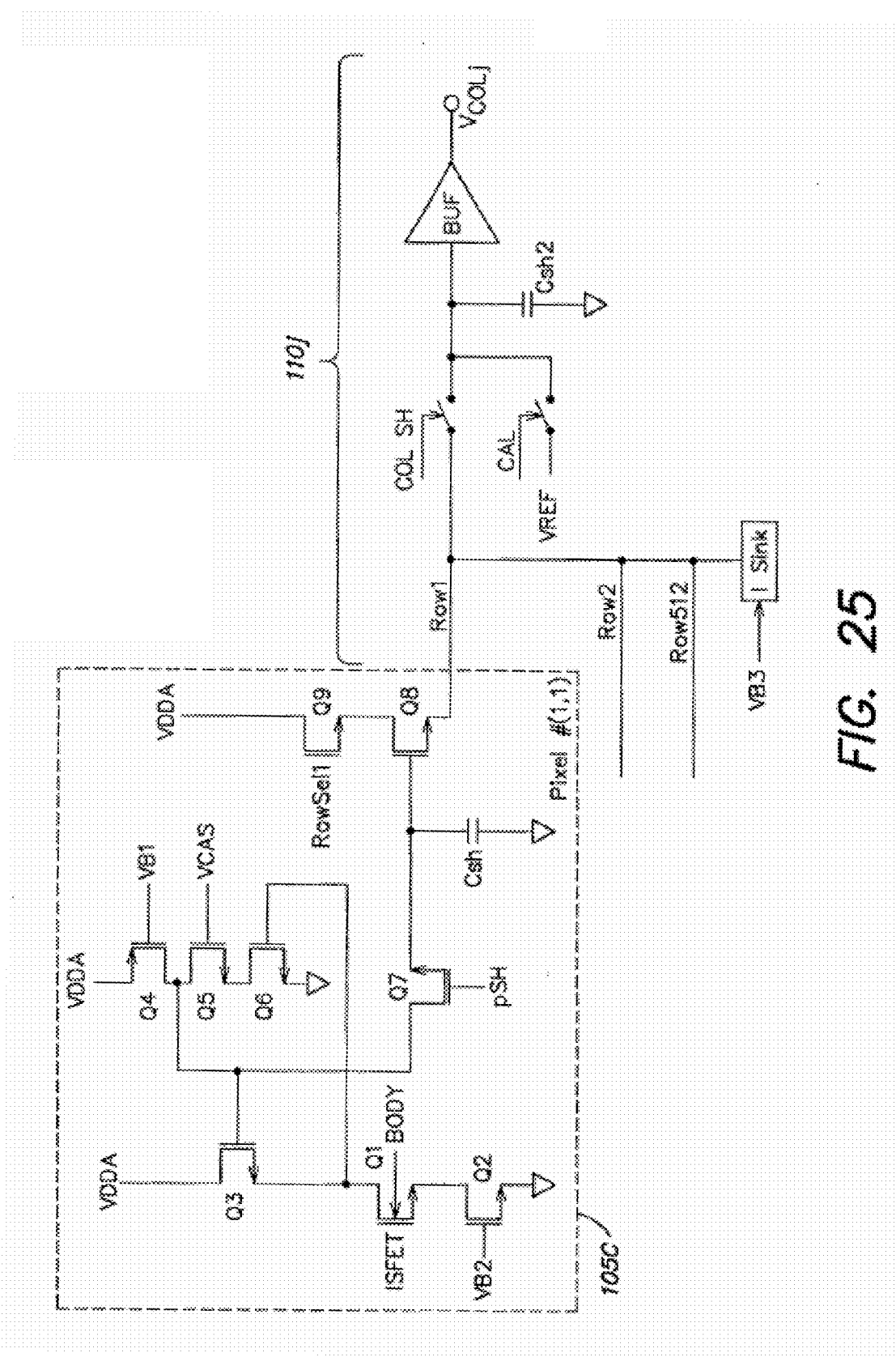
FIGS. 25-27 illustrate alternative pixel designs and associated column circuitry for chemFET arrays according to other inventive embodiments of the present disclosure.
Figure 26:
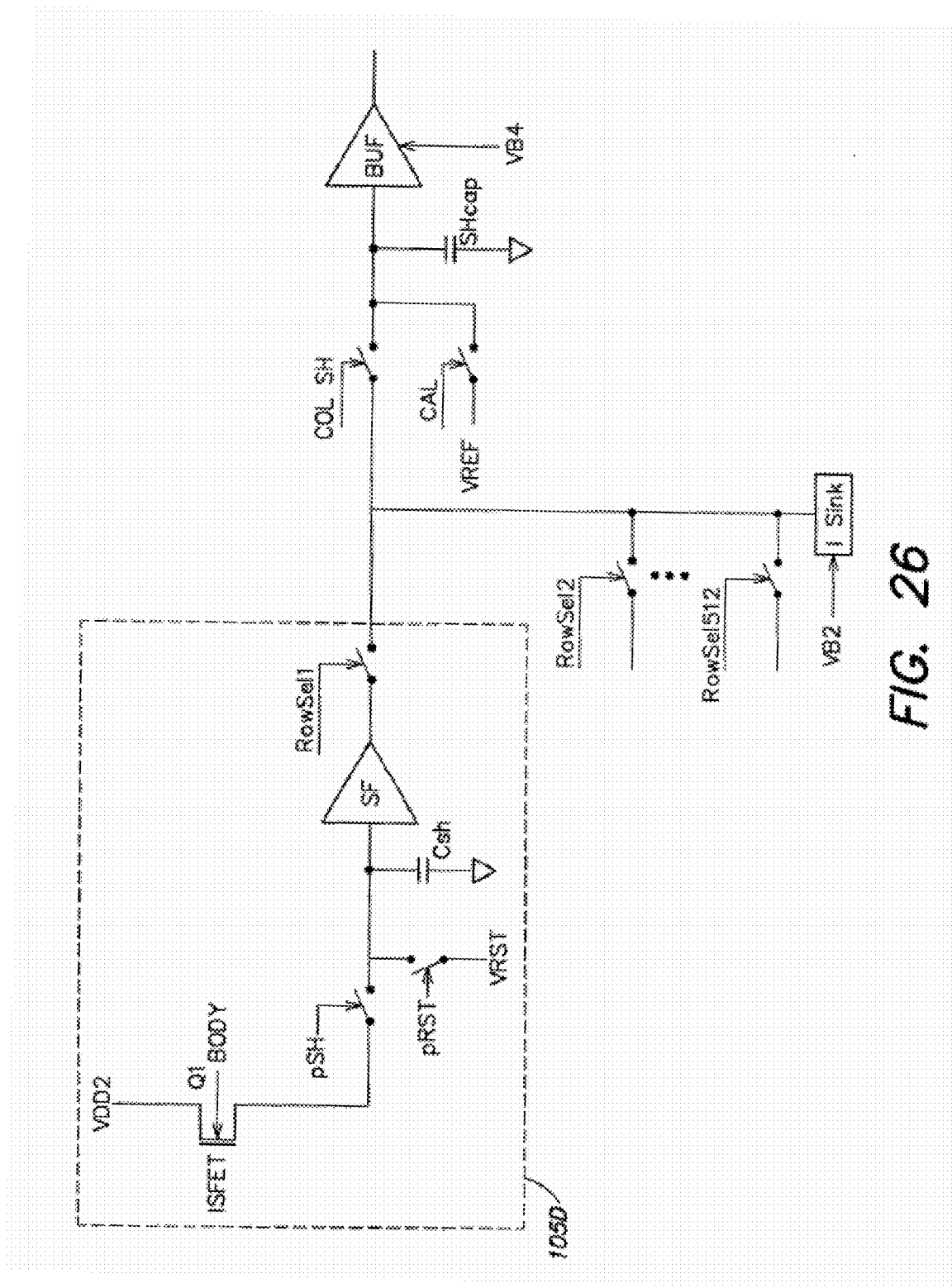
Figure 27:
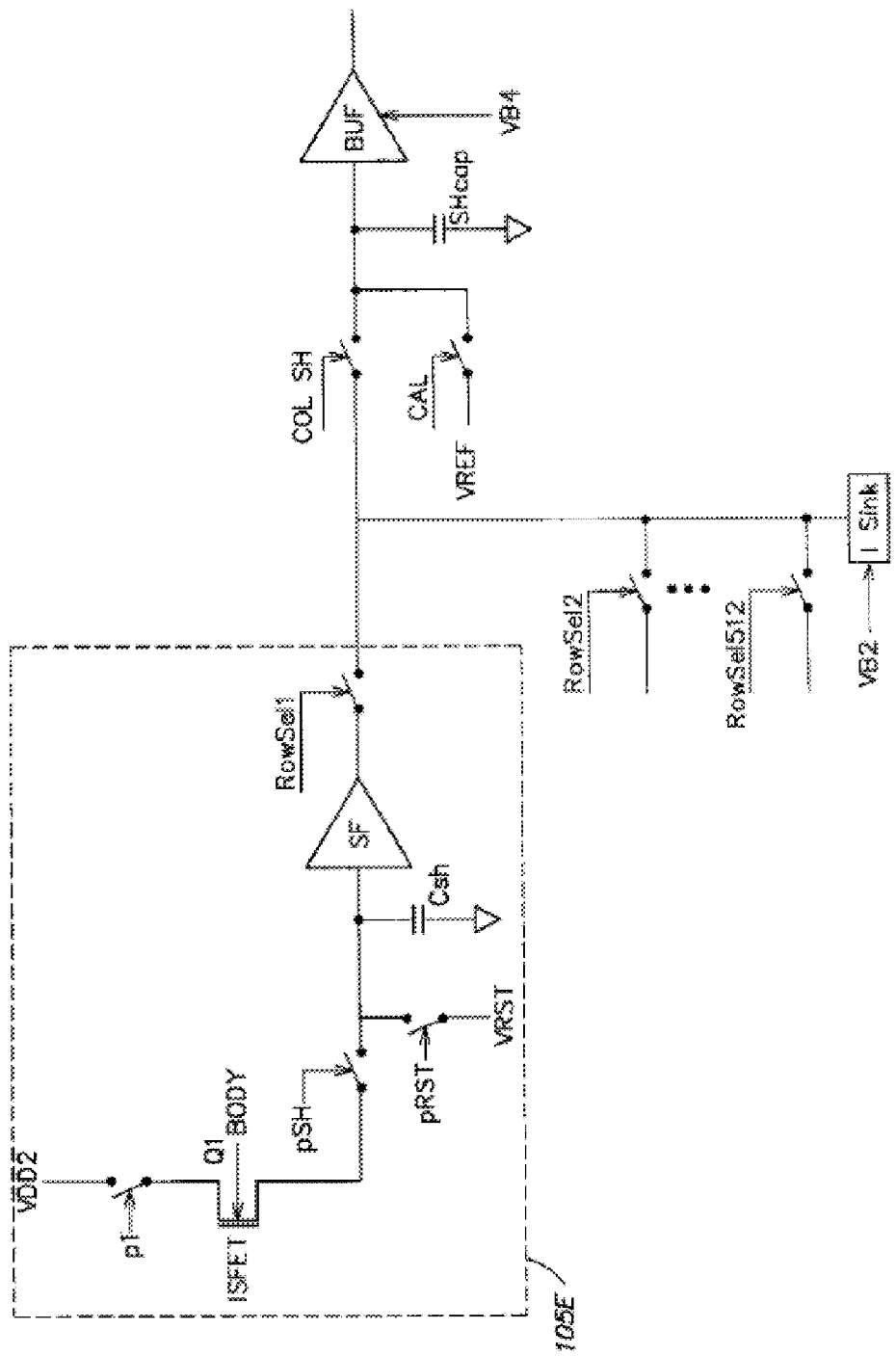

In addition to the pixel designs shown in FIGS. 9 and 24 (based on a constant ISFET drain current and constant ISFET drain-source voltage), alternative pixel designs are contemplated for ISFET arrays, based on both p-channel ISFETs and n-channel ISFETs, according to yet other inventive embodiments of the present disclosure, as illustrated in FIGS. 25-27. As discussed below, some alternative pixel designs may require additional and/or modified signals from the array controller 250 to facilitate data acquisition. In particular, a common feature of the pixel designs shown in FIGS. 25-27 includes a sample and hold capacitor within each pixel itself, in addition to a sample and hold capacitor for each column of the array. While the alternative pixel designs of FIGS. 25-27 generally include a greater number of components than the pixel designs of FIGS. 9 and 24, the feature of a pixel sample and hold capacitor enables "snapshot" types of arrays, in which all pixels of an array may be enabled simultaneously to sample a complete frame and acquire signals representing measurements of one or more analytes in proximity to respective ISFETs of the array. In some applications, this may provide for higher data acquisition speeds and/or improved signal sensitivity (e.g., higher signal-to-noise ratio).

FIG. 25 illustrates one such alternative design for a single pixel 105C and associated column circuitry $110j$. The pixel 105C employs an n-channel ISFET and is based generally on the premise of providing a constant voltage across the ISFET Q1 based on a feedback amplifier (Q4, Q5 and Q6). In particular, transistor Q4 constitutes the feedback amplifier load, and the amplifier current is set by the bias voltage VB1 (provided by the array controller). Transistor Q5 is a common gate amplifier and transistor Q6 is a common source amplifier. Again, the purpose of feedback amplifier is to hold the voltage across the ISFET Q1 constant by adjusting the current supplied by transistor Q3. Transistor Q2 limits the maximum current the ISFET Q1 can draw (e.g., so as to prevent damage from overheating a very large array of pixels). This maximum current is set by the bias voltage VB2 (also provided by the array controller). In one aspect of the pixel design shown in FIG. 25, power to the pixel 105C may be turned off by setting the bias voltage VB2 to 0 Volts and the bias voltage VB1 to 3.3 Volts. In this manner, the power supplied to large arrays of such pixels may be modulated (turned on for a short time period and then off by the array controller) to obtain ion concentration measurements while at the same time reducing overall power consumption of the array. Modulating power to the pixels also reduces heat dissipation of the array and potential heating of the analyte solution, thereby also reducing any potentially deleterious effects from sample heating.

In FIG. 25, the output of the feedback amplifier (the gate of transistor Q3) is sampled by MOS switch Q7 and stored on a pixel sample and hold capacitor Csh within the pixel itself. The switch Q7 is controlled by a pixel sample and hold signal pSH (provided to the array chip by the array controller), which is applied simultaneously to all pixels of the array so as to simultaneously store the readings of all the pixels on their respective sample and hold capacitors. In this manner, arrays based on the pixel design of FIG. 25 may be considered as "snapshot" arrays, in that a full frame of data is sampled at any given time, rather than sampling successive rows of the array. After each pixel value is stored on the corresponding pixel sample and hold capacitor Csh, each pixel 105C (ISFET and feedback amplifier) is free to acquire another pH reading or it can by turned off to conserve power.

In FIG. 25, the pixel values stored on all of the pixel sample and hold capacitors Csh are applied to the column circuitry $110j$ one row at a time through source follower Q8, which is enabled via the transistor Q9 in response to a row select signal (e.g., RowSel1). In particular, after a row is selected and has settled out, the values stored in the pixel sample and hold capacitors are then in turn stored on the column sample and hold capacitors Csh2, as enabled by the column sample and hold signal COL SH, and provided as the column output signal $V_{COLj}$.

FIG. 26 illustrates another alternative design for a single pixel 105D and associated column circuitry $110j$, according to one embodiment of the present disclosure. In this embodiment, the ISFET is shown as a p-channel device. At the start of a data acquisition cycle, CMOS switches controlled by the signals pSH (pixel sample/hold) and pRST (pixel reset) are closed (these signals are supplied by the array controller). This pulls the source of ISFET (Q1) to the voltage VRST. Subsequently, the switch controlled by the signal pRST is opened, and the source of ISFET Q1 pulls the pixel sample and hold capacitor Csh to a threshold below the level set by pH. The switch controlled by the signal pSH is then opened, and the pixel output value is coupled, via operation of a switch responsive to the row select signal RowSel1, to the column circuitry $110j$ to provide the column output signal $V_{COLj}$. Like the pixel design in the embodiment illustrated in FIG. 25, arrays based on the pixel 105D are "snapshot" type arrays in that all pixels of the array may be operated simultaneously. In one aspect, this design allows a long simultaneous integration time on all pixels followed by a high-speed read out of an entire frame of data.

FIG. 27 illustrates yet another alternative design for a single pixel 105E and associated column circuitry 110j, according to one embodiment of the present disclosure. In this embodiment, again the ISFET is shown as a p-channel device. At the start of a data acquisition cycle, the switches operated by the control signals p1 and pRST are briefly closed. This clears the value stored on the sampling capacitor Csh and allows a charge to be stored on ISFET (Q1). Subsequently, the switch controlled by the signal pSH is closed, allowing the charge stored on the ISFET Q1 to be stored on the pixel sample and hold capacitor Csh. The switch controlled by the signal pSH is then opened, and the pixel output value is coupled, via operation of a switch responsive to the row select signal RowSel1, to the column circuitry 110j to provide the column output signal $V_{COLj}$. Gain may be provided in the pixel 105E via the ratio of the ISFET capacitance to the Csh cap, i.e., gain=$C_{Q1}/C_{sh}$, or by enabling the pixel multiple times (i.e., taking multiple samples of the analyte measurement) and accumulating the ISFET output on the pixel sample and hold capacitor Csh without resetting the capacitor (i.e., gain is a function of the number of accumulations). Like the embodiments of FIGS. 25 and 26, arrays based on the pixel 105D are "snapshot" type arrays in that all pixels of the array may be operated simultaneously.

Figure 28A:
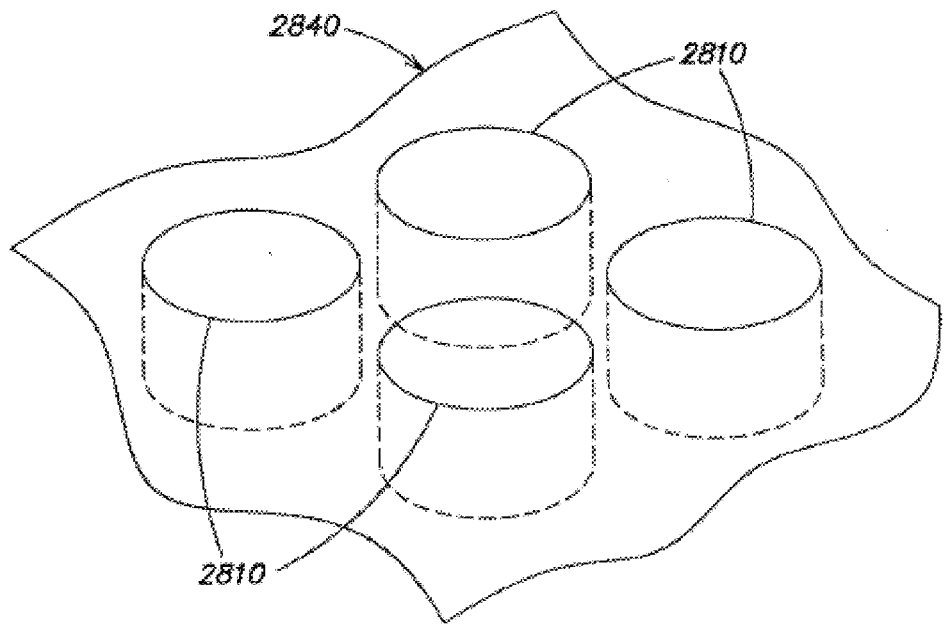
FIGS. 28A and 28B are isometric illustrations of portions of microwell arrays as employed herein, showing round wells and rectangular wells, to assist three-dimensional visualization of the array structures.
Figure 28B:
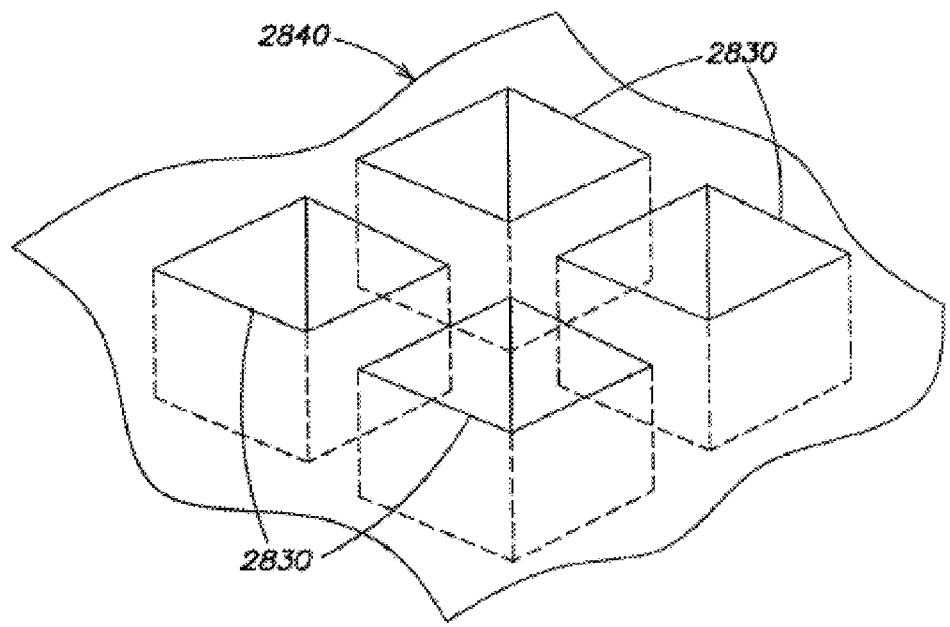

Turning from the sensor discussion, we will now be addressing the combining of the ISFET array with a microwell array and the attendant fluidics. As most of the drawings of the microwell array structure are presented only in cross-section or showing that array as only a block in a simplified diagram, FIGS. 28A and 28B are provided to assist the reader in beginning to visualize the resulting apparatus in three-dimensions. FIG. 28A shows a group of round cylindrical wells 2810 arranged in an array, while FIG. 28B shows a group of rectangular cylindrical wells 2830 arranged in an array. It will be seen that the wells are separated (isolated) from each other by the material 2839 forming the well walls. While it is certain possible to fabricate wells of other cross sections, it is not believed to be advantageous to do so. Such an array of microwells sits over the above-discussed ISFET array, with one or more ISFETs per well. In the subsequent drawings, when the microwell array is identified, one may picture one of these arrays.

Fluidic System: Apparatus and Method for Use with High Density Electronic Sensor Arrays For many uses, to complete a system for sensing chemical reactions or chemical agents using the above-explained high density electronic arrays, techniques and apparatus are required for delivery to the array elements (called "pixels") fluids containing chemical or biochemical components for sensing. In this section, exemplary techniques and methods will be illustrated, which are useful for such purposes, with desirable characteristics.

As high speed operation of the system may be desired, it is preferred that the fluid delivery system, insofar as possible, not limit the speed of operation of the overall system.

Accordingly, needs exist not only for high-speed, high-density arrays of ISFETs or other elements sensitive to ion concentrations or other chemical attributes, or changes in chemical attributes, but also for related mechanisms and techniques for supplying to the array elements the samples to be evaluated, in sufficiently small reaction volumes as to substantially advance the speed and quality of detection of the variable to be sensed.

There are two and sometimes three components or subsystems, and related methods, involved in delivery of the subject chemical samples to the array elements: (1) macrofluidic system of reagent and wash fluid supplies and appropriate valving and ancillary apparatus, (2) a flow cell and (3) in many applications, a microwell array. Each of these subsystems will be discussed, though in reverse order.

Microwell Array

As discussed elsewhere, for many uses, such as in DNA sequencing, it is desirable to provide over the array of semiconductor sensors a corresponding array of microwells, each microwell being small enough preferably to receive only one DNA-loaded bead, in connection with which an underlying pixel in the array will provide a corresponding output signal.

The use of such a microwell array involves three stages of fabrication and preparation, each of which is discussed separately: (1) creating the array of microwells to result in a chip having a coat comprising a microwell array layer; (2) mounting of the coated chip to a fluidic interface; and in the case of DNA sequencing, (3) loading DNA-loaded bead or beads into the wells. It will be understood, of course, that in other applications, beads may be unnecessary or beads having different characteristics may be employed.

Microwell Array Fabrication

Microwell fabrication may be accomplished in a number of ways. The actual details of fabrication may require some experimentation and vary with the processing capabilities that are available.

In general, fabrication of a high density array of microwells involves photo-lithographically patterning the well array configuration on a layer or layers of material such as photoresist (organic or inorganic), a dielectric, using an etching process. The patterning may be done with the material on the sensor array or it may be done separately and then transferred onto the sensor array chip, of some combination of the two. However, techniques other than photolithography are not to be excluded if they provide acceptable results.

Figure 29:
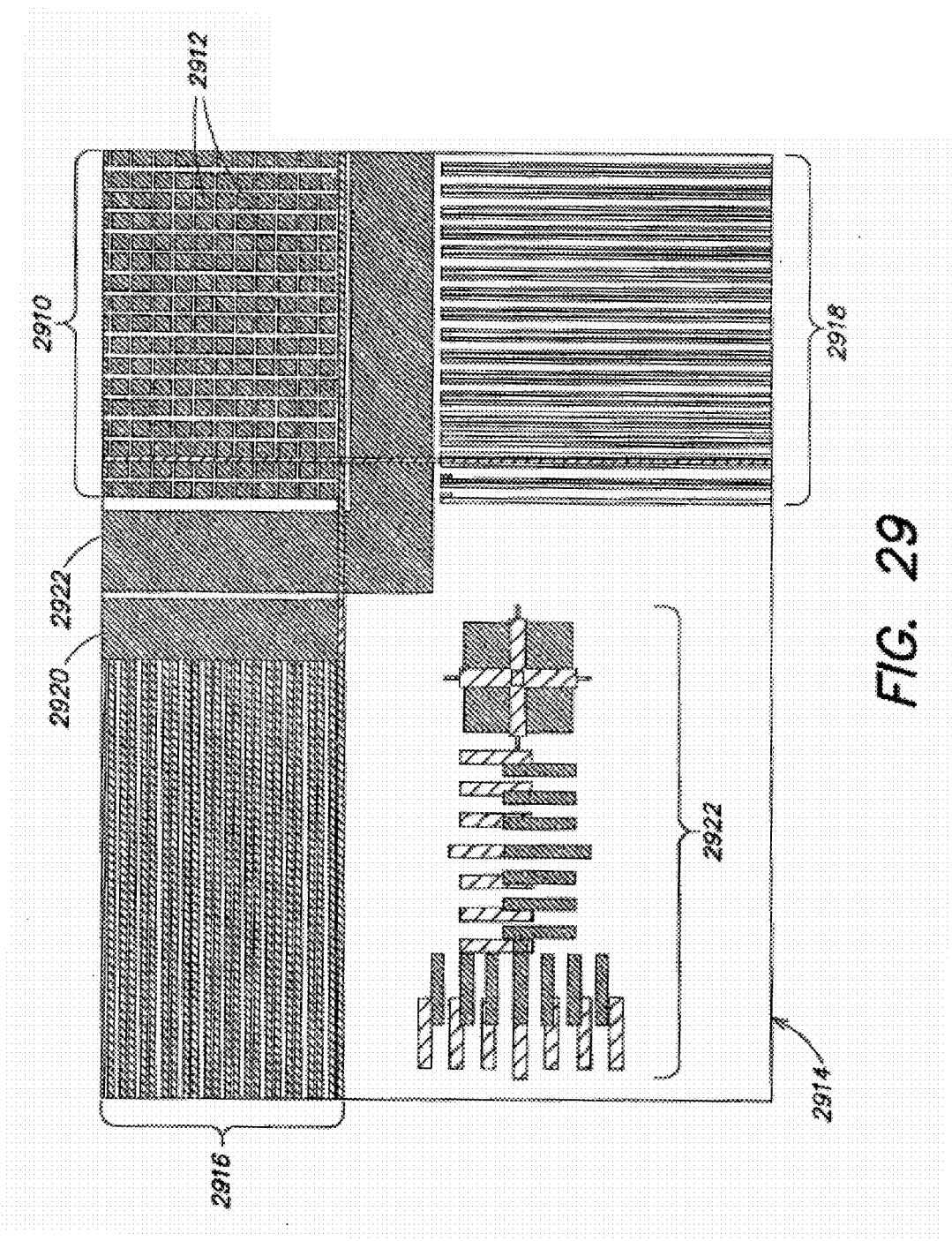
FIG. 29 is a diagrammatic depiction of a top view of one corner (i.e., the lower left corner) of the layout of a chip showing an array of individual ISFET sensors on a CMOS die.

One example of a method for forming a microwell array is now discussed, starting with reference to FIG. 29. That figure diagrammatically depicts a top view of one corner (i.e., the lower left corner) of the layout of a chip showing an array 2910 of the individual ISFET sensors 2912 on the CMOS die 2914. Signal lines 2916 and 2918 are used for addressing the array and reading its output. Block 2920 represents some of the electronics for the array, as discussed above, and layer 2922 represents a portion of a wall which becomes part of a microfluidics structure, the flow cell, as more fully explained below; the flow cell is that structure which provides a fluid flow over the microwell array or over the sensor surface directly, if there is no microwell structure. On the surface of the die, a pattern such as pattern 2922 at the bottom left of FIG. 29 may be formed during the semiconductor processing to form the ISFETs and associated circuitry, for use as alignment marks for locating the wells over the sensor pixels when the dielectric has covered the die's surface.

After the semiconductor structures, as shown, are formed, the microwell structure is applied to the die. That is, the microwell structure can be formed right on the die or it may be formed separately and then mounted onto the die, either approach being acceptable. To form the microwell structure on the die, various processes may be used. For example, the entire die may be spin-coated with, for example, a negative photoresist such as Microchem's SU-8 2015 or a positive resist/polyimide such as HD Microsystems HD8820, to the desired height of the microwells. The desired height of the wells (e.g., about 4-12 μm in the example of one pixel per well, though not so limited as a general matter) in the photoresist layer(s) can be achieved by spinning the appropriate resist at predetermined rates (which can be found by reference to the literature and manufacturer specifications, or empirically), in one or more layers. (Well height typically may be selected in correspondence with the lateral dimension of the sensor pixel, preferably for a nominal 1:1-1.5:1 aspect ratio, height:width or diameter. Based on signal-to-noise considerations, there is a relationship between dimensions and the required data sampling rates to achieve a desired level of performance. Thus there are a number of factors that will go into selecting optimum parameters for a given application.) Alternatively, multiple layers of different photoresists may be applied or another form of dielectric material may be deposited. Various types of chemical vapor deposition may also be used to build up a layer of materials suitable for microwell formation therein.

Once the photoresist layer (the singular form "layer" is used to encompass multiple layers in the aggregate, as well) is in place, the individual wells (typically mapped to have either one or four ISFET sensors per well) may be generated by placing a mask (e.g., of chromium) over the resist-coated die and exposing the resist to cross-linking (typically UV) radiation. All resist exposed to the radiation (i.e., where the mask does not block the radiation) becomes cross-linked and as a result will form a permanent plastic layer bonded to the surface of the chip (die). Unreacted resist (i.e., resist in areas which are not exposed, due to the mask blocking the light from reaching the resist and preventing cross-linking) is removed by washing the chip in a suitable solvent (i.e., developer) such as propyleneglycolmethylethylacetate (PGMEA) or other appropriate solvent. The resultant structure defines the walls of the microwell array.

Figure 30:
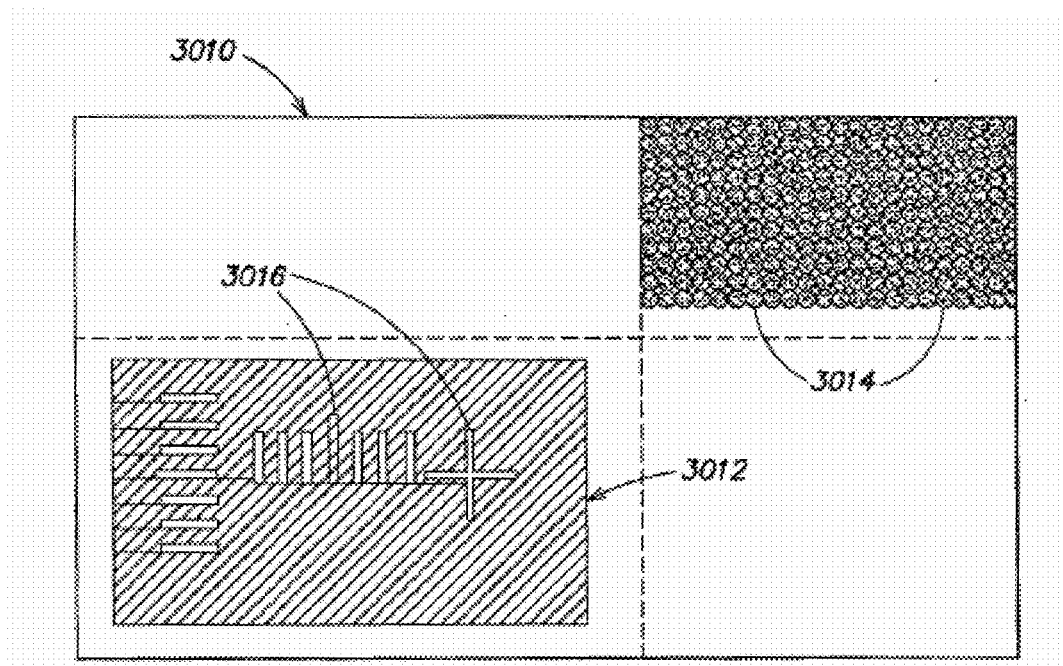
FIG. 30 is an illustration of an example of a layout for a portion of a (typically chromium) mask for a one-sensor-per-well embodiment of the above-described sensor array, corresponding to the portion of the die shown in FIG. 29.

FIG. 30 shows an example of a layout for a portion of a chromium mask 3010 for a one-sensor-per-well embodiment, corresponding to the portion of the die shown in FIG. 29. The grayed areas 3012, 3014 are those that block the UV radiation. The alignment marks in the white portions 3016 on the bottom left quadrant of FIG. 30, within gray area 3012, are used to align the layout of the wells with the ISFET sensors on the chip surface. The array of circles 3014 in the upper right quadrant of the mask block radiation from reaching the well areas, to leave unreacted resist which can be dissolved in forming the wells.

Figure 31:
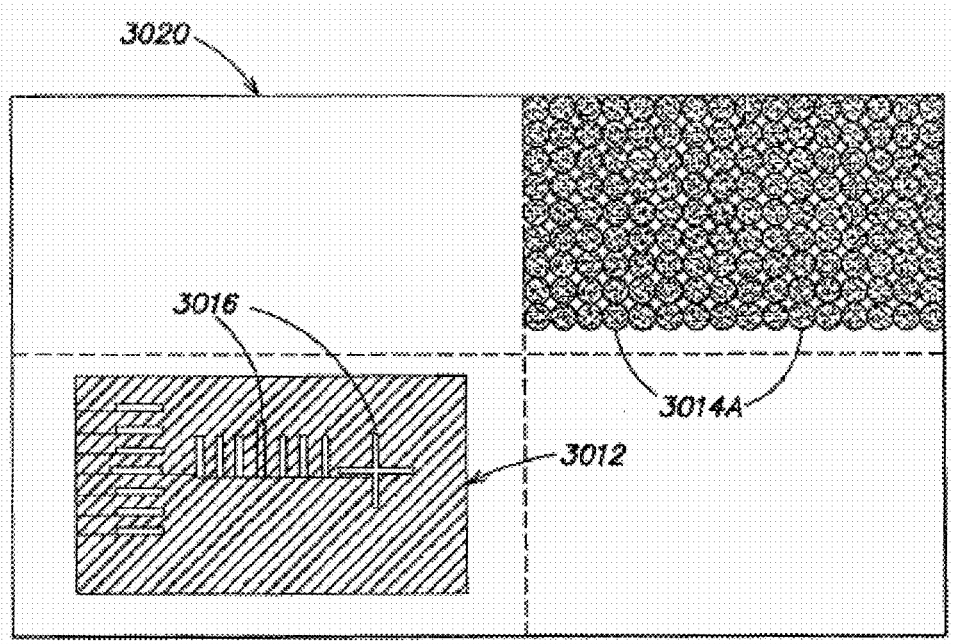
FIG. 31 is a corresponding layout for a mask for a 4-sensors-per-well embodiment.

FIG. 31 shows a corresponding layout for the mask 3020 for a 4-sensors-per-well embodiment. Note that the alignment pattern 3016 is still used and that the individual well-masking circles 3014A in the array 2910 now have twice the diameter as the wells 3014 in FIG. 30, for accommodating four sensors per well instead of one sensor-per-well.

Figure 32:
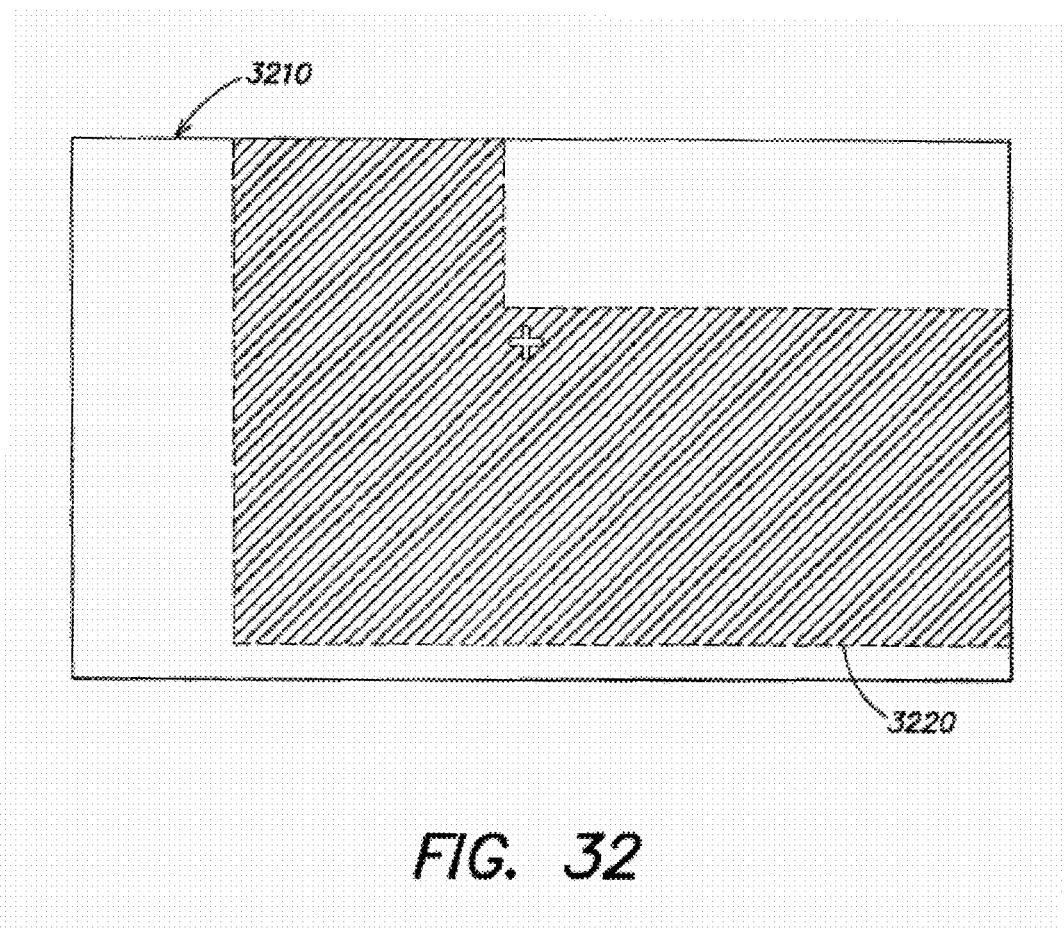
FIG. 32 is an illustration of a second mask used to mask an area which surrounds the array, to build a collar or wall (or basin, using that term in the geological sense) of resist which surrounds the active array of sensors on a substrate, as shown in FIG. 33A.
Figure 33:
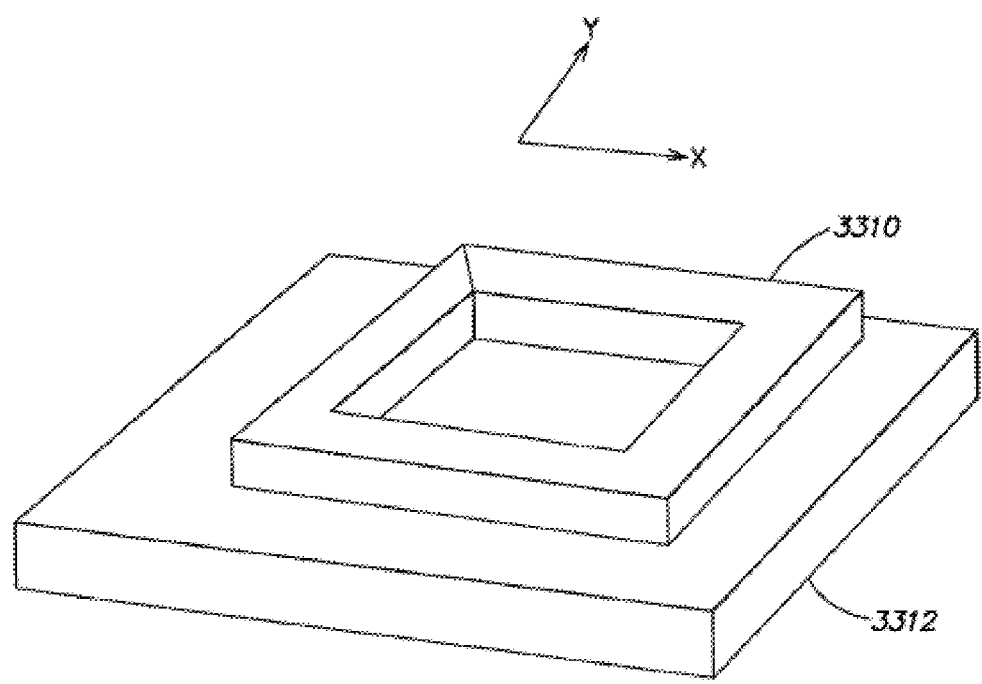
FIG. 33 is an illustration of the resulting basin.

After exposure of the die/resist to the UV radiation, a second layer of resist may be coated on the surface of the chip. This layer of resist may be relatively thick, such as about 400-450 μm thick, typically. A second mask 3210 (FIG. 32), which also may be of chromium, is used to mask an area 3220 which surrounds the array, to build a collar or wall (or basin, using that term in the geological sense) 3310 of resist which surrounds the active array of sensors on substrate 3312, as shown in FIG. 33. In the particular example being described, the collar is 150 μm wider than the sensor array, on each side of the array, in the x direction, and 9 μm wider on each side than the sensor array, in the y direction. Alignment marks on mask 3210 (most not shown) are matched up with the alignment marks on the first layer and the CMOS chip itself.

Other photolithographic approaches may be used for formation of the microwell array, of course, the foregoing being only one example.

For example, contact lithography of various resolutions and with various etchants and developers may be employed. Both organic and inorganic materials may be used for the layer(s) in which the microwells are formed. The layer(s) may be etched on a chip having a dielectric layer over the pixel structures in the sensor array, such as a passivation layer, or the layer(s) may be formed separately and then applied over the sensor array. The specific choice or processes will depend on factors such as array size, well size, the fabrication facility that is available, acceptable costs, and the like.

Among the various organic materials which may be used in some embodiments to form the microwell layer(s) are the above-mentioned SU-8 type of negative-acting photoresist, a conventional positive-acting photoresist and a positive-acting photodefineable polyimide. Each has its virtues and its drawbacks, well known to those familiar with the photolithographic art.

Naturally, in a production environment, modifications will be appropriate.

Contact lithography has its limitations and it may not be the production method of choice to produce the highest densities of wells—i.e., it may impose a higher than desired minimum pitch limit in the lateral directions. Other techniques, such as a deep UV step-and-repeat process, are capable of providing higher resolution lithography and can be used to produce small pitches and possibly smaller well diameters. Of course, for different desired specifications (e.g., numbers of sensors and wells per chip), different techniques may prove optimal. And pragmatic factors, such as the fabrication processes available to a manufacturer, may motivate the use of a specific fabrication method. While novel methods are discussed, various aspects of the invention are limited to use of these novel methods.

Preferably the CMOS wafer with the ISFET array will be planarized after the final metallization process. A chemical mechanical dielectric planarization prior to the silicon nitride passivation is suitable. This will allow subsequent lithographic steps to be done on very flat surfaces which are free of back-end CMOS topography.

By utilizing deep-UV step-and-repeat lithography systems, it is possible to resolve small features with superior resolution, registration, and repeatability. However, the high resolution and large numerical aperture (NA) of these systems precludes their having a large depth of focus. As such, it may be necessary, when using such a fabrication system, to use thinner photodefinable spin-on layers (i.e., resists on the order of 1-2 μm rather than the thicker layers used in contact lithography) to pattern transfer and then etch microwell features to underlying layer or layers. For example, four 1 μm plasma-enhanced chemical vapor thin-film depositions (standard fab process) may be done sequentially to render a target microwell thickness of 4 μm. High resolution lithography can then be used to pattern the microwell features and conventional SiO2 etch chemistries can be used—one each for the bondpad areas and then the microwell areas—having selective etch stops; the etch stops then can be on aluminum bondpads and silicon nitride passivation (or the like), respectively. Alternatively, other suitable substitute pattern transfer and etch processes can be employed to render microwells of inorganic materials.

Another approach is to form the microwell structure in an organic material. For example, a dual-resist "soft-mask" process may be employed, whereby a thin high-resolution deep-UV resist is used on top of a thicker organic material (e.g., cured polyimide or opposite-acting resist). The top resist layer is patterned. The pattern can be transferred using an oxygen plasma reactive ion etch process. This process sequence is sometimes referred to as the "portable conformable mask" (PCM) technique. See B. J. Lin et al., "Practicing the Novolac deep-UV portable conformable masking technique", Journal of Vacuum Science and Technology 19, No. 4, 1313-1319 (1981); and A. Cooper et al, "Optimization of a photosensitive spin-on dielectric process for copper inductor coil and interconnect protection in RF SoC devices."

Alternatively a "drill-focusing" technique may be employed, whereby several sequential step-and-repeat exposures are done at different focal depths to compensate for the limited depth of focus (DOF) of high-resolution steppers when patterning thick resist layers. This technique depends on the stepper NA and DOF as well as the contrast properties of the resist material.

Figure 33A:
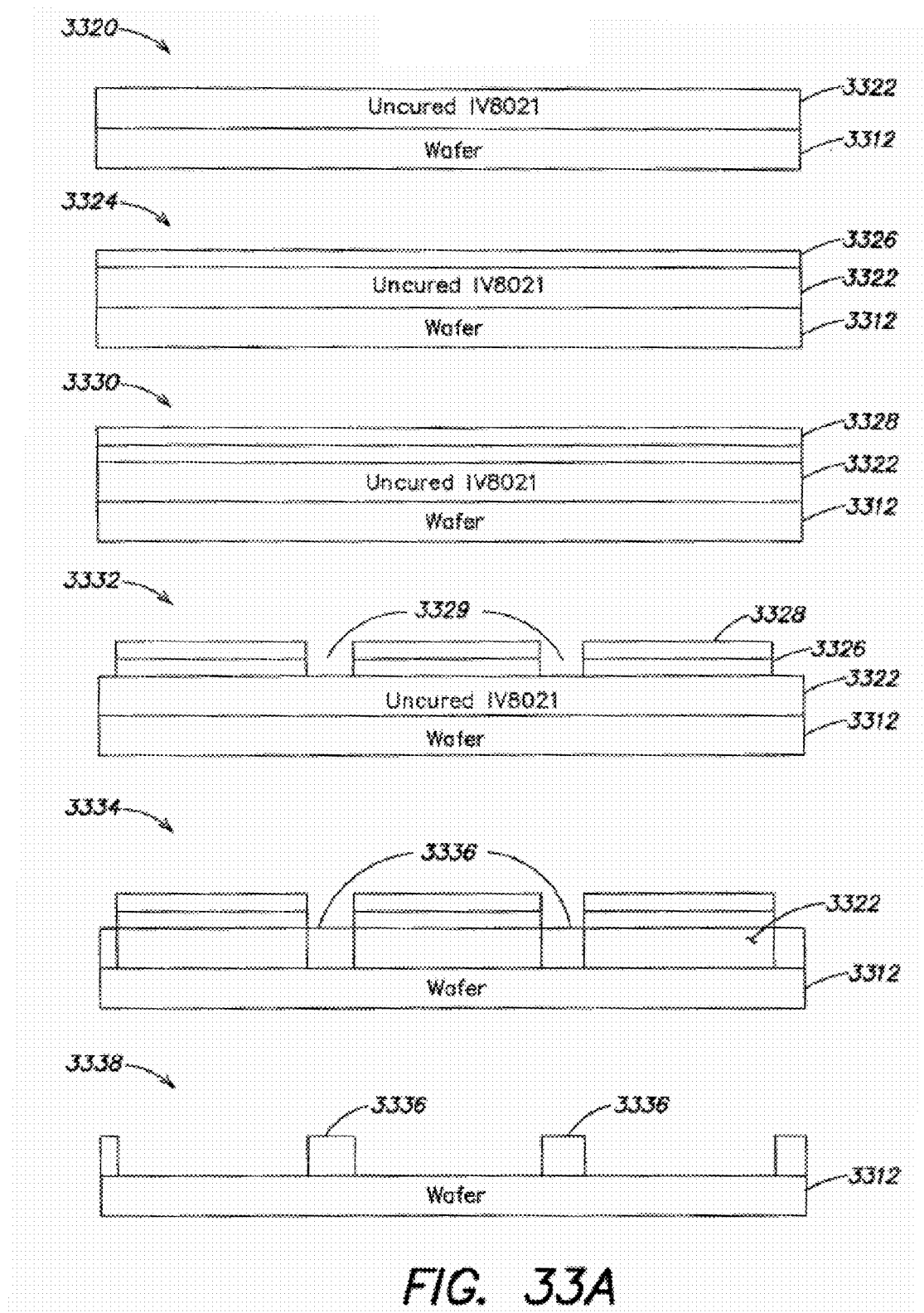
FIG. 33A is an illustration of a three-layer PCM process for making the microwell array.

Another PCM technique may be adapted to these purposes, such as that shown in U.S. patent application publication no. 2006/0073422 by Edwards et al. This is a three-layer PCM process and it is illustrated in FIG. 33A. As shown there, basically six major steps are required to produce the microwell array and the result is quite similar to what contact lithography would yield.

In a first step, 3320, a layer of high contrast negative-acting photoresist such as type Shipley InterVia Photodielectric Material 8021 (IV8021) 3322 is spun on the surface of a wafer, which we shall assume to be the wafer providing the substrate 3312 of FIG. 33 (in which the sensor array is fabricated), and a soft bake operation is performed. Next, in step 3324, a blocking anti-reflective coating (BARC) layer 3326, is applied and soft baked. On top of this structure, a thin resist layer 3328 is spun on and soft baked, step 3330, the thin layer of resist being suitable for fine feature definition. The resist layer 3328 is then patterned, exposed and developed, and the BARC in the exposed regions 3329, not protected any longer by the resist 3328, is removed, Step 3332. This opens up regions 3329 down to the uncured IV8021 layer. The BARC layer can now act like a conformal contact mask. A blanket exposure with a flooding exposure tool, Step 3334, cross-links the exposed IV8021, which is now shown as distinct from the uncured IV8021 at 3322. One or more developer steps 3338 are then performed, removing everything but the cross-linked IV8021 in regions 3336. Regions 3336 now constitute the walls of the microwells.

Although as shown above, the wells bottom out (i.e. terminate) on the top passivation layer of the ISFETs, it is believed that an improvement in ISFET sensor performance (i.e. such as signal-to-noise ratio) can be obtained if the active bead(s) is(are) kept slightly elevated from the ISFET passivation layer. One way to do so is to place a spacer "bump" within the boundary of the pixel microwell. An example of how this could be rendered would be not etching away a portion of the layer-or-layers used to form the microwell structure (i.e. two lithographic steps to form the microwells—one to etch part way done, the other to pattern the bump and finish the etch to bottom out), by depositing and lithographically defining and etching a separate layer to form the "bump", or by using a permanent photo-definable material for the bump once the microwells are complete. The bump feature is shown as 3350 in FIG. 33B. An alternative (or additional) non-integrated approach is to load the wells with a layer or two of very small packing beads before loading the DNA-bearing beads.

Mounting the Coated Chip to a Flow Cell (Fluidic Interface)

The process of using the assembly of an array of sensors on a chip combined with an array of microwells to sequence the DNA in a sample is referred to as an "experiment." Executing an experiment requires loading the wells with the DNA-bound beads and the flowing of several different solutions (i.e., reagents and washes) across the wells. A fluid delivery system coupled with a fluidic interface is needed which flows the various solutions across the wells in a controlled laminar flow with acceptably small dead volumes and small cross contamination between sequential solutions. The fluidic interface is sometimes referred to as a "flow cell."

Flow cell designs of many configurations are possible; the system and methods presented herein are not dependent on use of a specific flow cell configuration. It is desirable, though, that a suitable flow cell substantially conform to the following set of objectives:

suitable interconnections with a fluidics delivery system— e.g., via appropriately-sized tubing;

appropriate (for dna sequencing, approximately 300 μm) head space above wells;

minimization of dead volumes encountered by fluids prior to their entry to the flow chamber (i.e., the enclosed space above the microwell array).

elimination of small spaces in contact with liquid but not swept by through the flow cell (to minimize cross contamination).

uniform expansion of flow from the inlet tubing to a broad/ flat front at the entry to the flow chamber.

laminar flow characteristics such that the broad/flat front profile is maintained as it traverses across the chip from inlet side to outlet side.

adaptable to placement of a removable reference electrode inside or as close to the flow chamber as possible.

easy loading of beads.

manufacturable at acceptable cost easy assembly of flow cell and attachment to the chip package.

Each of several example designs will be discussed, meeting these criteria. In each instance, one typically may choose to implement the design in one of two ways: either by attaching the flow cell to a frame and gluing the frame (or otherwise attaching it) to the chip or by integrating the frame into the flow cell structure and attaching this unified assembly to the chip. Further, designs may be categorized by the way the reference electrode is integrated into the arrangement. Depending on the design, the reference electrode may be integrated into the flow cell (e.g., form part of the ceiling of the flow chamber) or be in the flow path (typically to the outlet or downstream side of the flow path, after the sensor array).

A first example of a suitable experiment apparatus 3410 incorporating such a fluidic interface is shown in FIGS. 34-37, the manufacture and construction of which will be discussed in greater detail below.

The apparatus comprises a semiconductor chip 3412 (indicated generally, though hidden) on or in which the arrays of wells and sensors are formed, and a fluidics assembly 3414 on top of the chip and delivering the sample to the chip for reading. The fluidics assembly includes a portion 3416 for introducing fluid containing the sample, a portion 3418 for allowing the fluid to be piped out, and a flow chamber portion 3420 for allowing the fluid to flow from inlet to outlet and along the way interact with the material in the wells. Those three portions are unified by an interface comprising a glass slide 3422 (e.g., Erie Microarray Cat #C22-5128-M20 from Erie Scientific Company, Portsmouth, N.H., cut in thirds of size about 25 mm×25 mm).

Mounted on the top face of the glass slide are two fittings, 3424 and 3426, such as nanoport fittings Part# N-333 from Upchurch Scientific of Oak Harbor, Wash. One port (e.g., 3424) serves as an inlet delivering liquids from the pumping/ valving system described below but not shown here. The second port (e.g., 3426) is the outlet which pipes the liquids to waste. Each port connects to a conduit 3428, 3432 such as flexible tubing of appropriate inner diameter. The nanoports are mounted such that the tubing can penetrate corresponding holes in the glass slide. The tube apertures should be flush with the bottom surface of the slide.

On the bottom of the glass slide, flow chamber 3420 may comprise various structures for promoting a substantially laminar flow across the microwell array. For example, a series of microfluidic channels fanning out from the inlet pipe to the edge of the flow chamber may be patterned by contact lithography using positive photoresists such as SU-8 photoresist from MicroChem. Corp. of Newton, Mass. Other structures will be discussed below.

The chip 3412 will in turn be mounted to a carrier 3430, for packaging and connection to connector pins 3432.

Figure 36:
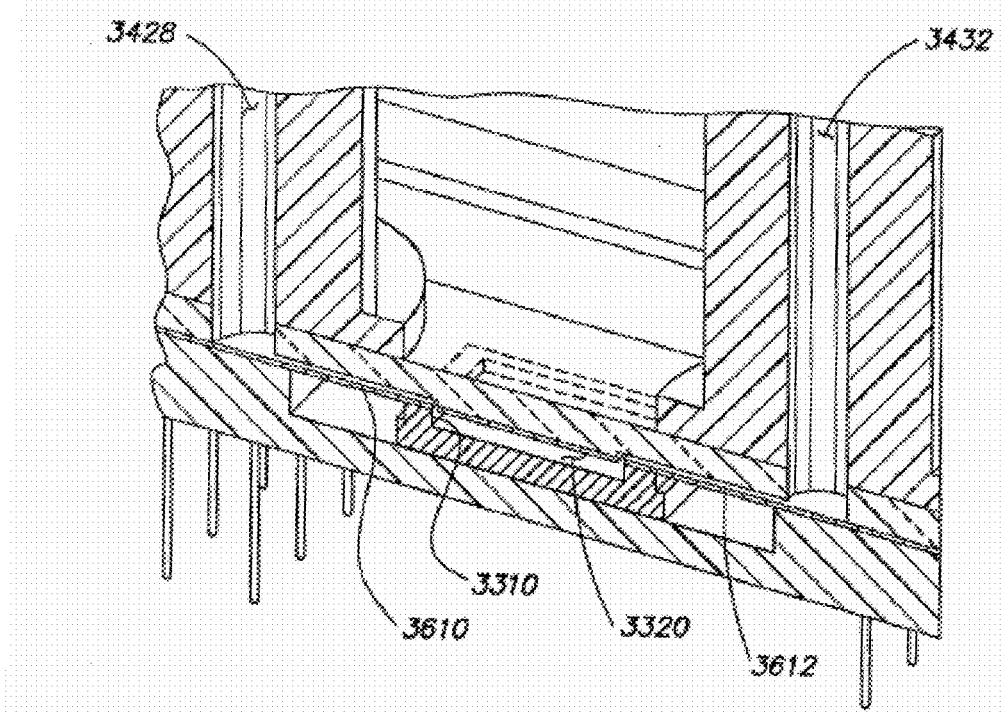
Figure 37:
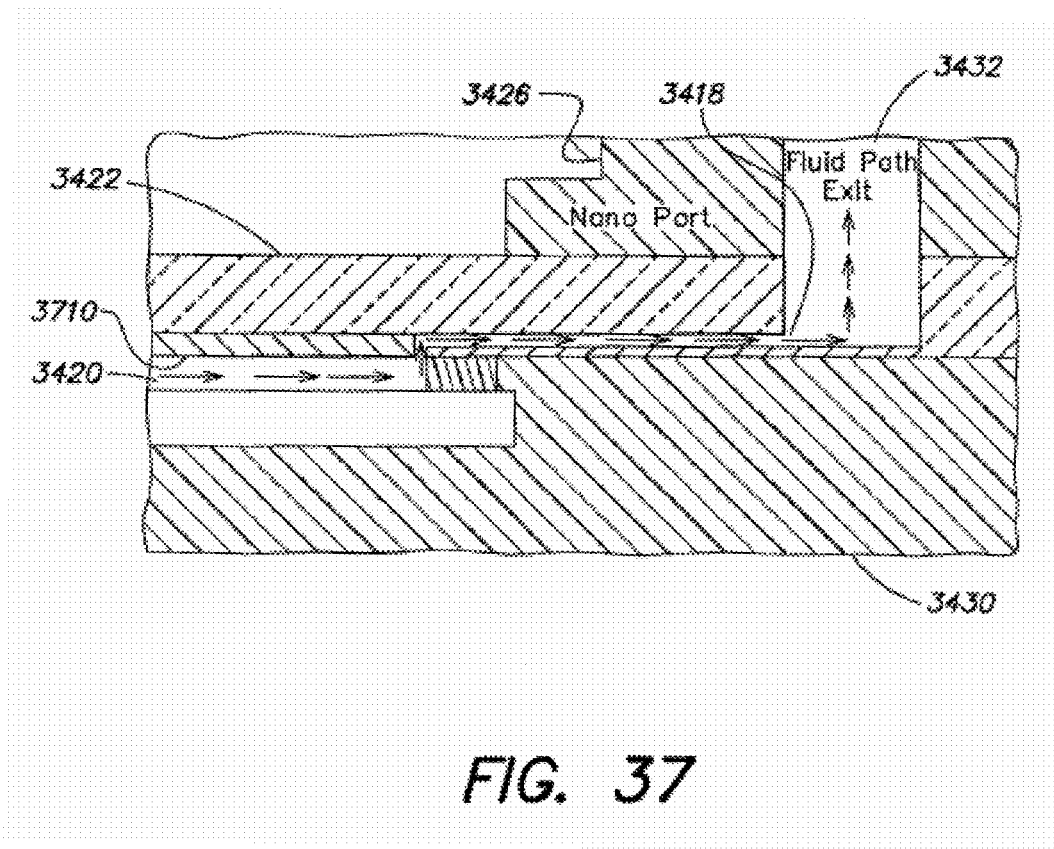
Figure 38:
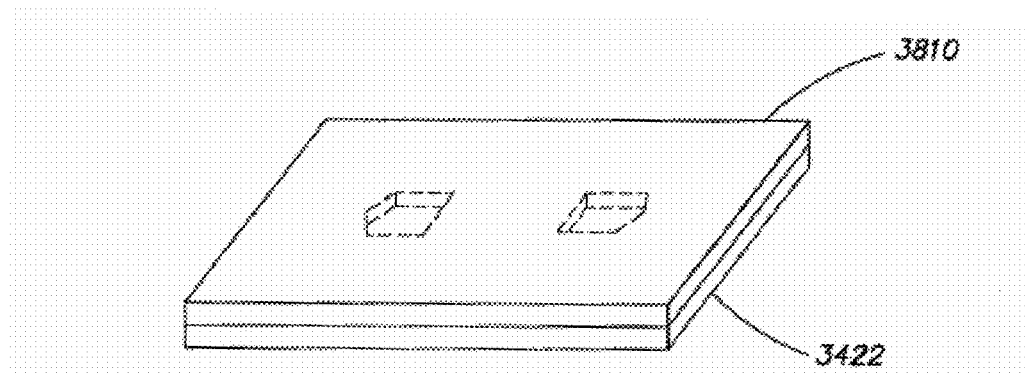
FIG. 38 is a diagrammatic illustration of a substrate with an etched photoresist layer beginning the formation of an example flow cell of a certain configuration.

For ease of description, to discuss fabrication starting with FIG. 38 we shall now consider the glass slide 3422 to be turned upside down relative to the orientation it has in FIGS. 34-37.

Figure 39:
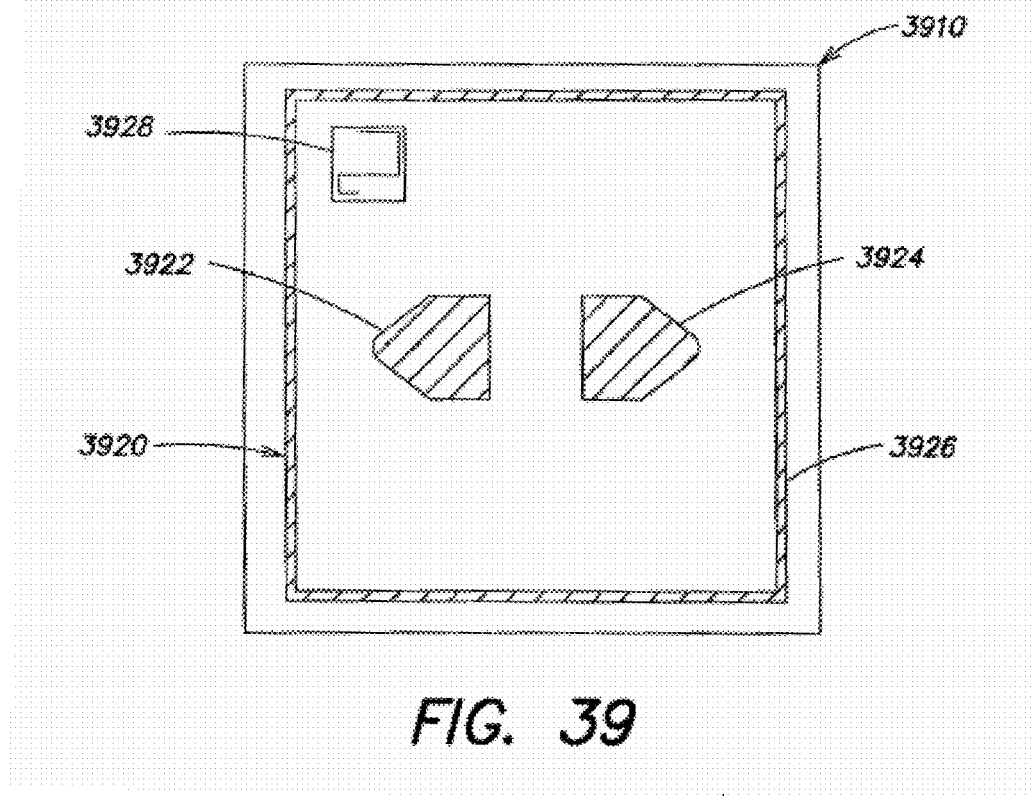
FIGS. 39-41 are diagrams of masks suitable for producing a first configuration of flow cell consistent with FIG. 38.
Figure 40:
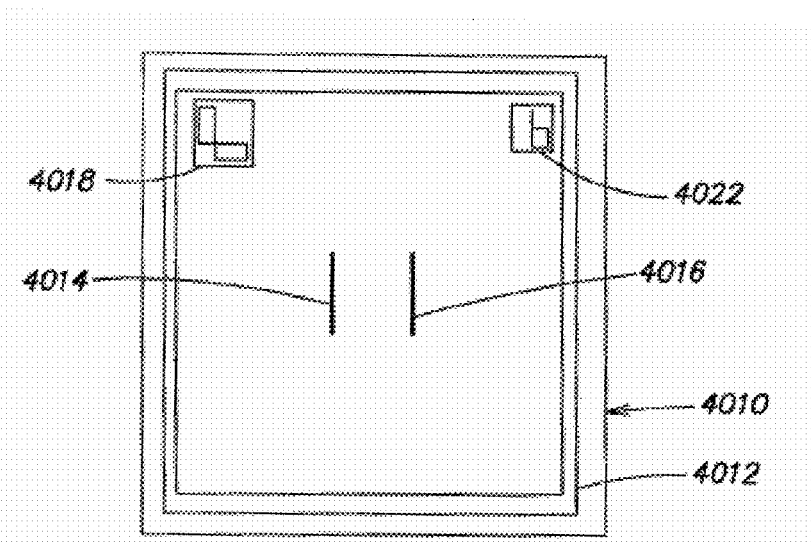

A layer of photoresist 3810 is applied to the "top" of the slide (which will become the "bottom" side when the slide and its additional layers is turned over and mounted to the sensor assembly of IS FET array with microwell array on it). Layer 3810 may be about 150 µm thick in this example, and it will form the primary fluid carrying layer from the end of the tubing in the nanoports to the edge of the sensor array chip. Layer 3810 is patterned using a mask such as the mask 3910 of FIG. 39 ("patterned" meaning that a radiation source is used to expose the resist through the mask and then the non-plasticized resist is removed). The mask 3910 has radiation-transparent regions which are shown as white and radiation-blocking regions 3920, which are shown in shading. The radiation-blocking regions are at 3922-3928. The region 3926 will form a channel around the sensor assembly; it is formed about 0.5 mm inside the outer boundary of the mask 3920, to avoid the edge bead that is typical. The regions 3922 and 3924 will block radiation so that corresponding portions of the resist are removed to form voids shaped as shown. Each of regions 3922, 3924 has a rounded end dimensioned to receive an end of a corresponding one of the tubes 3428, 3432 passing through a corresponding nanoport 3424, 3426. From the rounded end, the regions 3922, 3924 fan out in the direction of the sensor array to allow the liquid to spread so that the flow across the array will be substantially laminar. The region 3928 is simply an alignment pattern and may be any suitable alignment pattern or be replaced by a suitable substitute alignment mechanism. Dashed lines on FIG. 38 have been provided to illustrate the formation of the voids 3822 and 3824 under mask regions 3922 and 3924.

A second layer of photoresist is formed quite separately, not on the resist 3810 or slide 3422. Preferably it is formed on a flat, flexible surface (not shown), to create a peel-off, patterned plastic layer. This second layer of photoresist may be formed using a mask such as mask 4010, which will leave on the flexible substrate, after patterning, the border under region 4012, two slits under regions 4014, 4016, whose use will be discussed below, and alignment marks produced by patterned regions 4018 and 4022. The second layer of photoresist is then applied to the first layer of photoresist using one alignment mark or set of alignment marks, let's say produced by pattern 4018, for alignment of these layers. Then the second layer is peeled from its flexible substrate and the latter is removed.

The other alignment mark or set of marks produced by pattern 4022 is used for alignment with a subsequent layer to be discussed.

The second layer is preferably about 150 µm deep and it will cover the fluid-carrying channel with the exception of a slit about 150 µm long at each respective edge of the sensor array chip, under slit-forming regions 4014 and 4016.

Figure 41:
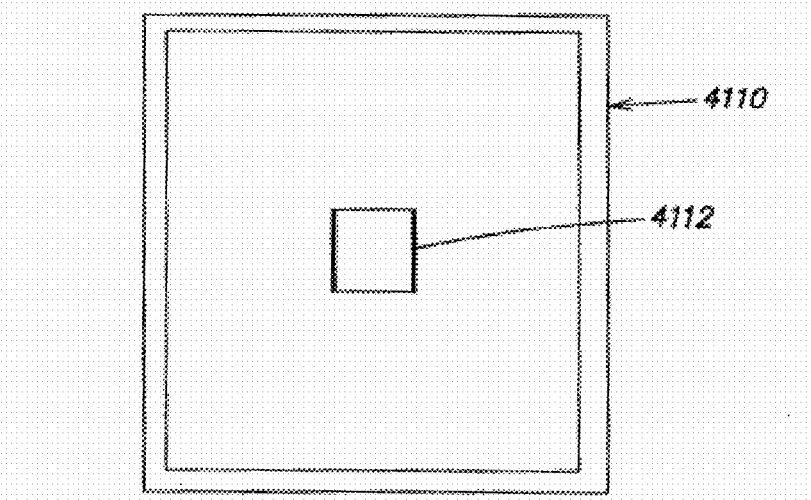

Once the second layer of photoresist is disposed on the first layer, a third patterned layer of photoresist is formed over the second layer, using a mask such as mask 4110, shown in FIG. 41. The third layer provides a baffle member under region 4112 which is as wide as the collar 3310 on the sensor chip array (see FIG. 33) but about 300 µm narrower to allow overlap with the fluid-carrying channel of the first layer. The third layer may be about 150 µm thick and will penetrate the chip collar 3310, toward the floor of the basin formed thereby, by 150 µm. This configuration will leave a headspace of about 300 µm above the wells on the sensor array chip. The liquids are flowed across the wells along the entire width of the sensor array through the 150 µm slits under 4014, 4016.

Figure 34:
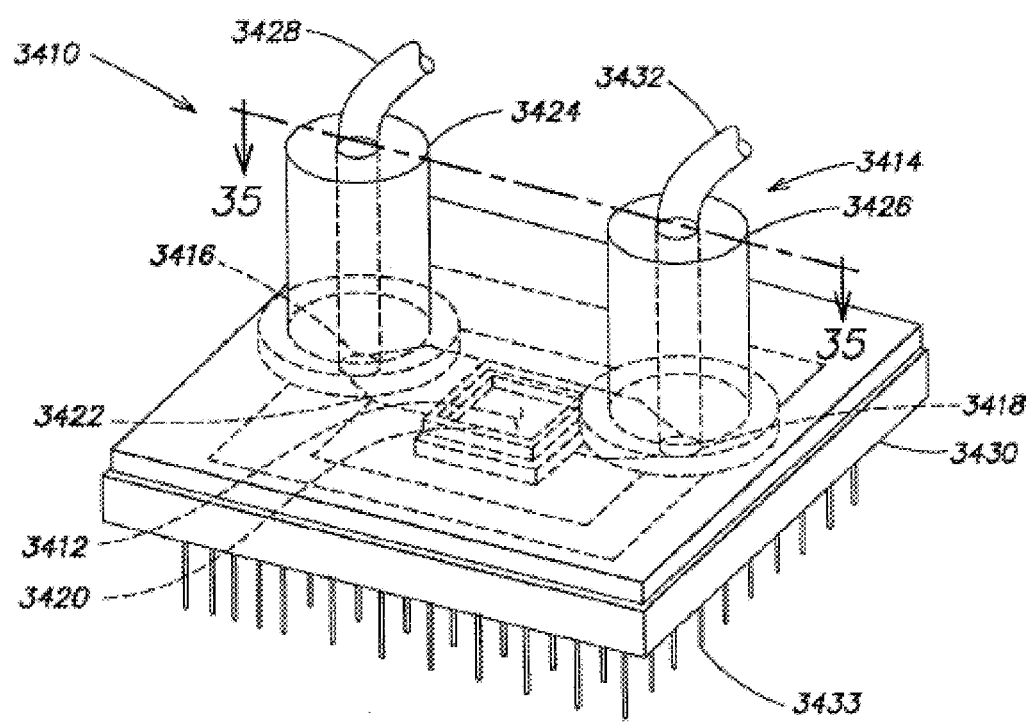
FIGS. 34-37 diagrammatically illustrate a first example of a suitable experiment apparatus incorporating a fluidic interface with the sensor array, with FIG. 35 providing a cross-section through the FIG. 34 apparatus along section line 35-35' and FIG. 36 expanding part of FIG. 35, in perspective, and FIG. 37 further expanding a portion of the structure to make the fluid flow more visible.
Figure 35:
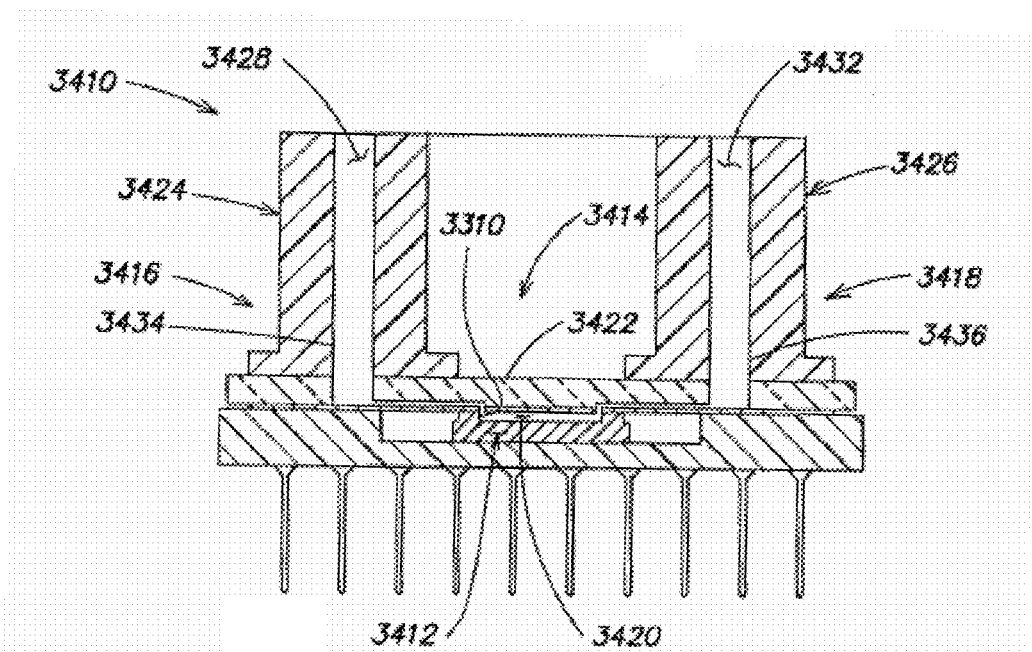

FIG. 36 shows a partial sectional view, in perspective, of the above-described example embodiment of a microfluidics and sensor assembly, also depicted in FIGS. 34 and 35, enlarged to make more visible the fluid flow path. (A further enlarged schematic of half of the flow path is shown in FIG. 37.) Here, it will be seen that fluid enters via the inlet pipe 3428 in inlet port 3424. At the bottom of pipe 3428, the fluid flows through the flow expansion chamber 3610 formed by mask area 3922, that the fluid flows over the collar 3310 and then down into the bottom 3320 of the basin, and across the die 3412 with its microwell array. After passing over the array, the fluid then takes a vertical turn at the far wall of the collar 3310 and flows over the top of the collar to and across the flow concentration chamber 3612 formed by mask area 3924, exiting via outlet pipe 3432 in outlet port 3426. Part of this flow, from the middle of the array to the outlet, may be seen also in the enlarged diagrammatic illustration of FIG. 37, wherein the arrows indicate the flow of the fluid.

The fluidics assembly may be secured to the sensor array chip assembly by applying an adhesive to parts of mating surfaces of those two assemblies, and pressing them together, in alignment.

Though not illustrated in FIGS. 34-36, the reference electrode may be understood to be a metallization 3710, as shown in FIG. 37, at the ceiling of the flow chamber.

Figure 42:
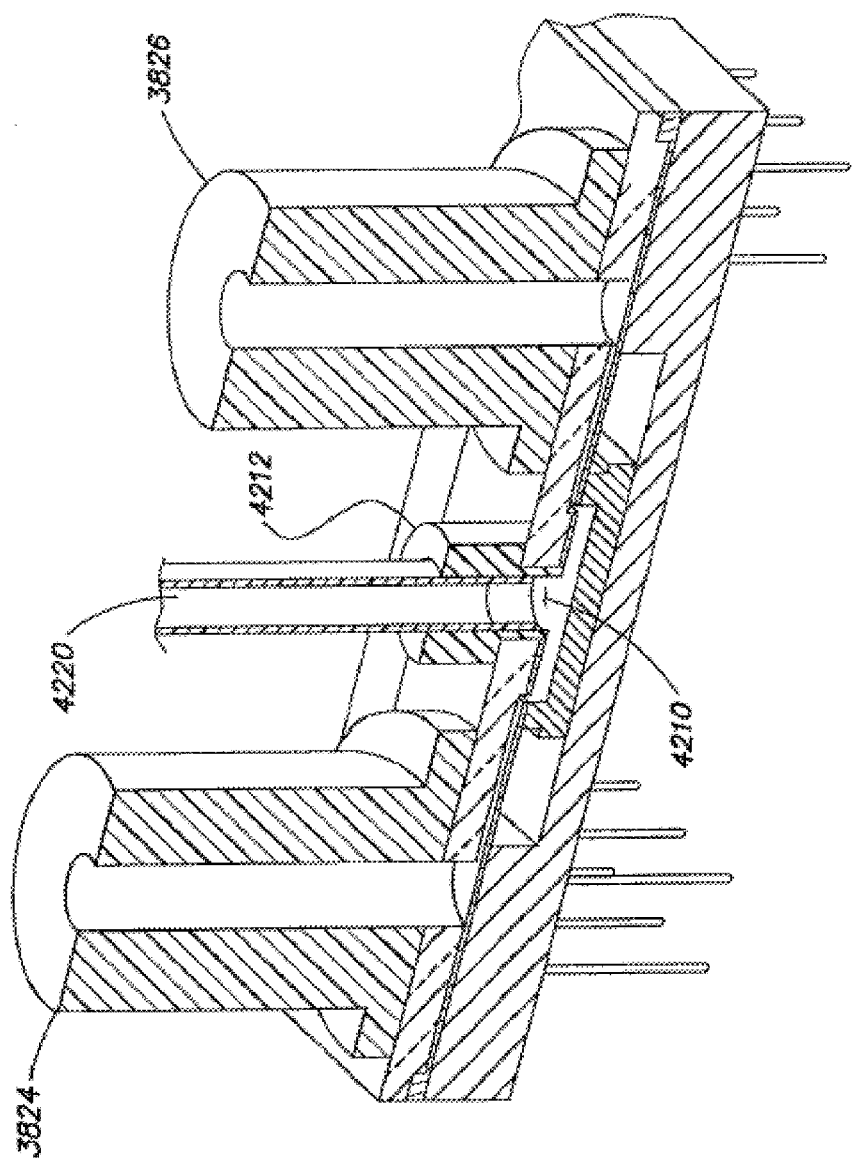
FIGS. 42-54 and 57-58 are pairs of partly isometric, sectional views of example apparatus and enlargements, showing ways of introducing a reference electrode into, and forming, a flow cell and flow chamber, using materials such as plastic and PDMS.

Another way to introduce the reference electrode is shown in FIG. 42. There, a hole 4210 is provided in the ceiling of the flow chamber and a grommet 4212 (e.g., of silicone) is fitted into that hole, providing a central passage or bore through which a reference electrode 4220 may be inserted. Baffles or other microfeatures (not shown) may be patterned into the flow channel to promote laminar flow over the microwell array.

Figure 43:
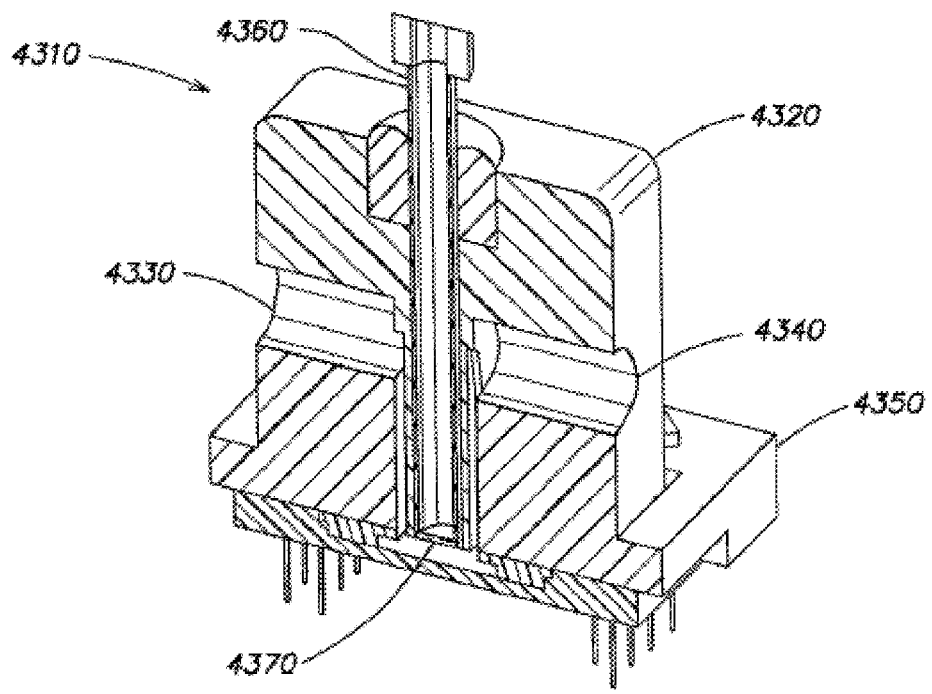
Figure 44:
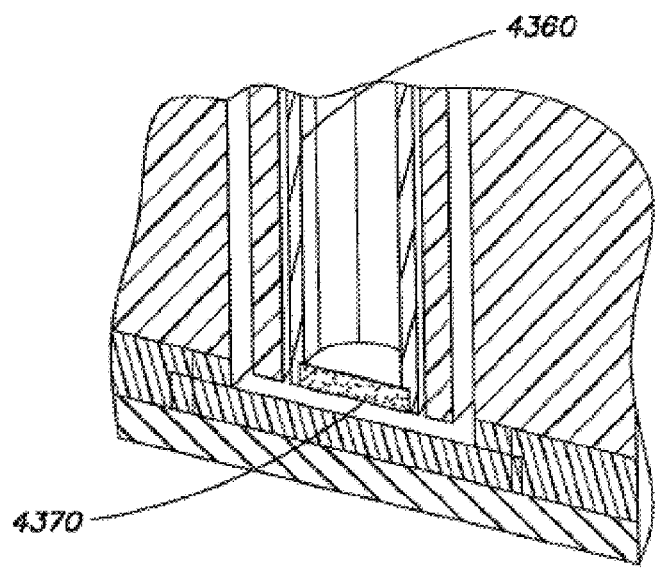

FIGS. 43-44 show another alternative flow cell design, 4310. This design relies on the molding of a single plastic piece or member 4320 to be attached to the chip to complete the flow cell. The connection to the fluidic system is made via threaded connections tapped into appropriate holes in the plastic piece at 4330 and 4340. Or, if the member 4320 is made of a material such as polydimethylsiloxane (PDMS), the connections may be made by simply inserting the tubing into an appropriately sized hole in the member 4320. A vertical cross section of this design is shown in FIGS. 43-44. This design may use an overhanging plastic collar 4350 (which may be a solid wall as shown or a series of depending, spaced apart legs forming a downwardly extending fence-like wall) to enclose the chip package and align the plastic piece with the chip package, or other suitable structure, and thereby to alignment the chip frame with the flow cell forming member

4320. Liquid is directed into the flow cell via one of apertures 4330, 4340, thence downwardly towards the flow chamber.

In the illustrated embodiment, the reference electrode is introduced to the top of the flow chamber via a bore 4325 in the member 4320. The placement of the removable reference electrode is facilitated by a silicone sleeve 4360 and an epoxy stop ring 4370 (see the blow-up of FIG. 44). The silicone sleeve provides a tight seal and the epoxy stop ring prevent the electrode from being inserted too far into the flow cell. Of course, other mechanisms may be employed for the same purposes, and it may not be necessary to employ structure to stop the electrode. And if a material such as PDMS is used for member 4320, the material itself may form a watertight seal when the electrode is inserted, obviating need for the silicone sleeve.

Figure 45:
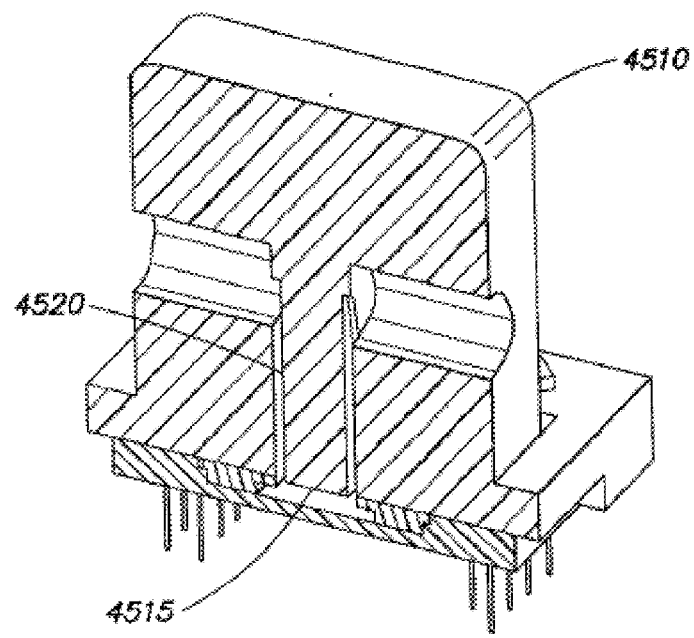
Figure 46:
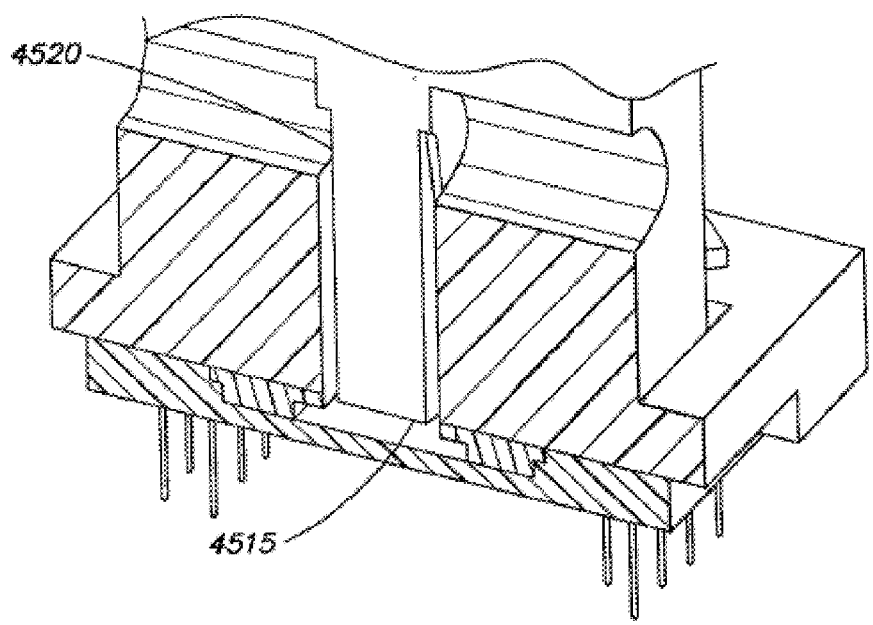

FIGS. 45 and 46 show a similar arrangement except that member 4510 lacks a bore for receiving a reference electrode. Instead, the reference electrode 4515 is formed on or affixed to the bottom of central portion 4520 and forms at least part of the flow chamber ceiling. For example, a metallization layer may be applied onto the bottom of central portion 4520 before member 4510 is mounted onto the chip package.

Figure 47:
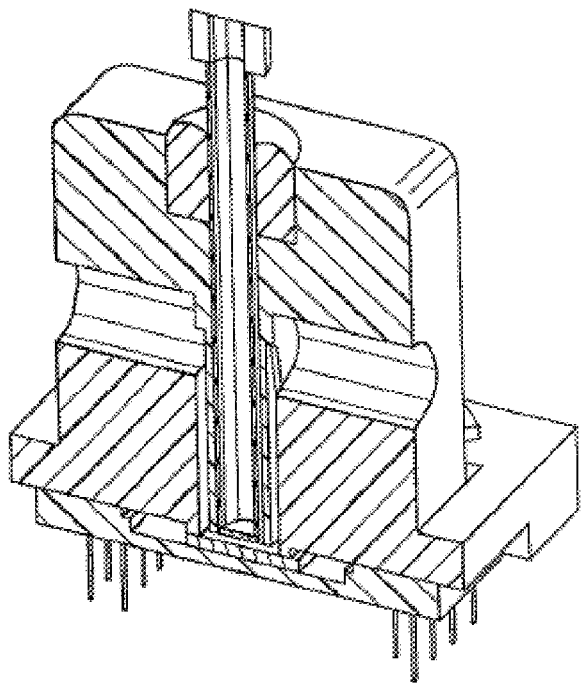
Figure 48:
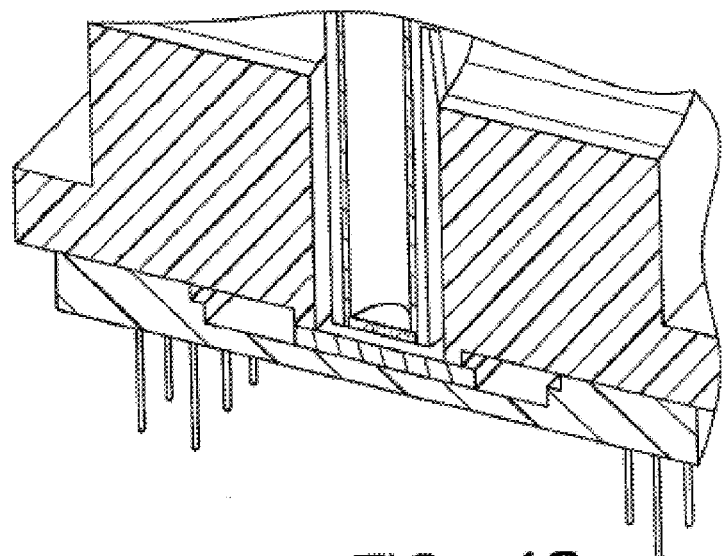
Figure 49:
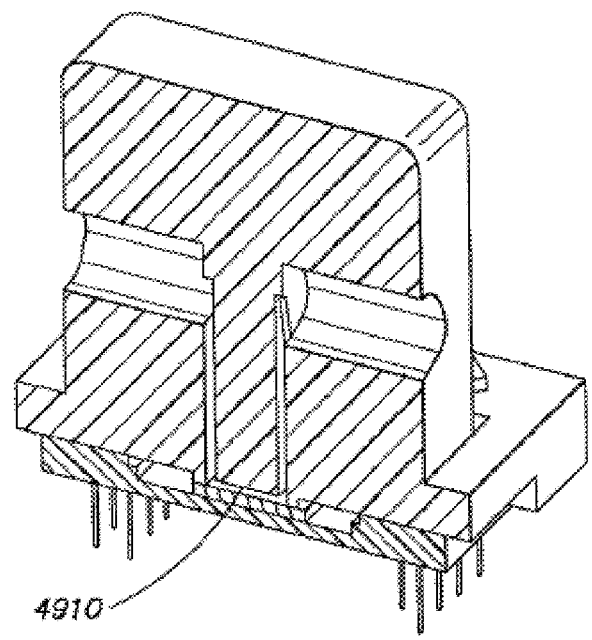
Figure 50:
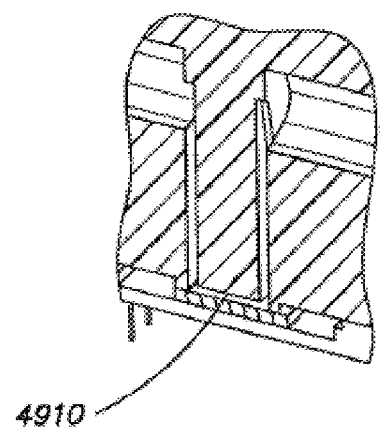

FIGS. 47-48 show another example, which is a variant of the embodiment shown in FIGS. 43-44, but wherein the frame is manufactured as part of the flow cell rather attaching a flow port structure to a frame previously attached to the chip surface. In designs of this type, assembly is somewhat more delicate since the wirebonds to the chip are not protected by the epoxy encapsulating the chip. The success of this design is dependent on the accurate placement and secure gluing of the integrated "frame" to the surface of the chip. A counterpart embodiment to that of FIGS. 45-46, with the reference electrode 4910 on the ceiling of the flow chamber, and with the frame manufactured as part of the flow cell, is shown in FIGS. 49-50.

Figure 51:
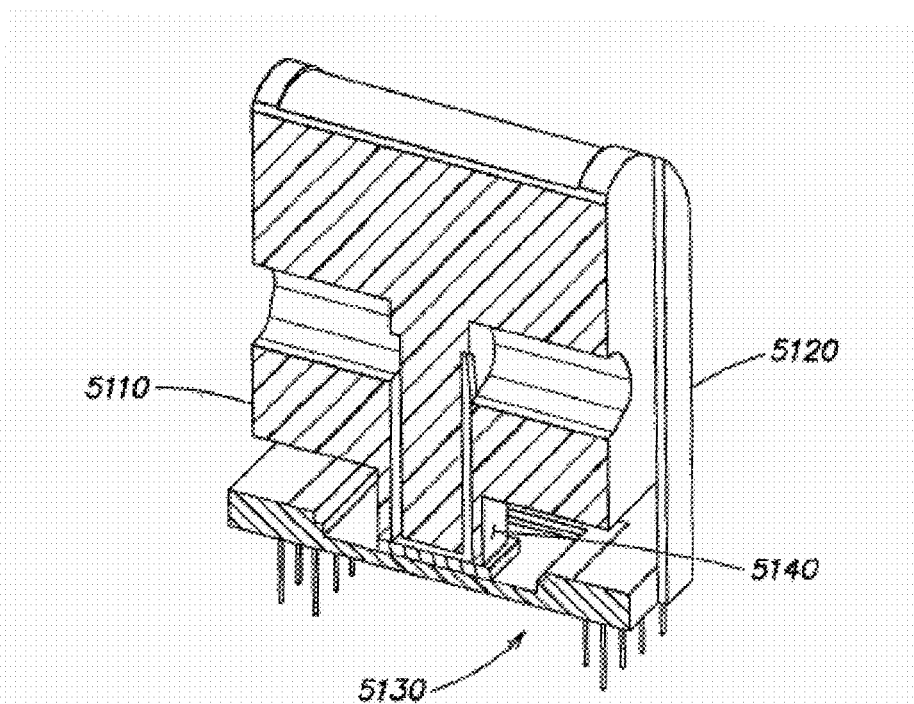
Figure 52:
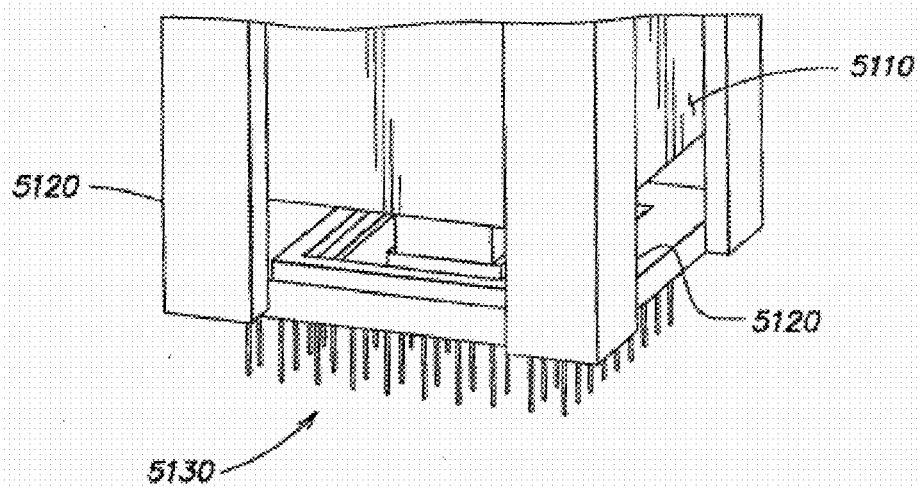

Yet another alternative for a fluidics assembly, as shown in FIGS. 51-52, has a fluidics member 5110 raised by about 5.5 mm on stand-offs 5120 from the top of the chip package 5130. This allows for an operator to visually inspect the quality of the bonding between plastic piece 5140 and chip surface and reinforce the bonding externally if necessary.

Figure 53:
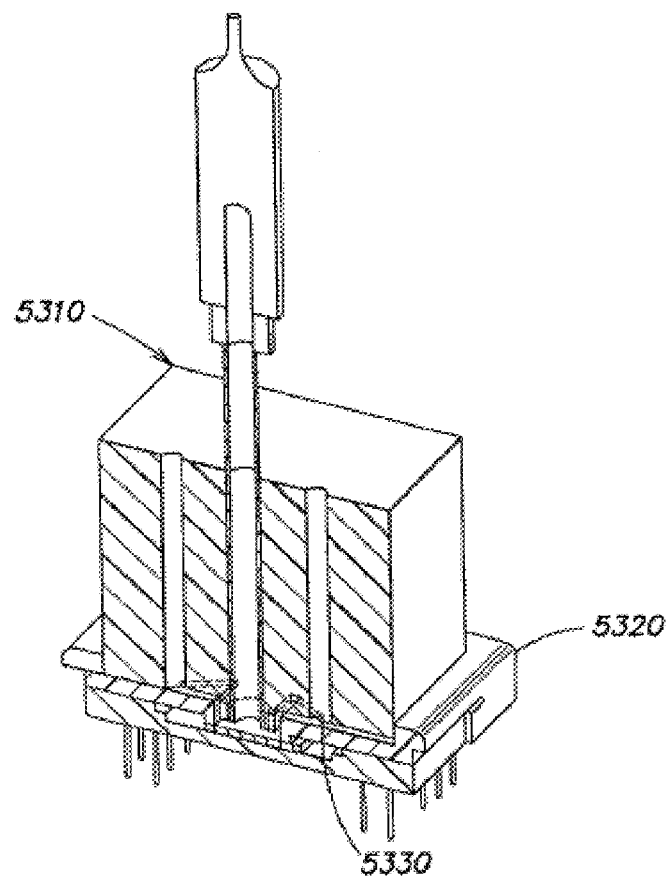
Figure 54:
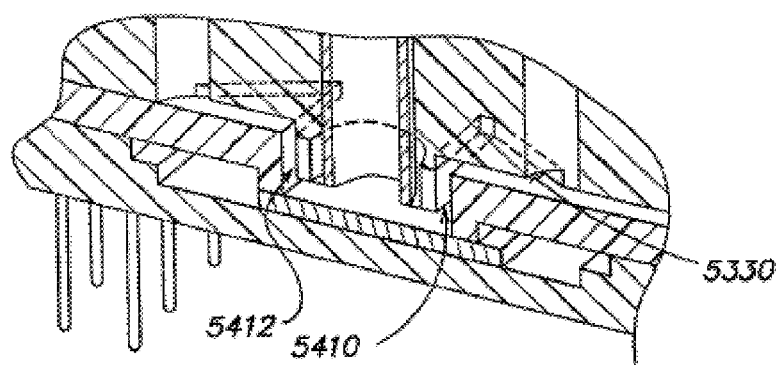

Some of the foregoing alternative embodiments also may be implemented in a hybrid plastic/PDMS configuration. For example, as shown in FIGS. 53-54, a plastic part 5310 may make up the frame and flow chamber, resting on a PDMS "base" portion 5320. The plastic part 5310 may also provides a region 5330 to the array, for expansion of the fluid flow from the inlet port; and the PDMS part may then include communicating slits 5410, 5412 through which liquids are passed from the PDMS part to and from the flow chamber below.

The fluidic structure may also be made from glass as discussed above, such as photo-definable (PD) glass. Such a glass may have an enhanced etch rate in hydrofluoric acid once selectively exposed to UV light and features may thereby be micromachined on the top-side and back-side, which when glued together can form a three-dimensional low aspect ratio fluidic cell.

Figure 55:
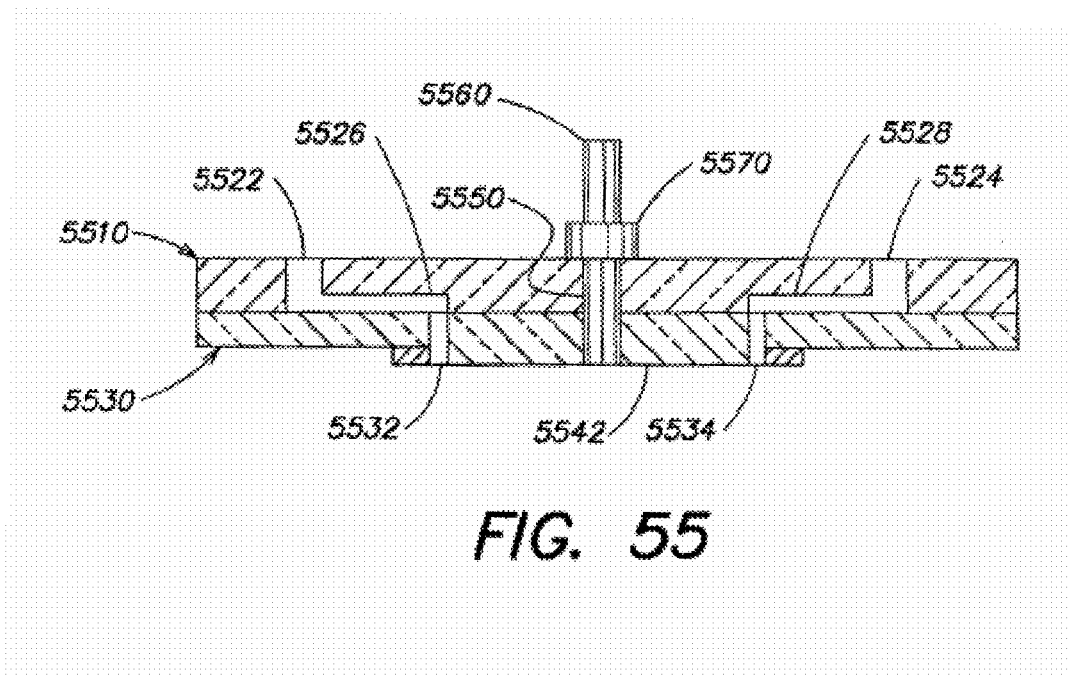
FIGS. 55 and 56 are schematic, cross-sectional views of two-layer glass (or plastic) arrangements for manufacturing fluidic apparatus for mounting onto a chip for use as taught herein.

An example is shown in FIG. 55. A first glass layer or sheet 5510 has been patterned and etched to create nanoport fluidic holes 5522 and 5524 on the top-side and fluid expansion channels 5526 and 5528 on the back-side. A second glass layer or sheet 5530 has been patterned and etched to provide downward fluid input/output channels 5532 and 5534, of about 300 μm height (the thickness of the layer). The bottom surface of layer 5530 is thinned to the outside of channels 5532 and 5534, to allow the layer 5530 to rest on the chip frame and protrusion area 5542 to be at an appropriate height to form the top of the flow channel. Two glass layers, or wafers, and four lithography steps required. Both wafers should be aligned and bonded (e.g., with an appropriate glue, not shown) such that the downward fluid input/output ports are aligned properly with the fluid expansion channels. Alignment targets may be etched into the glass to facilitate the alignment process.

Nanoports may be secured over the nanoport fluidic holes to facilitate connection of input and output tubing.

A central bore 5550 may be etched through the glass layers for receiving a reference electrode, 5560. The electrode may be secured and sealed in place with a silicone collar 5570 or like structure; or the electrode may be equipped integrally with a suitable washer for effecting the same purpose.

Figure 56:
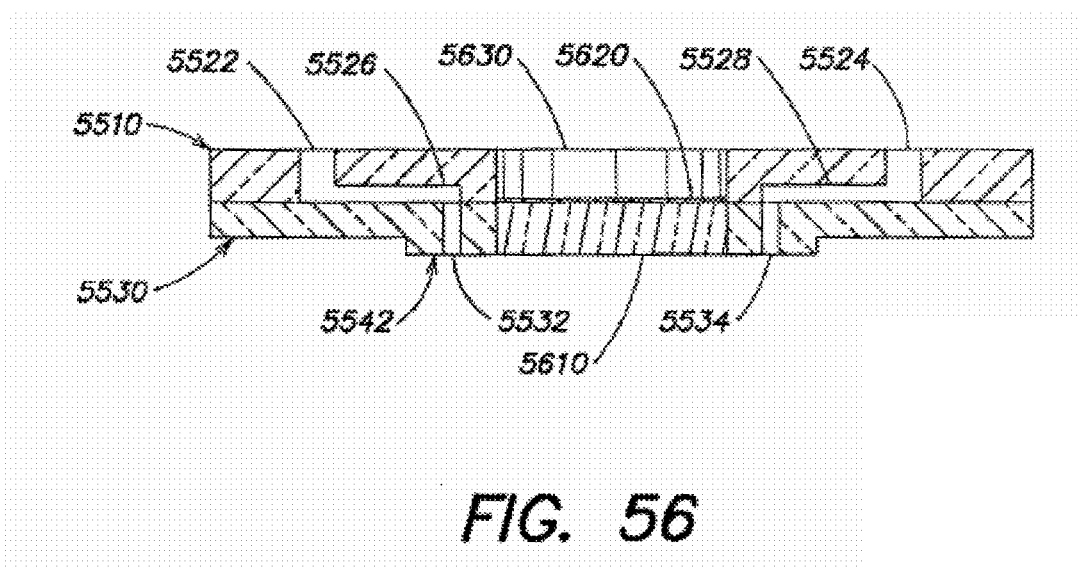

By using glass materials for the two-layer fluidic cell, the reference electrode may also be a conductive layer or pattern deposited on the bottom surface of the second glass layer (not shown). Or, as shown in FIG. 56, the protrusion region may be etched to form a permeable glass membrane 5610 on the top of which is coated a silver (or other material) thin-film 5620 to form an integrated reference electrode. A hole 5630 may be etched into the upper layer for accessing the electrode and if that hole is large enough, it can also serve as a reservoir for a silver chloride solution. Electrical connection to the thin-film silver electrode may be made in any suitable way, such as by using a clip-on pushpin connector or alternatively wirebonded to the ceramic ISFET package.

Figure 57:
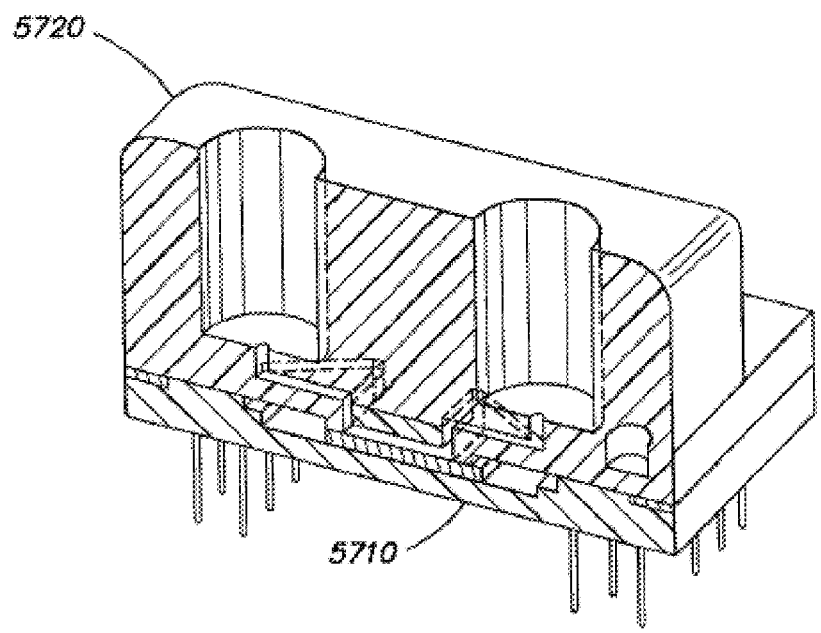
Figure 58:
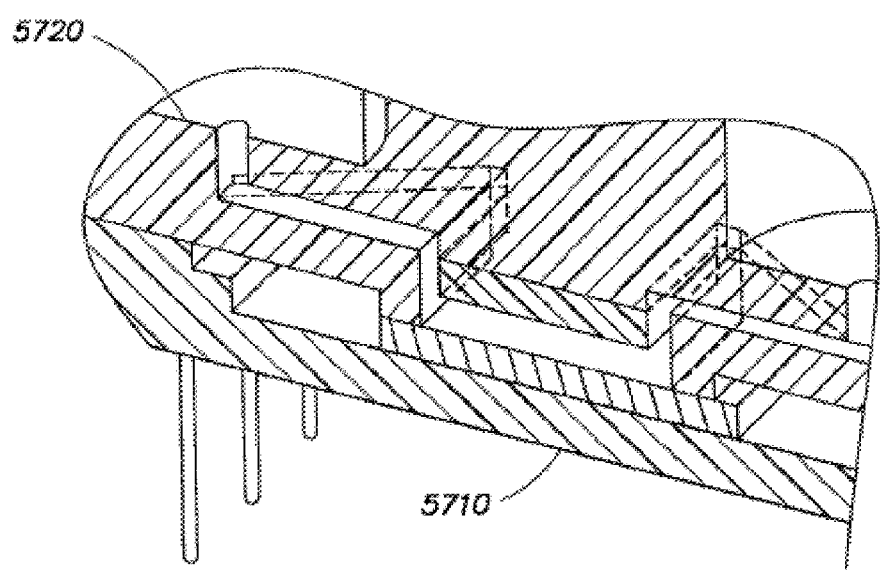

Still another example embodiment for a fluidic assembly is shown in FIGS. 57-58. This design is limited to a plastic piece 5710 which incorporates the frame and is attached directly to the chip surface, and to a second piece 5720 which is used to connect tubing from the fluidic system and similarly to the PDMS piece discussed above, distributes the liquids from the small bore tube to a wide flat slit. The two pieces are glued together and multiple (e.g., three) alignment markers (not shown) may be used to precisely align the two pieces during the gluing process. A hole may be provided in the bottom plate and the hole used to fill the cavity with an epoxy (for example) to protect the wirebonds to the chip and to fill in any potential gaps in the frame/chip contact. In the illustrated example, the reference electrode is external to the flow cell (downstream in the exhaust stream, through the outlet port—see below), though other configurations of reference electrode may, of course, be used.

Figure 59A:
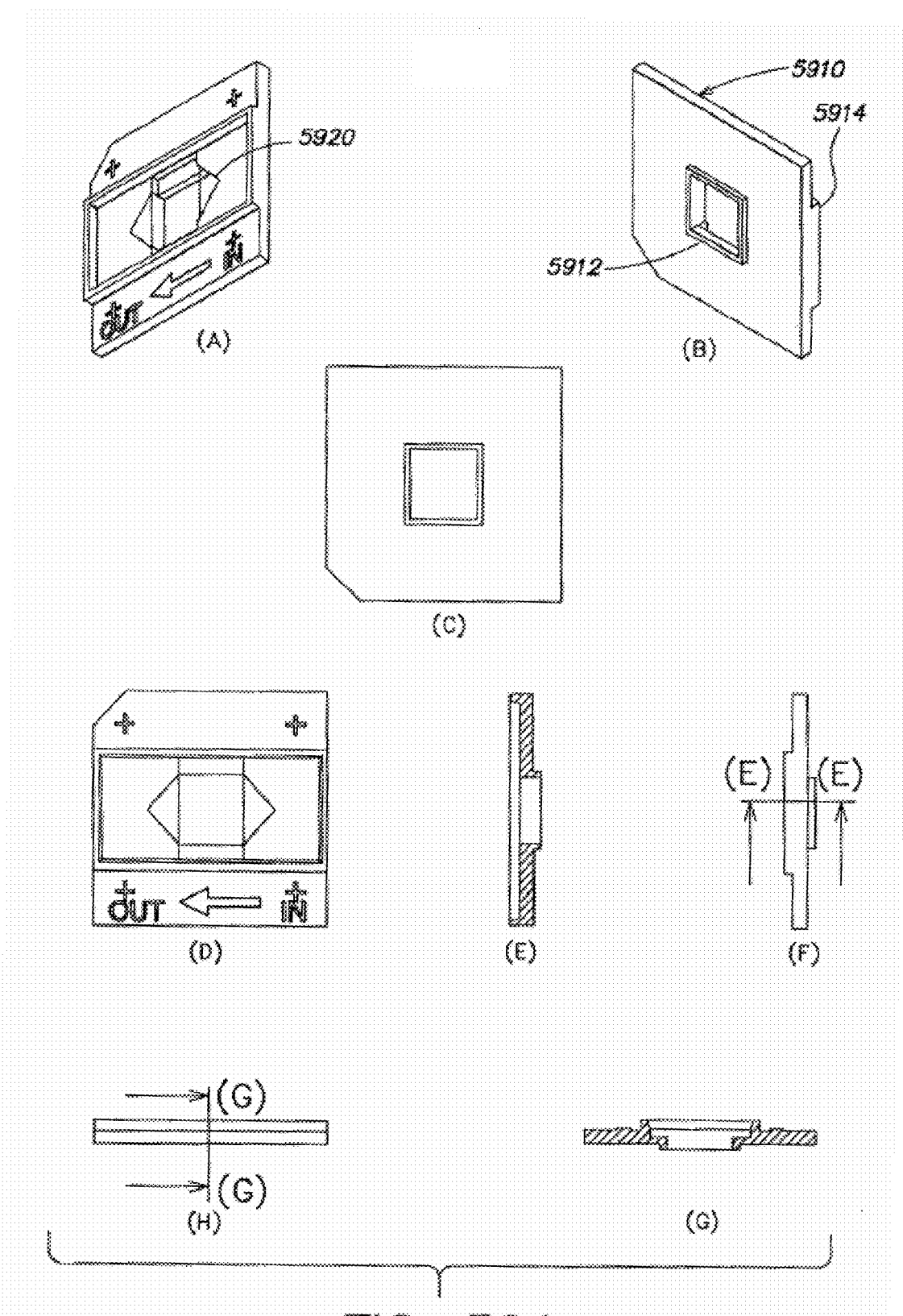
Figure 59C:
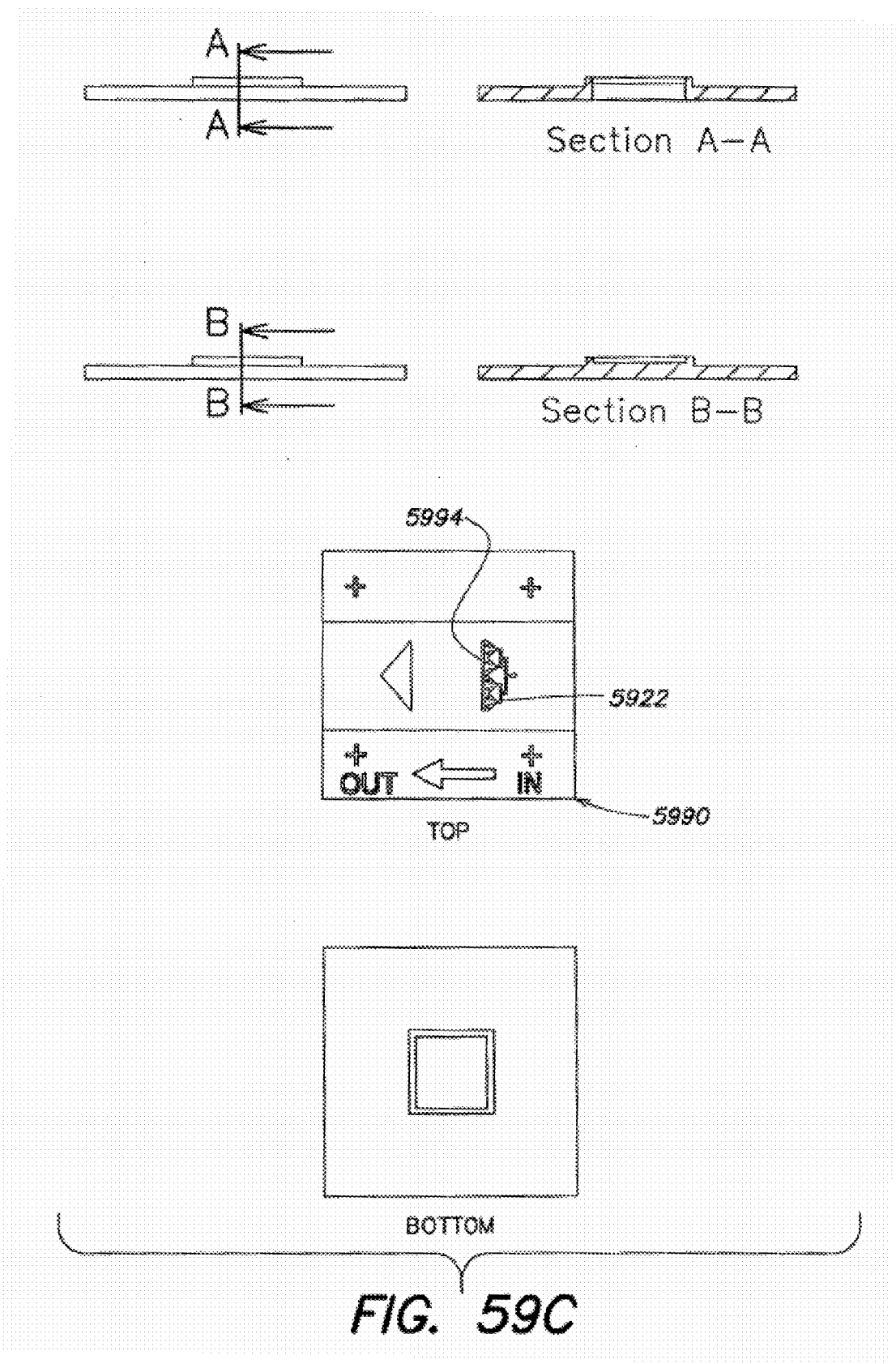
Figure 60:
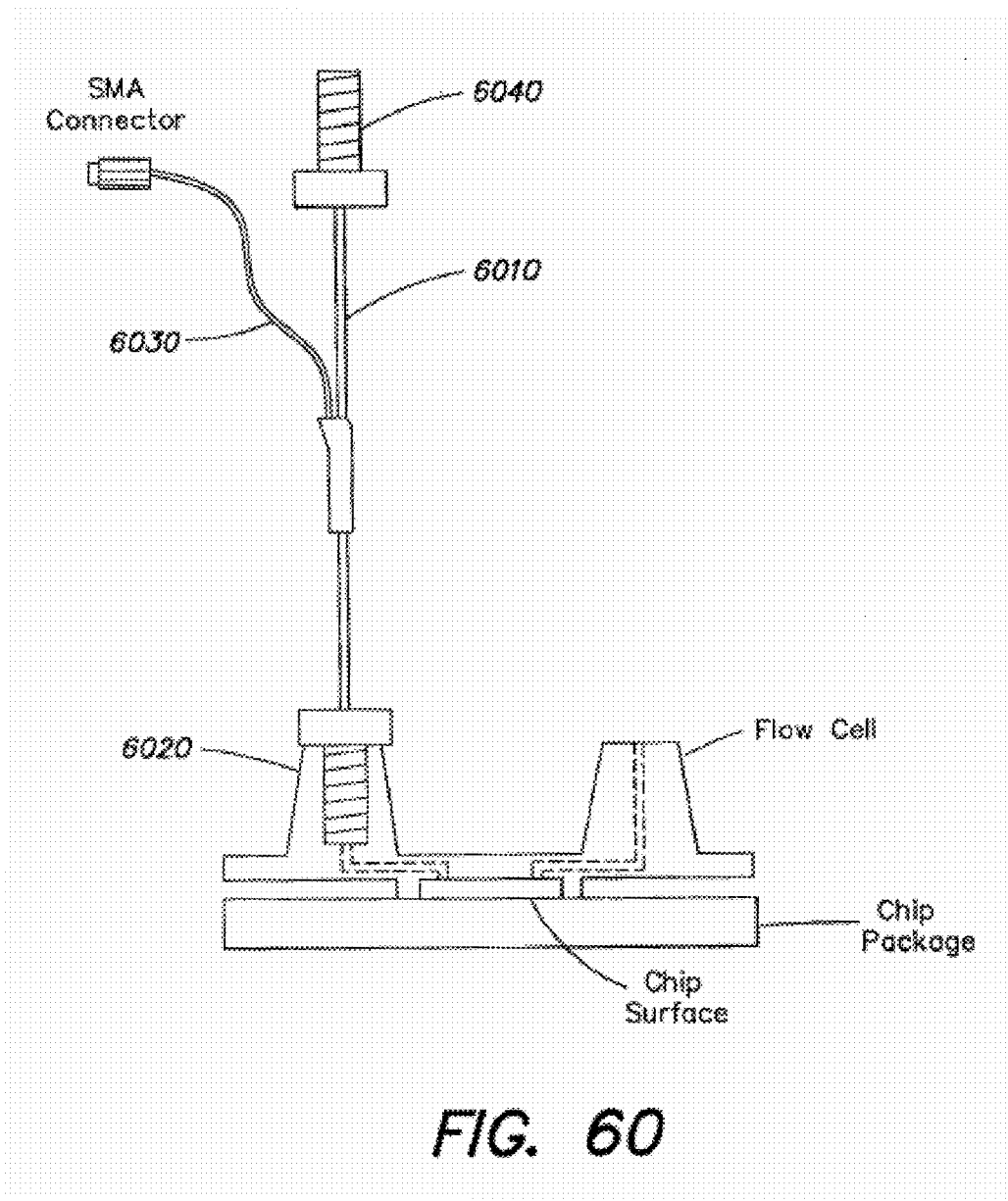
FIG. 60 is a schematic illustration, in cross-section, for introducing a stainless steel capillary tube as an electrode, into a downstream port of a flow cell such as the flow cells of FIGS. 59A-59C, or other flow cells.

Still further examples of flow cell structures are shown in FIGS. 59-60. FIG. 59A comprises eight views (A-H) of an injection molded bottom layer, or plate, 5910, for a flow cell fluidics interface, while FIG. 59B comprises seven views (A-G) of a mating, injection molded top plate, or layer, 5950. The bottom of plate 5910 has a downwardly depending rim 5912 configured and arranged to enclose the sensor chip and an upwardly extending rim 5914 for mating with the top plate 5610 along its outer edge. To form two fluid chambers (an inlet chamber and an outlet chamber) between them. A stepped, downwardly depending portion 5960 of top plate 5950, separates the input chamber from the output chamber. An inlet tube 5970 and an outlet tube 5980 are integrally molded with the rest of top plate 5950. From inlet tube 5970, which empties at the small end of the inlet chamber formed by a depression 5920 in the top of plate 5910, to the outlet edge of inlet chamber fans out to direct fluid across the whole array.

Whether glass or plastic or other material is used to form the flow cell, it may be desirable, especially with larger arrays, to include in the inlet chamber of the flow cell, between the inlet conduit and the front edge of the array, not just a gradually expanding (fanning out) space, but also some structure to facilitate the flow across the array being suitably laminar. Using the bottom layer 5990 of an injection molded flow cell as an example, one example type of structure for this purpose, shown in FIG. 59C, is a tree structure 5992 of channels from the inlet location of the flow cell to the front edge of the microwell array or sensor array, which should be understood to be under the outlet side of the structure, at 5994.

There are various other ways of providing a fluidics assembly for delivering an appropriate fluid flow across the microwell and sensor array assembly, and the forgoing examples are thus not intended to be exhaustive.

Reference Electrode

Commercial flow-type fluidic electrodes, such as silver chloride proton-permeable electrodes, may be inserted in series in a fluidic line and are generally designed to provide a stable electrical potential along the fluidic line for various electrochemical purposes. In the above-discussed system, however, such a potential must be maintained at the fluidic volume in contact with the microwell ISFET chip. With conventional silver chloride electrodes, it has been found difficult, due to an electrically long fluidic path between the chip surface and the electrode (through small channels in the flow cell), to achieve a stable potential. This led to reception of noise in the chip's electronics. Additionally, the large volume within the flow cavity of the electrode tended to trap and accumulate gas bubbles that degraded the electrical connection to the fluid. With reference to FIG. 60, a solution to this problem has been found in the use of a stainless steel capillary tube electrode 6010, directly connected to the chip's flow cell outlet port 6020 and connected to a voltage source (not shown) through a shielded cable 6030. The metal capillary tube 6010 has a small inner diameter (e.g., on the order of 0.01") that does not trap gas to any appreciable degree and effectively transports fluid and gas like other microfluidic tubing. Also, because the capillary tube can be directly inserted into the flow cell port 6020, it close to the chip surface, reducing possible electrical losses through the fluid. The large inner surface area of the capillary tube (typically about 2" long) may also contribute to its high performance. The stainless steel construction is highly chemically resistant, and should not be subject to electrochemical effects due to the very low electrical current use in the system (<1 µA). A fluidic fitting 6040 is attached to the end of the capillary that is not in the flow cell port, for connection to tubing to the fluid delivery and removal subsystem.

Fluidics System

A complete system for using the sensor array will include suitable fluid sources, valving and a controller for operating the valving to low reagents and washes over the microarray or sensor array, depending on the application. These elements are readily assembled from off-the-shelf components, with and the controller may readily be programmed to perform a desired experiment.

As already discussed, the apparatus and systems of the invention can be used to detect and/or monitor interactions between various entities. These interactions include chemical or enzymatic reactions in which substrates and/or reagents are consumed and/or reaction byproducts are generated. An example of an enzymatic reaction that can be monitored according to the invention is nucleic acid sequencing, which will be discussed in greater detail herein. In the context of a sequencing reaction, the apparatus and system provided herein is able to detect nucleotide incorporation based on changes in the chemFET current. Current changes may be the result of one or more of the following events either singly or some combination thereof: generation of PPi, generation of Pi (e.g., in the presence of pyrophosphatase), generation of hydrogen (and concomitant changes in pH for example in the presence of low strength buffer), reduced concentration of unincorporated dNTP at the chemFET surface, delayed arrival of dNTP at the chemFET surface, and the like. It is to be understood that the methods provided herein are not dependent upon the mechanism by which the current change is effected. And accordingly, the invention contemplates sequencing of nucleic acids based on changes in the chemFET current. The methods provided herein in regards to sequencing can be contrasted to those in the literature including Pourmand et al. PNAS 2006 103(17):6466-6470.

Figure 61:
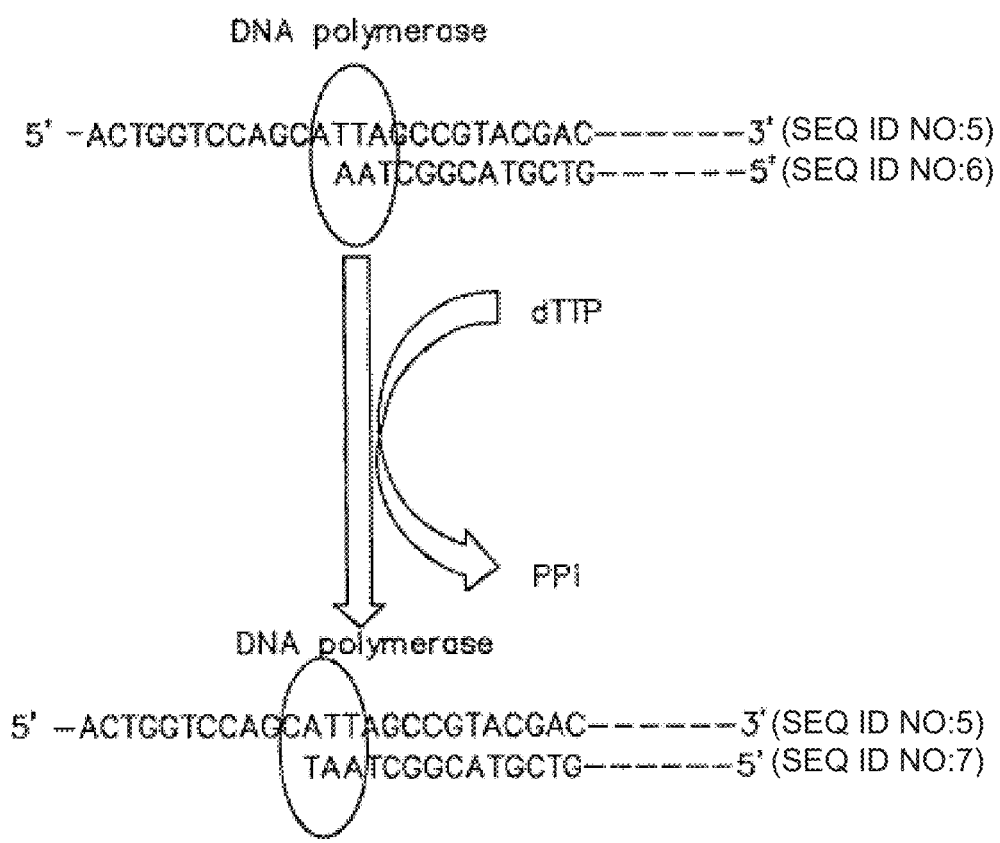
FIG. 61 is a schematic illustrating the incorporation of a dNTP into a synthesized nucleic acid strand with concomitant release of inorganic pyrophosphate (PPi).

FIG. 61 illustrates the production of PPi resulting from the incorporation of a nucleotide in a newly synthesized nucleic acid strand. PPi generated as a reaction byproduct of nucleotide incorporation in a nucleic acid strand can be detected directly even in the absence of a PPi receptor (such as those provided in FIG. 11B) and in the absence of a detectable pH change (e.g., as may occur in the presence of a strong buffer, as defined herein). The simple presence of PPi is sufficient, in some instances, to cause an electrical change in the chemFET surface, thereby resulting in a current change. The current change may result from PPi generation alone or in combination with other events such as those described above.

Thus, in one aspect, the invention contemplates sequencing nucleic acids using a chemFET array such as an ISFET array. The method of the invention is a "sequencing by synthesis" method since it requires synthesis of a new nucleic acid strand that is complementary to the strand being sequenced.

The release of PPi following incorporation of a nucleotide in a newly synthesized nucleic acid strand is shown in FIG. 61. The incorporation of a dNTP into the nucleic acid strand releases PPi which can then be hydrolyzed to two orthophosphates (Pi) and one hydrogen ion. The generation of the hydrogen ion therefore can facilitate detection of nucleotide incorporation on the basis of pH change. Alternatively, as discussed herein, PPi generation (as detected in the absence or presence of PPi receptors) can facilitate detection of nucleotide incorporation on the basis of pH change. And in still another embodiment, PPi may be converted to Pi using pyrophosphatase and Pi may be detected directly or indirectly. Any and all of these events (and more as described herein) may be involved in causing a current change in the chemFET that correlates with nucleotide incorporation.

The sequencing reactions aim to maximize complete incorporation across all wells for any given dNTP, reduce or decrease the number of unincorporated dNTPs that remain in the wells, and achieve as a high a signal to noise ratio as possible.

The nucleic acid being sequenced is referred to herein as the target nucleic acid. Target nucleic acids include but are not limited to DNA such as but not limited to genomic DNA, mitochondrial DNA, cDNA and the like, and RNA such as but not limited to mRNA, miRNA, and the like. The nucleic acid may be from any source including naturally occurring sources or synthetic sources. The nucleic acids may be PCR products, cosmids, plasmids, naturally occurring or synthetic libraries, and the like. The invention is not intended to be limited in this regard. The methods provided herein can be used to sequence nucleic acids of any length. To be clear, the Examples provide a proof of principle demonstration of the sequencing of four templates of known sequence. This artificial model is intended to show that the apparatus and system are able to readout nucleotide incorporation that correlates to the known sequence of the templates. This is not intended to represent typical use of the method or system in the field. The following is a brief description of these methods.

Target nucleic acids are prepared using any manner known in the art. As an example, genomic DNA may be harvested from a sample according to techniques known in the art (see for example Sambrook et al. "Maniatis"). Following harvest, the DNA may be fragmented to yield nucleic acids of smaller length. The resulting fragments may be on the order of hundreds, thousands, or tens of thousands nucleotides in length. In some embodiments, the fragments are 200-1000 base pairs in size, or 300-800 base pairs in size, although they are not so limited. Nucleic acids may be fragmented by any means including but not limited to mechanical, enzymatic or chemical means. Examples include shearing, sonication, nebulization and endonuclease (e.g., DNase I) digestion, or any other technique known in the art to produce nucleic acid fragments, preferably of a desired length. Fragmentation can be followed by size selection techniques can be used enrich or isolate fragments of a particular length or size. Such techniques are also known in the art and include but are not limited to gel electrophoresis or SPRI.

In some embodiments, the size selected target nucleic acids are ligated to adaptor sequences on both the 5' and 3' ends. These adaptor sequences comprise amplification primer sequences to be used in amplifying the target nucleic acids. One adaptor sequence may also comprise a sequence complementary to the sequencing primer. The opposite adaptor sequence may comprise a moiety that facilitates binding of the nucleic acid to a solid support such as but not limited to a bead. An example of such a moiety is a biotin molecule (or a double biotin moiety, as described by Diehl et al. Nature Methods, 2006, 3(7):551-559) and such a labeled nucleic acid can therefore be bound to a solid support having avidin or streptavidin groups. The resulting nucleic acid is referred to herein as a template nucleic acid. The template nucleic acid comprises at least the target nucleic acid and usually comprises nucleotide sequences in addition to the target.

In some instances a spacer is used to distance the template nucleic acid (and in particular the target nucleic acid sequence comprised therein) from the bead. This facilitates sequencing of the end of the target closest to the bead. Examples of suitable linkers are known in the art (see Diehl et al. Nature Methods, 2006, 3(7):551-559) and include but are not limited to carbon-carbon linkers such as but not limited to iSp18.

The solid support to which the template nucleic acids are bound is referred to herein as the "capture solid support". If the solid support is a bead, then such bead is referred to herein as a "capture bead". The beads can be made of any material including but not limited to cellulose, cellulose derivatives, gelatin, acrylic resins, glass, silica gels, polyvinyl pyrrolidine (PVP), co-polymers of vinyl and acrylamide, polystyrene, polystyrene cross-linked with divinylbenzene or the like (see, Merrifield Biochemistry 1964, 3, 1385-1390), polyacrylamides, latex gels, dextran, crosslinked dextrans (e.g., Sephadex™), rubber, silicon, plastics, nitrocellulose, natural sponges, metal, and agarose gel (Sepharose™). In one embodiment, the beads are streptavidin-coated beads. The bead diameter will depend on the density of the ISFET and well array used with larger arrays (and thus smaller sized wells) requiring smaller beads. Generally the bead size may be about 1-10 µM, and more preferably 2-6 µM. In some embodiments, the beads are about 5.91 µM while in other embodiments the beads are about 2.8 µM. It is to be understood that the beads may or may not be perfectly spherical in shape. It is to be understood that other beads may be used and other mechanisms for attaching the nucleic acid to the beads may be utilized.

As discussed herein, the sequencing reactions are carried out in wells that are situated above the chemFETs. The wells (referred to herein interchangeably as reaction chambers or microwells) may vary in size between arrays. Preferably the width to height ratio of the well is 1:1 to 1:1.5. The bead to well size is preferably in the range of 0.6-0.8.

A homogeneous population of amplified nucleic acids are conjugated to one or more beads with the proviso that each bead will ultimately be bound to a plurality of identical nucleic acid sequences. The degree of loading of nucleic acid templates onto beads will depend on a number of factors including the bead size and the length of the nucleic acid. In most aspects, maximal loading of the beads is desired. Amplification and conjugation of nucleic acids to solid support such as beads may be accomplished in a number of ways, including but not limited to emulsion PCR as described by Margulies et al. Nature 2005 437(15):376-380 and accompanying supplemental materials. In some embodiments, the amplification is a representative amplification. A representative amplification is an amplification that does not alter the relative representation of any nucleic acid species.

Before and/or while in the wells of the flow chamber, the beads are incubated with a sequencing primer that binds to its complementary sequence located on the 3' end of the template nucleic acid (i.e., either in the amplification primer sequence or in another adaptor sequence ligated to the 3' end of the target nucleic acid) and with a polymerase for a time and under conditions that promote hybridization of the primer to its complementary sequence and that promote binding of the polymerase to the template nucleic acid. The primer can be of virtually any sequence provided it is long enough to be unique. The hybridization conditions are such that the primer will hybridize to only its true complement on the 3' end of the template. Suitable conditions are disclosed in Margulies et al. Nature 2005 437(15):376-380 and accompanying supplemental materials.

Suitable polymerases include but are not limited to DNA polymerase, RNA polymerase, or a subunit thereof, provided it is capable of synthesizing a new nucleic acid strand based on the template and starting from the hybridized primer. An example of a suitable polymerase subunit is the exo-version of the Klenow fragment of E. coli DNA polymerase I which lacks 3' to 5' exonuclease activity. The enzyme is therefore bound to the bead (or corresponding solid support) but not to the ISFET surface itself. The template nucleic acid is also contacted with other reagents and/or cofactors including but not limited to buffer, detergent, reducing agents such as dithiothrietol (DTT, Cleland's reagent), single stranded binding proteins, and the like before and/or while in the well. In one embodiment, the template nucleic acid is contacted with the primer and the polymerase prior to its introduction into the flow chamber and wells thereof.

The nucleic acid loaded beads are introduced into the flow chamber and ultimately the wells situated above the ISFET array. The method requires that each well in the flow chamber contain only one nucleic acid loaded bead since the presence of two beads per well will yield one unusable sequencing information derived from two different nucleic acids. The Examples provides a brief description of an exemplary bead loading protocol in the context of magnetic beads. It is to be understood that a similar approach could be used to load other bead types. The protocol has been demonstrated to reduce the likelihood and incidence of trapped air in the wells of the flow chamber, uniformly distribute nucleic acid loaded beads in the totality of wells of the flow chamber, and avoid the presence and/or accumulation of excess beads in the flow chamber.

The percentage of occupied wells on the chip may vary depending on the methods being performed. If the method is aimed at extracting maximum sequence data in the shortest time possible, then higher occupancy is desirable. If speed and throughout is not as critical, then lower occupancy may be tolerated. Therefore depending on the embodiment, suitable occupancy percentages may be at least 10%, at least 20%, at least 30%, at least 40%, at least 50%, at least 60%, at least 70%, at least 80%, at least 90%, or 100% of the wells. As used herein, occupancy refers to the presence of one nucleic acid loaded bead in a well and the percentage occupancy refers to the proportion of total wells on a chip that are occupied by a single bead. Wells that are occupied by more than one bead cannot be used in the analyses contemplated by the invention.

Ultimately a homogeneous population of template nucleic acids is placed into one or more of a plurality of wells, each well situated over and thus corresponding to at least one ISFET. As discussed above, preferably the well contains at least 10, at least 100, at least 1000, at least $10^4$, at least $10^5$, at least $10^6$, or more copies of an identical template nucleic acid. Identical template nucleic acids means at a minimum that the templates are identical in sequence. Most and preferably all the template nucleic acids within a well are uniformly hybridized to a primer. Uniform hybridization of the template nucleic acids to the primers means that the primer hybridizes to the template at the same location (i.e., the sequence along the template that is complementary to the primer) as every other primer-template hybrid in the well. The uniform positioning of the primer on every template allows the co-ordinated synthesis of all new nucleic acid strands within a well, thereby resulting in a greater signal-to-noise ratio.

Nucleotides are then added in flow, or by any other suitable method, in sequential order to the flow chamber and thus the wells. The nucleotides can be added in any order provided it is known and for the sake of simplicity kept constant throughout a run. If the incorporation of nucleotides is based on detection of PPi rather than detection of pH change as a result of PPi release, then it is preferable to maintain a relatively constant level and concentration of nucleotides throughout the reactions and washes. One way of accomplishing this is to add ATP to the wash buffer such that dNTPs flowing into a well are displacing ATP from the well. The ATP matches the ionic strength of the dNTPs entering the wells and it also has a similar diffusion profile as those dNTPs. In this way, influx and efflux of dNTPs during the sequencing reaction do not interfere with measurements at the chemFET. The concentration of ATP used is on the order of the concentration of dNTP used.

A typical sequencing cycle proceeds as follows: washing of the flow chamber (and wells) with wash buffer containing ATP, introduction of a first dNTP species (e.g., dATP) into the flow chamber (and wells), release and detection of PPi (by any of the mechanisms described herein), washing of the flow chamber (and wells) with wash buffer containing ATP, washing of the flow chamber (and wells) with wash buffer containing apyrase, washing of the flow chamber (and wells) with wash buffer containing ATP, and introduction of a second dNTP species. This process is continued until all 4 dNTP (i.e., dATP, dCTP, dGTP and dTTP) have been flowed through the chamber and allowed to incorporate into the newly synthesized strands. This 4-nucleotide cycle may be repeated any number of times including but not limited to 10, 25, 50, 100, 200 or more times. The number of cycles will be governed by the length of the template being sequenced and the need to replenish reaction reagents, in particular the dNTP stocks and wash buffers.

As part of the sequencing reaction, a dNTP will be ligated to (or "incorporated into" as used herein) the 3' of the newly synthesized strand (or the 3' end of the sequencing primer in the case of the first incorporated dNTP) if its complementary nucleotide is present at that same location on the template nucleic acid. Incorporation of the introduced dNTP (and concomitant release of PPi) therefore indicates the identity of the corresponding nucleotide in the template nucleic acid. If no change in the electric field is detected by the ISFET, then the dNTP has not been incorporated and one can conclude that the complementary nucleotide was not present in the template at that location. If a change in the electric field is detected, then the introduced dNTP has been incorporated into the newly synthesized strand. There is a positive correlation between dNTP incorporation and PPi release and the response of the ISFET, and as a result it is further possible to quantitate the number of dNTP incorporated. In other words, the voltage change registered at the ISFET is related to the number of dNTP incorporated. The result is that no sequence information is lost through the sequencing of a homopolymer stretch (e.g., polyA, polyT, polyC, or polyG) in the template. As an example, if the template nucleic acid includes a sequence of 5' CAAAAG 3', the ISFET will register a signal (e.g., in terms of millivolt change) upon introduction of dCTP, and then it will register a signal of greater magnitude upon the introduction of dTTP, followed by another signal upon the introduction of dGTP. The magnitude of the signals arising upon introduction of dCTP and dTTP will be essentially equivalent and will correlate with the millivoltage change resulting from a single nucleotide incorporation. The magnitude of the signal arising upon introduction of dTTP will be greater than the signals arising from single dNTP incorporation. The magnitude of these signals may be additive, and depending on the length of the homopolymer stretch may not be readily apparent in a voltage versus time (or frame) plot (such as those shown in FIG. 71A-D, right panels). Signals may be measured using peak intensity or area under the curve from a voltage versus time (or frame) plot.

Apyrase is an enzyme that degrades residual unincorporated nucleotides converting them into monophosphate and releasing inorganic phosphate in the process. It is useful for degrading dNTPs that are not incorporated and/or that are in excess in any and all wells. It is important that excess and/or unreacted dNTP be washed away from any and all wells before introduction of the subsequent dNTP. Accordingly, addition of apyrase during the synthesis reaction and between the introduction of different dNTPs is useful to remove excess dNTPs that would otherwise obscure the sequencing data.

Additional sequencing reaction reagents such as those described above may be introduced throughout the reaction, although in some cases this may not be necessary. For example additional polymerase, DTT, SBB and the like may be added if necessary.

The invention therefore contemplates performing a plurality of different sequencing reactions simultaneously. A plurality of identical sequencing reactions is occurring in each occupied well simultaneously. It is this simultaneous and identical incorporation of dNTP within each well that increases the signal to noise ratio, thereby making detection of the sequencing reaction byproduct possible. By performing sequencing reactions in a plurality of wells simultaneously, a plurality of different sequencing reactions are also performed simultaneously.

The sequencing reaction can be run at a range of temperatures. Typically, the reaction is run in the range of 30-60° C., 35-55° C., or 40-45° C. It is preferable to run the reaction at temperatures that prevent formation of secondary structure in the nucleic acid. However this must be balanced with the binding of the primer (and the newly synthesized strand) to the template nucleic acid and the reduced half-life of apyrase at higher temperatures. A suitable temperature is about 41° C.

The solutions including the wash buffers and the dNTP solutions are generally warmed to these temperatures in order not to alter the temperature in the wells. The wash buffer containing apyrase however is preferably maintained at a lower temperature in order to extend the half-life of the enzyme. Typically, this solution is maintained at about 4-15° C., and more preferably 4-10° C.

The nucleotide incorporation reaction can occur very rapidly. As a result, it may be desirable in some instances to slow the reaction down in order to ensure maximal data capture during the reaction. The diffusion of reagents and/or byproducts can be slowed down in a number of ways including but not limited to addition of packing beads in the wells. The packing beads also tend to increase the concentration of reagents and/or byproducts at the chemFET surface, thereby increasing the potential for signal. The presence of packing beads generally allows a greater time to sample (e.g., by 2- or 4-fold).

Data capture rates can vary and be for example anywhere from 10-100 frames per second and the choice of which rate to use will be dictated at least in part by the well size and the presence of packing beads. Smaller well sizes generally require faster data capture rates.

In some aspects of the invention that are flow-based and where the top face of the well is open and in communication with fluid over the entirety of the chip, it is important to detect the released PPi or other byproduct (e.g., $H^+$) prior to diffusion out of the well. Diffusion of either reaction byproduct out of the well will lead to false negatives (because the byproduct is not detected in that well) and potential false positives in adjacent or downstream wells, and thus should be avoided. Packing beads may also help reduce the degree of diffusion and/or cross-talk between wells.

Thus in some embodiments packing beads are used in addition to the nucleic acid-loaded beads. The packing beads may be magnetic (including superparamagnetic) but they are not so limited. In some embodiments the packing beads and the capture beads are made of the same material (e.g., both are magnetic, both are polystyrene, etc.), while in other embodiment they are made of different materials (e.g., the packing beads are polystyrene and the capture beads are magnetic). The packing beads are generally smaller than the capture beads. The difference in size may be vary and may be 5-fold, 10-fold, 15-fold, 20-fold or more. As an example, 0.35 μm diameter packing beads have been used with 5.91 μm capture beads. Such packing beads are commercially available from sources such as Bang Labs. The placement of the packing beads relative to the capture bead may vary. For example, the packing beads may surround the capture bead and thereby prevent the capture bead from contacting the ISFET surface. As another example, the packing beads may be loaded into the wells following the capture beads in which case the capture bead is in contact with the ISFET surface. The presence of packing beads between the capture bead and the ISFET surface slows the diffusion of the sequencing byproducts such as PPi, thereby facilitating data capture.

The invention further contemplates the use of packing beads or modifications to the chemFET surface (as described herein) to prevent contact and thus interference of the chemFET surface with the template nucleic acids bound to the capture beads. A layer of packing beads that is 0.1-0.5 μm in depth or height would preclude this interaction.

The sequencing reaction may be preceded by an analysis of the arrays to determine the location of beads. It has been found that in the absence of flow the background signal (i.e., noise) is less than or equal to about 0.25 mV, but that in the presence of DNA-loaded capture beads that signal increases to about 1.0 mV+/−0.5 mV. This increase is sufficient to allow one to determine wells with beads.

The invention further contemplates kits comprising the various reagents necessary to perform a sequencing reaction and instructions of use according to the methods set forth herein.

One preferred kit comprises one or more containers housing wash buffer, one or more containers each containing one of the following reagents: dATP buffer, dCTP buffer, dGTP buffer or dTTP buffer, dATP, dCTP, dGTP and dTTP stocks, apyrase, SSB, polymerase, packing beads and optionally pyrophosphatase. Importantly the kits comprise only naturally occurring dNTPs.

The kits may also comprise one or more wash buffers comprising components as described in the Examples, but also not so limited. The kits may also comprise instructions for use including diagrams that demonstrate the methods of the invention.

It is to be understood that interactions between receptors and ligands or between two members of a binding pair or between components of a molecular complex can also be detected using the chemFET arrays. Examples of such interactions include hybridization of nucleic acids to each other, protein-nucleic acid binding, protein-protein binding, enzyme substrate binding, enzyme-inhibitor binding, antigen-antibody binding, and the like. Any binding or hybridization event that causes a change of the semiconductor charge density at the FET interface and thus changes the current that flows from the source to the drain of the sensors described herein can be detected according to the invention.

In these embodiments, the passivation layer (or possibly an intermediate layer coated onto the passivation layer) is functionalized with nucleic acids (e.g., DNA, RNA, miRNA, cDNA, and the like), antigens (which can be of any nature), proteins (e.g., enzymes, cofactors, antibodies, antibody fragments, and the like), and the like. Conjugation of these entities to the passivation layer can be direct or indirect (e.g., using bifunctional linkers that bind to both the passivation layer reactive group and the entity to be bound).

As an example, reaction groups such as amine or thiol groups may be added to a nucleic acid at any nucleotide during synthesis to provide a point of attachment for a bifunctional linker. As another example, the nucleic acid may be synthesized by incorporating conjugation-competent reagents such as Uni-Link AminoModifier, 3'-DMT-C6-Amine-ON CPG, AminoModifier II, N-TFA-C6-Amino-Modifier, C6-ThiolModifier, C6-Disulfide Phosphoramidite and C6-Disulfide CPG (Clontech, Palo Alto, Calif.). Other methods for attaching nucleic acids are discussed below.

In one aspect of the invention, the chemFET arrays are provided in combination with nucleic acid arrays. Nucleic acids in the form of short nucleic acids (e.g., oligonucleotides) or longer nucleic acids (e.g., full length cDNAs) can be provided on chemFET surfaces of the arrays described herein. Nucleic acid arrays generally comprise a plurality of physically defined regions on a planar surface (e.g., "spots") each of which has conjugated to it one and more preferably more nucleic acids. The nucleic acids are usually single stranded. The nucleic acids conjugated to a given spot are usually identical. In the context of an oligonucleotide array, these nucleic acids may be on the order of less 100 nucleotides in length (including about 10, 20, 25, 30, 40, 50, 60, 70, 80, 90 or 100 nucleotides in length). If the arrays are used to detect certain genes (including mutations in such genes or expression levels of such genes), then the array may include a number of spots each of which contains oligonucleotides that span a defined and potentially different sequence of the gene.

These spots are then located across the planar surface in order to exclude position related effects in the hybridization and readout means of the array.

The arrays are contacted with a sample being tested. The sample may be a genomic DNA sample, a cDNA sample from a cell, a tissue or a mass (e.g., a tumor), a population of cells that are grown on the array, potentially in a two dimensional array that corresponds to the underlying sensor array, and the like. Such arrays are therefore useful for determining presence and/or level of a particular gene or of its expression, detecting mutations within particular genes (such as but not limited to deletions, additions, substitutions, including single nucleotide polymorphisms), and the like.

The binding or hybridization of the sample nucleic acids and the immobilized nucleic acids is generally performed under stringent hybridization conditions as that term is understood in the art. (See for example Sambrook et al. "Maniatis".) Examples of relevant conditions include (in order of increasing stringency): incubation temperatures of 25° C., 37° C., 50° C. and 68° C.; buffer concentrations of 10×SSC, 6×SSC, 4×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water. By way of example hybridization may be performed at 50% formamide and 4×SSC followed by washes of 2×SSC/formamide at 50° C. and with 1×SSC.

Nucleic acid arrays include those in which already formed nucleic acids such as cDNAs are deposited (or "spotted") on the array in a specific location. Nucleic acids can be spotted onto a surface by piezoelectrically deposition, UV crosslinking of nucleic acids to polymer layers such as but not limited to poly-L-lysine or polypyrrole, direct conjugation to silicon coated $SiO_2$ as described in published US patent application 2003/0186262, direct conjugation to a silanised chemFET surface (e.g., a surface treated with 3-aminopropyltriethoxysilane (APTES) as described by Uslu et al. Biosensors and Bioelectronics 2004, 19: 1723-1731, for example.

Nucleic acid arrays also include those in which nucleic acids (such as oligonucleotides of known sequence) are synthesized directly on the array. Nucleic acids can be synthesized on arrays using art-recognized techniques such as but not limited to printing with fine-pointed pins onto glass slides, photolithography using pre-made masks, photolithography using dynamic micromirror devices (such as DLP mirrors), ink-jet printing, or electrochemistry on microelectrode arrays. Reference can also be made to Nuwaysir et al. 2002 "Gene expression analysis using oligonucleotide arrays produced by maskless photolithography.". Genome Res 12: 1749-1755. Commercial sources of this latter type of array include Agilent, Affymetrix, and NimbleGen.

Thus the chemFET passivation layer may be coated with an intermediate layer of reactive molecules (and therefore reactive groups) to which the nucleic acids are bound and/or from which they are synthesized.

The invention contemplates combining such nucleic acid arrays with the chemFET arrays and particularly the "large scale" chemFET arrays described herein. The chemFET/nucleic acid array can be used in a variety of applications, some of which will not require the wells (or microwells or reaction chambers, as they are interchangeably referred to herein). Since analyses may still be carried out in flow, including in a "closed" system (i.e., where the flow of reagents and wash solutions and the like is automated), there will be one or more flow chambers situated above and in contact with the array. The use of multiple flow chambers allows multiple samples (or nucleic acid libraries) to be analyzed simultaneously. There may be 2, 3, 4, 5, 6, 7, 8, 9, 10 or more flow chambers. This configuration applies equally to other biological arrays including those discussed herein such as protein arrays, antibody arrays, enzyme arrays, chemical arrays, and the like.

Since the binding event between binding partners or between components of a complex is detected electronically via the underlying FET, such assays may be carried out without the need to manipulate (e.g., extrinsically label) the sample being assayed. This is advantageous since such manipulation invariably results in loss of sample and generally requires increased time and work up. In addition, the present method allows binding interactions to be studied in real time.

Protein arrays used in combination with the chemFET arrays of the invention are also contemplated. Protein arrays comprise proteins or peptides or other amino acid comprising biological moiety bound to a planar surface in an organized and predetermined manner. Such proteins include but are not limited to enzymes, antibodies and antibody fragments or antibody mimics (e.g., single chain antibodies).

In one embodiment, a protein array may comprise a plurality of different proteins (or other amino acid containing biological moieties). Each protein, and preferably a plurality of proteins, is present in a predetermined region or "cell" of the array. The regions (or cells) are aligned with the sensors in the sensor array such that there is one sensor for each region (or cell). The plurality of proteins in a single region (or cell) may vary depending on the size of the protein and the size of the region (or cell) and may be but is not limited to at least 10, 50, 100, 500, $10^3$, $10^4$ or more. The array itself may have any number of cells, including but not limited to at least 10, $10^2$, $10^3$, $10^4$, $10^5$, $10^6$, $10^7$, or more. In one application, the array is exposed to a sample that is known to contain or is suspected of containing an analyte that binds to the protein. The analyte may be a substrate or an inhibitor if the protein is an enzyme. The analyte may be any molecule that binds to the protein including another protein, a nucleic acid, a chemical species (whether synthetic or naturally occurring), and the like.

It is to be understood that, like the nucleic acid arrays contemplated herein, the readout from the protein arrays will be a change in current through the chemFET and thus no additional step of labeling and/or label detection is required in these array methods.

In another embodiment, the protein array may comprise a plurality of identical proteins (or other amino acid containing biological moieties). The identical proteins may be uniformly distributed on a planar surface or they may be organized into discrete regions (or cells) on that surface. In these latter embodiments, the regions (or cells) are aligned with the sensors in the sensor array such that there is one sensor for each region (or cell).

The proteins may be synthesised off-chip, then purified and attached to the array. Alternatively they can be synthesised on-chip, similarly to the nucleic acids discussed above. Synthesis of proteins using cell-free DNA expression or chemical synthesis is amenable to on-chip synthesis. Using cell-free DNA expression, proteins are attached to the solid support once synthesized. Alternatively, proteins may be chemically synthesized on the solid support using solid phase peptide synthesis. Selective deprotection is carried out through lithographic methods or by SPOT-synthesis. Reference can be made to at least MacBeath and Schreiber, Science, 2000, 289:1760-1763, or Jones et al. Nature, 2006, 439:168-174. Reference can also be made to U.S. Pat. No. 6,919,211 to Fodor et al.

Chemical compound microarrays in combination with chemFET arrays are also envisioned. Chemical compound microarrays can be made by covalently immobilizing the compounds (e.g., organic compounds) on the solid surface with diverse linking techniques (may be referred to in the literature as "small molecule microarray"), by spotting and drying compounds (e.g., organic compounds) on the solid surface without immobilization (may be referred to in the literature as "micro arrayed compound screening (μARCS)"), or by spotting organic compounds in a homogenous solution without immobilization and drying effect (commercialized as DiscoveryDot™ technology by Reaction Biology Corporation).

Tissue microarrays in combination with chemFET arrays are further contemplated by the invention. Tissue microarrays are discussed in greater detail in Battifora Lab Invest 1986, 55:244-248; Battifora and Mehta Lab Invest 1990, 63:722-724; and Kononen et al. Nat Med 1998, 4:844-847.

The configurations of the chemFET arrays and the biological or chemical arrays are similar in each instance and the discussion of one combination array will apply to others described herein or otherwise known in the art.

In yet another aspect, the invention contemplates analysis of cell cultures (e.g., two-dimensional cells cultures) (see for example Baumann et al. Sensors and Actuators B 55 1999 77:89), and tissue sections placed in contact with the chemFET array. As an example, a brain section may be placed in contact with the chemFET array of the invention and changes in the section may be detected either in the presence or absence of stimulation such as but not limited to neurotoxins and the like. Transduction of neural processes and/or stimulation can thereby be analyzed. In these embodiments, the chemFETs may operate by detecting calcium and/or potassium fluxes via the passivation layer itself or via receptors for these ions that are coated onto the passivation layer.

In yet another aspect, the invention contemplates the use of chemFET arrays, functionalized as described herein or in another manner, for use in vivo. Such an array may be introduced into a subject (e.g., in the brain or other region that is subject to ion flux) and then analyzed for changes based on the status of the subject.

Methods for attaching nucleic acids, proteins, molecules, and the like to solid supports, particularly in the context of an array, have been described in the art. See for example Lipshutz et al. Nature Genetics (supplement) 1999 21:20-24; Li et al. Proc. Natl. Acad. Sci., 2001, 98:31-36; Lockhart et al. Nat. Biotechnol. 1996 14:1675-1680; Wodicka et al. Nat. Biotechnol. 1997 15: 1359-1367; Chen et al. Journal of Biomedical Optics 1997 2:364; Duggan et al. Nat. Genet. 1991 21 (1 Suppl):10-4; Marton et al. Nat. Med. 1998 4(11):1293-301; Kononen et al. Nat Med 1998 4(7):844-847; MacBeath et al., Science 2000 289(5485):1760-1763; Haab et al. Genome Biology 2001 2 (2); Pollack et al. Nat. Genet. 1999 23(1):41-6; Wang D G et al. Science 1998 280(5366):1077-82; Fodor et al. Science 1991 251:767-773; Fodor et al. Nature 1993 364:555-556; Pease et al. Proc. Natl. Acad. Sci. USA 1994 91:5022-5026; Fodor Science 1997 277:393-395; Southern et al. Genomics 1992 13: 1008-1017; Schena et al. Science 1995 270(5235):467-70; Shalon et al. Genome Res 1996 6(7):639-45; Jongsma Proteomics 2006, 6:2650-2655; Sakata, Biosensors and Bioelectronics 2007, 22: 1311-1316.

The following examples are included for purposes of illustration and are not intended to limit the scope of the invention.

EXAMPLES

The following is an example of a proof of principle for rapid sequencing of single-stranded oligonucleotides using an ISFET array.

1.1. Binding of Single-Stranded Oligonucleotides to Streptavidin-Coated Magnetic Beads.

Single-stranded DNA oligonucleotide templates with a 5' Dual Biotin tag (HPLC purified), and a 20-base universal primer were ordered from IDT (Integrated DNA Technologies, Coralville, Ind.). Templates were 60 bases in length, and were designed to include 20 bases at the 3' end that were complementary to the 20-base primer (Table 1, italics). The lyophilized and biotinylated templates and primer were re-suspended in TE buffer (10 mM Tris-HCl, 1 mM EDTA, pH 8) as 40 μM stock solutions and as a 400 μM stock solution, respectively, and stored at −20° C. until use.

For each template, 60 μl of magnetic 5.91 μm (Bangs Laboratories, Inc. Fishers, Ind.) streptavidin-coated beads, stored as an aqueous, buffered suspension ($8.57 \times 10^4$ beads/μL), at 4° C., were prepared by washing with 120 μl bead wash buffer three times and then incubating with templates 1, 2, 3 and 4 (T1, T2, T3, T4: Table 1) with biotin on the 5' end, respectively.

Due to the strong covalent binding affinity of streptavidin for biotin (Kd ~10-15), these magnetic beads are used to immobilize the templates on a solid support, as described below. The reported binding capacity of these beads for free biotin is 0.650 pmol/μL of bead stock solution. For a small (<100 bases) biotinylated ssDNA template, it was conservatively calculated that $9.1 \times 10^5$ templates could be bound per bead. The beads are easily concentrated using simple magnets, as with the Dynal Magnetic Particle Concentrator or MPC-s (Invitrogen, Carlsbad, Calif.). The MPC-s was used in the described experiments.

An MPC-s was used to concentrate the beads for 1 minute between each wash, buffer was then added and the beads were resuspended. Following the third wash the beads were resuspended in 120 μL bead wash buffer plus 1 μl of each template (40 μM). Beads were incubated for 30 minutes with rotation (Labquake Tube Rotator, Barnstead, Dubuque, Iowa). Following the incubation, beads were then washed three times in 120 μL Annealing Buffer (20 mM Tris-HCl, 5 mM magnesium acetate, pH 7.5), and re-suspended in 60 μL of the same buffer.

TABLE 1

| Sequences for Templates 1, 2, 3, and 4 |
| --- |
| T1: 5'/52Bio/GCA AGT GCC CTT AGG CTT CAT TTC AAA AGT CCT AAC TGG GCA *AGG CAC ACA GGG GAT AGG*-3' (SEQ ID NO: 1) |
| T2: 5'/52Bio/CCA TGT CCC CTT AAG CCC CCC CCA TTC CCC CCT GAA CCC CCA *AGG CAC ACA GGG GAT AGG*-3' (SEQ ID NO: 2) |
| T3: 5'/52Bio/AAG CTC AAA AAC GGT AAA AAA AAG CCA AAA AAC TGG AAA ACA *AGG CAC ACA GGG GAT AGG*-3' (SEQ ID NO: 3) |
| T4: 5'/52Bio/TTC GAG TTT TTG CCA TTT TTT TTC GGT TTT TTG ACC TTT TCA *AGG CAC ACA GGG GAT AGG*-3' (SEQ ID NO: 4) |

1.2. Annealing of Sequencing Primer.

The immobilized templates, bound at the 5' end to 5.91 μm magnetic beads, are then annealed to a 20-base primer complementary to the 3' end of the templates (Table 1). A 1.0 μL aliquot of the 400 μM primer stock solution, representing a 20-fold excess of primer to immobilized template, is then added and then the beads plus template are incubated with primer for 15 minutes at 95° C. and the temperature was then slowly lowered to room temperature. The beads were then washed 3 times in 120 µL of 25 mM Tricine buffer (25 mM Tricine, 0.4 mg/ml PVP, 0.1% Tween 20, 8.8 mM Magnesium Acetate; ph 7.8) as described above using the MPC-s. Beads were resuspended in 25 mM Tricine buffer.

1.3. Incubation of Hybridized Templates/Primer with DNA Polymerase.

Template and primer hybrids are incubated with polymerase essentially as described by Margulies et al. Nature 2005 437(15):376-380 and accompanying supplemental materials.

2. Loading of Prepared Test Samples onto the Isfet Sensor Array.

The dimensions and density of the ISFET array and the microfluidics positioned thereon may vary depending on the application. A non-limiting example is a 512×512 array. Each grid of such an array (of which there would be 262144) has a single ISFET. Each grid also has a well (or as they may be interchangeably referred to herein as a "microwell") positioned above it. The well (or microwell) may have any shape including columnar, conical, square, rectangular, and the like. In one exemplary conformation, the wells are square wells having dimensions of 7×7×10 µm. The center-to-center distance between wells is referred to herein as the "pitch". The pitch may be any distance although it is preferably to have shorter pitches in order to accommodate as large of an array as possible. The pitch may be less than 50 less than 40 less than 30 less than 20 or less than 10 µm. In one embodiment, the pitch is about 9 µm. The entire chamber above the array (within which the wells are situated) may have a volume of equal to or less than about 30 µL, equal to or less than about 20 µL, equal to or less than about 15 µL, or equal to or less than 10 µL. These volumes therefore correspond to the volume of solution within the chamber as well.

2.1 Loading of Beads in an 'Open' System.

Beads with templates 1-4 were loaded on the chip (10 µL of each template). Briefly, an aliquot of each template was added onto the chip using an Eppendorf pipette. A magnet was then used to pull the beads into the wells.

2.2 Loading of Beads in a 'Closed' System.

Figure 62:
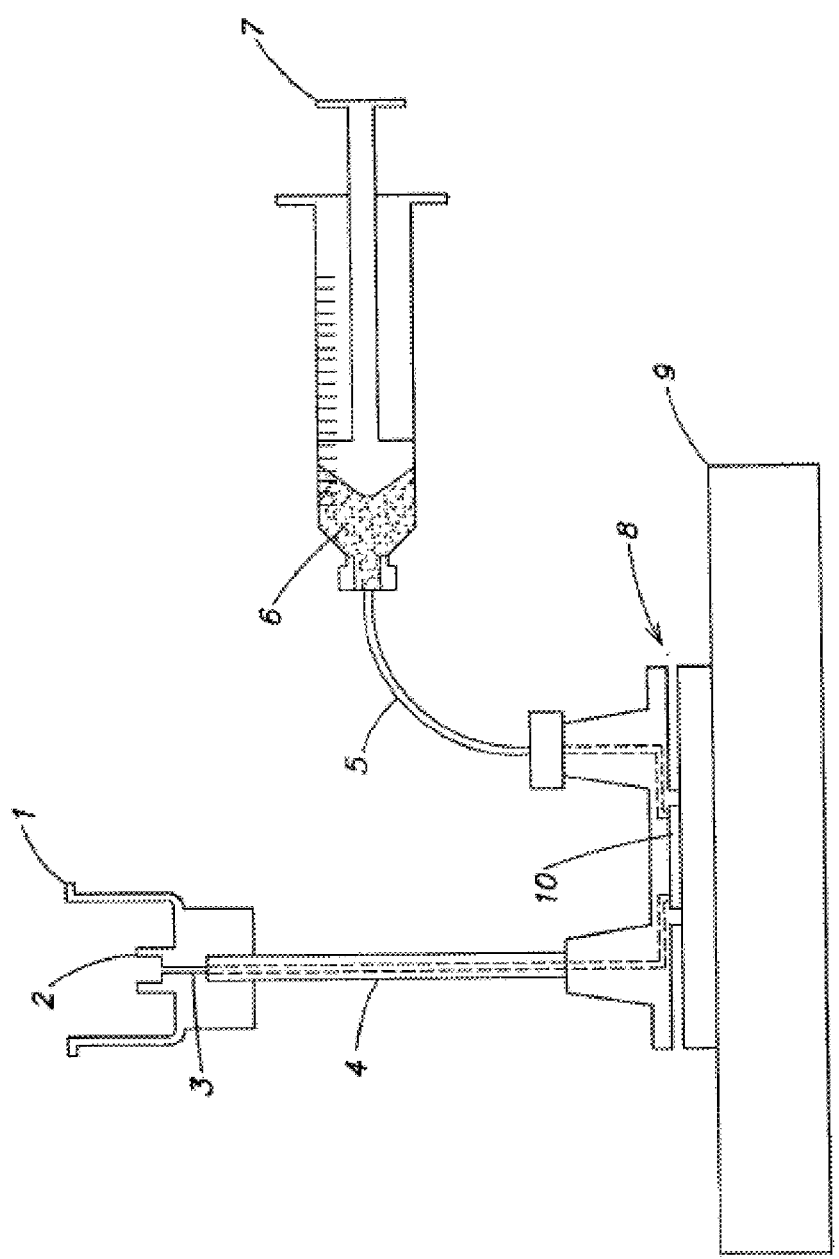
FIGS. 62-70 illustrate bead loading into the microfluidic arrays of the invention.

Both the capture beads the packing beads are loaded using flow. Microliter precision of bead solution volume, as well as positioning of the bead solution through the fluidics connections, is achieved as shown in FIG. 62 using the bead loading fitting, which includes a major reservoir (approx. 1 mL in volume), minor reservoir (approx. 10 µL in volume), and a microfluidic channel for handling small volumes of bead solution. This method also leverages the microliter precision of fluid application allowed by precision pipettes.

The chip comprising the ISFET array and flow cell is seated in the ZIF (zero insertion force) socket of the loading fixture, then attaching a stainless steel capillary to one port of the flow cell and flexible nylon tubing on the other port. Both materials are microfluidic-type fluid paths (e.g., on the order of <0.01" inner diameter). The bead loading fitting, consisting of the major and minor reservoirs, it attached to the end of the capillary. A common plastic syringe is filled with buffer solution, then connected to the free end of the nylon tubing. The electrical leads protruding from the bottom of the chip are inserted into a socket on the top of a fixture unit (not shown).

Figure 63:
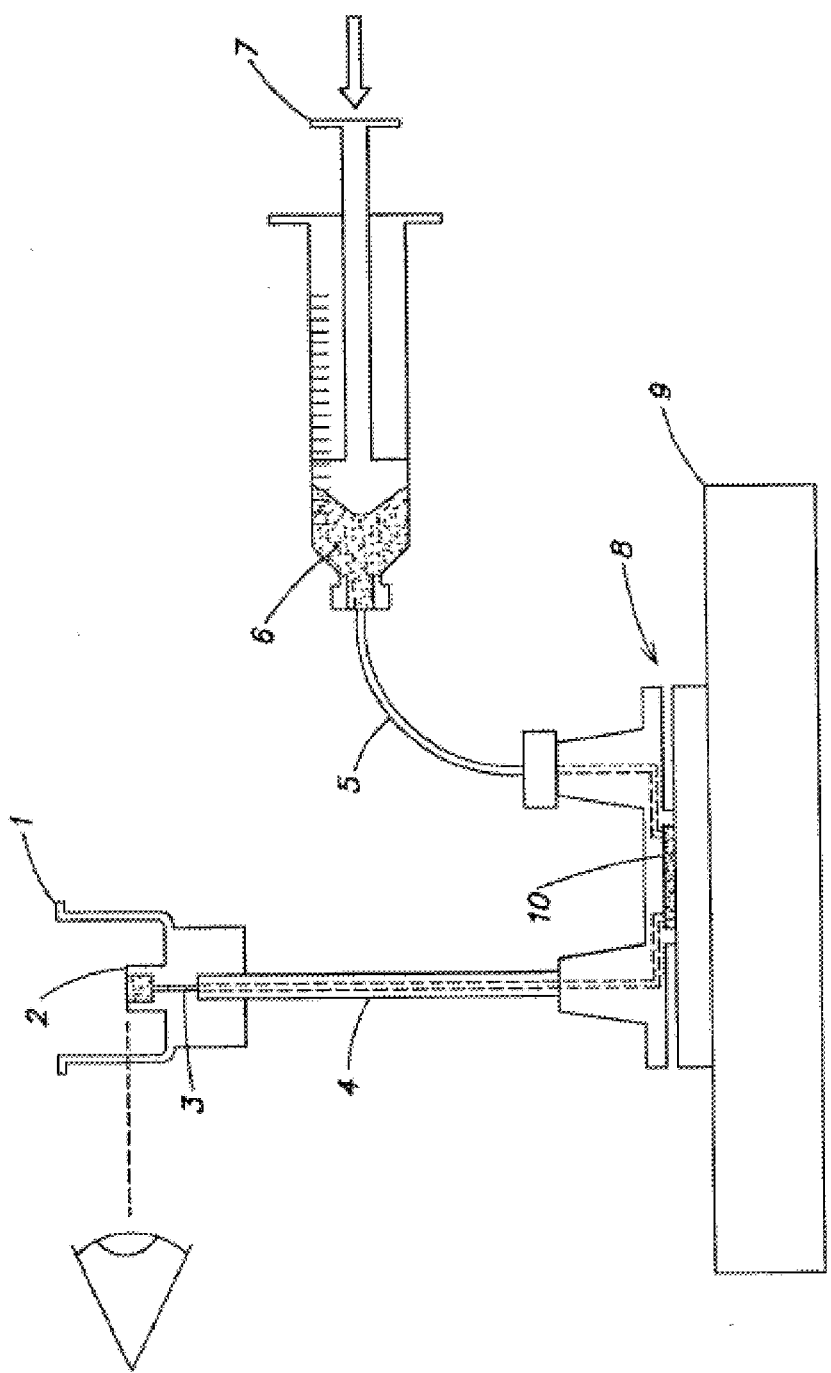

The syringe is pushed to inject the buffer solution through the tubing, across the flow cell (and chip surface) and up through the capillary as shown in FIG. 63. This process is called priming, and ensures that the fluidic circuit is free of air. The buffer is injected until the level of the liquid can be seen at the top of the minor reservoir, through the transparent major reservoir.

Figure 64:
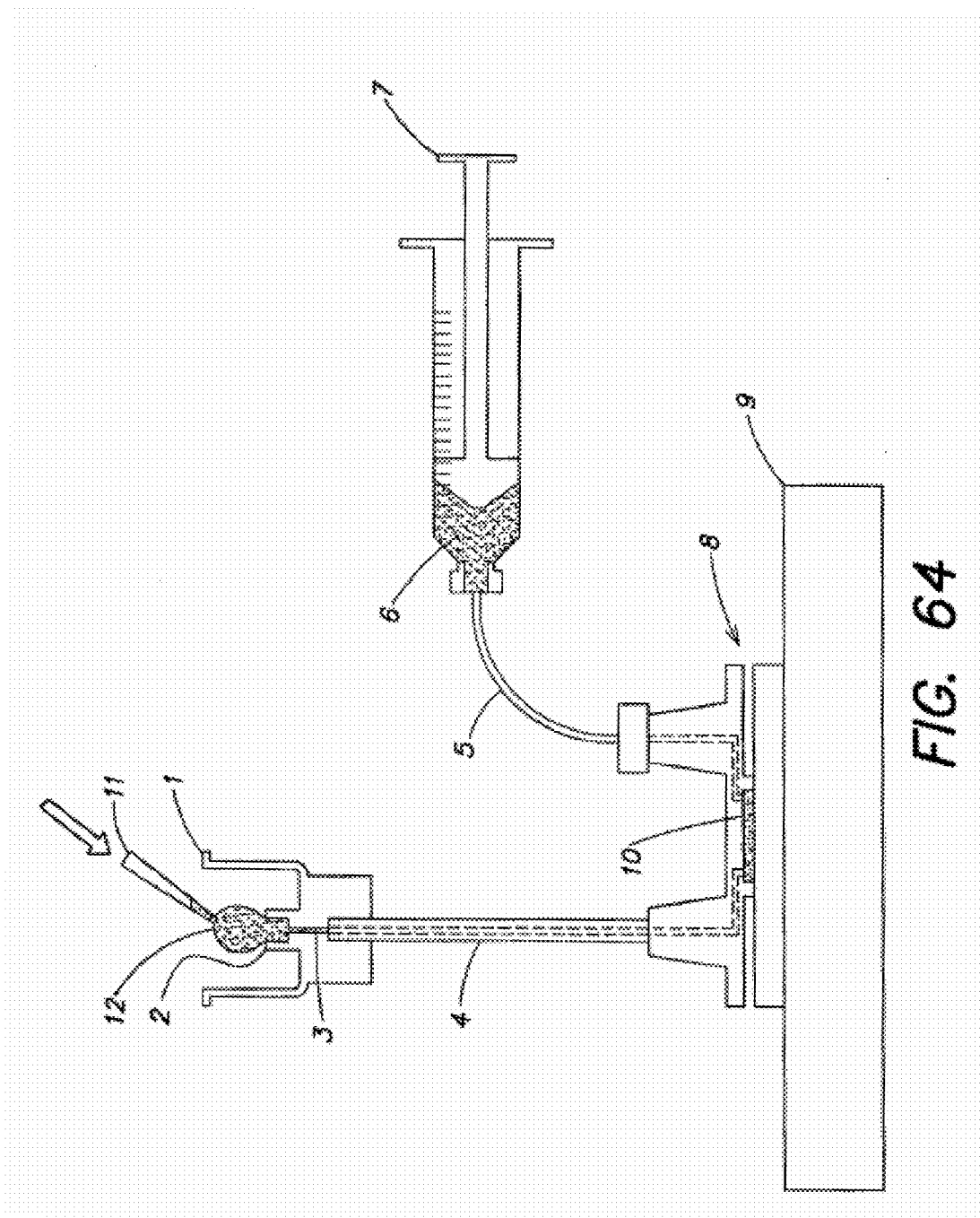
Figure 65:
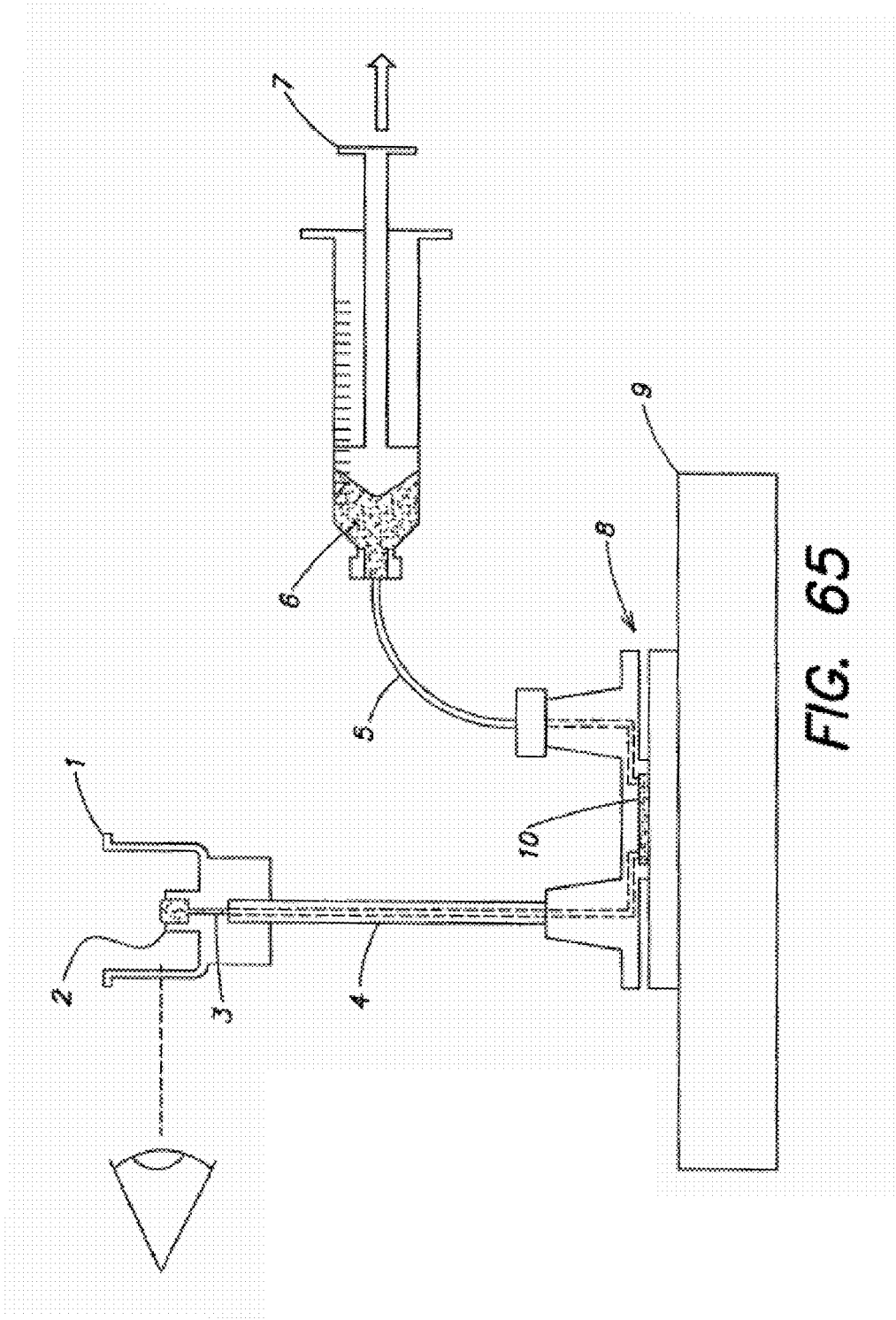

Next, a solution containing the nucleic acid-coated beads is applied with a precision pipette to the minor reservoir, as shown in FIG. 64. This application produces a large droplet at the top of the reservoir. The volume of solution added is equal to the volume of the flow chamber (e.g., on the order of 10 µL), and has a concentration of beads, such that when added to the volume of buffer solution initially in the minor reservoir, produces the desired concentration of beads to be delivered to the flow cell. The pipette is retracted, and the syringe is pulled carefully and slowly until the droplet recedes to the top of the minor reservoir, again viewed through the transparent major reservoir as shown in FIG. 65. Because the microfluidic channel extending down from the minor reservoir is very small (e.g., on the order of 0.01" diameter), very little mixing occurs between the bead solution and buffer solution in the fluidic path during this process.

Figure 66:
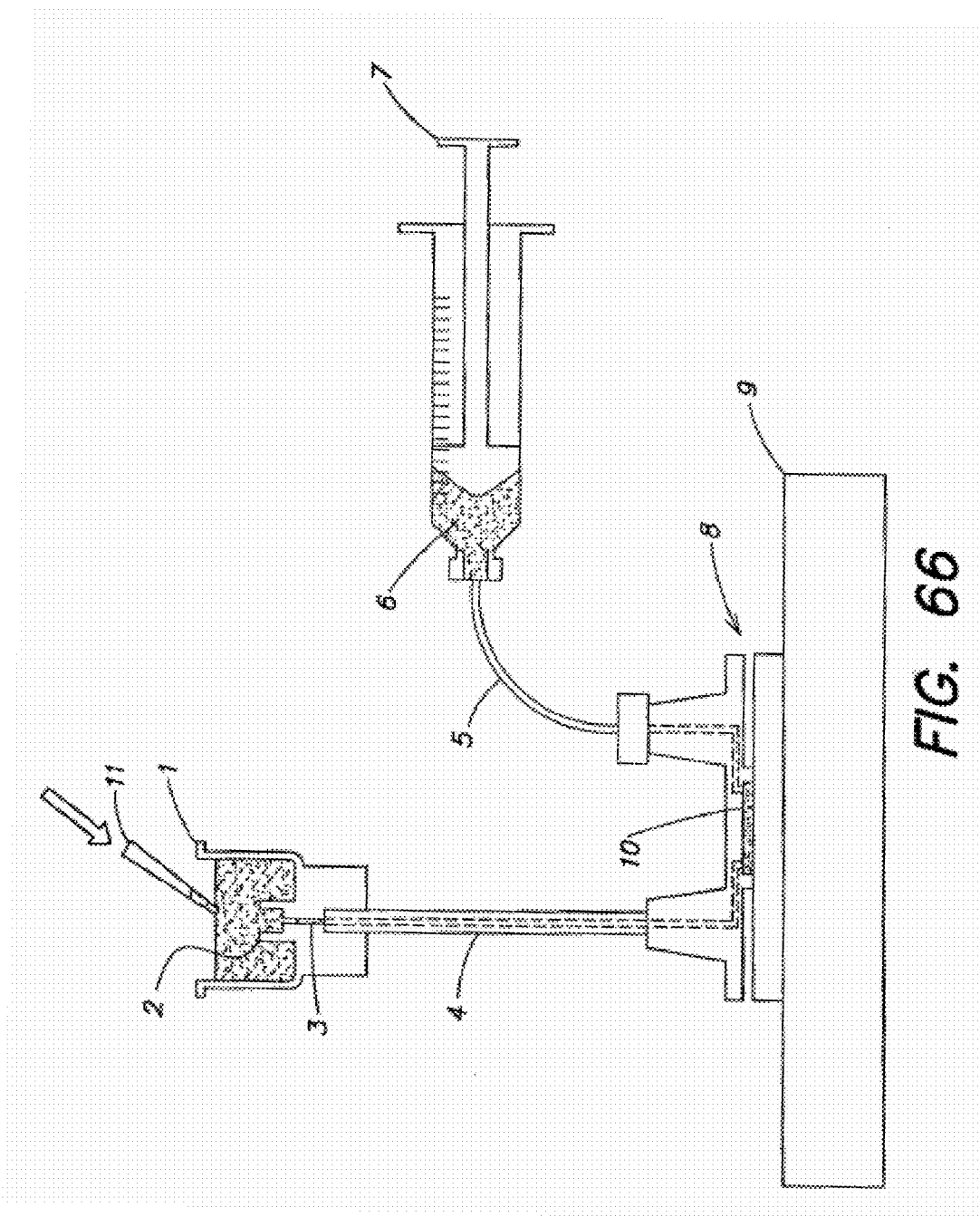
Figure 67:
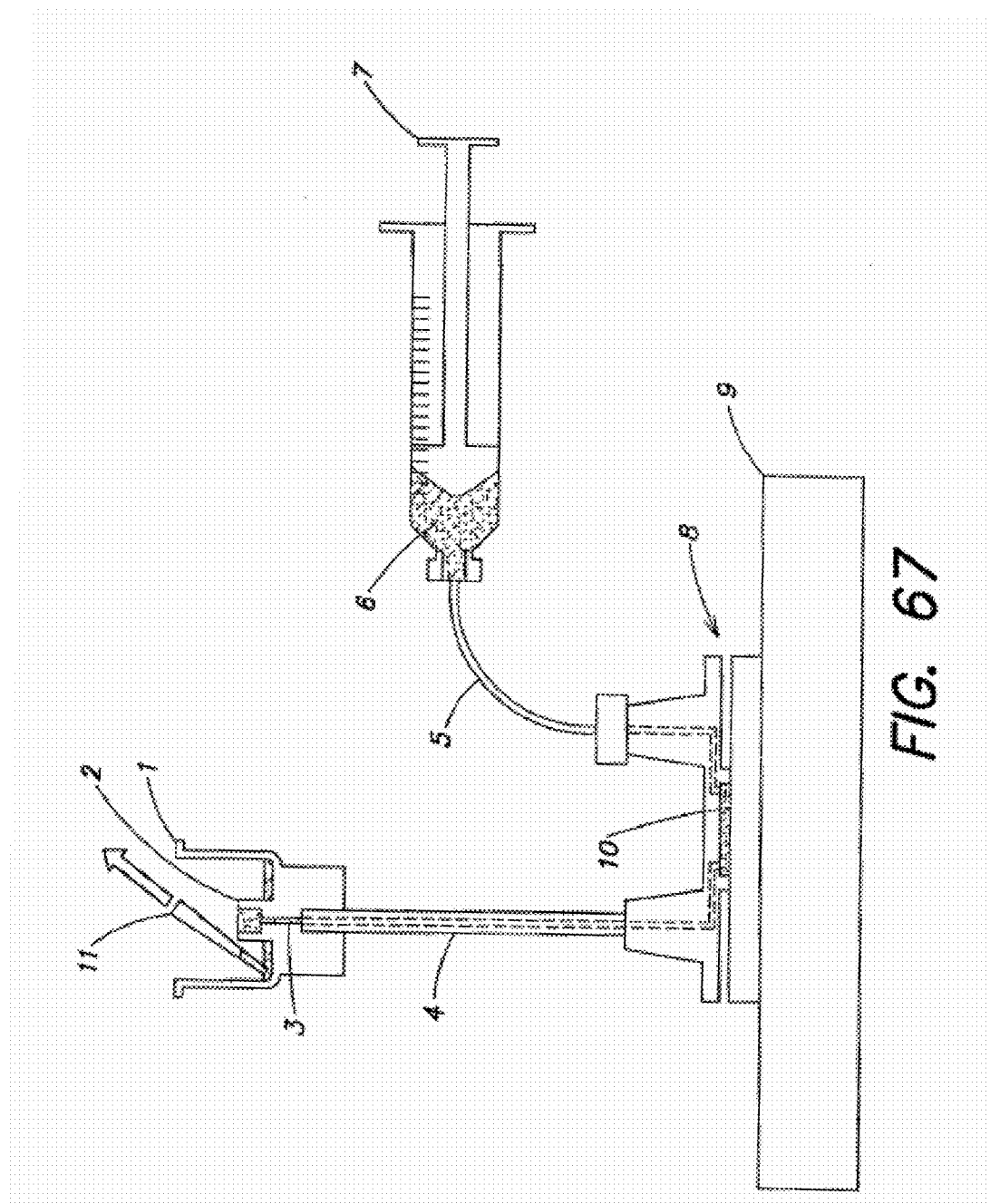

At this point, the bead solution is loaded into the fluidic path, but is not yet at the location of flow cell. Before transferring the bead solution plug, or volume of bead solution in the fluidic path, the solution in the minor reservoir is cleaned. First, approximately 1 mL of buffer solution is injected into the major reservoir, effectively diluting the bead solution left in the minor reservoir, as shown in FIG. 66. Then, the solution is pipetted out by placing a pipette tip along the bottom edge of the major reservoir. The level of solution in the minor reservoir is left at its top as shown in FIG. 67.

Figure 68:
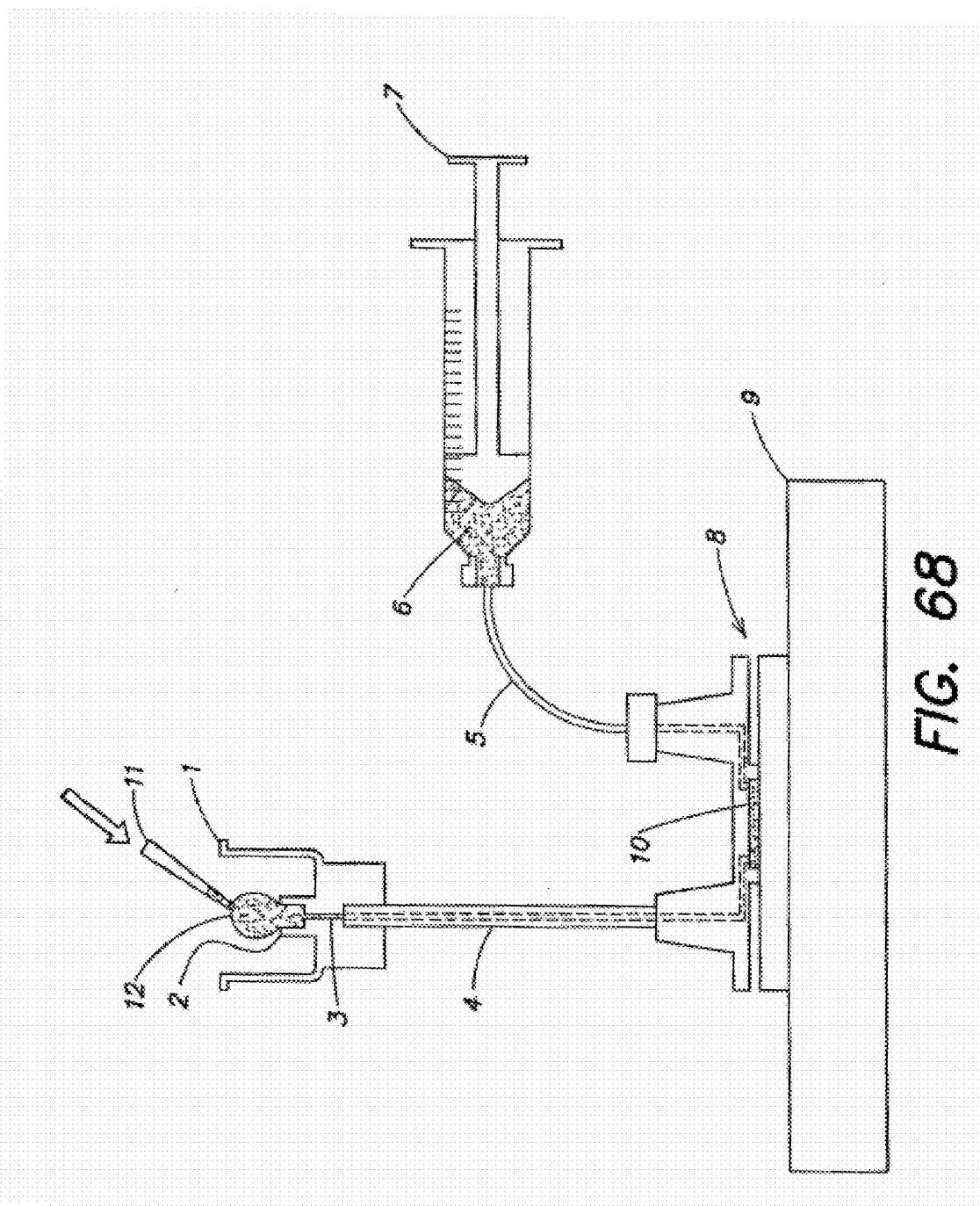
Figure 69:
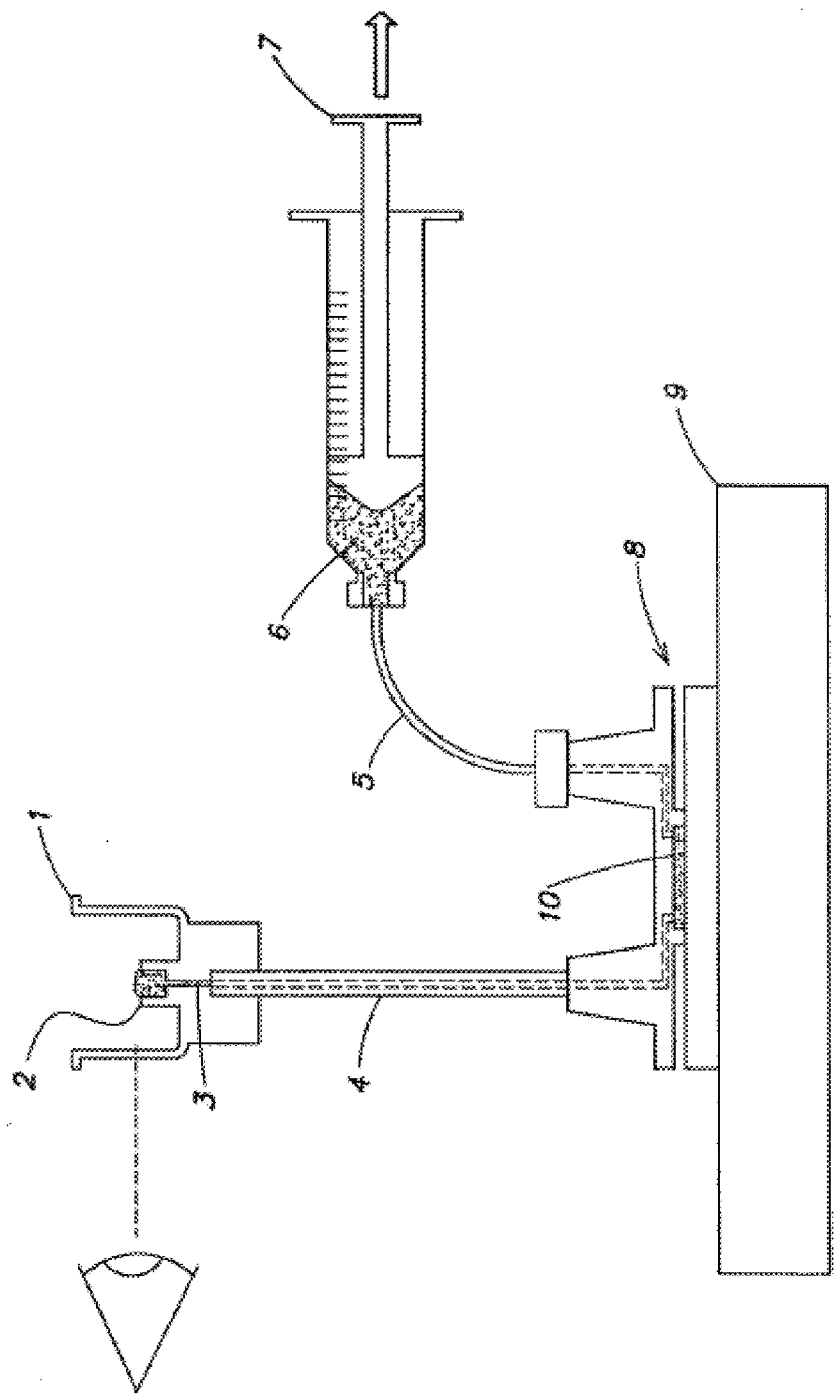

A volume of buffer solution is then added as droplet above the minor reservoir, as in prior bead solution application as shown in FIG. 68. The volume of this solution is equal to the volume of the fluidic path between the minor reservoir and the flow chamber of the flow cell (i.e., the microfluidic channel volume plus the capillary volume plus the volume of flow cell before the flow chamber). Again, the syringe is pulled until the droplet retracts to the top of the minor reservoir as shown in FIG. 69. Now the bead solution plug is loaded into the flow cell's flow chamber.

Figure 70:
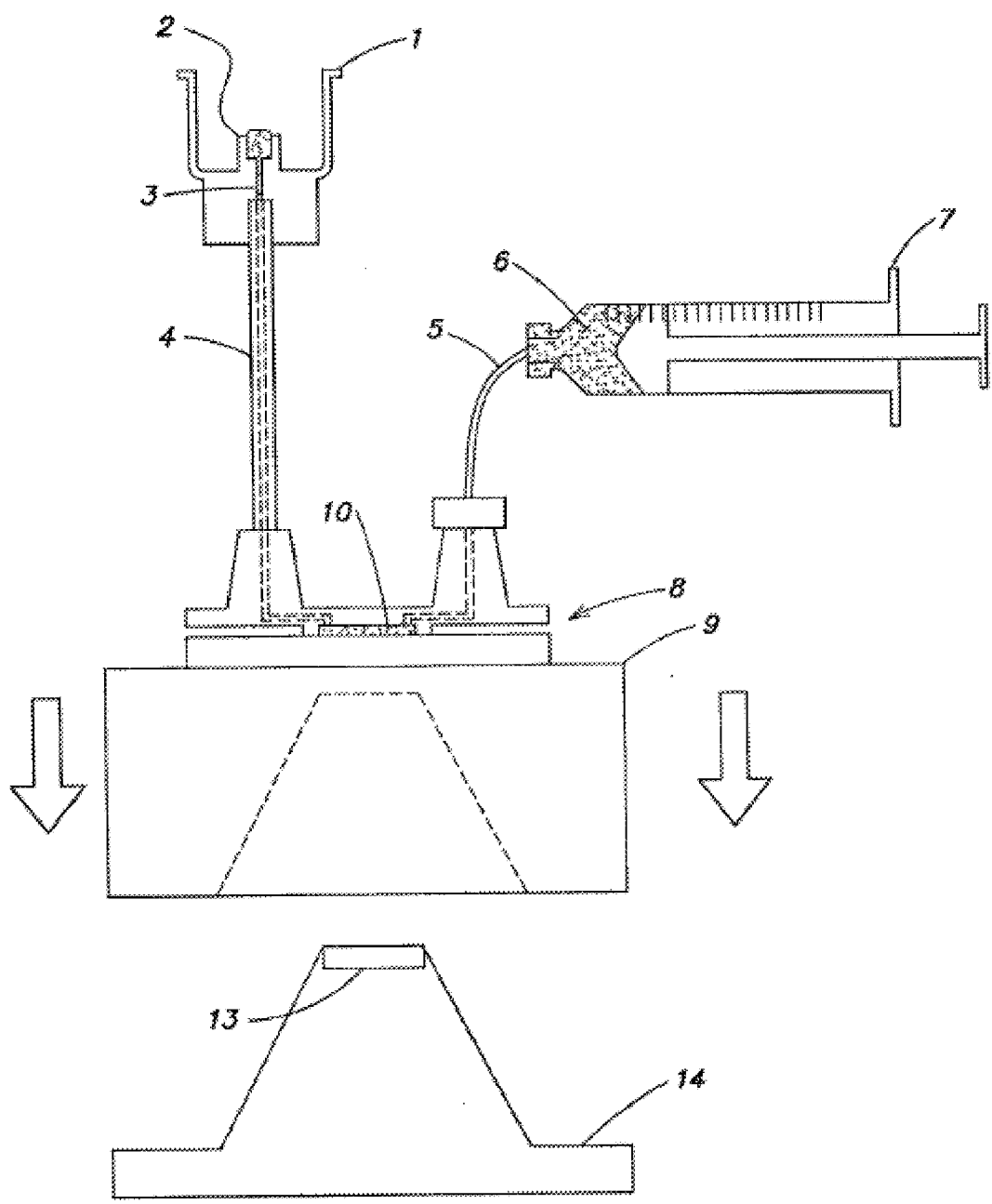

The loading fixture is now lifted and placed over a pyramidal base, containing a magnet at its apex, as shown in FIG. 70. The magnet pulls the beads from the bead solution into the microwells of the chip. The fixture is removed from the base after a few seconds. The entire process, excluding the initial priming of the fluidics with buffer solution, can be repeated for the loading of small packing beads into the microwells, if necessary.

It will be appreciated that there will be other ways of drawing the beads into the wells of the flow chamber, including centrifugation or gravity. The invention is not limited in this respect.

3. Dna Sequencing Using the ISFET Sensor Array.

3.1 DNA Sequencing in an 'Open' System.

The results shown are representative of an experiment carried out in an 'open' system (i.e., the ISFET chip is placed on the platform of the ISFET apparatus and then each nucleotide (5 µL resulting in 6.5 µM each) was manually added in the following order: dATP, dCTP, dGTP and dTTP (100 mM stock solutions, Pierce, Milwaukee, Wis.), by pipetting the given nucleotide into the liquid already on the surface of the chip and collecting data from the chip at a rate of 2.5 mHz. This resulted in data collection over 7.5 seconds at approximately 18 frames/second. Data were then analyzed using LabView.

Given the sequences of the templates, addition of dATP resulted in a 4 base extension in template 4. Addition of dCTP resulted in a 4 base extension in template 1. Addition of dGTP caused template 1, 2 and 4 to extend as indicated in Table 2 and addition of dTTP results in a run-off (extension of all templates as indicated).

FIG. 71 (A-D) illustrates the extension reactions. In the left panel, all pixels for one snapshot in time are shown, and on the right, mV vs. time graphs are shown for four selected pixels from the set on the left. White arrows indicate active pixels where extensions are taking place. In the run-off (FIG. 71D) in addition to the wells marked in FIG. 71C, an additional arrow indicates a well where an extension did not take place following the addition of dGTP, but rather dATP and is then seen again during the run-off.

Preferably when the method is performed in a non-automated manner (i.e., in the absence of automated flow and reagent introduction), each well contains apyrase in order to degrade the unincorporated dNTPs, or alternatively apyrase is added into each well following the addition and incorporation of each dNTP (e.g. dATP) and prior to the addition of another dNTP (e.g. dTTP). It is to be understood that apyrase can be substituted, in this embodiment or in any other embodiment discussed herein, with another compound (or enzyme) capable of degrading dNTPs.

TABLE 2

Set-up of experiment and order of nucleotide addition.

|    | dATP | dCTP         | dGTP | dTTP         |
|----|------|--------------|------|--------------|
| T1 | 0    | (3: C; 1: A)4 | 1    | Run-off (25) |
| T2 | 0    | 0            | 4    | Run-off (26) |
| T3 | 0    | 0            | 0    | Run-off (30) |
| T4 | 4    | 0            | 2    | Run-off (24) |

3.2 DNA Sequencing Using Microfluidics on Sensor Chip

Sequencing in the flow regime is an extension of open application of nucleotide reagents for incorporation into DNA. Rather than add the reagents into a bulk solution on the ISFET chip, the reagents are flowed in a sequential manner across the chip surface, extending a single DNA base(s) at a time. The dNTPs are flowed sequentially, beginning with dTTP, then dATP, dCTP, and dGTP. Due to the laminar flow nature of the fluid movement over the chip, diffusion of the nucleotide into the microwells and finally around the nucleic acid loaded bead is the main mechanism for delivery. The flow regime also ensures that the vast majority of nucleotide solution is washed away between applications. This involves rinsing the chip with buffer solution and apyrase solution following every nucleotide flow. The nucleotides and wash solutions are stored in chemical bottles in the system, and are flowed over the chip using a system of fluidic tubing and automated valves. The ISFET chip is activated for sensing chemical products of the DNA extension during nucleotide flow.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A sensor comprising:
a chemically-sensitive field effect transistor (chemFET) to detect a chemical reaction occurring proximate to the chemFET; and
bias circuitry coupled to the chemFET, the bias circuitry including a diode-connected transistor maintaining a substantially constant bias voltage between a source terminal of the chemFET and a drain terminal of the chemFET.

2. The sensor of claim 1, wherein a first terminal of the diode-connected transistor is coupled to a gate terminal of the diode-connected transistor and to the source terminal of the chemFET, and a second terminal of the chemFET is coupled to the drain terminal of the chemFET.

3. The sensor of claim 2, wherein the bias circuitry further includes a current sink to draw a current through the diode-connect transistor to establish the bias voltage between the first terminal and the second terminal of the diode-connected transistor.

4. The sensor of claim 1, wherein the chemFET generates a sensor signal in response to detecting the chemical reaction.

5. The sensor of claim 4, further comprising readout circuitry to produce an output signal based on the sensor signal.

6. The sensor of claim 4, wherein the sensor signal is based on a threshold voltage of the chemFET.

7. The sensor of claim 4, wherein the sensor signal is a voltage level at one of the source terminal and the drain terminal of the chemFET.

8. The sensor of claim 1, wherein the bias circuitry further applies a read voltage to the drain terminal of the chemFET.

9. The sensor of claim 1, wherein the chemical reaction is a sequencing reaction.

10. The sensor of claim 9, wherein the sequencing reaction includes incorporation of one or more nucleotides into at least one template nucleic acid.

11. The sensor of claim 1, wherein the bias circuitry further includes a current source to provide a bias current through the chemFET, and the chemFET generates a voltage level at one of the source terminal and the drain terminal of the chemFET in response to the chemical reaction.

* * * * *